US008877200B2

United States Patent
(12) United States Patent
Shriver et al.

(10) Patent No.: US 8,877,200 B2
(45) Date of Patent: Nov. 4, 2014

(54) HA BINDING AGENTS

(71) Applicant: Visterra, Inc., Cambridge, MA (US)

(72) Inventors: Zachary Shriver, Cambridge, MA (US); Karthik Viswanathan, Waltham, MA (US); Vidya Subramanian, Somerville, MA (US); Sasisekharan Raguram, Cambridge, MA (US)

(73) Assignee: Visterra, Inc., Cambridge, MA (US)

(*) Notice: Subject to any disclaimer, the term of this patent is extended or adjusted under 35 U.S.C. 154(b) by 0 days.

(21) Appl. No.: 14/051,405

(22) Filed: Oct. 10, 2013

(65) Prior Publication Data

US 2014/0148581 A1 May 29, 2014

Related U.S. Application Data

(63) Continuation of application No. 13/830,367, filed on Mar. 14, 2013.

(60) Provisional application No. 61/716,447, filed on Oct. 19, 2012, provisional application No. 61/645,554, filed on May 10, 2012.

(51) Int. Cl.

| | |
|---|---|
| *A61K 39/42* | (2006.01) |
| *C07K 16/00* | (2006.01) |
| *C07K 16/10* | (2006.01) |
| *A61K 45/06* | (2006.01) |
| *A61K 39/00* | (2006.01) |

(52) U.S. Cl.

CPC ............. *C07K 16/1018* (2013.01); *A61K 39/42* (2013.01); *A61K 45/06* (2013.01); *A61K 2039/505* (2013.01); *C07K 2317/33* (2013.01); *C07K 2317/34* (2013.01); *C07K 2317/565* (2013.01); *C07K 2317/567* (2013.01); *C07K 2317/56* (2013.01); *C07K 2317/76* (2013.01); *C07K 2317/92* (2013.01)

USPC .................. 424/159.1; 530/387.1; 530/388.3

(58) Field of Classification Search

CPC .................................................. A61K 2300/00

See application file for complete search history.

(56) References Cited

U.S. PATENT DOCUMENTS

| | | | |
|---|---|---|---|
| 4,474,757 | A | 10/1984 | Arnon et al. |
| 4,625,015 | A | 11/1986 | Green et al. |
| 5,589,174 | A | 12/1996 | Okuno et al. |
| 5,631,350 | A | 5/1997 | Okuno et al. |

(Continued)

FOREIGN PATENT DOCUMENTS

| | | | |
|---|---|---|---|
| EP | 0044710 | A1 | 1/1982 |
| EP | 2363415 | A2 | 9/2011 |

(Continued)

OTHER PUBLICATIONS

Smith, G.P. Filamentous Fusion Phage: Novel Expression Vectors That Display Cloned Antigens on the Virion Surface. Science, 1985; 228: 1315-1316.*

(Continued)

*Primary Examiner* — Zachariah Lucas
*Assistant Examiner* — Stuart W Snyder
(74) *Attorney, Agent, or Firm* — Lando & Anastasi, LLP

(57) ABSTRACT

This disclosure relates to novel peptide agents, e.g., antibodies and antigen-binding fragments thereof, that bind hemagglutinin protein of influenza viruses, and methods of their use.

9 Claims, 28 Drawing Sheets

(56) References Cited

U.S. PATENT DOCUMENTS

| | | |
|---|---|---|
| 5,684,146 A | 11/1997 | Okuno et al. |
| 6,337,070 B1 | 1/2002 | Okuno et al. |
| 6,720,409 B2 | 4/2004 | Okuno et al. |
| 7,255,859 B1 | 8/2007 | Emrich et al. |
| 7,527,800 B2 | 5/2009 | Yang et al. |
| 7,537,768 B2 | 5/2009 | Luke et al. |
| 7,566,454 B2 | 7/2009 | Lu et al. |
| 7,566,458 B2 | 7/2009 | Yang et al. |
| 7,572,620 B2 | 8/2009 | Olsen et al. |
| 7,879,326 B2 | 2/2011 | Foung et al. |
| 8,124,092 B2 | 2/2012 | Lanzavecchia |
| 8,192,927 B2 | 6/2012 | Van Den Brink et al. |
| 8,383,121 B2 | 2/2013 | Qian et al. |
| 8,444,986 B2 | 5/2013 | Qian et al. |
| 8,470,327 B2 | 6/2013 | Throsby et al. |
| 8,486,406 B2 | 7/2013 | Burioni et al. |
| 8,540,994 B2 | 9/2013 | Ho et al. |
| 8,540,995 B2 | 9/2013 | Mookkan et al. |
| 8,540,996 B2 | 9/2013 | Qian et al. |
| 8,574,581 B2 | 11/2013 | Qian et al. |
| 8,574,830 B2 | 11/2013 | Mookkan et al. |
| 8,603,467 B2 | 12/2013 | Chen et al. |
| 8,637,456 B2 | 1/2014 | Sasisekharan et al. |
| 8,637,644 B2 | 1/2014 | Ho et al. |
| 8,637,645 B2 | 1/2014 | Ho et al. |
| 2002/0054882 A1 | 5/2002 | Okuno et al. |
| 2005/0042229 A1 | 2/2005 | Yang et al. |
| 2005/0287172 A1 | 12/2005 | Yang et al. |
| 2006/0153871 A1 | 7/2006 | Olsen et al. |
| 2006/0217338 A1 | 9/2006 | Lu et al. |
| 2007/0286869 A1 | 12/2007 | Luke et al. |
| 2008/0014205 A1 | 1/2008 | Horowitz et al. |
| 2009/0060949 A1 | 3/2009 | Ho et al. |
| 2009/0092620 A1 | 4/2009 | Moste et al. |
| 2009/0106864 A1 | 4/2009 | Henry et al. |
| 2009/0136530 A1 | 5/2009 | Yang et al. |
| 2009/0234096 A1 | 9/2009 | Garry et al. |
| 2009/0264362 A1 | 10/2009 | Garry et al. |
| 2009/0291472 A1 | 11/2009 | Lu et al. |
| 2009/0311265 A1 | 12/2009 | Van Den Brink et al. |
| 2010/0021489 A1 | 1/2010 | Arnon et al. |
| 2010/0040635 A1 | 2/2010 | Horowitz et al. |
| 2010/0041740 A1 | 2/2010 | Wong et al. |
| 2010/0080813 A1 | 4/2010 | Lanzavecchia |
| 2010/0086555 A1 | 4/2010 | Lanzavecchia |
| 2010/0145031 A1 | 6/2010 | Lanzavecchia et al. |
| 2010/0278834 A1 | 11/2010 | Lanzavecchia |
| 2010/0316654 A1 | 12/2010 | Horowitz et al. |
| 2011/0014187 A1 | 1/2011 | Burioni et al. |
| 2011/0038935 A1 | 2/2011 | Marasco et al. |
| 2011/0065095 A1 | 3/2011 | Kida et al. |
| 2011/0201547 A1 | 8/2011 | Sasisekharan et al. |
| 2011/0274702 A1 | 11/2011 | Lanzavecchia |
| 2011/0319600 A1 | 12/2011 | Ikuta et al. |
| 2012/0020971 A1 | 1/2012 | Kauvar et al. |
| 2012/0039898 A1 | 2/2012 | Throsby et al. |
| 2012/0039899 A1 | 2/2012 | Olsen et al. |
| 2012/0058124 A1 | 3/2012 | Kurosawa et al. |
| 2012/0093823 A1 | 4/2012 | Van Den Brink et al. |
| 2012/0093834 A1 | 4/2012 | Horowitz et al. |
| 2012/0100142 A1 | 4/2012 | Crowe, Jr. et al. |
| 2012/0100150 A1 | 4/2012 | Jiang et al. |
| 2012/0107326 A1 | 5/2012 | Horowitz et al. |
| 2012/0114664 A1 | 5/2012 | Lanzavecchia |
| 2012/0128671 A1 | 5/2012 | Horowitz et al. |
| 2012/0128684 A1 | 5/2012 | Marasco et al. |
| 2012/0276115 A1 | 11/2012 | Van Den Brink et al. |
| 2012/0282273 A1 | 11/2012 | Wrammert et al. |
| 2013/0004505 A1 | 1/2013 | Chang et al. |
| 2013/0022608 A1 | 1/2013 | Burioni et al. |
| 2013/0202608 A1 | 8/2013 | Mookkan et al. |
| 2013/0243792 A1 | 9/2013 | Vogels et al. |
| 2013/0289246 A1 | 10/2013 | Crowe et al. |
| 2013/0302348 A1 | 11/2013 | Raguram et al. |
| 2013/0309248 A1 | 11/2013 | Throsby et al. |
| 2014/0011982 A1 | 1/2014 | Marasco et al. |
| 2014/0046039 A1 | 2/2014 | Ahmed et al. |

FOREIGN PATENT DOCUMENTS

| | | |
|---|---|---|
| JP | 62-051700 | 3/1987 |
| JP | 2008104450 A | 5/2008 |
| JP | 2011-160681 A | 8/2011 |
| WO | 84/00687 A1 | 3/1984 |
| WO | 02/46235 A1 | 6/2002 |
| WO | 2007/089753 A2 | 8/2007 |
| WO | 2007/134327 A2 | 11/2007 |
| WO | 2007/149715 A2 | 12/2007 |
| WO | 2008/028946 A2 | 3/2008 |
| WO | 2008/033105 A1 | 3/2008 |
| WO | 2008/091657 A1 | 7/2008 |
| WO | 2008/110937 A2 | 9/2008 |
| WO | 2008/118970 A2 | 10/2008 |
| WO | 2008/140415 A1 | 11/2008 |
| WO | 2008/154813 A1 | 12/2008 |
| WO | 2009/035412 A1 | 3/2009 |
| WO | 2009/035420 A1 | 3/2009 |
| WO | 2009/073163 A1 | 6/2009 |
| WO | 2009/073330 A2 | 6/2009 |
| WO | 2009/079259 A2 | 6/2009 |
| WO | 2009/099394 A1 | 8/2009 |
| WO | 2009/111865 A1 | 9/2009 |
| WO | 2009/115972 A1 | 9/2009 |
| WO | 2009/119722 A1 | 10/2009 |
| WO | 2009/121004 A2 | 10/2009 |
| WO | 2009/133249 A1 | 11/2009 |
| WO | 2009/144667 A1 | 12/2009 |
| WO | 2009/147248 A2 | 12/2009 |
| WO | 2010/006144 A2 | 1/2010 |
| WO | 2010/010466 A2 | 1/2010 |
| WO | 2010/010467 A2 | 1/2010 |
| WO | 2010/027818 A2 | 3/2010 |
| WO | 2010/040281 A1 | 4/2010 |
| WO | 2010/040572 A2 | 4/2010 |
| WO | 2010/046775 A2 | 4/2010 |
| WO | 2010/073647 A1 | 7/2010 |
| WO | 2010/074656 A1 | 7/2010 |
| WO | 2010/127252 A2 | 11/2010 |
| WO | 2010/130636 A1 | 11/2010 |
| WO | 2010/132604 A2 | 11/2010 |
| WO | 2010/140114 A1 | 12/2010 |
| WO | 2011/041391 A1 | 4/2011 |
| WO | 2011/044570 A2 | 4/2011 |
| WO | 2011/068143 A1 | 6/2011 |
| WO | 2011/087092 A1 | 7/2011 |
| WO | 2011/093217 A1 | 8/2011 |
| WO | 2011/096302 A1 | 8/2011 |
| WO | 2011/117848 A1 | 9/2011 |
| WO | 2011/160083 A1 | 12/2011 |
| WO | 2012/021786 A2 | 2/2012 |
| WO | 2012/026878 A1 | 3/2012 |
| WO | 2012/029997 A1 | 3/2012 |
| WO | 2012/045001 A2 | 4/2012 |
| WO | 2012/054745 A1 | 4/2012 |
| WO | 2012/072788 A1 | 6/2012 |
| WO | 2012/096994 A2 | 7/2012 |
| WO | 2013/007770 A1 | 1/2013 |
| WO | 2013/011347 A1 | 1/2013 |
| WO | 2013/020074 A2 | 2/2013 |
| WO | 2013/030604 A1 | 3/2013 |
| WO | 2013/044840 A1 | 4/2013 |
| WO | 2013/048153 A1 | 4/2013 |
| WO | 2013/059524 A2 | 4/2013 |
| WO | 2013/081371 A1 | 6/2013 |
| WO | 2013/081463 A2 | 6/2013 |
| WO | 2013/086052 A2 | 6/2013 |
| WO | 2013/089496 A1 | 6/2013 |
| WO | 2013/114885 A1 | 8/2013 |
| WO | 2013/132007 A1 | 9/2013 |

(56) References Cited

FOREIGN PATENT DOCUMENTS

| WO | 2013/169377 A1 | 11/2013 |
| WO | 2013/170139 A1 | 11/2013 |

OTHER PUBLICATIONS

Chen et al "Humanized antibodies with broad-spectrum neutralization to avian influenza virus H1N1", Antiviral Research, vol. 87, No. 1, Jul. 1, 2010 pp. 81-84.

Corti et al. "A Neutralizing Antibody Selected from Plasma Cells that Binds to Group 1 and Group 2 Influenza A Hemagglutinins", Science vol. 333, No. 6044, Aug. 2011, pp. 850-856.

Ekiert et al, "A Highly Conserved Neutralizing Epitope on Group 2 Influenza A Viruses", Science, vol. 333, No. 6044, Aug. 2011 pp. 843-850.

Ekiert et al."Broadly neutralizing antibodies against influenza virus and prospects for universal therapeies", Current Opinion in Virology, vol. 2, No. 2, Apr. 2012, pp. 134-141.

International Search Report and Written Opinion for PCT/US2013/040534 dated Feb. 9, 2013.

Krause et al. "A Broadly Neutralizing Human Monoclonal Antibody That Recognizes a Conserved, Novel Epitope on the Globular Head of the Influenza H1N1 Virus Hemagglutinin", Journal of Virology, vol. 85, No. 20, Oct. 15, 2011, pp. 10905-10908.

Kubota-Koketsu et al "Broad neutralizing human monoclonal antibodies against influenza virus from vaccinated healthy donors", Biochemical and Biophysical Research Communications, vol. 387, No. 1, Sep. 11, 2009 pp. 180-185.

Laursen et al. "Broadly neutralizing antibodies against influenza viruses", Antiviral Research, vol. 98, No. 3, Jun. 2013, pp. 476-483.

Shriver et al. "DEsign of a Broadly Neutralizing Antibody Targeting Influenza A", Internet citation, Sep. 10, 2012, pp. 1-18. Retrieved on Aug. 8, 2013.

Soundararajan et al. "Networks link antigenic and receptor-binding sites of influenza hemagglutinin: Mechanistic insight into filter strain propagation", Scientific Reports, vol. 1, Dec. 2011, pp. 1-7.

Whittle et al. "Broadly neutralizing human antibody that recognizes the receptor-binding pocket of influenza virus hemagglutinin", National Academy of Sciences Proceedings, vol. 108, No. 34, Aug. 23, 2011, pp. 14216-14221.

Dreyfus et al., "Highly conserved protective epitopes on influenza B viruses" Science 337(6100):1343-1348 (2012).

Ekiert et al., "Antibody recognition of a highly conserved influenza virus epitope" Science 324(5924):246-251 (2009).

Okuno et al., "A common neutralizing epitope conserved between the hemagglutinins of influenza a virus H1 and H2 strains." J Virol. 67(5):2552-2558 (1993).

Rogers and Paulson "Receptor determinants of human and animal influenza virus isolates: differences in receptor specificity of the H3 hemagglutinin based on species of origin" Virology. 127(2):361-373 (1983).

Rogers et al. "Single amino acid substitutions in influenza haemagglutinin change receptor binding specificity" Nature. 304(5921):76-78 (1983).

Sauter et al. "Binding of influenza virus hemagglutinin to analogs of its cell-surface receptor, sialic acid: analysis by proton nuclear magnetic resonance spectroscopy and X-ray crystallography" Biochemistry. 31(40):9609-9621 (1992).

Skehel and Wiley "Receptor binding and membrane fusion in virus entry: the influenza hemagglutinin" Annu Rev Biochem. 69:531-569 (2000).

Sui et al., "Structural and functional bases for broad-spectrum neutralization of avian and human influenza A viruses." Nat Struct Mol Biol. 16(3):265-273 (2009).

Sui et al., "Wide prevalence of heterosubtypic broadly neutralizing human anti-influenza A antibodies" Clin Infect Dis. 52(8):1003-1009 (2011).

Tan et al., "A pan-H1 anti-hemagglutinin monoclonal antibody with potent broad-spectrum efficacy in vivo" J Virol. 86 (11):6179-6188 (2012).

Wang et al., "Broadly protective monoclonal antibodies against H3 influenza viruses following sequential immunization with different hemagglutinins" PLoS Pathog. 6(2):e1000796 (2010).

Wrammert et al., "Broadly cross-reactive antibodies dominate the human B cell response against 2009 pandemic H1N1 influenza virus infection" J Exp Med. 208(1):181-193 (2011).

Communication Made to Inventors Prior to Mar. 14, 2013.

* cited by examiner

Heavy Chain

EVQLLESGGGLVKPGQSLKLSCAASGFTFT<u>SYGMH</u>WVRQPPGKGLEWVA<u>VISYDGSYKYYADSVQG</u>
RFTISRDNSKNTLYLQMNSLRAEDTAVYYCAK<u>DSRLRSLLYFEWLSQGYFNPWGAGTTLTVSS</u>*AST*
*KGPSVFPLAPSSKSTSGGTAALGCLVKDYFPEPVTVSWNSGALTSGVHTFPAVLQSSGLYSLSSVV*
*TVPSSSLGTQTYICNVNHKPSNTKVDKKVEPPKSCDKTHTCPPCPGTELLGGPSVFLFPPKPKDTL*
*MISRTPEVTCVVVDVSHEDPEVKFNWYVDGVEVHNAKTKPREEQYNSTYRVVSVLTVLHQDWLNGK*
*EYKCKVSNKALPAPIEKTISKAKGEPREPQVYTLPPSRDELTKNQVSLTCLVKGFYPSDIAVEWES*
*NGQPENNYKTTPPVLDSDGSFFLYSKLTVDKSRWQQGNVFSCSVMHEALHNHYTQKSLSLSPGK*
(SEQ ID NO: 94)

Light Chain

EIVMTQSPDSLAVSLGERATINCKS<u>SQSVTYNYKNYLA</u>WYQQKPGQPPKLLIY<u>WASTRESG</u>VPDRFSGSGSGT
DFTLTISSLQAEDVAVYYC<u>QQYYRTPPT</u>FGGGTKLDIK*GSVAAPSVFIFPPSDEQLKSGTASVVCLLNNFYPREAK*
*VQWKVDNALQSGNSQESVTEQDSKDSTYSLSSTLTLSKADYEKHKVYACEVTHQGLSSPVTKSFNRGEC*
(SEQ ID NO: 95)

Fig. 1

|  | 10 | 20 | 30 | 40 | 50 | 60 | 70 | 80 | 90 | 100 | 110 | 120 | 129 |
|---|---|---|---|---|---|---|---|---|---|---|---|---|---|
|  |  |  |  |  | CDR-H1 |  | CDR-H2 |  |  |  | CDR-H3 |  |  |
| VH15 | EVQLLESGGG | LVKPGQSLKL | SCAASGFTFT | SYGMHWVRQP | PGKGLEWVAV | ISYDGSYKYY | ADSVQGRFTI | SRDNSKNTLY | LQMNSLRAED | TAVYYCAKDS | RLRSLLYFEW | LSQGYFNPWG | AGTTLTVSS |
| VH16 | EVQLLESGGG | LVKPGQSLKL | SCAASGFTFS | SYGMHWVRQP | PGKGLEWVAV | VSYDGSNKYY | ADSVQGRFTI | SRDNSKNTLY | LQMNSLRAED | TAVYYCAKDT | KLRSLLYFEW | LSSGLLDYWG | QGAMVTVSS |
| VH17 | EVQLLESGGG | LVKPGQSLKL | SCAASGFTFT | SYGMHWVRQP | PGKGLEWVAV | VSYDGNYKYY | ADSVQGRFTI | SRDNSKNTLY | LQMNSLRAED | TAVYYCAKDS | RLRSLLYFEW | LSQGYFNPWG | AGTTLTVSS |
| VH18 | EVQLLESGGG | LVKPGQSLKL | SCAASGFTFT | SYGMHWVRQP | PGKGLEWVAV | LSYDGNYKYY | ADSVQGRFTI | SRDNSKNTLY | LQMNSLRAED | TAVYYCAKDS | RLRSLLYFEW | LSQGYFNPWG | AGTTLTVSS |
| VH19 | EVQLLESGGG | LVKPGQSLKL | SCAASGFTFT | TYAMHWVRQP | PGKGLEWVAV | LSYDGNYKYY | ADSVQGRFTI | SRDNSKNTLY | LQMNSLRAED | TAVYYCAKDS | RLRSLLYFEW | LSQGYFNPWG | AGTTLTVSS |
| VH21 | EVQLLESGGG | LVKPGQSLKL | SCAASGFTFT | SYGMHWVRQP | PGKGLEWVAV | VSYDGNNKYY | ADSVQGRFTI | SRDNSKNTLY | LQMNSLRAED | TAVYYCAKDS | KLRSLLYFEW | LSSGLLDYWG | QGAMVTVSS |
| VH22 | EVQLLESGGG | LVKPGQSLKL | SCAASGFTFT | TYAMHWVRQP | PGKGLEWVAV | VSFDGNNRYY | ADSVQGRFTI | SRDNSKNTLY | LQMNSLRAED | TAVYYCAKDS | QLRSLLYFEW | LSSGVLDYWG | QGAMVTVSS |
| VH20 | EVQLLESGGG | LVKPGQSLKL | SCAASGFTFT | SYGMHWVRQP | PGKGLEWVAV | VSYDNYKYY | ADSVQGRFTI | SRDNSKNTLY | LQMNSLRAED | TAVYYCAKDS | KLRSLLYFEW | LSQGYFNPWG | AGTTLTVSS |
| VH23 | EVQLLESGGG | LVKPGQSLKL | SCAASGFTFT | SYAMHWVRQP | PGKGLEWVAV | VSYDGNYKYY | ADSVQGRFTI | SRDNSKNTLY | LQMNSLRAED | TAVYYCAKDS | RLRSLLYFEW | LSQGYFNPWG | QGTTLTVSS |
| VH24 | EVQLLESGGG | LVKPGQSLKL | SCAASGFTFT | SYAMHWVRQP | PGKGLEWVAV | VSYDGNYKYY | ADSVQGRFTI | SRDNSKNTLY | LQMNSLRAED | TAVYYCAKDS | RLRSLLYFEW | LSQGYFNPWG | QGTTLTVSS |
| VH25 | QVQLLETGGG | LVKPGQSLKL | SCAASGFTFT | SYAMHWVRQP | PGKGLEWVAV | VSYDGNYKYY | ADSVQGRFTI | SRDNSKNTLY | LQMNSLRAED | TAVYYCAKDS | RLRSLLYFEW | LSQGYFNPWG | QGTTLTVSS |
| VH26 | EVQLLESGGG | LVKPGQSLKL | SCAASGFTFT | SYAMHWVRQP | PGKGLEWVAV | VSYDGNYKYY | ADSVQGRFTI | SRDNSKNTLY | LQMNSLRAED | TAVYYCAKDS | QLRTLLYFEW | LSQGYFNPWG | QGTTLTVSS |
| VH27 | EVQLLESGGG | LVKPGQSLKL | SCAASGFTFT | SYAMHWVRQP | PGKGLEWVAV | VSYDGNYKYY | ADSVQGRFTI | SRDNSKNTLY | LQMNSLRAED | TAVYYCAKDS | RLRTLLYFEW | LSQGYFRDPWG | QGTTLTVSS |
| VH161 | EVQLLESGGG | LVKPGQSLKL | SCAASGFTFS | SYGMHWVRQP | PGKGLEWVAV | VSYDGSNKYY | ADSVQGRFTI | SRDNSKNTLY | LQMNSLRAED | TAVYYCAKDS | KLRSLLYFEW | LSSGLLDYWG | QGAMVTVSS |

Fig. 2

|      |            |            | CDR-L1      |            |            | CDR-L2     |            |            |            | CDR-L3     |            |   |
|------|------------|------------|-------------|------------|------------|------------|------------|------------|------------|------------|------------|---|
|      | 10         | 20         | 30          | 40         | 50         | 60         | 70         | 80         | 90         | 100        | 110        |   |
| VL28 | EIVMTQSPDS | LAVSLGERAT | INCKSSQSVT  | YNVKNYLAWY | QQKPGQPPKL | LIYWASTRES | GVPDRFSGSG | SGTDFTLTIS | SLQAEDVAVY | YCQQYRTPP  | TFGGGTKLDI | K |
| VL29 | EIVMTQSPDS | LAVSLGERAT | INCKSSQSVT  | FSYKNYLAWY | QQKPGQPPKL | LIYWASTRES | GVPDRFSGSG | SGTDFTLTIS | SLQAEDVAVY | YCQQYRTPP  | TFGGGTKLDI | K |
| VL30 | EIVMTQSPDS | LAVSLGERAT | INCKSSQSVT  | FDYKNYLAWY | QQKPGQPPKL | LIYWASTRES | GVPDRFSGSG | SGTDFTLTIS | SLQAEDVAVY | YCQQYRTPP  | TFGGGTKLDI | K |
| VL35 | EIVMTQSPDS | LAVSLGERAT | INCKSSQSVT  | WSYKNYLAWY | QQKPGQPPKL | LIYWASTRES | GVPDRFSGSG | SGTDFTLTIS | SLQAEDVAVY | YCQQYRTPP  | TFGGGTKLDI | K |
| VL31 | EIVMTQSPDS | LAVSLGERAT | INCKSSQTVT  | FNYKNYLAWY | QQKPGQPPKL | LIYWASTRES | GVPDRFSGSG | SGTDFTLTIS | SLQAEDVAVY | YCQQHYRTPP | SFGGGTKLDI | K |
| VL32 | EIVMTQSPDS | LAVSLGERAT | INCKSSQTLS  | FNYKNYLAWY | QQKPGQPPKL | LIYWASTRES | GVPDRFSGSG | SGTDFTLTIS | SLQAEDVAVY | YCQQHYRTPP | SFGGGTKLDI | K |
| VL33 | EIVMTQSPDS | LAVSLGERAT | INCKSSQTLS  | FNYKNYLAWY | QQKPGQPPKL | LIYWASTRES | GVPDRFSGSG | SGTDFTLTIS | SLQAEDVAVY | YCQQHYRTPP | SFGGGTKLDI | K |
| VL34 | EIVMTQSPDS | LAVSLGERAT | INCKSSQTLS  | FNYKNYLAWY | QQKPGQPPKL | LIYFASTRES | GVPDRFSGSG | SGTDFTLTIS | SLQAEDVAVY | YCQQHYRTPP | SFGGGTKLEI | K |
| VL36 | EIVMTQSPDS | LAVTLGERAS | INCKSSQTLS  | FNYKNYLAWY | QQKPGQPPKV | LIYFASTRES | GVPERFSGSG | SGTDFTLTIS | SLQAEDVAVY | YCQQHYRTPP | SFGQGTKVDI | K |
| VL45 | EIVMSQSPDT | LAVTLGERAS | ITCRSSQSIT  | FNYKNYLAWY | QQKPGKAPKL | LIYWASARET | GVPSRFSGSG | SGTDFTLTIS | SLQPEDFATY | YCQQHYRTPP | SFGQGTKVEI | K |
| VL46 | DIQMTQSPSS | LSASVGDRVT | ITCRSSQSIT  | FNYKNYLGWY | QQKPGKAPKL | LIYWGSYLES | GVPSRFSGSG | SGTDFTLTIS | SLQPEDFATY | YCQQHYRTPP | SFGTGTKVEI | K |
| VL37 | DIQMTQSPSS | LSASVGDRVT | ITCRSSQSIT  | FNYKNYLGWY | QQKPGQPPKL | LIYWGSYLES | GVPDRFSGSG | SGTDFTLTIS | SLQAEDVAVY | YCQQHYRTPP | SFGSGTKLDI | K |
| VL38 | EIVMTQSPDS | LAVSLGERAT | INCKSSQTVT  | FNYKNYLAWY | QQKPGQPPKL | LIYWASTRES | GVPDRFSGSG | SGTDFTLTIS | SLQAEDVAVY | YCQQHYRTPP | SFGQGTKLDI | K |
| VL39 | EIVMTQSPDS | LAVSLGERAT | INCKSSQTVT  | FNYKNYLAWY | QQKPGQPPKL | LIYWASTRES | GVPDRFSGSG | SGTDFTLTIS | SLQAEDVAVY | YCQQHYRTPP | SFGNGTKLDI | K |
| VL40 | EIVMTQSPDS | LAVSLGERAT | INCKSSQTVT  | FNYKNYLAWY | QQKPGQPPKL | LIYWASTRES | GVPDRFSGSG | SGTDFTLTIS | SLQAEDVAVY | YCQQHYRTPP | SFGTGTKLDI | K |
| VL41 | EIVMTQSPDS | LAVSLGERAT | INCKSSQTLS  | FNYKNYLAWY | QQKPGQPPKL | LIYWASTRES | GVPDRFSGSG | SGTDFTLTIS | SLQAEDVAVY | YCQQHYRTPP | SFGSGTKLDI | K |
| VL42 | EIVMTQSPDS | LAVSLGERAT | INCKSSQTLS  | FNYKNYLAWY | QQKPGQPPKL | LIYWASTRES | GVPDRFSGSG | SGTDFTLTIS | SLQAEDVAVY | YCQQHYRTPP | SFGQGTKLDI | K |
| VL43 | EIVMTQSPDS | LAVSLGERAT | INCKSSQTLS  | FNYKNYLAWY | QQKPGQPPKL | LIYWASTRES | GVPDRFSGSG | SGTDFTLTIT | SLQAEDVAVY | YCQQHYRTPP | SFGNGTKLDI | K |
| VL44 | EIVMTQSPDS | LAVSLGERAT | IQCKSSQTLS  | FNYKNYLAWY | QQKPGQPPKL | LIYWASTRES | GVPDRFSGSG | SGTDFTLTIS | SLQAEDVAVY | YCQQHYRTPP | SFGQGTKLDI | K |
| VL47 | DIVMTQSPDT | LAVTLGERAT | INCKSSQTVT  | FNYKNYLAWY | QQKPGQPPKL | LIYWASTRES | GVPDRFSGSG | SGTDFTLTIS | SLQAEDVAVY | YCQQHYRTPP | SFGSGTKLDI | K |
| VL48 | DIVMTQSPDT | VAVTVGERAT | INCKSSQTVT  | FNYKNYLAWY | QQKPGQPPKL | LIYWASTRES | GVPDRFSGSG | SGTDFTLTIS | SLQAEDVAVY | YCQQHYRTPP | SFGQGTKLDI | K |

Fig. 3

```
                                                                    CDR-L1                                        CDR-L2                                                              CDR-L3
              10         20            30         40         50           60            70         80         90        100        110
VL49   DIVMTQSPDT VAVTLGERAT IDCKSSQTVT FNYKNYLAWY QQKPGQPPKL LIYWASTRES GVPDRFSGSG SGTDFTLTIS SLQAEDVAVY YCQQHYRTPP SFGQGTKLDI K
VL50   DIVMTQSPDT LAVTVGERAT IRCKSSQTVT FNYKNYLAWY QQKPGQPPKL LIYWASTRES GVPDRFSGSG SGTDFTLTIS SLQAEDVAVY YCQQHYRTPP SFGQGTKLDI K
VL51   DIVMTQSPDT LAVSRGERAT IDCKSSQTVT FDYKNYLAWY QQKPGQPPKL LIYWASTRES GVPDRFSGSG SGTDFTLTIS SLQAEDEAVY YCQQHYRTPP SFGQGTKLDI K
VL52   DIQMTQSPSS LSASVGDRVT ITCRSSQSIT FNYKNYLAWY QQKPGKAPKL LIYWGSYLES GVPSRFSGSG SGTDFTLTIS SLQPEDFATY YCQQHYRTPP SFGQGTKVEI K
VL53   DIQMTQSPSS LSASVGDRVT ITCRSSQSIT FNYKNYLAWY QQKPGKAPKL LIYWGSTLES GVPSRFSGSG SGTDFTLTIS SLQPEDFATY YCQQHYRTPP SFGQGTKVEI K
VL54   DIQMTQSPSS LSASVGDRVT ITCRSSQSIT FNYKNYLAWY QQKPGKAPKL LIYWGSHLES GVPSRFSGSG SGTDFTLTIS SLQPEDFATY YCQQHYRTPP SFGQGTKVEI K
VL55   DIQMTQSPSS LSASVGDRVT ITCRSSQSIT FNYKNYLAWY QQKPGKAPKL LIYWGSKLES GVPSRFSGSG SGTDFTLTIS SLQPEDFATY YCQQHYRTPP SFGQGTKVEI K
VL56   DIQMTQSPSS LSASVGDRVT ITCRSSQSIT FNYKNYLAWY QQKPGKAPKL LIYWGSDLES GVPSRFSGSG SGTDFTLTIS SLQPEDVATY YCQQHYRTPP SFGQGTKVEI K
VL57   DIQMTQSPSS LSASVGDRVT ITCRSSQSIT FNYKNYLAWY QQKPGKAPKL LIYWGSYLES GVPSRFSGSG SGTDFTLTIS SLQPEDKATY YCQQHYRTPP SFGQGTKVEI K
VL58   DIQMTQSPSS LSASVGDRVT ITCRSSQSIT FNYKNYLAWY QQKPGKAPKL LIYWGSYLES GVPSRFSGSG SGTDFTLTIS SLQPEDDATY YCQQHYRTPP SFGQGTKVEI K
VL59   DIQMTQSPSS LSASVGDRVT ITCRSSQSIT FNYKNYLAWY QQKPGKAPKL LIYWGSYLES GVPSRFSGSG SGTDFTLTIS SLQPEDFATY YCQQHYRTPP SFGQGTKVEI K
VL60   DIQMTQSPSS LSASVGDRVT ITCRSSQSIT FNYKNYLAWY QQKPGKAPKL LIYWGSYLES GVPSRFSGSG SGTDFTLTIS SLQPEDFATY YCQQHYRTPP SFGQGTKVEI K
VL61   DIQMTQSPSS LSASVGDRVT ITCRSSQSIT FQYKNYLAWY QQKPGKAPKL LIYWGSTRES GVPSRFSGSG SGTDFTLTIS SLQPEDFATY YCQQHYRTPP SFGQGTKVEI K
VL153  DIQMTQSPSS LSASVGDRVT ITCRSSQSIT FRYKNYLAWY QQKPGKAPKL LIYWGSYLES GVPSRFSGSG SGTDFTLTIS SLQPEDFATY YCQQYYRTPP SFGQGTKVEI K
VL154  DIQMTQSPSS LSASVGDRVT ITCRSSQSIT FEYKNYLAWY QQKPGKAPKL LIYWGSYLES GVPSRFSGSG SGTDFTLTIS SLQPEDFATY YCQQHYRTPP SFGQGTKVEI K
VL155  DIQMTQSPSS LSASVGDRVT ITCRSSQSIT FDYKNYLAWY QQKPGKAPKL LIYWGSTRES GVPSRFSGSG SGTDFTLTIS SLQPEDFATY YCQQHYRTPP SFGQGTKVEI K
VL156  DIQMTQSPSS LSASVGDRVT ITCRSSQSIT FNYKNYLAWY QQKPGKAPKL LIYWGSTRES GVPSRFSGSG SGTDFTLTIS SLQPEDFATY YCQQHYRTPP SFGQGTKVEI K
VL62   DIQMTQSPSS LSASVGDRVT ITCRSSQSIT FNYKNYLAWY QQKPGKAPKL LIYWGSYLES GVPSRFSGSG SGTDFTLTIS SLQPEDFATY YCQQHYRTPP SFGQGTKVEI K
```

Fig. 3 (Continued)

```
FI6   VH       QVQLVQSGGGVVQPGRSLRLRLSCVASGFTFSTYAMHWVRQAPGRGLEWVAVISYDGNYKYYADSVKGRFSISRDNSNNTLHLEMNTLRTEDTALYYCAKDSQLRSLLYFEWLSQGYFDPWGQGTLVTVTS
FI370 VH       QVQLVQSGGGVVPPGRSLRLRLSCAASGFTFSTYGMHWVRQAPGKGLEWVAVISYDGNYKYYADSVRGRFTISRDNSKNTLNLDMNSLRTEDTALYYCAKDSQLRSLLYFDWLSQGYFDHWGQGTLVTVSS
FI6  VHv1     QVQLVESGGGVVQPGRSLRLRLSCAASGFTFSSYGMHWVRQAPGKGLEWVAVISYDGSNKYYADSVKGRFTISRDNSKNTLYLQMNSLRAEDTAVYYCAKDSQLRSLLYFDWLSQGYFDYWGQGTLVTVSS
FI6  VHv3     QVQLVESGGGVVQPGRSLRLRLSCAASGFTFSTYAMHWVRQAPGKGLEWVAVISYDGSNKYYADSVKGRFTISRDNSKNTLYLQMNSLRAEDTAVYYCAKDSQLRSLLYFEWLSQGYFDYWGQGTLVTVSS
FI6/370 VH    QVQLVQSGGGVVQPGRSLRLRLSCAASGFTFSTYGMHWVRQAPGKGLEWVAVISYDGNYKYYADSVKGRFTISRDNSKNTLYLEMNSLRTEDTALYYCAKDSQLRSLLYFDWLSQGYFDHWGQGTLVTVSS
FI6VK          DIQMTSQPDSLAVSLGARATINCKSSQSVTFNYKNYLAWYQQKPGQPPKVLIYWASARESGVPDRFSGSGSGTDFTLTISSLQAEDVAVYYCQQHYRTPPTFGQGTKVEIK
```

Fig. 12

```
                     CDR-H1
                  ---|  |---           10         20         30         40         50
VH15-ID   IDEVQLLESG GGLVKPGQSL KLSCAASGFT FTSYGMHWVR QPPGKGLEWV
VH16-ID   IDEVQLLESG GGLVKPGQSL KLSCAASGFT FSSYGMHWVR QPPGKGLEWV
VH17-ID   IDEVQLLESG GGLVKPGQSL KLSCAASGFT FTSYGMHWVR QPPGKGLEWV
VH18-ID   IDEVQLLESG GGLVKPGQSL KLSCAASGFT FTSYGMHWVR QPPGKGLEWV
VH19-ID   IDEVQLLESG GGLVKPGQSL KLSCAASGFT FTTYAMHWVR QPPGKGLEWV
VH21-ID   IDEVQLLESG GGLVKPGQSL KLSCAASGFT FSSYGMHWVR QPPGKGLEWV
VH22-ID   IDEVQLLESG GGLVKPGQSL KLSCAASGFT FTTYAMHWVR QPPGKGLEWV
VH20-ID   IDEVQLLESG GGLVKPGQSL KLSCAASGFT FTTYAMHWVR QPPGKGLEWV
VH23-ID   IDEVQLLESG GGLVKPGQSL KLSCAASGFT FTSYGMHWVR QPPGKGLEWV
VH24-ID   IDEVQLLESG GGLVKPGQSL KLSCAASGFT FTSYGMHWVR QPPGKGLEWV
VH25-ID   IDQYQLLETG GGLVKPGQSL KLSCAASGFT FTSYGMHWVR QPPGKGLEWV
VH26-ID   IDEVQLLESG GGLVKPGQSL KLSCAASGFT FTSYAMHWVR QPPGKGLEWV
VH27-ID   IDEVQLLESG GGLVKPGQSL KLSCAASGFT FTTYAMHWVR QPPGKGLEWV
VH161-ID  IDEVQLLESG GGLVKPGQSL KLSCAASGFT FSSYGMHWVR QPPGKGLEWV

CDR-H2
             ---|         |---         60         70         80         90
VH15-ID   AVLSYDGSYK YYADSVQGRF TISRDNSKNT LYLQMNSLRA EDTAVYYCAK
VH16-ID   AVVSYDGSNK YYADSVQGRF TISRDNSKNT LYLQMNSLRA EDTAVYYCAK
VH17-ID   AVVSYDGNYK YYADSVQGRF TISRDNSKNT LYLQMNSLRA EDTAVYYCAK
VH18-ID   AVLSYDGNYK YYADSVQGRF TISRDNSKNT LYLQMNSLRA EDTAVYYCAK
VH19-ID   AVLSYDGNYK YYADSVQGRF TISRDNSKNT LYLQMNSLRA EDTAVYYCAK
VH21-ID   AVVSYDGNNK YYADSVQGRF TISRDNSKNT LYLQMNSLRA EDTAVYYCAK
VH22-ID   AVVSYDGNNR YYADSVQGRF TISRDNSKNT LYLQMNSLRA EDTAVYYCAK
VH20-ID   AVVSFDGNNR YYADSVQGRF TISRDNSKNT LYLQMNSLRA EDTAVYYCAK
VH23-ID   AVVSYDGNYK YYADSVQGRF TISRDNSKNT LYLQMNSLRA EDTAVYYCAK
VH24-ID   AVVSYDGNYK YYADSVQGRF TISRDNSKNT LYLQMNSLRA EDTAVYYCAK
VH25-ID   AVVSYDGNYK YYADSVQGRF TISRDNSKNT LYLQMNSLRA EDTAVYYCAK
VH26-ID   AVVSYDGNYK YYADSVQGRF TISRDNSKNT LYLQMNSLRA EDTAVYYCAK
VH27-ID   AVVSYDGNYK YYADSVQGRF TISRDNSKNT LYLQMNSLRA EDTAVYYCAK
VH161-ID  AVVSYDGSNK YYADSVQGRF TISRDNSKNT LYLQMNSLRA EDTAVYYCAK

CDR-H3
                           ---|                     |---
                    110        120        130
VH15-ID   DSRLRSLLYF EWLSQGYFNP WGAGTTLTVS S
VH16-ID   DTKLRSLLYF EWLSSGLLDY WGQGAMVTVS S
VH17-ID   DSRLRSLLYF EWLSQGYFNP WGAGTTLTVS S
VH18-ID   DSRLRSLLYF EWLSQGYFNP WGAGTTLTVS S
VH19-ID   DSRLRSLLYF EWLSQGYFNP WGAGTTLTVS S
VH21-ID   DSKLRSLLYF EWLSQGYFNP WGAGTTLTVS S
VH22-ID   DSKLRSLLYF EWLSSGLLDY WGQGAMVTVS S
VH20-ID   DSQLRSLLYF EWLSSGVLDY WGQGAMVTVS S
VH23-ID   DSKLRSLLYF EWLSQGYFNP WGAGTTLTVS S
VH24-ID   DSRLRSLLYF EWLSQGYFNP WGQGTTLTVS S
VH25-ID   DSRLRSLLYF EWLSQGYFNP WGQGTTLTVS S
VH26-ID   DSQLRTLLYF EWLSQGYFDP WGQGTTLTVS S
VH27-ID   DSRLRTLLYF EWLSQGYFNP WGQGTTLTVS S
VH161-ID  DSKLRSLLYF EWLSSGLLDY WGQGAMVTVS S
```

Fig. 13

|  |  | CDR-L1 |  |  | CDR-L2 |  |  |  |  | CDR-L3 |  |  |
|---|---|---|---|---|---|---|---|---|---|---|---|---|---|
|  | 10 | 20 | 30 | 40 | 50 | 60 | 70 | 80 | 90 | 100 | 110 |  |
| VL28-ID | IDEIVMTQSP | DSLAVSLGER | ATINCKSSQS | VTYNYKNYLA | WYQQKPGQPP | KLLIYWASTR | ESGVPDRFSG | SGSGTDFTLT | ISSLQAEDVA | VYYCQQYYRT | PPTFGGGTKL | DIK |
| VL29-ID | IDEIVMTQSP | DSLAVSLGER | ATINCKSSQS | VTFSYKNYLA | WYQQKPGQPP | KLLIYWASTR | ESGVPDRFSG | SGSGTDFTLT | ISSLQAEDVA | VYYCQQYYRT | PPTFGGGTKL | DIK |
| VL30-ID | IDEIVMTQSP | DSLAVSLGER | ATINCKSSQS | VTFDYKNYLA | WYQQKPGQPP | KLLIYWASTR | ESGVPDRFSG | SGSGTDFTLT | ISSLQAEDVA | VYYCQQYYRT | PPTFGGGTKL | DIK |
| VL35-ID | IDEIVMTQSP | DSLAVSLGER | ATINCKSSQS | VTWSYKNYLA | WYQQKPGQPP | KLLIYWASTR | ESGVPDRFSG | SGSGTDFTLT | ISSLQAEDVA | VYYCQQYYRT | PPTFGGGTKL | DIK |
| VL31-ID | IDEIVMTQSP | DSLAVSLGER | ATINCKSSQT | VTFNYKNYLA | WYQQKPGQPP | KLLIYWASTR | ESGVPDRFSG | SGSGTDFTLT | ISSLQAEDVA | VYYCQQYYRT | PPTFGGGTKL | DIK |
| VL32-ID | IDEIVMTQSP | DSLAVSLGER | ATINCKSSQT | LSFNYKNYLA | WYQQKPGQPP | KLLIYWASTR | ESGVPDRFSG | SGSGTDFTLT | ISSLQAEDVA | VYYCQQHYRT | PPSFGGGTKL | DIK |
| VL33-ID | IDEIVMTQSP | DSLAVSLGER | ATINCKSSQT | VTFNYKNYLA | WYQQKPGQPP | KLLIYWASTR | ESGVPDRFSG | SGSGTDFTLT | ISSLQAEDVA | VYYCQQHYRT | PPSFGGGTKL | DIK |
| VL34-ID | IDEIVMTQSP | DSLAVSLGER | ATINCKSSQT | LSFNYKNYLA | WYQQKPGQPP | KLLIYFASTR | ESGVPDRFSG | SGSGTDFTLT | ISSLQAEDVA | VYYCQQHYRT | PPSFGGGTKL | DIK |
| VL36-ID | IDEIVMSQSP | DTLAVTLGER | ASINCKSSQT | VTFNYKNYLA | WYQQKPGQPP | KLLIYFASTR | ETGVPERFSG | SGSGTDFTLT | ISSLQAEDVA | VYYCQQHYRT | PPSFGGGTKL | DIK |
| VL45-ID | IDDIQMTQSP | SSLSASVGDR | VTITCRSSQS | VTFNYKNYLA | WYQQKPGQPP | KVLIYWASAR | ESGVPSRFSG | SGSGTDFTLT | ISSLQPEDFA | TYYCQQHYRT | PPSFGQGTKV | EIK |
| VL46-ID | IDDIQMTQSP | SSLSASVGDR | VTITCRSSQS | ITFNYKNYLG | WYQQKPGKAP | KLLIYWGSYL | ESGVPSRFSG | SGSGTDFTLT | ISSLQPEDFA | TYYCQQHYRT | PPSFGQGTKV | EIK |
| VL37-ID | IDEIVMTQSP | DSLAVSLGER | ATINCKSSQT | ITFNYKNYLA | WYQQKPGKAP | KLLIYWGSYL | ESGVPDRFSG | SGSGTDFTLT | ISSLQAEDVA | VYYCQQHYRT | PPSFGQGTKL | EIK |
| VL38-ID | IDEIVMTQSP | DSLAVSLGER | ATINCKSSQT | VTFNYKNYLA | WYQQKPGQPP | KLLIYWASTR | ESGVPDRFSG | SGSGTDFTLT | ISSLQAEDVA | VYYCQQHYRT | PPSFGTGTKL | DIK |
| VL39-ID | IDEIVMTQSP | DSLAVSLGER | ATINCKSSQT | VTFNYKNYLA | WYQQKPGQPP | KLLIYWASTR | ESGVPDRFSG | SGSGTDFTLT | ISSLQAEDVA | VYYCQQHYRT | PPSFGSGTKL | DIK |
| VL40-ID | IDEIVMTQSP | DSLAVSLGER | ATINCKSSQT | VTFNYKNYLA | WYQQKPGQPP | KLLIYWASTR | ESGVPDRFSG | SGSGTDFTLT | ISSLQAEDVA | VYYCQQHYRT | PPSFGQGTKL | DIK |
| VL41-ID | IDEIVMTQSP | DSLAVSLGER | ATINCKSSQT | LSFNYKNYLA | WYQQKPGQPP | KLLIYWASTR | ESGVPDRFSG | SGSGTDFTLT | ISSLQAEDVA | VYYCQQHYRT | PPSFGNGTKL | DIK |
| VL42-ID | IDEIVMTQSP | DSLAVSLGER | ATINCKSSQT | LSFNYKNYLA | WYQQKPGQPP | KLLIYWASTR | ESGVPDRFSG | SGSGTDFTLT | ISSLQAEDVA | VYYCQQHYRT | PPSFGTGTKL | DIK |
| VL43-ID | IDEIVMTQSP | DSLAVSLGER | ATINCKSSQT | LSFNYKNYLA | WYQQKPGQPP | KLLIYWASTR | ESGVPDRFSG | SGSGTDFTLT | ISSLQAEDVA | VYYCQQHYRT | PPSFGSGTKL | DIK |
| VL44-ID | IDEIVMTQSP | DSLAVSLGER | ATINCKSSQT | LSFNYKNYLA | WYQQKPGQPP | KLLIYWASTR | ESGVPDRFSG | SGSGTDFTLT | ISSLQAEDVA | VYYCQQHYRT | PPSFGNGTKL | DIK |

Fig. 14

```
                      10         20         30         40         50         60         70         80         90        100       110
                                                      CDR-L1                    CDR-L2                                        CDR-L3
VL47-ID   IDDIVMTQSP DTLAVTLGER ATIQCKSSQT VTFNYKNYLA WYQQKPGQPP KLLIYWASTR ESGVPDRFSG SGSGTDFTLT ITSLQAEDVA VYYCQQHYRT PPSFGQGTKL DIK
VL48-ID   IDDIVMTQSP DTVAVTVGER ATINCKSSQT VTFNYKNYLA WYQQKPGQPP KLLIYWASTR ESGVPDRFSG SGSGTDFTLT ISSLQAEDVA VYYCQQHYRT PPSFGQGTKL DIK
VL49-ID   IDDIVMTQSP DTVAVTLGER ATIDCKSSQT VTFNYKNYLA WYQQKPGQPP KLLIYWASTR ESGVPDRFSG SGSGTDFTLT ISSLQAEDVA VYYCQQHYRT PPSFGQGTKL DIK
VL50-ID   IDDIVMTQSP DTLAVTVGER ATIRCKSSQT VTFNYKNYLA WYQQKPGQPP KLLIYWASTR ESGVPDRFSG SGSGTDFTLT ISSLQAEDVA VYYCQQHYRT PPSFGQGTKL DIK
VL51-ID   IDDIVMTQSP DTLAVSRGER ATIDCKSSQT VTFNYKNYLA WYQQKPGQPP KLLIYWASTR ESGVPDRFSG SGSGTDFTLT ISSLQAEDEA VYYCQQHYRT PPSFGQGTKL DIK
VL52-ID   IDDIQMTQSP SSLSASVGDR VTITCRSSQS ITFDYKNYLA WYQQKPGKAP KLLIYWGSYL ESGVPSRFSG SGSGTDFTLT ISSLQPEDFA TYYCQQHYRT PPSFGQGTKV EIK
VL53-ID   IDDIQMTQSP SSLSASVGDR VTITCRSSQS ITFNYKNYLA WYQQKPGKAP KLLIYWASTR ESGVPSRFSG SGSGTDFTLT ISSLQPEDFA TYYCQQHYRT PPSFGQGTKV EIK
VL54-ID   IDDIQMTQSP SSLSASVGDR VTITCRSSQS ITFNYKNYLA WYQQKPGKAP KLLIYWGSHL ESGVPSRFSG SGSGTDFTLT ISSLQPEDFA TYYCQQHYRT PPSFGQGTKV EIK
VL55-ID   IDDIQMTQSP SSLSASVGDR VTITCRSSQS ITFNYKNYLA WYQQKPGKAP KLLIYWGSKL ESGVPSRFSG SGSGTDFTLT ISSLQPEDFA TYYCQQHYRT PPSFGQGTKV EIK
VL56-ID   IDDIQMTQSP SSLSASVGDR VTITCRSSQS ITFNYKNYLA WYQQKPGKAP KLLIYWGSDL ESGVPSRFSG SGSGTDFTLT ISSLQPEDFA TYYCQQHYRT PPSFGQGTKV EIK
VL57-ID   IDDIQMTQSP SSLSASVGDR VTITCRSSQS ITFNYKNYLA WYQQKPGKAP KLLIYWGSYL ESGVPSRFSG SGSGTDFTLT ISSLQPEDVA TYYCQQHYRT PPSFGQGTKV EIK
VL58-ID   IDDIQMTQSP SSLSASVGDR VTITCRSSQS ITFNYKNYLA WYQQKPGKAP KLLIYWGSYL ESGVPSRFSG SGSGTDFTLT ISSLQPEDKA TYYCQQHYRT PPSFGQGTKV EIK
VL59-ID   IDDIQMTQSP SSLSASVGDR VTITCRSSQS ITFNYKNYLA WYQQKPGKAP KLLIYWGSYL ESGVPSRFSG SGSGTDFTLT ISSLQPEDDA TYYCQQHYRT PPSFGQGTKV EIK
VL60-ID   IDDIQMTQSP SSLSASVGDR VTITCRSSQS ITFNYKNYLA WYQQKPGKAP KLLIYWGSTR ESGVPSRFSG SGSGTDFTLT ISSLQPEDFA TYYCQQHYRT PPSFGQGTKV EIK
VL61-ID   IDDIQMTQSP SSLSASVGDR VTITCRSSQS ITFNYKNYLA WYQQKPGKAP KLLIYWGSYL ESGVPSRFSG SGSGTDFTLT ISSLQPEDFA TYYCQQHYRT PPSFGQGTKV EIK
VL153-ID  IDDIQMTQSP SSLSASVGDR VTITCRSSQS ITFQYKNYLA WYQQKPGKAP KLLIYWGSYL ESGVPSRFSG SGSGTDFTLT ISSLQPEDFA TYYCQQHYRT PPSFGQGTKV EIK
VL154-ID  IDDIQMTQSP SSLSASVGDR VTITCRSSQS ITFRYKNYLA WYQQKPGKAP KLLIYWGSYL ESGVPSRFSG SGSGTDFTLT ISSLQPEDFA TYYCQQHYRT PPSFGQGTKV EIK
VL155-ID  IDDIQMTQSP SSLSASVGDR VTITCRSSQS ITFEYKNYLA WYQQKPGKAP KLLIYWGSYL ESGVPSRFSG SGSGTDFTLT ISSLQPEDFA TYYCQQHYRT PPSFGQGTKV EIK
VL156-ID  IDDIQMTQSP SSLSASVGDR VTITCRSSQS ITFDYKNYLA WYQQKPGKAP KLLIYWGSTR ESGVPSRFSG SGSGTDFTLT ISSLQPEDFA TYYCQQHYYT PPSFGQGTKV EIK
VH62-ID   IDDIQMTQSP SSLSASVGDR VTITCRSSQS ITFNYKNYLA WYQQKPGKAP KLLIYWGSYL ESGVPSRFSG SGSGTDFTLT ISSLQPEDFA TYYCQQHYRT PPSFGQGTKV EIK
```

Fig. 14 (Continued)

Additional Light Chain Variable Regions

VL165
DIQMTQSPSSLSASVGDRVTITCRSSQSITWNYKNYLAWYQQKPGKAPKLLIYWGSYLESGVPSRFSGSGSGTD
FTLTISSLQPEDFATYYCQQHYRTPPSFGQGTKVEIK

VL166
DIQMTQSPSSLSASVGDRVTITCRSSQSITWDYKNYLAWYQQKPGKAPKLLIYWGSYLESGVPSRFSGSGSGTD
FTLTISSLQPEDFATYYCQQHYRTPPSFGQGTKVEIK

VL167
DIQMTQSPSSLSASVGDRVTITCRSSQSITWQYKNYLAWYQQKPGKAPKLLIYWGSYLESGVPSRFSGSGSGTD
FTLTISSLQPEDFATYYCQQHYRTPPSFGQGTKVEIK

VL168
DIQMTQSPSSLSASVGDRVTITCRSSQSITWRYKNYLAWYQQKPGKAPKLLIYWGSYLESGVPSRFSGSGSGTD
FTLTISSLQPEDFATYYCQQHYRTPPSFGQGTKVEIK

VL169
DIQMTQSPSSLSASVGDRVTITCRSSQSITWEYKNYLAWYQQKPGKAPKLLIYWGSYLESGVPSRFSGSGSGTD
FTLTISSLQPEDFATYYCQQHYRTPPSFGQGTKVEIK

Additional Heavy Chain Variable Regions

VH164
QVQLLETGGGLVKPGQSLKLSCAASGFTFTSYAMHWVRQPPGKGLEWVAVVSYDGNYKYYADSVQGRFTISR
DNSKNTLYLQMNSLRAEDTAVYYCAKDSRLRSLLYFEWLSQGYFNPWGQGTTVTVSS

VH162
EVQLLESGGGLVKPGQSLKLSCAASGFSFSTYAMHWVRQPPGKGLEWVAVVSYDGNYKYYADTVQGRFTISRD
NSKNTLYLQMNSLRAEDTAVYYCAKDSRLRSLLYFEWLSQGYFNPWGQGTTLTVSS

VH163
EVQLLESGGGLRKPGQSLKLSCAASGFSFSTYAMHWVRQPPGKGLEWVAVVSYDGNYKYYADSVQGRFTISR
DNSKNTLYLQMNSLRAEDTAVYYCAKDSRLRSLLYFEWLSQGYFNPWGQGTTLTVSS

Fig. 17

| Treatment Group | Lung Viral Load H1N1 (PFU/ml) |
|---|---|
| Untreated | 6.03 |
| Ab 044 Prophylaxis 10 mg/Kg | 4.45 |
| Ab 044 Prophylaxis 2.5 mg/Kg | 4.08 |
| Ab 044 Prophylaxis 0.6 mg/Kg | 5.38 |
| Ab 044 Therapy 10 mg/Kg (48hpi) | 5.34 |
| Ab 044 Therapy 2.5 mg/Kg (48 hpi) | 5.49 |
| Ab 044 Therapy 0.6 mg/Kg (48hpi) | 5.74 |
| Ab 044 Therapy 20 mg/Kg (72hpi) | 5.29 |

Fig. 21A

| Treatment Group | Lung Viral Load H3N2 (PFU/ml) |
|---|---|
| Untreated | 6.48 |
| Ab 044 Prophylaxis 10 mg/Kg | 5.42 |
| Ab 044 Therapy 10 mg/Kg (48hpi) | 5.46 |
| Ab 044 Therapy 2.5 mg/Kg (48 hpi) | 5.99 |
| Ab 044 Therapy 0.6 mg/Kg (48hpi) | 6.44 |
| Ab 044 Therapy 20 mg/Kg (72hpi) | 5.64 |

Fig. 21B

SEQUENCE LISTING

```
<160> NUMBER OF SEQ ID NOS: 188

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser or Thr
<220> FEATURE:
<221> NAME/KEY: MOD_RES
<222> LOCATION: (3)..(3)
<223> OTHER INFORMATION: Ala or Gly

<400> SEQUENCE: 1

Xaa Tyr Xaa Met His
1               5

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ile, Val or Leu
<220> FEATURE:
<221> NAME/KEY: MOD_RES
<222> LOCATION: (4)..(4)
<223> OTHER INFORMATION: Tyr or Phe
<220> FEATURE:
<221> NAME/KEY: MOD_RES
<222> LOCATION: (7)..(7)
<223> OTHER INFORMATION: Ser or Asn
<220> FEATURE:
<221> NAME/KEY: MOD_RES
<222> LOCATION: (8)..(8)
<223> OTHER INFORMATION: Tyr or Asn
<220> FEATURE:
<221> NAME/KEY: MOD_RES
<222> LOCATION: (9)..(9)
<223> OTHER INFORMATION: Lys or Arg

<400> SEQUENCE: 2

Val Xaa Ser Xaa Asp Gly Xaa Xaa Xaa Tyr Tyr Ala Asp Ser Val Gln
1               5                   10                  15

Gly

<210> SEQ ID NO 3
<211> LENGTH: 20
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ser or Thr
<220> FEATURE:
<221> NAME/KEY: MOD_RES
<222> LOCATION: (3)..(3)
<223> OTHER INFORMATION: Arg, Lys or Gln
<220> FEATURE:
<221> NAME/KEY: MOD_RES
<222> LOCATION: (6)..(6)
<223> OTHER INFORMATION: Ser or Thr
<220> FEATURE:
<221> NAME/KEY: MOD_RES
<222> LOCATION: (15)..(15)
<223> OTHER INFORMATION: Gln or Ser
<220> FEATURE:
<221> NAME/KEY: MOD_RES
<222> LOCATION: (17)..(17)
<223> OTHER INFORMATION: Tyr, Leu or Val
<220> FEATURE:
<221> NAME/KEY: MOD_RES
<222> LOCATION: (18)..(18)
<223> OTHER INFORMATION: Phe or Leu
<220> FEATURE:
<221> NAME/KEY: MOD_RES
<222> LOCATION: (19)..(19)
<223> OTHER INFORMATION: Asn or Asp
<220> FEATURE:
<221> NAME/KEY: MOD_RES
<222> LOCATION: (20)..(20)
<223> OTHER INFORMATION: Pro or Tyr

<400> SEQUENCE: 3

Asp Xaa Xaa Leu Arg Xaa Leu Leu Tyr Phe Glu Trp Leu Ser Xaa Gly
1               5                   10                  15

Xaa Xaa Xaa Xaa
            20

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ser or Thr
<220> FEATURE:
<221> NAME/KEY: MOD_RES
<222> LOCATION: (3)..(3)
<223> OTHER INFORMATION: Val, Leu or Ile
<220> FEATURE:
<221> NAME/KEY: MOD_RES
<222> LOCATION: (4)..(4)
<223> OTHER INFORMATION: Thr or Ser
<220> FEATURE:
<221> NAME/KEY: MOD_RES
<222> LOCATION: (5)..(5)
<223> OTHER INFORMATION: Tyr, Phe or Trp
<220> FEATURE:
<221> NAME/KEY: MOD_RES
<222> LOCATION: (6)..(6)
<223> OTHER INFORMATION: Asn, Ser or Asp

<400> SEQUENCE: 4

Gln Xaa Xaa Xaa Xaa Xaa Tyr Lys Asn Tyr Leu Ala
1               5                   10

<210> SEQ ID NO 5
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ala or Gly
<220> FEATURE:
<221> NAME/KEY: MOD_RES
<222> LOCATION: (4)..(4)
<223> OTHER INFORMATION: Thr, Ala, Tyr, His, Lys or Asp
<220> FEATURE:
<221> NAME/KEY: MOD_RES
<222> LOCATION: (5)..(5)
<223> OTHER INFORMATION: Arg or Leu
<220> FEATURE:
<221> NAME/KEY: MOD_RES
<222> LOCATION: (7)..(7)
<223> OTHER INFORMATION: Ser or Thr

<400> SEQUENCE: 5

Trp Xaa Ser Xaa Xaa Glu Xaa
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Tyr or His
<220> FEATURE:
<221> NAME/KEY: MOD_RES
<222> LOCATION: (9)..(9)
<223> OTHER INFORMATION: Thr or Ser

<400> SEQUENCE: 6

Gln Gln Xaa Tyr Arg Thr Pro Pro Xaa
1               5

<210> SEQ ID NO 7
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Glu or Gln
<220> FEATURE:
<221> NAME/KEY: MOD_RES
<222> LOCATION: (7)..(7)
<223> OTHER INFORMATION: Ser or Thr
<220> FEATURE:
<221> NAME/KEY: MOD_RES
<222> LOCATION: (30)..(30)
<223> OTHER INFORMATION: Ser or Thr

<400> SEQUENCE: 7

Xaa Val Gln Leu Leu Glu Xaa Gly Gly Gly Leu Val Lys Pro Gly Gln
1               5                   10                  15

Ser Leu Lys Leu Ser Cys Ala Ala Ser Gly Phe Thr Phe Xaa
            20                  25                  30
```

<210> SEQ ID NO 8
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Trp Val Arg Gln Pro Pro Gly Lys Gly Leu Glu Trp Val Ala
1               5                   10

<210> SEQ ID NO 9
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Lys
            20                  25                  30

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ala or Gln
<220> FEATURE:
<221> NAME/KEY: MOD_RES
<222> LOCATION: (5)..(5)
<223> OTHER INFORMATION: Thr or Ala
<220> FEATURE:
<221> NAME/KEY: MOD_RES
<222> LOCATION: (6)..(6)
<223> OTHER INFORMATION: Thr or Met
<220> FEATURE:
<221> NAME/KEY: MOD_RES
<222> LOCATION: (7)..(7)
<223> OTHER INFORMATION: Leu or Val

<400> SEQUENCE: 10

Trp Gly Xaa Gly Xaa Xaa Xaa Thr Val Ser Ser
1               5                   10

<210> SEQ ID NO 11
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Glu or Asp
<220> FEATURE:
<221> NAME/KEY: MOD_RES
<222> LOCATION: (3)..(3)
<223> OTHER INFORMATION: Val or Gln
<220> FEATURE:
<221> NAME/KEY: MOD_RES

```
<222> LOCATION: (9)..(9)
<223> OTHER INFORMATION: Asp or Ser
<220> FEATURE:
<221> NAME/KEY: MOD_RES
<222> LOCATION: (10)..(10)
<223> OTHER INFORMATION: Ser or Thr
<220> FEATURE:
<221> NAME/KEY: MOD_RES
<222> LOCATION: (11)..(11)
<223> OTHER INFORMATION: Leu or Val
<220> FEATURE:
<221> NAME/KEY: MOD_RES
<222> LOCATION: (12)..(12)
<223> OTHER INFORMATION: Ala or Ser
<220> FEATURE:
<221> NAME/KEY: MOD_RES
<222> LOCATION: (13)..(13)
<223> OTHER INFORMATION: Val or Ala
<220> FEATURE:
<221> NAME/KEY: MOD_RES
<222> LOCATION: (14)..(14)
<223> OTHER INFORMATION: Ser or Thr
<220> FEATURE:
<221> NAME/KEY: MOD_RES
<222> LOCATION: (15)..(15)
<223> OTHER INFORMATION: Leu, Val or Arg
<220> FEATURE:
<221> NAME/KEY: MOD_RES
<222> LOCATION: (17)..(17)
<223> OTHER INFORMATION: Glu or Asp
<220> FEATURE:
<221> NAME/KEY: MOD_RES
<222> LOCATION: (19)..(19)
<223> OTHER INFORMATION: Ala or Val
<220> FEATURE:
<221> NAME/KEY: MOD_RES
<222> LOCATION: (20)..(20)
<223> OTHER INFORMATION: Thr or Ser
<220> FEATURE:
<221> NAME/KEY: MOD_RES
<222> LOCATION: (22)..(22)
<223> OTHER INFORMATION: Asn, Thr, Gln, Asp or Arg
<220> FEATURE:
<221> NAME/KEY: MOD_RES
<222> LOCATION: (24)..(24)
<223> OTHER INFORMATION: Lys or Arg

<400> SEQUENCE: 11

Xaa Ile Xaa Met Thr Gln Ser Pro Xaa Xaa Xaa Xaa Xaa Xaa Xaa Gly
1               5                   10                  15

Xaa Arg Xaa Xaa Ile Xaa Cys Xaa Ser Ser
            20                  25

<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Gln or Lys
<220> FEATURE:
<221> NAME/KEY: MOD_RES
<222> LOCATION: (9)..(9)
<223> OTHER INFORMATION: Pro or Ala

<400> SEQUENCE: 12

Trp Tyr Gln Gln Lys Pro Gly Xaa Xaa Pro Lys Leu Leu Ile Tyr
1               5                   10                  15

<210> SEQ ID NO 13
```

```
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Asp, Glu or Ser
<220> FEATURE:
<221> NAME/KEY: MOD_RES
<222> LOCATION: (24)..(24)
<223> OTHER INFORMATION: Ala or Pro
<220> FEATURE:
<221> NAME/KEY: MOD_RES
<222> LOCATION: (27)..(27)
<223> OTHER INFORMATION: Val, Phe, Lys or Asp
<220> FEATURE:
<221> NAME/KEY: MOD_RES
<222> LOCATION: (29)..(29)
<223> OTHER INFORMATION: Val or Thr

<400> SEQUENCE: 13

Gly Val Pro Xaa Arg Phe Ser Gly Ser Gly Ser Gly Thr Asp Phe Thr
1               5                   10                  15

Leu Thr Ile Ser Ser Leu Gln Xaa Glu Asp Xaa Ala Xaa Tyr Tyr Cys
            20                  25                  30

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Gly, Gln, Thr, Ser or Asn
<220> FEATURE:
<221> NAME/KEY: MOD_RES
<222> LOCATION: (7)..(7)
<223> OTHER INFORMATION: Leu or Val
<220> FEATURE:
<221> NAME/KEY: MOD_RES
<222> LOCATION: (8)..(8)
<223> OTHER INFORMATION: Asp or Glu

<400> SEQUENCE: 14

Phe Gly Xaa Gly Thr Lys Xaa Xaa Ile Lys
1               5                   10

<210> SEQ ID NO 15
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Glu Val Gln Leu Leu Glu Ser Gly Gly Gly Leu Val Lys Pro Gly Gln
1               5                   10                  15

Ser Leu Lys Leu Ser Cys Ala Ala Ser Gly Phe Thr Phe Thr Ser Tyr
            20                  25                  30

Gly Met His Trp Val Arg Gln Pro Pro Gly Lys Gly Leu Glu Trp Val
        35                  40                  45

Ala Val Ile Ser Tyr Asp Gly Ser Tyr Lys Tyr Tyr Ala Asp Ser Val
    50                  55                  60
```

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Arg Leu Arg Ser Leu Leu Tyr Phe Glu Trp Leu Ser
            100                 105                 110

Gln Gly Tyr Phe Asn Pro Trp Gly Ala Gly Thr Thr Leu Thr Val Ser
        115                 120                 125

Ser

<210> SEQ ID NO 16
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Glu Val Gln Leu Leu Glu Ser Gly Gly Gly Leu Val Lys Pro Gly Gln
1               5                   10                  15

Ser Leu Lys Leu Ser Cys Ala Ala Ser Gly Phe Thr Phe Ser Ser Tyr
            20                  25                  30

Gly Met His Trp Val Arg Gln Pro Pro Gly Lys Gly Leu Glu Trp Val
        35                  40                  45

Ala Val Val Ser Tyr Asp Gly Ser Asn Lys Tyr Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Thr Lys Leu Arg Ser Leu Leu Tyr Phe Glu Trp Leu Ser
            100                 105                 110

Ser Gly Leu Leu Asp Tyr Trp Gly Gln Gly Ala Met Val Thr Val Ser
        115                 120                 125

Ser

<210> SEQ ID NO 17
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Glu Val Gln Leu Leu Glu Ser Gly Gly Gly Leu Val Lys Pro Gly Gln
1               5                   10                  15

Ser Leu Lys Leu Ser Cys Ala Ser Gly Phe Thr Phe Thr Ser Tyr
            20                  25                  30

Gly Met His Trp Val Arg Gln Pro Pro Gly Lys Gly Leu Glu Trp Val
        35                  40                  45

Ala Val Val Ser Tyr Asp Gly Asn Tyr Lys Tyr Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys

```
                    85                  90                  95

Ala Lys Asp Ser Arg Leu Arg Ser Leu Leu Tyr Phe Glu Trp Leu Ser
                100                 105                 110

Gln Gly Tyr Phe Asn Pro Trp Gly Ala Gly Thr Thr Leu Thr Val Ser
            115                 120                 125

Ser

<210> SEQ ID NO 18
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Glu Val Gln Leu Leu Glu Ser Gly Gly Gly Leu Val Lys Pro Gly Gln
1               5                   10                  15

Ser Leu Lys Leu Ser Cys Ala Ala Ser Gly Phe Thr Phe Thr Ser Tyr
            20                  25                  30

Gly Met His Trp Val Arg Gln Pro Pro Gly Lys Gly Leu Glu Trp Val
        35                  40                  45

Ala Val Leu Ser Tyr Asp Gly Asn Tyr Lys Tyr Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Arg Leu Arg Ser Leu Leu Tyr Phe Glu Trp Leu Ser
                100                 105                 110

Gln Gly Tyr Phe Asn Pro Trp Gly Ala Gly Thr Thr Leu Thr Val Ser
            115                 120                 125

Ser

<210> SEQ ID NO 19
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Glu Val Gln Leu Leu Glu Ser Gly Gly Gly Leu Val Lys Pro Gly Gln
1               5                   10                  15

Ser Leu Lys Leu Ser Cys Ala Ala Ser Gly Phe Thr Phe Thr Thr Tyr
            20                  25                  30

Ala Met His Trp Val Arg Gln Pro Pro Gly Lys Gly Leu Glu Trp Val
        35                  40                  45

Ala Val Leu Ser Tyr Asp Gly Asn Tyr Lys Tyr Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Arg Leu Arg Ser Leu Leu Tyr Phe Glu Trp Leu Ser
                100                 105                 110
```

Gln Gly Tyr Phe Asn Pro Trp Gly Ala Gly Thr Thr Leu Thr Val Ser
            115                 120                 125

Ser

<210> SEQ ID NO 20
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Glu Val Gln Leu Leu Glu Ser Gly Gly Gly Leu Val Lys Pro Gly Gln
1               5                   10                  15

Ser Leu Lys Leu Ser Cys Ala Ala Ser Gly Phe Thr Phe Thr Thr Tyr
            20                  25                  30

Ala Met His Trp Val Arg Gln Pro Pro Gly Lys Gly Leu Glu Trp Val
        35                  40                  45

Ala Val Val Ser Phe Asp Gly Asn Asn Arg Tyr Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Gln Leu Arg Ser Leu Leu Tyr Phe Glu Trp Leu Ser
            100                 105                 110

Ser Gly Val Leu Asp Tyr Trp Gly Gln Gly Ala Met Val Thr Val Ser
        115                 120                 125

Ser

<210> SEQ ID NO 21
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Glu Val Gln Leu Leu Glu Ser Gly Gly Gly Leu Val Lys Pro Gly Gln
1               5                   10                  15

Ser Leu Lys Leu Ser Cys Ala Ala Ser Gly Phe Thr Phe Ser Ser Tyr
            20                  25                  30

Gly Met His Trp Val Arg Gln Pro Pro Gly Lys Gly Leu Glu Trp Val
        35                  40                  45

Ala Val Val Ser Tyr Asp Gly Asn Asn Lys Tyr Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Lys Leu Arg Ser Leu Leu Tyr Phe Glu Trp Leu Ser
            100                 105                 110

Ser Gly Leu Leu Asp Tyr Trp Gly Gln Gly Ala Met Val Thr Val Ser
        115                 120                 125

Ser

<210> SEQ ID NO 22
<211> LENGTH: 129
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 22

Glu Val Gln Leu Leu Glu Ser Gly Gly Gly Leu Val Lys Pro Gly Gln
1               5                   10                  15

Ser Leu Lys Leu Ser Cys Ala Ala Ser Gly Phe Thr Phe Thr Thr Tyr
            20                  25                  30

Ala Met His Trp Val Arg Gln Pro Pro Gly Lys Gly Leu Glu Trp Val
        35                  40                  45

Ala Val Val Ser Tyr Asp Gly Asn Asn Lys Tyr Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Lys Leu Arg Ser Leu Leu Tyr Phe Glu Trp Leu Ser
            100                 105                 110

Ser Gly Leu Leu Asp Tyr Trp Gly Gln Gly Ala Met Val Thr Val Ser
        115                 120                 125

Ser

<210> SEQ ID NO 23
<211> LENGTH: 129
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 23

Glu Val Gln Leu Leu Glu Ser Gly Gly Gly Leu Val Lys Pro Gly Gln
1               5                   10                  15

Ser Leu Lys Leu Ser Cys Ala Ala Ser Gly Phe Thr Phe Thr Ser Tyr
            20                  25                  30

Gly Met His Trp Val Arg Gln Pro Pro Gly Lys Gly Leu Glu Trp Val
        35                  40                  45

Ala Val Val Ser Tyr Asp Gly Asn Tyr Lys Tyr Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Lys Leu Arg Ser Leu Leu Tyr Phe Glu Trp Leu Ser
            100                 105                 110

Gln Gly Tyr Phe Asn Pro Trp Gly Ala Gly Thr Thr Leu Thr Val Ser
        115                 120                 125

Ser

<210> SEQ ID NO 24
<211> LENGTH: 129
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 24

Glu Val Gln Leu Leu Glu Ser Gly Gly Gly Leu Val Lys Pro Gly Gln
1               5                   10                  15

Ser Leu Lys Leu Ser Cys Ala Ala Ser Gly Phe Thr Phe Thr Ser Tyr
            20                  25                  30

Ala Met His Trp Val Arg Gln Pro Pro Gly Lys Gly Leu Glu Trp Val
        35                  40                  45

Ala Val Val Ser Tyr Asp Gly Asn Tyr Lys Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Arg Leu Arg Ser Leu Leu Tyr Phe Glu Trp Leu Ser
            100                 105                 110

Gln Gly Tyr Phe Asn Pro Trp Gly Gln Gly Thr Thr Leu Thr Val Ser
        115                 120                 125

Ser

<210> SEQ ID NO 25
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Val Gln Leu Leu Glu Thr Gly Gly Gly Leu Val Lys Pro Gly Gln
1               5                   10                  15

Ser Leu Lys Leu Ser Cys Ala Ala Ser Gly Phe Thr Phe Thr Ser Tyr
            20                  25                  30

Ala Met His Trp Val Arg Gln Pro Pro Gly Lys Gly Leu Glu Trp Val
        35                  40                  45

Ala Val Val Ser Tyr Asp Gly Asn Tyr Lys Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Arg Leu Arg Ser Leu Leu Tyr Phe Glu Trp Leu Ser
            100                 105                 110

Gln Gly Tyr Phe Asn Pro Trp Gly Gln Gly Thr Thr Leu Thr Val Ser
        115                 120                 125

Ser

<210> SEQ ID NO 26
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26
```

Glu Val Gln Leu Leu Glu Ser Gly Gly Gly Leu Val Lys Pro Gly Gln
1               5                   10                  15

Ser Leu Lys Leu Ser Cys Ala Ala Ser Gly Phe Thr Phe Thr Ser Tyr
            20                  25                  30

Ala Met His Trp Val Arg Gln Pro Pro Gly Lys Gly Leu Glu Trp Val
        35                  40                  45

Ala Val Val Ser Tyr Asp Gly Asn Tyr Lys Tyr Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Gln Leu Arg Thr Leu Leu Tyr Phe Glu Trp Leu Ser
            100                 105                 110

Gln Gly Tyr Phe Asn Pro Trp Gly Gln Gly Thr Thr Leu Thr Val Ser
        115                 120                 125

Ser

<210> SEQ ID NO 27
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Glu Val Gln Leu Leu Glu Ser Gly Gly Gly Leu Val Lys Pro Gly Gln
1               5                   10                  15

Ser Leu Lys Leu Ser Cys Ala Ala Ser Gly Phe Thr Phe Thr Ser Tyr
            20                  25                  30

Ala Met His Trp Val Arg Gln Pro Pro Gly Lys Gly Leu Glu Trp Val
        35                  40                  45

Ala Val Val Ser Tyr Asp Gly Asn Tyr Lys Tyr Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Arg Leu Arg Thr Leu Leu Tyr Phe Glu Trp Leu Ser
            100                 105                 110

Gln Gly Tyr Phe Asp Pro Trp Gly Gln Gly Thr Thr Leu Thr Val Ser
        115                 120                 125

Ser

<210> SEQ ID NO 28
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Thr Tyr Asn

```
                        20                  25                  30

Tyr Lys Asn Tyr Leu Ala Trp Tyr Gln Gln Lys Pro Gly Gln Pro Pro
                35                  40                  45

Lys Leu Leu Ile Tyr Trp Ala Ser Thr Arg Glu Ser Gly Val Pro Asp
        50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Tyr Tyr
                85                  90                  95

Arg Thr Pro Pro Thr Phe Gly Gly Gly Thr Lys Leu Asp Ile Lys
                100                 105                 110
```

<210> SEQ ID NO 29
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

```
Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Thr Phe Ser
                20                  25                  30

Tyr Lys Asn Tyr Leu Ala Trp Tyr Gln Gln Lys Pro Gly Gln Pro Pro
                35                  40                  45

Lys Leu Leu Ile Tyr Trp Ala Ser Thr Arg Glu Ser Gly Val Pro Asp
        50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Tyr Tyr
                85                  90                  95

Arg Thr Pro Pro Thr Phe Gly Gly Gly Thr Lys Leu Asp Ile Lys
                100                 105                 110
```

<210> SEQ ID NO 30
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

```
Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Thr Phe Asp
                20                  25                  30

Tyr Lys Asn Tyr Leu Ala Trp Tyr Gln Gln Lys Pro Gly Gln Pro Pro
                35                  40                  45

Lys Leu Leu Ile Tyr Trp Ala Ser Thr Arg Glu Ser Gly Val Pro Asp
        50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Tyr Tyr
                85                  90                  95

Arg Thr Pro Pro Thr Phe Gly Gly Gly Thr Lys Leu Asp Ile Lys
```

<210> SEQ ID NO 31
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Val Thr Phe Asn
            20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln His Tyr
                85                  90                  95

Arg Thr Pro Pro Ser Phe Gly Gly Gly Thr Lys Leu Asp Ile Lys
            100                 105                 110

<210> SEQ ID NO 32
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Leu Ser Phe Asn
            20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln His Tyr
                85                  90                  95

Arg Thr Pro Pro Ser Phe Gly Gly Gly Thr Lys Leu Asp Ile Lys
            100                 105                 110

<210> SEQ ID NO 33
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Glu Ile Val Met Thr Gln Ser Pro Asp Ser Leu Ala Val Ser Leu Gly
1               5                   10                  15

```
Glu Arg Ala Thr Ile Asn Cys Lys Ser Ser Gln Thr Val Thr Phe Asn
                20                  25                  30

Tyr Lys Asn Tyr Leu Ala Trp Tyr Gln Gln Lys Pro Gly Gln Pro Pro
            35                  40                  45

Lys Leu Leu Ile Tyr Phe Ala Ser Thr Arg Glu Ser Gly Val Pro Asp
50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln His Tyr
                85                  90                  95

Arg Thr Pro Pro Ser Phe Gly Gly Gly Thr Lys Leu Asp Ile Lys
            100                 105                 110

<210> SEQ ID NO 34
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Leu Ser Phe Asn
                20                  25                  30

Tyr Lys Asn Tyr Leu Ala Trp Tyr Gln Gln Lys Pro Gly Gln Pro Pro
            35                  40                  45

Lys Leu Leu Ile Tyr Phe Ala Ser Thr Arg Glu Ser Gly Val Pro Asp
50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln His Tyr
                85                  90                  95

Arg Thr Pro Pro Ser Phe Gly Gly Gly Thr Lys Leu Asp Ile Lys
            100                 105                 110

<210> SEQ ID NO 35
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Thr Trp Ser
                20                  25                  30

Tyr Lys Asn Tyr Leu Ala Trp Tyr Gln Gln Lys Pro Gly Gln Pro Pro
            35                  40                  45

Lys Leu Leu Ile Tyr Trp Ala Ser Thr Arg Glu Ser Gly Val Pro Asp
50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Tyr Tyr
                85                  90                  95
```

```
Arg Thr Pro Pro Thr Phe Gly Gly Gly Thr Lys Leu Asp Ile Lys
                100                 105                 110
```

<210> SEQ ID NO 36
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

```
Glu Ile Val Met Ser Gln Ser Pro Asp Thr Leu Ala Val Thr Leu Gly
1               5                   10                  15

Glu Arg Ala Ser Ile Asn Cys Lys Ser Ser Gln Thr Val Thr Phe Asn
            20                  25                  30

Tyr Lys Asn Tyr Leu Ala Trp Tyr Gln Gln Lys Pro Gly Gln Pro Pro
        35                  40                  45

Lys Val Leu Ile Tyr Trp Ala Ser Ala Arg Glu Thr Gly Val Pro Glu
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln His Tyr
                85                  90                  95

Arg Thr Pro Pro Ser Phe Gly Gln Gly Thr Lys Leu Glu Ile Lys
                100                 105                 110
```

<210> SEQ ID NO 37
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

```
Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Val Thr Phe Asn
            20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln His Tyr
                85                  90                  95

Arg Thr Pro Pro Ser Phe Gly Thr Gly Thr Lys Leu Asp Ile Lys
                100                 105                 110
```

<210> SEQ ID NO 38
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Val Thr Phe Asn
            20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln His Tyr
                85                  90                  95

Arg Thr Pro Pro Ser Phe Gly Ser Gly Thr Lys Leu Asp Ile Lys
            100                 105                 110

<210> SEQ ID NO 39
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Val Thr Phe Asn
            20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln His Tyr
                85                  90                  95

Arg Thr Pro Pro Ser Phe Gly Gln Gly Thr Lys Leu Asp Ile Lys
            100                 105                 110

<210> SEQ ID NO 40
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Val Thr Phe Asn
            20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln His Tyr
                85                  90                  95

Arg Thr Pro Pro Ser Phe Gly Asn Gly Thr Lys Leu Asp Ile Lys
            100                 105                 110

<210> SEQ ID NO 41
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Leu Ser Phe Asn
            20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln His Tyr
                85                  90                  95

Arg Thr Pro Pro Ser Phe Gly Thr Gly Thr Lys Leu Asp Ile Lys
            100                 105                 110

<210> SEQ ID NO 42
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Leu Ser Phe Asn
            20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln His Tyr
                85                  90                  95

Arg Thr Pro Pro Ser Phe Gly Ser Gly Thr Lys Leu Asp Ile Lys
            100                 105                 110

<210> SEQ ID NO 43
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 43

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Leu Ser Phe Asn
            20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln His Tyr
                85                  90                  95

Arg Thr Pro Pro Ser Phe Gly Gln Gly Thr Lys Leu Asp Ile Lys
            100                 105                 110

<210> SEQ ID NO 44
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Leu Ser Phe Asn
            20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln His Tyr
                85                  90                  95

Arg Thr Pro Pro Ser Phe Gly Asn Gly Thr Lys Leu Asp Ile Lys
            100                 105                 110

<210> SEQ ID NO 45
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Phe Asn
            20                  25                  30

Tyr Lys Asn Tyr Leu Ala Trp Tyr Gln Gln Lys Pro Gly Lys Ala Pro
        35                  40                  45

Lys Leu Leu Ile Tyr Trp Gly Ser Tyr Leu Glu Ser Gly Val Pro Ser
50                  55                  60

Arg Phe Ser Gly Ser Gly Ser Gly Thr Asp Phe Thr Leu Thr Ile Ser

```
                65                  70                  75                  80
Ser Leu Gln Pro Glu Asp Phe Ala Thr Tyr Tyr Cys Gln Gln His Tyr
                    85                  90                  95

Arg Thr Pro Pro Ser Phe Gly Gln Gly Thr Lys Val Glu Ile Lys
                100                 105                 110

<210> SEQ ID NO 46
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Arg Ser Gln Ser Ile Thr Phe Asn
                20                  25                  30

Tyr Lys Asn Tyr Leu Gly Trp Tyr Gln Gln Lys Pro Gly Lys Ala Pro
            35                  40                  45

Lys Leu Leu Ile Tyr Trp Gly Ser Tyr Leu Glu Ser Gly Val Pro Ser
        50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln His Tyr
                    85                  90                  95

Arg Thr Pro Pro Ser Phe Gly Gln Gly Thr Lys Val Glu Ile Lys
                100                 105                 110

<210> SEQ ID NO 47
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Asp Ile Val Met Thr Gln Ser Pro Asp Thr Leu Ala Val Thr Leu Gly
1               5                   10                  15

Glu Arg Ala Thr Ile Gln Cys Lys Ser Ser Gln Thr Val Thr Phe Asn
                20                  25                  30

Tyr Lys Asn Tyr Leu Ala Trp Tyr Gln Gln Lys Pro Gly Gln Pro Pro
            35                  40                  45

Lys Leu Leu Ile Tyr Trp Ala Ser Thr Arg Glu Ser Gly Val Pro Asp
        50                  55                  60

Arg Phe Ser Gly Ser Gly Ser Gly Thr Asp Phe Thr Leu Thr Ile Thr
65                  70                  75                  80

Ser Leu Gln Ala Glu Asp Val Ala Val Tyr Tyr Cys Gln Gln His Tyr
                    85                  90                  95

Arg Thr Pro Pro Ser Phe Gly Gln Gly Thr Lys Leu Asp Ile Lys
                100                 105                 110

<210> SEQ ID NO 48
<211> LENGTH: 111
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 48

Asp Ile Val Met Thr Gln Ser Pro Asp Thr Val Ala Val Thr Val Gly
1               5                   10                  15

Glu Arg Ala Thr Ile Asn Cys Lys Ser Ser Gln Thr Val Thr Phe Asn
            20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln His Tyr
                85                  90                  95

Arg Thr Pro Pro Ser Phe Gly Gln Gly Thr Lys Leu Asp Ile Lys
            100                 105                 110

<210> SEQ ID NO 49
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Asp Ile Val Met Thr Gln Ser Pro Asp Thr Val Ala Val Thr Leu Gly
1               5                   10                  15

Glu Arg Ala Thr Ile Asp Cys Lys Ser Ser Gln Thr Val Thr Phe Asn
            20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln His Tyr
                85                  90                  95

Arg Thr Pro Pro Ser Phe Gly Gln Gly Thr Lys Leu Asp Ile Lys
            100                 105                 110

<210> SEQ ID NO 50
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Asp Ile Val Met Thr Gln Ser Pro Asp Thr Leu Ala Val Thr Val Gly
1               5                   10                  15

Glu Arg Ala Thr Ile Arg Cys Lys Ser Ser Gln Thr Val Thr Phe Asn
            20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
    50                  55                  60

```
Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln His Tyr
                 85                  90                  95

Arg Thr Pro Pro Ser Phe Gly Gln Gly Thr Lys Leu Asp Ile Lys
                100                 105                 110

<210> SEQ ID NO 51
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Asp Ile Val Met Thr Gln Ser Pro Asp Thr Leu Ala Val Ser Arg Gly
 1               5                  10                  15

Glu Arg Ala Thr Ile Asp Cys Lys Ser Ser Gln Thr Val Thr Phe Asn
                 20                  25                  30

Tyr Lys Asn Tyr Leu Ala Trp Tyr Gln Gln Lys Pro Gly Gln Pro Pro
             35                  40                  45

Lys Leu Leu Ile Tyr Trp Ala Ser Thr Arg Glu Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Glu Ala Val Tyr Tyr Cys Gln Gln His Tyr
                 85                  90                  95

Arg Thr Pro Pro Ser Phe Gly Gln Gly Thr Lys Leu Asp Ile Lys
                100                 105                 110

<210> SEQ ID NO 52
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Asp Ile Gln Met Thr Gln Ser Pro Ser Ser Leu Ser Ala Ser Val Gly
 1               5                  10                  15

Asp Arg Val Thr Ile Thr Cys Arg Ser Ser Gln Ser Ile Thr Phe Asp
                 20                  25                  30

Tyr Lys Asn Tyr Leu Ala Trp Tyr Gln Gln Lys Pro Gly Lys Ala Pro
             35                  40                  45

Lys Leu Leu Ile Tyr Trp Gly Ser Tyr Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln His Tyr
                 85                  90                  95

Arg Thr Pro Pro Ser Phe Gly Gln Gly Thr Lys Val Glu Ile Lys
                100                 105                 110

<210> SEQ ID NO 53
<211> LENGTH: 111
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 53

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Phe Asn
            20                  25                  30

Tyr Lys Asn Tyr Leu Ala Trp Tyr Gln Gln Lys Pro Gly Lys Ala Pro
        35                  40                  45

Lys Leu Leu Ile Tyr Trp Gly Ser Thr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln His Tyr
                85                  90                  95

Arg Thr Pro Pro Ser Phe Gly Gln Gly Thr Lys Val Glu Ile Lys
            100                 105                 110

<210> SEQ ID NO 54
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Phe Asn
            20                  25                  30

Tyr Lys Asn Tyr Leu Ala Trp Tyr Gln Gln Lys Pro Gly Lys Ala Pro
        35                  40                  45

Lys Leu Leu Ile Tyr Trp Gly Ser His Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln His Tyr
                85                  90                  95

Arg Thr Pro Pro Ser Phe Gly Gln Gly Thr Lys Val Glu Ile Lys
            100                 105                 110

<210> SEQ ID NO 55
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Phe Asn
            20                  25                  30

Tyr Lys Asn Tyr Leu Ala Trp Tyr Gln Gln Lys Pro Gly Lys Ala Pro
        35                  40                  45
```

```
Lys Leu Leu Ile Tyr Trp Gly Ser Lys Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln His Tyr
                 85                  90                  95

Arg Thr Pro Pro Ser Phe Gly Gln Gly Thr Lys Val Glu Ile Lys
            100                 105                 110

<210> SEQ ID NO 56
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Asp Ile Gln Met Thr Gln Ser Pro Ser Ser Leu Ser Ala Ser Val Gly
 1               5                  10                  15

Asp Arg Val Thr Ile Thr Cys Arg Ser Ser Gln Ser Ile Thr Phe Asn
             20                  25                  30

Tyr Lys Asn Tyr Leu Ala Trp Tyr Gln Gln Lys Pro Gly Lys Ala Pro
         35                  40                  45

Lys Leu Leu Ile Tyr Trp Gly Ser Asp Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln His Tyr
                 85                  90                  95

Arg Thr Pro Pro Ser Phe Gly Gln Gly Thr Lys Val Glu Ile Lys
            100                 105                 110

<210> SEQ ID NO 57
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Asp Ile Gln Met Thr Gln Ser Pro Ser Ser Leu Ser Ala Ser Val Gly
 1               5                  10                  15

Asp Arg Val Thr Ile Thr Cys Arg Ser Ser Gln Ser Ile Thr Phe Asn
             20                  25                  30

Tyr Lys Asn Tyr Leu Ala Trp Tyr Gln Gln Lys Pro Gly Lys Ala Pro
         35                  40                  45

Lys Leu Leu Ile Tyr Trp Gly Ser Tyr Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Val Ala Thr Tyr Tyr Cys Gln Gln His Tyr
                 85                  90                  95

Arg Thr Pro Pro Ser Phe Gly Gln Gly Thr Lys Val Glu Ile Lys
            100                 105                 110

<210> SEQ ID NO 58
<211> LENGTH: 111
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Phe Asn
            20                  25                  30

Tyr Lys Asn Tyr Leu Ala Trp Tyr Gln Gln Lys Pro Gly Lys Ala Pro
        35                  40                  45

Lys Leu Leu Ile Tyr Trp Gly Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Lys Ala Thr Tyr Tyr Cys Gln Gln His Tyr
                85                  90                  95

Arg Thr Pro Pro Ser Phe Gly Gln Gly Thr Lys Val Glu Ile Lys
            100                 105                 110

<210> SEQ ID NO 59
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Phe Asn
            20                  25                  30

Tyr Lys Asn Tyr Leu Ala Trp Tyr Gln Gln Lys Pro Gly Lys Ala Pro
        35                  40                  45

Lys Leu Leu Ile Tyr Trp Gly Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Asp Ala Thr Tyr Tyr Cys Gln Gln His Tyr
                85                  90                  95

Arg Thr Pro Pro Ser Phe Gly Gln Gly Thr Lys Val Glu Ile Lys
            100                 105                 110

<210> SEQ ID NO 60
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Phe Asn
            20                  25                  30

Tyr Lys Asn Tyr Leu Ala Trp Tyr Gln Gln Lys Pro Gly Lys Ala Pro
```

```
                35                  40                  45
Lys Leu Leu Ile Tyr Trp Gly Ser Tyr Leu Glu Ser Gly Val Pro Ser
         50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln Tyr Tyr
                 85                  90                  95

Arg Thr Pro Pro Ser Phe Gly Gln Gly Thr Lys Val Glu Ile Lys
             100                 105                 110

<210> SEQ ID NO 61
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Asp Ile Gln Met Thr Gln Ser Pro Ser Ser Leu Ser Ala Ser Val Gly
 1               5                  10                  15

Asp Arg Val Thr Ile Thr Cys Arg Ser Ser Gln Ser Ile Thr Phe Asn
             20                  25                  30

Tyr Lys Asn Tyr Leu Ala Trp Tyr Gln Gln Lys Pro Gly Lys Ala Pro
         35                  40                  45

Lys Leu Leu Ile Tyr Trp Gly Ser Thr Arg Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln His Tyr
                 85                  90                  95

Arg Thr Pro Pro Ser Phe Gly Gln Gly Thr Lys Val Glu Ile Lys
             100                 105                 110

<210> SEQ ID NO 62
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Asp Ile Gln Met Thr Gln Ser Pro Ser Ser Leu Ser Ala Ser Val Gly
 1               5                  10                  15

Asp Arg Val Thr Ile Thr Cys Arg Ser Ser Gln Ser Ile Thr Phe Asn
             20                  25                  30

Tyr Lys Asn Tyr Leu Ala Trp Tyr Gln Gln Lys Pro Gly Lys Ala Pro
         35                  40                  45

Lys Leu Leu Ile Tyr Trp Gly Ser Tyr Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln His Tyr
                 85                  90                  95

Arg Thr Pro Pro Ser Phe Gly Gln Gly Thr Lys Val Glu Ile Lys
             100                 105                 110
```

```
<210> SEQ ID NO 63
<211> LENGTH: 405
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63
gaggtacagc tcctcgaatc gggaggggga ctggtcaaac ccggtcaatc gctcaaactc     60
tcgtgtgcag cgtcaggttt tacgttcagc tcatatggga tgcactgggt ccgccagcct    120
ccgggaaagg gactggagtg ggtggcagtc gtgtcgtatg acgggagcaa taagtactac    180
gccgattcag tgcaaggtcg gtttaccatt tcgagggata acagcaagaa cacgctctac    240
ttgcagatga actcacttag agcggaagat acggctgtgt actattgcgc caaagacaca    300
aagctgcgat ccctgttgta cttcgaatgg ttgtcctcgg gcttgcttga ctattggggg    360
cagggcgcca tggtcacagt atccagcgcg tcgactaagg ggccc                    405

<210> SEQ ID NO 64
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64
gagatcgtga tgacgcagag ccccgatagc ctcgctgtct cattggggga acgggccacg     60
attaactgca aatcctcaca gtcggtgact ttcagctata agaattaccct ggcatggtat   120 cagcagaagc cgggtcaacc cccaaaactg ttgatctact gggcctccac acgcgagtcg    180
ggagtcccgg accgattttc gggttcaggg tccggcactg actttaccct cacaatttca    240
tcgcttcaag cggaggatgt agcagtgtac tattgtcagc agtattacag aacacctccc    300
accttcggag ggggaacgaa acttgacatc aagggatcc                           339

<210> SEQ ID NO 65
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65
gagatcgtga tgacgcagag ccccgatagc ctcgctgtct cattggggga acgggccacg     60
attaactgca aatcctcaca gtcggtgact ttcgactata agaattaccct ggcatggtat   120 cagcagaagc cgggtcaacc cccaaaactg ttgatctact gggcctccac acgcgagtcg    180
ggagtcccgg accgattttc gggttcaggg tccggcactg actttaccct cacaatttca    240
tcgcttcaag cggaggatgt agcagtgtac tattgtcagc agtattacag aacacctccc    300
accttcggag ggggaacgaa acttgacatc aagggatcc                           339

<210> SEQ ID NO 66
<211> LENGTH: 405
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 66

```
gaagtgcaac tcctcgagtc aggaggaggt ttggtgaaac cgggtcagtc cttgaaactg    60
agctgtgcag caagcgggtt cacgtttacg tcgtacggca tgcactgggt acggcagcct   120
cccgggaagg gacttgaatg ggtcgccgtc atctcatacg acgggtcgta caaatactat   180
gcggatagcg tgcaaggtcg cttcacaatt tcccgggaca attcgaagaa tacactgtat   240
cttcagatga actcgctcag ggctgaggac acggcggtct attactgcgc gaaggattcg   300
cgactcagat cccttttgta ctttgagtgg ctgtcgcagg ggtatttcaa cccatgggga   360
gccggaacca ctttgaccgt atcaagcgcg tcaacaaagg ggccc                    405
```

<210> SEQ ID NO 67
<211> LENGTH: 654
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67

```
gaaattgtaa tgacgcagag ccctgatagc cttgccgtgt ccctgggtga gagggcgaca    60
atcaattgta agtcatcaca gtcggtcacg tacaactaca gaactacctg gcgtggtat   120
caacagaaac ccgggcagcc gcccaaattg ctcatctatt gggcttcgac acgggagtcg   180
ggtgtgccag accgcttctc cgggtcagga tcgggaactg acttcacgtt gactatttcg   240
tccctccagg cagaagatgt agccgtctac tattgccaac agtattacag aacgccgcct   300
acatttggag gcgggaccaa acttgacatc aagggatccg tggccgcccc cagcgtcttc   360
atcttcccgc ccagcgacga gcagctgaag tcgggcacgg ccagcgtggt gtgcctcctg   420
aacaacttct acccccgcga ggcgaaggtc cagtggaagg tggacaacgc cctgcagagc   480
gggaacagcc aggagagcgt gaccgagcag gactcgaagg acagcaccta cagcctcagc   540
agcaccctga cgctgagcaa ggccgactac gagaagcaca aggtctacgc ctgcgaggtg   600
acccaccagg ggctctcgag ccccgtgacc aagagcttca accggggcga gtgc         654
```

<210> SEQ ID NO 68
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ser Tyr Ala Met His
1               5

<210> SEQ ID NO 69
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Val Val Ser Tyr Asp Gly Asn Tyr Lys Tyr Tyr Ala Asp Ser Val Gln
1               5                   10                  15
Gly

```
<210> SEQ ID NO 70
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Asp Ser Arg Leu Arg Ser Leu Leu Tyr Phe Glu Trp Leu Ser Gln Gly
1               5                   10                  15

Tyr Phe Asn Pro
            20

<210> SEQ ID NO 71
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gln Ser Ile Thr Phe Asn Tyr Lys Asn Tyr Leu Ala
1               5                   10

<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Trp Gly Ser Tyr Leu Glu Ser
1               5

<210> SEQ ID NO 73
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gln Gln His Tyr Arg Thr Pro Pro Ser
1               5

<210> SEQ ID NO 74
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Gln Val Gln Leu Leu Glu Thr Gly Gly Gly Leu Val Lys Pro Gly Gln
1               5                   10                  15

Ser Leu Lys Leu Ser Cys Ala Ala Ser Gly Phe Thr Phe Thr
            20                  25                  30

<210> SEQ ID NO 75
<211> LENGTH: 14
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Trp Val Arg Gln Pro Pro Gly Lys Gly Leu Glu Trp Val Ala
1               5                   10

<210> SEQ ID NO 76
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Lys
            20                  25                  30

<210> SEQ ID NO 77
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Trp Gly Gln Gly Thr Thr Leu Thr Val Ser Ser
1               5                   10

<210> SEQ ID NO 78
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Asp Ile Gln Met Thr Gln Ser Pro Ser Ser Leu Ser Ala Ser Val Gly
1               5                   10                  15

Asp Arg Val Thr Ile Thr Cys Arg Ser Ser
            20                  25

<210> SEQ ID NO 79
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Trp Tyr Gln Gln Lys Pro Gly Lys Ala Pro Lys Leu Leu Ile Tyr
1               5                   10                  15

<210> SEQ ID NO 80
<211> LENGTH: 32
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 80

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 81
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Phe Gly Gln Gly Thr Lys Val Glu Ile Lys
1               5                   10

<210> SEQ ID NO 82
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Glu Val Gln Leu Leu Glu Ser Gly Gly Gly Leu Val Lys Pro Gly Gln
1               5                   10                  15

Ser Leu Lys Leu Ser Cys Ala Ala Ser Gly Phe Thr Phe Thr
            20                  25                  30

<210> SEQ ID NO 83
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Lys Ser Ser Gln Ser Val Thr Tyr Asn Tyr Lys Asn Tyr Leu Ala
1               5                   10                  15

<210> SEQ ID NO 84
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Trp Ala Ser Thr Arg Glu Ser
1               5

<210> SEQ ID NO 85
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 85

Gln Gln Tyr Tyr Arg Thr Pro Pro Thr
1               5

<210> SEQ ID NO 86
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Ser Tyr Gly Met His
1               5

<210> SEQ ID NO 87
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Val Ile Ser Tyr Asp Gly Ser Tyr Lys Tyr Tyr Ala Asp Ser Val Gln
1               5                   10                  15

Gly

<210> SEQ ID NO 88
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Asp Ser Glu Leu Arg Ser Leu Leu Tyr Phe Glu Trp Leu Ser Gln Gly
1               5                   10                  15

Tyr Phe Asn Pro
            20

<210> SEQ ID NO 89
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Trp Gly Ala Gly Thr Thr Leu Thr Val Ser Ser
1               5                   10

<210> SEQ ID NO 90
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Glu Ile Val Met Thr Gln Ser Pro Asp Ser Leu Ala Val Ser Leu Gly
1               5                   10                  15
```

Glu Arg Ala Thr Ile Asn Cys
            20

<210> SEQ ID NO 91
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Trp Tyr Gln Gln Lys Pro Gly Gln Pro Pro Lys Leu Leu Ile Tyr
1               5                   10                  15

<210> SEQ ID NO 92
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 93
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Phe Gly Gly Gly Thr Lys Leu Asp Ile Lys
1               5                   10

<210> SEQ ID NO 94
<211> LENGTH: 460
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Glu Val Gln Leu Leu Glu Ser Gly Gly Gly Leu Val Lys Pro Gly Gln
1               5                   10                  15

Ser Leu Lys Leu Ser Cys Ala Ala Ser Gly Phe Thr Phe Thr Ser Tyr
            20                  25                  30

Gly Met His Trp Val Arg Gln Pro Pro Gly Lys Gly Leu Glu Trp Val
        35                  40                  45

Ala Val Ile Ser Tyr Asp Gly Ser Tyr Lys Tyr Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Arg Leu Arg Ser Leu Leu Tyr Phe Glu Trp Leu Ser

```
            100                 105                 110
Gln Gly Tyr Phe Asn Pro Trp Gly Ala Gly Thr Thr Leu Thr Val Ser
        115                 120                 125

Ser Ala Ser Thr Lys Gly Pro Ser Val Phe Pro Leu Ala Pro Ser Ser
130                 135                 140

Lys Ser Thr Ser Gly Gly Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
            180                 185                 190

Ser Leu Ser Ser Val Val Thr Val Pro Ser Ser Ser Leu Gly Thr Gln
        195                 200                 205

Thr Tyr Ile Cys Asn Val Asn His Lys Pro Ser Asn Thr Lys Val Asp
    210                 215                 220

Lys Lys Val Glu Pro Lys Ser Cys Asp Lys Thr His Thr Cys Pro
225                 230                 235                 240

Pro Cys Pro Gly Thr Glu Leu Leu Gly Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Lys Phe
        275                 280                 285

Asn Trp Tyr Val Asp Gly Val Glu Val His Asn Ala Lys Thr Lys Pro
    290                 295                 300

Arg Glu Glu Gln Tyr Asn Ser Thr Tyr Arg Val Val Ser Val Leu Thr
305                 310                 315                 320

Val Leu His Gln Asp Trp Leu Asn Gly Lys Glu Tyr Lys Cys Lys Val
                325                 330                 335

Ser Asn Lys Ala Leu Pro Ala Pro Ile Glu Lys Thr Ile Ser Lys Ala
            340                 345                 350

Lys Gly Glu Pro Arg Glu Pro Gln Val Tyr Thr Leu Pro Pro Ser Arg
        355                 360                 365

Asp Glu Leu Thr Lys Asn Gln Val Ser Leu Thr Cys Leu Val Lys Gly
    370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
                405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
        435                 440                 445

Tyr Thr Gln Lys Ser Leu Ser Leu Ser Pro Gly Lys
    450                 455                 460
```

<210> SEQ ID NO 95
<211> LENGTH: 218
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 95

```
Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Thr Tyr Asn
            20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Tyr Tyr
                85                  90                  95

Arg Thr Pro Pro Thr Phe Gly Gly Gly Thr Lys Leu Asp Ile Lys Gly
            100                 105                 110

Ser Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 96
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Ile Asp Glu Val Gln Leu Leu Glu Ser Gly Gly Gly Leu Val Lys Pro
1               5                   10                  15

Gly Gln Ser Leu Lys Leu Ser Cys Ala Ala Ser Gly Phe Thr Phe Thr
            20                  25                  30

Ser Tyr Gly Met His Trp Val Arg Gln Pro Pro Gly Lys Gly Leu Glu
        35                  40                  45

Trp Val Ala Val Ile Ser Tyr Asp Gly Ser Tyr Lys Tyr Tyr Ala Asp
    50                  55                  60

Ser Val Gln Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Asp Ser Arg Leu Arg Ser Leu Leu Tyr Phe Glu Trp
            100                 105                 110

Leu Ser Gln Gly Tyr Phe Asn Pro Trp Gly Ala Gly Thr Thr Leu Thr
        115                 120                 125

Val Ser Ser
    130
```

<210> SEQ ID NO 97
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Ile Asp Glu Val Gln Leu Leu Glu Ser Gly Gly Gly Leu Val Lys Pro
1               5                   10                  15

Gly Gln Ser Leu Lys Leu Ser Cys Ala Ala Ser Gly Phe Thr Phe Ser
            20                  25                  30

Ser Tyr Gly Met His Trp Val Arg Gln Pro Pro Gly Lys Gly Leu Glu
        35                  40                  45

Trp Val Ala Val Val Ser Tyr Asp Gly Ser Asn Lys Tyr Tyr Ala Asp
    50                  55                  60

Ser Val Gln Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Asp Thr Lys Leu Arg Ser Leu Leu Tyr Phe Glu Trp
            100                 105                 110

Leu Ser Ser Gly Leu Leu Asp Tyr Trp Gly Gln Gly Ala Met Val Thr
        115                 120                 125

Val Ser Ser
    130

<210> SEQ ID NO 98
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Ile Asp Glu Val Gln Leu Leu Glu Ser Gly Gly Gly Leu Val Lys Pro
1               5                   10                  15

Gly Gln Ser Leu Lys Leu Ser Cys Ala Ala Ser Gly Phe Thr Phe Thr
            20                  25                  30

Ser Tyr Gly Met His Trp Val Arg Gln Pro Pro Gly Lys Gly Leu Glu
        35                  40                  45

Trp Val Ala Val Val Ser Tyr Asp Gly Asn Tyr Lys Tyr Tyr Ala Asp
    50                  55                  60

Ser Val Gln Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Asp Ser Arg Leu Arg Ser Leu Leu Tyr Phe Glu Trp
            100                 105                 110

Leu Ser Gln Gly Tyr Phe Asn Pro Trp Gly Ala Gly Thr Thr Leu Thr
        115                 120                 125

Val Ser Ser
    130

<210> SEQ ID NO 99

<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Ile Asp Glu Val Gln Leu Leu Glu Ser Gly Gly Gly Leu Val Lys Pro
1               5                   10                  15

Gly Gln Ser Leu Lys Leu Ser Cys Ala Ala Ser Gly Phe Thr Phe Thr
                20                  25                  30

Ser Tyr Gly Met His Trp Val Arg Gln Pro Pro Gly Lys Gly Leu Glu
            35                  40                  45

Trp Val Ala Val Leu Ser Tyr Asp Gly Asn Tyr Lys Tyr Tyr Ala Asp
    50                  55                  60

Ser Val Gln Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Asp Ser Arg Leu Arg Ser Leu Leu Tyr Phe Glu Trp
                100                 105                 110

Leu Ser Gln Gly Tyr Phe Asn Pro Trp Gly Ala Gly Thr Thr Leu Thr
            115                 120                 125

Val Ser Ser
    130

<210> SEQ ID NO 100
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Ile Asp Glu Val Gln Leu Leu Glu Ser Gly Gly Gly Leu Val Lys Pro
1               5                   10                  15

Gly Gln Ser Leu Lys Leu Ser Cys Ala Ala Ser Gly Phe Thr Phe Thr
                20                  25                  30

Thr Tyr Ala Met His Trp Val Arg Gln Pro Pro Gly Lys Gly Leu Glu
            35                  40                  45

Trp Val Ala Val Leu Ser Tyr Asp Gly Asn Tyr Lys Tyr Tyr Ala Asp
    50                  55                  60

Ser Val Gln Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Asp Ser Arg Leu Arg Ser Leu Leu Tyr Phe Glu Trp
                100                 105                 110

Leu Ser Gln Gly Tyr Phe Asn Pro Trp Gly Ala Gly Thr Thr Leu Thr
            115                 120                 125

Val Ser Ser
    130

<210> SEQ ID NO 101
<211> LENGTH: 131
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 101

Ile Asp Glu Val Gln Leu Leu Glu Ser Gly Gly Gly Leu Val Lys Pro
1               5                   10                  15

Gly Gln Ser Leu Lys Leu Ser Cys Ala Ala Ser Gly Phe Thr Phe Ser
            20                  25                  30

Ser Tyr Gly Met His Trp Val Arg Gln Pro Pro Gly Lys Gly Leu Glu
        35                  40                  45

Trp Val Ala Val Val Ser Tyr Asp Gly Asn Asn Lys Tyr Tyr Ala Asp
50                  55                  60

Ser Val Gln Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Asp Ser Lys Leu Arg Ser Leu Leu Tyr Phe Glu Trp
            100                 105                 110

Leu Ser Ser Gly Leu Leu Asp Tyr Trp Gly Gln Gly Ala Met Val Thr
        115                 120                 125

Val Ser Ser
    130

<210> SEQ ID NO 102
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Ile Asp Glu Val Gln Leu Leu Glu Ser Gly Gly Gly Leu Val Lys Pro
1               5                   10                  15

Gly Gln Ser Leu Lys Leu Ser Cys Ala Ala Ser Gly Phe Thr Phe Thr
            20                  25                  30

Thr Tyr Ala Met His Trp Val Arg Gln Pro Pro Gly Lys Gly Leu Glu
        35                  40                  45

Trp Val Ala Val Val Ser Tyr Asp Gly Asn Asn Lys Tyr Tyr Ala Asp
50                  55                  60

Ser Val Gln Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Asp Ser Lys Leu Arg Ser Leu Leu Tyr Phe Glu Trp
            100                 105                 110

Leu Ser Ser Gly Leu Leu Asp Tyr Trp Gly Gln Gly Ala Met Val Thr
        115                 120                 125

Val Ser Ser
    130

<210> SEQ ID NO 103
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 103

Ile Asp Glu Val Gln Leu Leu Glu Ser Gly Gly Gly Leu Val Lys Pro
1               5                   10                  15

Gly Gln Ser Leu Lys Leu Ser Cys Ala Ala Ser Gly Phe Thr Phe Thr
            20                  25                  30

Thr Tyr Ala Met His Trp Val Arg Gln Pro Pro Gly Lys Gly Leu Glu
        35                  40                  45

Trp Val Ala Val Ser Phe Asp Gly Asn Asn Arg Tyr Tyr Ala Asp
50                  55                  60

Ser Val Gln Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Asp Ser Gln Leu Arg Ser Leu Leu Tyr Phe Glu Trp
            100                 105                 110

Leu Ser Ser Gly Val Leu Asp Tyr Trp Gly Gln Gly Ala Met Val Thr
            115                 120                 125

Val Ser Ser
    130

<210> SEQ ID NO 104
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Ile Asp Glu Val Gln Leu Leu Glu Ser Gly Gly Gly Leu Val Lys Pro
1               5                   10                  15

Gly Gln Ser Leu Lys Leu Ser Cys Ala Ala Ser Gly Phe Thr Phe Thr
            20                  25                  30

Ser Tyr Gly Met His Trp Val Arg Gln Pro Pro Gly Lys Gly Leu Glu
        35                  40                  45

Trp Val Ala Val Ser Tyr Asp Gly Asn Tyr Lys Tyr Tyr Ala Asp
50                  55                  60

Ser Val Gln Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Asp Ser Lys Leu Arg Ser Leu Leu Tyr Phe Glu Trp
            100                 105                 110

Leu Ser Gln Gly Tyr Phe Asn Pro Trp Gly Ala Gly Thr Thr Leu Thr
            115                 120                 125

Val Ser Ser
    130

<210> SEQ ID NO 105
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Ile Asp Glu Val Gln Leu Leu Glu Ser Gly Gly Leu Val Lys Pro
1               5                   10                  15

Gly Gln Ser Leu Lys Leu Ser Cys Ala Ala Ser Gly Phe Thr Phe Thr
            20                  25                  30

Ser Tyr Ala Met His Trp Val Arg Gln Pro Pro Gly Lys Gly Leu Glu
        35                  40                  45

Trp Val Ala Val Val Ser Tyr Asp Gly Asn Tyr Lys Tyr Tyr Ala Asp
    50                  55                  60

Ser Val Gln Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Asp Ser Arg Leu Arg Ser Leu Leu Tyr Phe Glu Trp
            100                 105                 110

Leu Ser Gln Gly Tyr Phe Asn Pro Trp Gly Gln Gly Thr Thr Leu Thr
            115                 120                 125

Val Ser Ser
        130

<210> SEQ ID NO 106
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Ile Asp Gln Val Gln Leu Leu Glu Thr Gly Gly Leu Val Lys Pro
1               5                   10                  15

Gly Gln Ser Leu Lys Leu Ser Cys Ala Ala Ser Gly Phe Thr Phe Thr
            20                  25                  30

Ser Tyr Ala Met His Trp Val Arg Gln Pro Pro Gly Lys Gly Leu Glu
        35                  40                  45

Trp Val Ala Val Val Ser Tyr Asp Gly Asn Tyr Lys Tyr Tyr Ala Asp
    50                  55                  60

Ser Val Gln Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Asp Ser Arg Leu Arg Ser Leu Leu Tyr Phe Glu Trp
            100                 105                 110

Leu Ser Gln Gly Tyr Phe Asn Pro Trp Gly Gln Gly Thr Thr Leu Thr
            115                 120                 125

Val Ser Ser
        130

<210> SEQ ID NO 107
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Ile Asp Glu Val Gln Leu Leu Glu Ser Gly Gly Leu Val Lys Pro
1               5                   10                  15

```
Gly Gln Ser Leu Lys Leu Ser Cys Ala Ala Ser Gly Phe Thr Phe Thr
            20                  25                  30

Ser Tyr Ala Met His Trp Val Arg Gln Pro Pro Gly Lys Gly Leu Glu
        35                  40                  45

Trp Val Ala Val Val Ser Tyr Asp Gly Asn Tyr Lys Tyr Tyr Ala Asp
    50                  55                  60

Ser Val Gln Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Asp Ser Gln Leu Arg Thr Leu Leu Tyr Phe Glu Trp
            100                 105                 110

Leu Ser Gln Gly Tyr Phe Asn Pro Trp Gly Gln Gly Thr Thr Leu Thr
            115                 120                 125

Val Ser Ser
    130

<210> SEQ ID NO 108
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Ile Asp Glu Val Gln Leu Leu Glu Ser Gly Gly Gly Leu Val Lys Pro
1               5                   10                  15

Gly Gln Ser Leu Lys Leu Ser Cys Ala Ala Ser Gly Phe Thr Phe Thr
            20                  25                  30

Ser Tyr Ala Met His Trp Val Arg Gln Pro Pro Gly Lys Gly Leu Glu
        35                  40                  45

Trp Val Ala Val Val Ser Tyr Asp Gly Asn Tyr Lys Tyr Tyr Ala Asp
    50                  55                  60

Ser Val Gln Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Asp Ser Arg Leu Arg Thr Leu Leu Tyr Phe Glu Trp
            100                 105                 110

Leu Ser Gln Gly Tyr Phe Asp Pro Trp Gly Gln Gly Thr Thr Leu Thr
            115                 120                 125

Val Ser Ser
    130

<210> SEQ ID NO 109
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Ile Asp Glu Val Gln Leu Leu Glu Ser Gly Gly Gly Leu Val Lys Pro
1               5                   10                  15

Gly Gln Ser Leu Lys Leu Ser Cys Ala Ala Ser Gly Phe Thr Phe Ser
            20                  25                  30
```

```
Ser Tyr Gly Met His Trp Val Arg Gln Pro Pro Lys Gly Leu Glu
         35                  40                  45

Trp Val Ala Val Val Ser Tyr Asp Gly Ser Asn Lys Tyr Tyr Ala Asp
 50                  55                  60

Ser Val Gln Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Ala Lys Asp Ser Lys Leu Arg Ser Leu Leu Tyr Phe Glu Trp
                100                 105                 110

Leu Ser Ser Gly Leu Leu Asp Tyr Trp Gly Gln Gly Ala Met Val Thr
            115                 120                 125

Val Ser Ser
    130

<210> SEQ ID NO 110
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Ile Asp Glu Ile Val Met Thr Gln Ser Pro Asp Ser Leu Ala Val Ser
 1               5                  10                  15

Leu Gly Glu Arg Ala Thr Ile Asn Cys Lys Ser Ser Gln Ser Val Thr
                20                  25                  30

Tyr Asn Tyr Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Arg Thr Pro Pro Thr Phe Gly Gly Gly Thr Lys Leu Asp Ile
                100                 105                 110

Lys

<210> SEQ ID NO 111
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Ile Asp Glu Ile Val Met Thr Gln Ser Pro Asp Ser Leu Ala Val Ser
 1               5                  10                  15

Leu Gly Glu Arg Ala Thr Ile Asn Cys Lys Ser Ser Gln Ser Val Thr
                20                  25                  30

Phe Ser Tyr Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
```

```
65                  70                  75                  80

Ile Ser Ser Leu Gln Ala Glu Asp Val Ala Val Tyr Tyr Cys Gln Gln
                85                  90                  95

Tyr Tyr Arg Thr Pro Pro Thr Phe Gly Gly Gly Thr Lys Leu Asp Ile
            100                 105                 110

Lys

<210> SEQ ID NO 112
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Ile Asp Glu Ile Val Met Thr Gln Ser Pro Asp Ser Leu Ala Val Ser
1               5                   10                  15

Leu Gly Glu Arg Ala Thr Ile Asn Cys Lys Ser Ser Gln Ser Val Thr
            20                  25                  30

Phe Asp Tyr Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Arg Thr Pro Pro Thr Phe Gly Gly Gly Thr Lys Leu Asp Ile
            100                 105                 110

Lys

<210> SEQ ID NO 113
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Ile Asp Glu Ile Val Met Thr Gln Ser Pro Asp Ser Leu Ala Val Ser
1               5                   10                  15

Leu Gly Glu Arg Ala Thr Ile Asn Cys Lys Ser Ser Gln Ser Val Thr
            20                  25                  30

Trp Ser Tyr Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Arg Thr Pro Pro Thr Phe Gly Gly Gly Thr Lys Leu Asp Ile
            100                 105                 110

Lys
```

```
<210> SEQ ID NO 114
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Ile Asp Glu Ile Val Met Thr Gln Ser Pro Asp Ser Leu Ala Val Ser
1               5                   10                  15

Leu Gly Glu Arg Ala Thr Ile Asn Cys Lys Ser Ser Gln Thr Val Thr
            20                  25                  30

Phe Asn Tyr Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Arg Thr Pro Pro Ser Phe Gly Gly Gly Thr Lys Leu Asp Ile
            100                 105                 110

Lys

<210> SEQ ID NO 115
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Ile Asp Glu Ile Val Met Thr Gln Ser Pro Asp Ser Leu Ala Val Ser
1               5                   10                  15

Leu Gly Glu Arg Ala Thr Ile Asn Cys Lys Ser Ser Gln Thr Leu Ser
            20                  25                  30

Phe Asn Tyr Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Arg Thr Pro Pro Ser Phe Gly Gly Gly Thr Lys Leu Asp Ile
            100                 105                 110

Lys

<210> SEQ ID NO 116
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Ile Asp Glu Ile Val Met Thr Gln Ser Pro Asp Ser Leu Ala Val Ser
```

```
                1               5                   10                  15
Leu Gly Glu Arg Ala Thr Ile Asn Cys Lys Ser Ser Gln Thr Val Thr
                20                  25                  30

Phe Asn Tyr Lys Asn Tyr Leu Ala Trp Tyr Gln Gln Lys Pro Gly Gln
                35                  40                  45

Pro Pro Lys Leu Leu Ile Tyr Phe Ala Ser Thr Arg Glu Ser Gly Val
                50                  55                  60

Pro Asp Arg Phe Ser Gly Ser Gly Ser Gly Thr Asp Phe Thr Leu Thr
 65                 70                  75                  80

Ile Ser Ser Leu Gln Ala Glu Asp Val Ala Val Tyr Tyr Cys Gln Gln
                85                  90                  95

His Tyr Arg Thr Pro Pro Ser Phe Gly Gly Gly Thr Lys Leu Asp Ile
                100                 105                 110

Lys

<210> SEQ ID NO 117
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Ile Asp Glu Ile Val Met Thr Gln Ser Pro Asp Ser Leu Ala Val Ser
 1              5                   10                  15

Leu Gly Glu Arg Ala Thr Ile Asn Cys Lys Ser Ser Gln Thr Leu Ser
                20                  25                  30

Phe Asn Tyr Lys Asn Tyr Leu Ala Trp Tyr Gln Gln Lys Pro Gly Gln
                35                  40                  45

Pro Pro Lys Leu Leu Ile Tyr Phe Ala Ser Thr Arg Glu Ser Gly Val
                50                  55                  60

Pro Asp Arg Phe Ser Gly Ser Gly Ser Gly Thr Asp Phe Thr Leu Thr
 65                 70                  75                  80

Ile Ser Ser Leu Gln Ala Glu Asp Val Ala Val Tyr Tyr Cys Gln Gln
                85                  90                  95

His Tyr Arg Thr Pro Pro Ser Phe Gly Gly Gly Thr Lys Leu Asp Ile
                100                 105                 110

Lys

<210> SEQ ID NO 118
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Ile Asp Glu Ile Val Met Ser Gln Ser Pro Asp Thr Leu Ala Val Thr
 1              5                   10                  15

Leu Gly Glu Arg Ala Ser Ile Asn Cys Lys Ser Ser Gln Thr Val Thr
                20                  25                  30

Phe Asn Tyr Lys Asn Tyr Leu Ala Trp Tyr Gln Gln Lys Pro Gly Gln
                35                  40                  45

Pro Pro Lys Val Leu Ile Tyr Trp Ala Ser Ala Arg Glu Thr Gly Val
                50                  55                  60
```

```
Pro Glu Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

His Tyr Arg Thr Pro Pro Ser Phe Gly Gln Gly Thr Lys Leu Glu Ile
            100                 105                 110

Lys
```

<210> SEQ ID NO 119
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

```
Ile Asp Asp Ile Gln Met Thr Gln Ser Pro Ser Ser Leu Ser Ala Ser
 1               5                  10                  15

Val Gly Asp Arg Val Thr Ile Thr Cys Arg Ser Ser Gln Ser Ile Thr
                20                  25                  30

Phe Asn Tyr Lys Asn Tyr Leu Ala Trp Tyr Gln Gln Lys Pro Gly Lys
            35                  40                  45

Ala Pro Lys Leu Leu Ile Tyr Trp Gly Ser Tyr Leu Glu Ser Gly Val
         50                 55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

His Tyr Arg Thr Pro Pro Ser Phe Gly Gln Gly Thr Lys Val Glu Ile
            100                 105                 110

Lys
```

<210> SEQ ID NO 120
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

```
Ile Asp Asp Ile Gln Met Thr Gln Ser Pro Ser Ser Leu Ser Ala Ser
 1               5                  10                  15

Val Gly Asp Arg Val Thr Ile Thr Cys Arg Ser Ser Gln Ser Ile Thr
                20                  25                  30

Phe Asn Tyr Lys Asn Tyr Leu Gly Trp Tyr Gln Gln Lys Pro Gly Lys
            35                  40                  45

Ala Pro Lys Leu Leu Ile Tyr Trp Gly Ser Tyr Leu Glu Ser Gly Val
         50                 55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

His Tyr Arg Thr Pro Pro Ser Phe Gly Gln Gly Thr Lys Val Glu Ile
            100                 105                 110

Lys
```

<210> SEQ ID NO 121
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Ile Asp Glu Ile Val Met Thr Gln Ser Pro Asp Ser Leu Ala Val Ser
1               5                   10                  15

Leu Gly Glu Arg Ala Thr Ile Asn Cys Lys Ser Ser Gln Thr Val Thr
                20                  25                  30

Phe Asn Tyr Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Arg Thr Pro Pro Ser Phe Gly Thr Gly Thr Lys Leu Asp Ile
            100                 105                 110

Lys

<210> SEQ ID NO 122
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Ile Asp Glu Ile Val Met Thr Gln Ser Pro Asp Ser Leu Ala Val Ser
1               5                   10                  15

Leu Gly Glu Arg Ala Thr Ile Asn Cys Lys Ser Ser Gln Thr Val Thr
                20                  25                  30

Phe Asn Tyr Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Arg Thr Pro Pro Ser Phe Gly Ser Gly Thr Lys Leu Asp Ile
            100                 105                 110

Lys

<210> SEQ ID NO 123
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Ile Asp Glu Ile Val Met Thr Gln Ser Pro Asp Ser Leu Ala Val Ser
1               5                   10                  15

Leu Gly Glu Arg Ala Thr Ile Asn Cys Lys Ser Ser Gln Thr Val Thr
            20                  25                  30

Phe Asn Tyr Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Arg Thr Pro Pro Ser Phe Gly Gln Gly Thr Lys Leu Asp Ile
            100                 105                 110

Lys

<210> SEQ ID NO 124
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Ile Asp Glu Ile Val Met Thr Gln Ser Pro Asp Ser Leu Ala Val Ser
1               5                   10                  15

Leu Gly Glu Arg Ala Thr Ile Asn Cys Lys Ser Ser Gln Thr Val Thr
            20                  25                  30

Phe Asn Tyr Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Arg Thr Pro Pro Ser Phe Gly Asn Gly Thr Lys Leu Asp Ile
            100                 105                 110

Lys

<210> SEQ ID NO 125
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Ile Asp Glu Ile Val Met Thr Gln Ser Pro Asp Ser Leu Ala Val Ser
1               5                   10                  15

Leu Gly Glu Arg Ala Thr Ile Asn Cys Lys Ser Ser Gln Thr Leu Ser
            20                  25                  30

Phe Asn Tyr Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

```
Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

His Tyr Arg Thr Pro Pro Ser Phe Gly Thr Gly Thr Lys Leu Asp Ile
            100                 105                 110

Lys

<210> SEQ ID NO 126
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Ile Asp Glu Ile Val Met Thr Gln Ser Pro Asp Ser Leu Ala Val Ser
 1               5                  10                  15

Leu Gly Glu Arg Ala Thr Ile Asn Cys Lys Ser Ser Gln Thr Leu Ser
                20                  25                  30

Phe Asn Tyr Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

His Tyr Arg Thr Pro Pro Ser Phe Gly Ser Gly Thr Lys Leu Asp Ile
            100                 105                 110

Lys

<210> SEQ ID NO 127
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Ile Asp Glu Ile Val Met Thr Gln Ser Pro Asp Ser Leu Ala Val Ser
 1               5                  10                  15

Leu Gly Glu Arg Ala Thr Ile Asn Cys Lys Ser Ser Gln Thr Leu Ser
                20                  25                  30

Phe Asn Tyr Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

His Tyr Arg Thr Pro Pro Ser Phe Gly Gln Gly Thr Lys Leu Asp Ile
            100                 105                 110

Lys
```

<210> SEQ ID NO 128
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Ile Asp Glu Ile Val Met Thr Gln Ser Pro Asp Ser Leu Ala Val Ser
1               5                   10                  15

Leu Gly Glu Arg Ala Thr Ile Asn Cys Lys Ser Ser Gln Thr Leu Ser
            20                  25                  30

Phe Asn Tyr Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Arg Thr Pro Pro Ser Phe Gly Asn Gly Thr Lys Leu Asp Ile
            100                 105                 110

Lys

<210> SEQ ID NO 129
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Ile Asp Asp Ile Val Met Thr Gln Ser Pro Asp Thr Leu Ala Val Thr
1               5                   10                  15

Leu Gly Glu Arg Ala Thr Ile Gln Cys Lys Ser Ser Gln Thr Val Thr
            20                  25                  30

Phe Asn Tyr Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Thr Ser Leu Gln Ala Glu Asp Val Ala Val Tyr Tyr Cys Gln Gln
                85                  90                  95

His Tyr Arg Thr Pro Pro Ser Phe Gly Gln Gly Thr Lys Leu Asp Ile
            100                 105                 110

Lys

<210> SEQ ID NO 130
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

```
Ile Asp Asp Ile Val Met Thr Gln Ser Pro Asp Thr Val Ala Val Thr
1               5                   10                  15

Val Gly Glu Arg Ala Thr Ile Asn Cys Lys Ser Ser Gln Thr Val Thr
            20                  25                  30

Phe Asn Tyr Lys Asn Tyr Leu Ala Trp Tyr Gln Gln Lys Pro Gly Gln
                35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Arg Thr Pro Pro Ser Phe Gly Gln Gly Thr Lys Leu Asp Ile
                100                 105                 110

Lys
```

<210> SEQ ID NO 131
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

```
Ile Asp Asp Ile Val Met Thr Gln Ser Pro Asp Thr Val Ala Val Thr
1               5                   10                  15

Leu Gly Glu Arg Ala Thr Ile Asp Cys Lys Ser Ser Gln Thr Val Thr
            20                  25                  30

Phe Asn Tyr Lys Asn Tyr Leu Ala Trp Tyr Gln Gln Lys Pro Gly Gln
                35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Arg Thr Pro Pro Ser Phe Gly Gln Gly Thr Lys Leu Asp Ile
                100                 105                 110

Lys
```

<210> SEQ ID NO 132
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

```
Ile Asp Asp Ile Val Met Thr Gln Ser Pro Asp Thr Leu Ala Val Thr
1               5                   10                  15

Val Gly Glu Arg Ala Thr Ile Arg Cys Lys Ser Ser Gln Thr Val Thr
            20                  25                  30

Phe Asn Tyr Lys Asn Tyr Leu Ala Trp Tyr Gln Gln Lys Pro Gly Gln
                35                  40                  45

Pro Pro Lys Leu Leu Ile Tyr Trp Ala Ser Thr Arg Glu Ser Gly Val
```

```
            50                  55                  60
Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

His Tyr Arg Thr Pro Pro Ser Phe Gly Gln Gly Thr Lys Leu Asp Ile
            100                 105                 110

Lys

<210> SEQ ID NO 133
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Ile Asp Asp Ile Val Met Thr Gln Ser Pro Asp Thr Leu Ala Val Ser
 1               5                  10                  15

Arg Gly Glu Arg Ala Thr Ile Asp Cys Lys Ser Ser Gln Thr Val Thr
             20                  25                  30

Phe Asn Tyr Lys Asn Tyr Leu Ala Trp Tyr Gln Gln Lys Pro Gly Gln
         35                  40                  45

Pro Pro Lys Leu Leu Ile Tyr Trp Ala Ser Thr Arg Glu Ser Gly Val
     50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Glu Ala Val Tyr Tyr Cys Gln Gln
                 85                  90                  95

His Tyr Arg Thr Pro Pro Ser Phe Gly Gln Gly Thr Lys Leu Asp Ile
            100                 105                 110

Lys

<210> SEQ ID NO 134
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Ile Asp Asp Ile Gln Met Thr Gln Ser Pro Ser Ser Leu Ser Ala Ser
 1               5                  10                  15

Val Gly Asp Arg Val Thr Ile Thr Cys Arg Ser Ser Gln Ser Ile Thr
             20                  25                  30

Phe Asp Tyr Lys Asn Tyr Leu Ala Trp Tyr Gln Gln Lys Pro Gly Lys
         35                  40                  45

Ala Pro Lys Leu Leu Ile Tyr Trp Gly Ser Tyr Leu Glu Ser Gly Val
     50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

His Tyr Arg Thr Pro Pro Ser Phe Gly Gln Gly Thr Lys Val Glu Ile
            100                 105                 110
```

Lys

<210> SEQ ID NO 135
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Ile Asp Asp Ile Gln Met Thr Gln Ser Pro Ser Ser Leu Ser Ala Ser
1               5                   10                  15

Val Gly Asp Arg Val Thr Ile Thr Cys Arg Ser Ser Gln Ser Ile Thr
            20                  25                  30

Phe Asn Tyr Lys Asn Tyr Leu Ala Trp Tyr Gln Gln Lys Pro Gly Lys
        35                  40                  45

Ala Pro Lys Leu Leu Ile Tyr Trp Gly Ser Thr Leu Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

His Tyr Arg Thr Pro Pro Ser Phe Gly Gln Gly Thr Lys Val Glu Ile
            100                 105                 110

Lys

<210> SEQ ID NO 136
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Ile Asp Asp Ile Gln Met Thr Gln Ser Pro Ser Ser Leu Ser Ala Ser
1               5                   10                  15

Val Gly Asp Arg Val Thr Ile Thr Cys Arg Ser Ser Gln Ser Ile Thr
            20                  25                  30

Phe Asn Tyr Lys Asn Tyr Leu Ala Trp Tyr Gln Gln Lys Pro Gly Lys
        35                  40                  45

Ala Pro Lys Leu Leu Ile Tyr Trp Gly Ser His Leu Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

His Tyr Arg Thr Pro Pro Ser Phe Gly Gln Gly Thr Lys Val Glu Ile
            100                 105                 110

Lys

<210> SEQ ID NO 137
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 137

Ile Asp Asp Ile Gln Met Thr Gln Ser Pro Ser Ser Leu Ser Ala Ser
1               5                   10                  15

Val Gly Asp Arg Val Thr Ile Thr Cys Arg Ser Ser Gln Ser Ile Thr
            20                  25                  30

Phe Asn Tyr Lys Asn Tyr Leu Ala Trp Tyr Gln Gln Lys Pro Gly Lys
        35                  40                  45

Ala Pro Lys Leu Leu Ile Tyr Trp Gly Ser Lys Leu Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

His Tyr Arg Thr Pro Pro Ser Phe Gly Gln Gly Thr Lys Val Glu Ile
            100                 105                 110

Lys

<210> SEQ ID NO 138
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Ile Asp Asp Ile Gln Met Thr Gln Ser Pro Ser Ser Leu Ser Ala Ser
1               5                   10                  15

Val Gly Asp Arg Val Thr Ile Thr Cys Arg Ser Ser Gln Ser Ile Thr
            20                  25                  30

Phe Asn Tyr Lys Asn Tyr Leu Ala Trp Tyr Gln Gln Lys Pro Gly Lys
        35                  40                  45

Ala Pro Lys Leu Leu Ile Tyr Trp Gly Ser Asp Leu Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

His Tyr Arg Thr Pro Pro Ser Phe Gly Gln Gly Thr Lys Val Glu Ile
            100                 105                 110

Lys

<210> SEQ ID NO 139
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Ile Asp Asp Ile Gln Met Thr Gln Ser Pro Ser Ser Leu Ser Ala Ser
1               5                   10                  15

Val Gly Asp Arg Val Thr Ile Thr Cys Arg Ser Ser Gln Ser Ile Thr
            20                  25                  30

Phe Asn Tyr Lys Asn Tyr Leu Ala Trp Tyr Gln Gln Lys Pro Gly Lys
        35                  40                  45
```

```
Ala Pro Lys Leu Leu Ile Tyr Trp Gly Ser Tyr Leu Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Val Ala Thr Tyr Tyr Cys Gln Gln
                85                  90                  95

His Tyr Arg Thr Pro Pro Ser Phe Gly Gln Gly Thr Lys Val Glu Ile
            100                 105                 110

Lys

<210> SEQ ID NO 140
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Ile Asp Asp Ile Gln Met Thr Gln Ser Pro Ser Ser Leu Ser Ala Ser
1               5                   10                  15

Val Gly Asp Arg Val Thr Ile Thr Cys Arg Ser Ser Gln Ser Ile Thr
            20                  25                  30

Phe Asn Tyr Lys Asn Tyr Leu Ala Trp Tyr Gln Gln Lys Pro Gly Lys
        35                  40                  45

Ala Pro Lys Leu Leu Ile Tyr Trp Gly Ser Tyr Leu Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Lys Ala Thr Tyr Tyr Cys Gln Gln
                85                  90                  95

His Tyr Arg Thr Pro Pro Ser Phe Gly Gln Gly Thr Lys Val Glu Ile
            100                 105                 110

Lys

<210> SEQ ID NO 141
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Ile Asp Asp Ile Gln Met Thr Gln Ser Pro Ser Ser Leu Ser Ala Ser
1               5                   10                  15

Val Gly Asp Arg Val Thr Ile Thr Cys Arg Ser Ser Gln Ser Ile Thr
            20                  25                  30

Phe Asn Tyr Lys Asn Tyr Leu Ala Trp Tyr Gln Gln Lys Pro Gly Lys
        35                  40                  45

Ala Pro Lys Leu Leu Ile Tyr Trp Gly Ser Tyr Leu Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Asp Ala Thr Tyr Tyr Cys Gln Gln
                85                  90                  95

His Tyr Arg Thr Pro Pro Ser Phe Gly Gln Gly Thr Lys Val Glu Ile
            100                 105                 110
```

Lys

<210> SEQ ID NO 142
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Ile Asp Asp Ile Gln Met Thr Gln Ser Pro Ser Ser Leu Ser Ala Ser
1               5                   10                  15

Val Gly Asp Arg Val Thr Ile Thr Cys Arg Ser Ser Gln Ser Ile Thr
            20                  25                  30

Phe Asn Tyr Lys Asn Tyr Leu Ala Trp Tyr Gln Gln Lys Pro Gly Lys
        35                  40                  45

Ala Pro Lys Leu Leu Ile Tyr Trp Gly Ser Tyr Leu Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Tyr Arg Thr Pro Pro Ser Phe Gly Gln Gly Thr Lys Val Glu Ile
            100                 105                 110

Lys

<210> SEQ ID NO 143
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Ile Asp Asp Ile Gln Met Thr Gln Ser Pro Ser Ser Leu Ser Ala Ser
1               5                   10                  15

Val Gly Asp Arg Val Thr Ile Thr Cys Arg Ser Ser Gln Ser Ile Thr
            20                  25                  30

Phe Asn Tyr Lys Asn Tyr Leu Ala Trp Tyr Gln Gln Lys Pro Gly Lys
        35                  40                  45

Ala Pro Lys Leu Leu Ile Tyr Trp Gly Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

His Tyr Arg Thr Pro Pro Ser Phe Gly Gln Gly Thr Lys Val Glu Ile
            100                 105                 110

Lys

<210> SEQ ID NO 144
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Ile Asp Asp Ile Gln Met Thr Gln Ser Pro Ser Ser Leu Ser Ala Ser
1               5                   10                  15

Val Gly Asp Arg Val Thr Ile Thr Cys Arg Ser Ser Gln Ser Ile Thr
            20                  25                  30

Phe Asn Tyr Lys Asn Tyr Leu Ala Trp Tyr Gln Gln Lys Pro Gly Lys
        35                  40                  45

Ala Pro Lys Leu Leu Ile Tyr Trp Gly Ser Tyr Leu Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

His Tyr Arg Thr Pro Pro Ser Phe Gly Gln Gly Thr Lys Val Glu Ile
            100                 105                 110

Lys

<210> SEQ ID NO 145
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Gln Ser Ile Thr Phe Asp Tyr Lys Asn Tyr Leu Ala
1               5                   10

<210> SEQ ID NO 146
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Lys Ser Ser Gln Ser Val Thr Phe Asn Tyr Lys Asn Tyr Leu Ala
1               5                   10                  15

<210> SEQ ID NO 147
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Trp Ala Ser Ala Arg Glu Ser
1               5

<210> SEQ ID NO 148
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Gln Gln His Tyr Arg Thr Pro Pro Thr
1               5

<210> SEQ ID NO 149
<211> LENGTH: 657
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 149

```
gacattcaga tgactcagtc gccttcgtca ttgtccgcct ccgtgggtga tagggtcacg      60
atcacgtgcc ggagcagcca gtccatcacc ttcaattaca aaaactattt ggcatggtat     120
caacagaaac ccggaaaggc gccgaagctc ctgatctact ggggttcata tcttgagtcg     180
ggggtgccgt cgagattttc gggcagcgga tcagggacgg atttcacgct gaccatttcg     240
tcactccagc ccgaggactt tgcgacatat tactgtcaac agcactacag gacacccccca    300 tctttcggac aggggactaa agtagaaatc aagggatccg tggccgcccc cagcgtcttc     360
atcttcccgc ccagcgacga gcagctgaag tcgggcacgg ccagcgtggt gtgcctcctg     420
aacaacttct accccgcga ggcgaaggtc cagtggaagg tggacaacgc cctgcagagc      480
gggaacagcc aggagagcgt gaccgagcag gactcgaagg acagcaccta cagcctcagc     540
agcaccctga cgctgagcaa ggccgactac gagaagcaca aggtctacgc ctgcgaggtg     600
acccaccagg ggctctcgag ccccgtgacc aagagcttca ccggggcga gtgctga         657
```

<210> SEQ ID NO 150
<211> LENGTH: 663
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 150

```
gacattcaga tgactcagtc gccttcgtca ttgtccgcct ccgtgggtga tagggtcacg      60
atcacgtgcc ggagcagcca gtccatcacc ttcaattaca aaaactattt ggcatggtat     120
caacagaaac ccggaaaggc gccgaagctc ctgatctact ggggttcata tcttgagtcg     180
ggggtgccgt cgagattttc gggcagcgga tcagggacgg atttcacgct gaccatttcg     240
tcactccagc ccgaggactt tgcgacatat tactgtcaac agcactacag gacacccccca    300 tctttcggac aggggactaa agtagaaatc aagggatccg tggccgcccc cagcgtcttc     360
atcttcccgc ccagcgacga gcagctgaag tcgggcacgg ccagcgtggt gtgcctcctg     420
aacaacttct accccgcga ggcgaaggtc cagtggaagg tggacaacgc cctgcagagc      480
gggaacagcc aggagagcgt gaccgagcag gactcgaagg acagcaccta cagcctcagc     540
agcaccctga cgctgagcaa ggccgactac gagaagcaca aggtctacgc ctgcgaggtg     600
acccaccagg ggctctcgag ccccgtgacc aagagcttca ccggggcga gtgctgagaa      660 ttc                                                                  663
```

<210> SEQ ID NO 151
<211> LENGTH: 1383
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 151

```
caggtacaat tgcttgagac aggtggagga ctcgtgaagc caggtcagtc attgaaactg      60
agctgtgccg catccgggtt cacattcact cctacgcga tgcactgggt ccgccagcct     120
cccggaaagg gacttgagtg ggtcgctgtg gtatcgtatg atgggaatta caaatactat    180
gcagactccg tgcaaggccg gtttacgatt agcagggaca actcgaagaa taccctttac    240
ctccaaatga actcgctccg agcggaggac acggcgtgt attactgcgc gaaggattca     300
cggttgagat cgctgctcta ttttgaatgg ttgtcacagg ggtacttcaa cccgtggggt    360
cagggaacaa cactgaccgt cagctcagcc tcgactaaag gcccagcgt gttcccgctg     420
gcccccagca gcaagagcac cagcggcggg accgccgccc tgggctgcct cgtcaaggac    480
tacttccccg agcccgtgac cgtgtcgtgg aacagcggcg cgctgacgag cggggtccac    540
accttcccgg ccgtgctgca gagcagcggc ctctactcgc tgagcagcgt ggtcaccgtg    600
cccagcagca gctggggac ccagacgtac atctgcaacg tgaaccacaa gccctcgaac     660
accaaggtcg acaagaaggt ggagcccccg aagagctgcg acaaaactca cacatgccca    720
ccgtgcccag gtactgaact cctgggggga ccgtcagtct tcctcttccc cccaaaaccc    780
aaggacaccc tcatgatctc ccggacccct gaggtcacat gcgtggtggt ggacgtgagc    840
cacgaagacc ctgaggtcaa gttcaactgg tacgtggacg gcgtggaggt gcataatgcc    900
aagacaaagc cgcgggagga gcagtacaac agcacgtacc gtgtggtcag cgtcctcacc    960
gtcctgcacc aggactggct gaatggcaag gagtacaagt gcaaggtctc caacaaagcc   1020
ctcccagccc ccatcgagaa aaccatctcc aaagccaaag gtgagcccg agaaccacag    1080
gtgtacaccc tgcccccatc ccgggatgag ctgaccaaga accaggtcag cctgacctgc   1140
ctggtcaaag gcttctatcc cagcgacatc gccgtggagt gggagagcaa tgggcagccg   1200
gagaacaact acaagaccac gcctcccgtg ctggactccg acggctcctt cttcctctac   1260
agcaagctca ccgtggacaa gagcaggtgg cagcagggga acgtcttctc atgctccgtg   1320
atgcatgagg ctctgcacaa ccactacacg cagaagagcc tctccctgtc tccgggtaaa   1380
tga                                                                 1383
```

<210> SEQ ID NO 152
<211> LENGTH: 1383
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 152

```
gaagtacaat tgcttgagtc gggtggagga ctcgtgaagc caggtcagtc attgaaactg      60
agctgtgccg catccgggtt cacattcact cctacgcga tgcactgggt ccgccagcct     120
cccggaaagg gacttgagtg ggtcgctgtg gtatcgtatg atgggaatta caaatactat    180
gcagactccg tgcaaggccg gtttacgatt agcagggaca actcgaagaa taccctttac    240
ctccaaatga actcgctccg agcggaggac acggcgtgt attactgcgc gaaggattca     300
cggttgagat cgctgctcta ttttgaatgg ttgtcacagg ggtacttcaa cccgtggggt    360
cagggaacaa cactgaccgt cagctcagcc tcgactaaag gcccagcgt gttcccgctg     420
gcccccagca gcaagagcac cagcggcggg accgccgccc tgggctgcct cgtcaaggac    480
tacttccccg agcccgtgac cgtgtcgtgg aacagcggcg cgctgacgag cggggtccac    540
```

```
accttcccgg ccgtgctgca gagcagcggc ctctactcgc tgagcagcgt ggtcaccgtg      600
cccagcagca gcctggggac ccagacgtac atctgcaacg tgaaccacaa gccctcgaac      660
accaaggtcg acaagaaggt ggagcccccg aagagctgcg acggtaccca cacatgccca      720
ccgtgcccag gtactgaact cctgggggga ccgtcagtct tcctcttccc cccaaaaccc      780
aaggacaccc tcatgatctc ccggacccct gaggtcacat gcgtggtggt ggacgtgagc      840
cacgaagacc ctgaggtcaa gttcaactgg tacgtggacg gcgtggaggt gcataatgcc      900
aagacaaagc cgcgggagga gcagtacaac agcacgtacc gtgtggtcag cgtcctcacc      960
gtcctgcacc aggactggct gaatggcaag gagtacaagt gcaaggtctc caacaaagcc     1020
ctcccagccc ccatcgagaa aaccatctcc aaagccaaag gtgagccccg agaaccacag     1080
gtgtacaccc tgcccccatc ccgggatgag ctgaccaaga accaggtcag cctgacctgc     1140
ctggtcaaag gcttctatcc cagcgacatc gccgtggagt gggagagcaa tgggcagccg     1200
gagaacaact acaagaccac gcctcccgtg ctggactccg acggctcctt cttcctctac     1260
agcaagctca ccgtggacaa gagcaggtgg cagcagggga acgtcttctc atgctccgtg     1320
atgcatgagg ctctgcacaa ccactacacg cagaagagcc tctccctgtc tccgggtaaa     1380
tga                                                                    1383
```

<210> SEQ ID NO 153
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Phe Gln
            20                  25                  30

Tyr Lys Asn Tyr Leu Ala Trp Tyr Gln Gln Lys Pro Gly Lys Ala Pro
        35                  40                  45

Lys Leu Leu Ile Tyr Trp Gly Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln His Tyr
                85                  90                  95

Arg Thr Pro Pro Ser Phe Gly Gln Gly Thr Lys Val Glu Ile Lys
            100                 105                 110

<210> SEQ ID NO 154
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Phe Arg
            20                  25                  30

```
Tyr Lys Asn Tyr Leu Ala Trp Tyr Gln Gln Lys Pro Gly Lys Ala Pro
            35                  40                  45

Lys Leu Leu Ile Tyr Trp Gly Ser Tyr Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln His Tyr
                 85                  90                  95

Arg Thr Pro Pro Ser Phe Gly Gln Gly Thr Lys Val Glu Ile Lys
            100                 105                 110

<210> SEQ ID NO 155
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Asp Ile Gln Met Thr Gln Ser Pro Ser Ser Leu Ser Ala Ser Val Gly
 1               5                  10                  15

Asp Arg Val Thr Ile Thr Cys Arg Ser Ser Gln Ser Ile Thr Phe Glu
             20                  25                  30

Tyr Lys Asn Tyr Leu Ala Trp Tyr Gln Gln Lys Pro Gly Lys Ala Pro
            35                  40                  45

Lys Leu Leu Ile Tyr Trp Gly Ser Tyr Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln His Tyr
                 85                  90                  95

Arg Thr Pro Pro Ser Phe Gly Gln Gly Thr Lys Val Glu Ile Lys
            100                 105                 110

<210> SEQ ID NO 156
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Asp Ile Gln Met Thr Gln Ser Pro Ser Ser Leu Ser Ala Ser Val Gly
 1               5                  10                  15

Asp Arg Val Thr Ile Thr Cys Arg Ser Ser Gln Ser Ile Thr Phe Asp
             20                  25                  30

Tyr Lys Asn Tyr Leu Ala Trp Tyr Gln Gln Lys Pro Gly Lys Ala Pro
            35                  40                  45

Lys Leu Leu Ile Tyr Trp Gly Ser Thr Arg Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln His Tyr
                 85                  90                  95

Arg Thr Pro Pro Ser Phe Gly Gln Gly Thr Lys Val Glu Ile Lys
            100                 105                 110
```

<210> SEQ ID NO 157
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Ile Asp Asp Ile Gln Met Thr Gln Ser Pro Ser Ser Leu Ser Ala Ser
1               5                   10                  15

Val Gly Asp Arg Val Thr Ile Thr Cys Arg Ser Ser Gln Ser Ile Thr
            20                  25                  30

Phe Gln Tyr Lys Asn Tyr Leu Ala Trp Tyr Gln Gln Lys Pro Gly Lys
        35                  40                  45

Ala Pro Lys Leu Leu Ile Tyr Trp Gly Ser Tyr Leu Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

His Tyr Arg Thr Pro Pro Ser Phe Gly Gln Gly Thr Lys Val Glu Ile
            100                 105                 110

Lys

<210> SEQ ID NO 158
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Ile Asp Asp Ile Gln Met Thr Gln Ser Pro Ser Ser Leu Ser Ala Ser
1               5                   10                  15

Val Gly Asp Arg Val Thr Ile Thr Cys Arg Ser Ser Gln Ser Ile Thr
            20                  25                  30

Phe Arg Tyr Lys Asn Tyr Leu Ala Trp Tyr Gln Gln Lys Pro Gly Lys
        35                  40                  45

Ala Pro Lys Leu Leu Ile Tyr Trp Gly Ser Tyr Leu Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

His Tyr Arg Thr Pro Pro Ser Phe Gly Gln Gly Thr Lys Val Glu Ile
            100                 105                 110

Lys

<210> SEQ ID NO 159
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

```
Ile Asp Asp Ile Gln Met Thr Gln Ser Pro Ser Ser Leu Ser Ala Ser
1               5                   10                  15

Val Gly Asp Arg Val Thr Ile Thr Cys Arg Ser Ser Gln Ser Ile Thr
            20                  25                  30

Phe Glu Tyr Lys Asn Tyr Leu Ala Trp Tyr Gln Gln Lys Pro Gly Lys
        35                  40                  45

Ala Pro Lys Leu Leu Ile Tyr Trp Gly Ser Tyr Leu Glu Ser Gly Val
50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

His Tyr Arg Thr Pro Pro Ser Phe Gly Gln Gly Thr Lys Val Glu Ile
            100                 105                 110

Lys

<210> SEQ ID NO 160
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Ile Asp Asp Ile Gln Met Thr Gln Ser Pro Ser Ser Leu Ser Ala Ser
1               5                   10                  15

Val Gly Asp Arg Val Thr Ile Thr Cys Arg Ser Ser Gln Ser Ile Thr
            20                  25                  30

Phe Asp Tyr Lys Asn Tyr Leu Ala Trp Tyr Gln Gln Lys Pro Gly Lys
        35                  40                  45

Ala Pro Lys Leu Leu Ile Tyr Trp Gly Ser Thr Arg Glu Ser Gly Val
50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

His Tyr Arg Thr Pro Pro Ser Phe Gly Gln Gly Thr Lys Val Glu Ile
            100                 105                 110

Lys

<210> SEQ ID NO 161
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Glu Val Gln Leu Leu Glu Ser Gly Gly Gly Leu Val Lys Pro Gly Gln
1               5                   10                  15

Ser Leu Lys Leu Ser Cys Ala Ala Ser Gly Phe Thr Phe Ser Ser Tyr
            20                  25                  30

Gly Met His Trp Val Arg Gln Pro Pro Gly Lys Gly Leu Glu Trp Val
        35                  40                  45

Ala Val Val Ser Tyr Asp Gly Ser Asn Lys Tyr Tyr Ala Asp Ser Val
```

```
                50                  55                  60
Gln Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Ser Lys Leu Arg Ser Leu Leu Tyr Phe Glu Trp Leu Ser
                100                 105                 110

Ser Gly Leu Leu Asp Tyr Trp Gly Gln Gly Ala Met Val Thr Val Ser
            115                 120                 125

Ser

<210> SEQ ID NO 162
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Glu Val Gln Leu Leu Glu Ser Gly Gly Gly Leu Val Lys Pro Gly Gln
 1               5                  10                  15

Ser Leu Lys Leu Ser Cys Ala Ala Ser Gly Phe Ser Phe Ser Thr Tyr
                 20                  25                  30

Ala Met His Trp Val Arg Gln Pro Pro Gly Lys Gly Leu Glu Trp Val
             35                  40                  45

Ala Val Val Ser Tyr Asp Gly Asn Tyr Lys Tyr Tyr Ala Asp Thr Val
         50                  55                  60

Gln Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Ser Arg Leu Arg Ser Leu Leu Tyr Phe Glu Trp Leu Ser
                100                 105                 110

Gln Gly Tyr Phe Asn Pro Trp Gly Gln Gly Thr Thr Leu Thr Val Ser
            115                 120                 125

Ser

<210> SEQ ID NO 163
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Glu Val Gln Leu Leu Glu Ser Gly Gly Gly Leu Arg Lys Pro Gly Gln
 1               5                  10                  15

Ser Leu Lys Leu Ser Cys Ala Ala Ser Gly Phe Ser Phe Ser Thr Tyr
                 20                  25                  30

Ala Met His Trp Val Arg Gln Pro Pro Gly Lys Gly Leu Glu Trp Val
             35                  40                  45

Ala Val Val Ser Tyr Asp Gly Asn Tyr Lys Tyr Tyr Ala Asp Ser Val
         50                  55                  60

Gln Gly Arg Phe Thr Ile Ser Arg Asp Asn Ser Lys Asn Thr Leu Tyr
 65                  70                  75                  80
```

-continued

Leu Gln Met Asn Ser Leu Arg Ala Glu Asp Thr Ala Val Tyr Tyr Cys
                85                  90                  95

Ala Lys Asp Ser Arg Leu Arg Ser Leu Leu Tyr Phe Glu Trp Leu Ser
            100                 105                 110

Gln Gly Tyr Phe Asn Pro Trp Gly Gln Gly Thr Thr Leu Thr Val Ser
        115                 120                 125

Ser

<210> SEQ ID NO 164
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Gln Val Gln Leu Leu Glu Thr Gly Gly Gly Leu Val Lys Pro Gly Gln
1               5                   10                  15

Ser Leu Lys Leu Ser Cys Ala Ala Ser Gly Phe Thr Phe Thr Ser Tyr
            20                  25                  30

Ala Met His Trp Val Arg Gln Pro Pro Gly Lys Gly Leu Glu Trp Val
        35                  40                  45

Ala Val Val Ser Tyr Asp Gly Asn Tyr Lys Tyr Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Arg Leu Arg Ser Leu Leu Tyr Phe Glu Trp Leu Ser
            100                 105                 110

Gln Gly Tyr Phe Asn Pro Trp Gly Gln Gly Thr Thr Val Thr Val Ser
        115                 120                 125

Ser

<210> SEQ ID NO 165
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Trp Asn
            20                  25                  30

Tyr Lys Asn Tyr Leu Ala Trp Tyr Gln Gln Lys Pro Gly Lys Ala Pro
        35                  40                  45

Lys Leu Leu Ile Tyr Trp Gly Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln His Tyr
                85                  90                  95

Arg Thr Pro Pro Ser Phe Gly Gln Gly Thr Lys Val Glu Ile Lys
            100                 105                 110

<210> SEQ ID NO 166
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

Asp Ile Gln Met Thr Gln Ser Pro Ser Ser Leu Ser Ala Ser Val Gly
1               5                   10                  15

Asp Arg Val Thr Ile Thr Cys Arg Ser Gln Ser Ile Thr Trp Asp
            20                  25                  30

Tyr Lys Asn Tyr Leu Ala Trp Tyr Gln Gln Lys Pro Gly Lys Ala Pro
        35                  40                  45

Lys Leu Leu Ile Tyr Trp Gly Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln His Tyr
                85                  90                  95

Arg Thr Pro Pro Ser Phe Gly Gln Gly Thr Lys Val Glu Ile Lys
            100                 105                 110

<210> SEQ ID NO 167
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Asp Ile Gln Met Thr Gln Ser Pro Ser Ser Leu Ser Ala Ser Val Gly
1               5                   10                  15

Asp Arg Val Thr Ile Thr Cys Arg Ser Gln Ser Ile Thr Trp Gln
            20                  25                  30

Tyr Lys Asn Tyr Leu Ala Trp Tyr Gln Gln Lys Pro Gly Lys Ala Pro
        35                  40                  45

Lys Leu Leu Ile Tyr Trp Gly Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln His Tyr
                85                  90                  95

Arg Thr Pro Pro Ser Phe Gly Gln Gly Thr Lys Val Glu Ile Lys
            100                 105                 110

<210> SEQ ID NO 168
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

Asp Ile Gln Met Thr Gln Ser Pro Ser Ser Leu Ser Ala Ser Val Gly
1               5                   10                  15

```
Asp Arg Val Thr Ile Thr Cys Arg Ser Ser Gln Ser Ile Thr Trp Arg
            20                  25                  30

Tyr Lys Asn Tyr Leu Ala Trp Tyr Gln Gln Lys Pro Gly Lys Ala Pro
        35                  40                  45

Lys Leu Leu Ile Tyr Trp Gly Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln His Tyr
                85                  90                  95

Arg Thr Pro Pro Ser Phe Gly Gln Gly Thr Lys Val Glu Ile Lys
            100                 105                 110

<210> SEQ ID NO 169
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Trp Glu
            20                  25                  30

Tyr Lys Asn Tyr Leu Ala Trp Tyr Gln Gln Lys Pro Gly Lys Ala Pro
        35                  40                  45

Lys Leu Leu Ile Tyr Trp Gly Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln His Tyr
                85                  90                  95

Arg Thr Pro Pro Ser Phe Gly Gln Gly Thr Lys Val Glu Ile Lys
            100                 105                 110

<210> SEQ ID NO 170
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ser or Thr
<220> FEATURE:
<221> NAME/KEY: MOD_RES
<222> LOCATION: (3)..(3)
<223> OTHER INFORMATION: Val, Leu or Ile
<220> FEATURE:
<221> NAME/KEY: MOD_RES
<222> LOCATION: (4)..(4)
<223> OTHER INFORMATION: Thr or Ser
<220> FEATURE:
<221> NAME/KEY: MOD_RES
<222> LOCATION: (5)..(5)
<223> OTHER INFORMATION: Tyr, Phe or Trp
<220> FEATURE:
<221> NAME/KEY: MOD_RES
<222> LOCATION: (6)..(6)
<223> OTHER INFORMATION: Asn, Ser, Asp, Gln, Arg or Glu
```

<400> SEQUENCE: 170

Gln Xaa Xaa Xaa Xaa Tyr Lys Asn Tyr Leu Ala
1               5                   10

<210> SEQ ID NO 171
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Trp Gly Gln Gly Thr Thr Val Thr Val Ser Ser
1               5                   10

<210> SEQ ID NO 172
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Gln Ser Ile Thr Phe Glu Tyr Lys Asn Tyr Leu Ala
1               5                   10

<210> SEQ ID NO 173
<211> LENGTH: 329
<212> TYPE: PRT
<213> ORGANISM: Influenza A virus

<400> SEQUENCE: 173

Gln Asp Leu Pro Gly Asn Asp Asn Ser Thr Ala Thr Leu Cys Leu Gly
1               5                   10                  15

His His Ala Val Pro Asn Gly Thr Leu Val Lys Thr Ile Thr Asp Asp
            20                  25                  30

Gln Ile Glu Val Thr Asn Ala Thr Glu Leu Val Gln Ser Ser Ser Thr
        35                  40                  45

Gly Lys Ile Cys Asn Asn Pro His Arg Ile Leu Asp Gly Ile Asp Cys
    50                  55                  60

Thr Leu Ile Asp Ala Leu Leu Gly Asp Pro His Cys Asp Val Phe Gln
65                  70                  75                  80

Asn Glu Thr Trp Asp Leu Phe Val Glu Arg Ser Lys Ala Phe Ser Asn
                85                  90                  95

Cys Tyr Pro Tyr Asp Val Pro Asp Tyr Ala Ser Leu Arg Ser Leu Val
            100                 105                 110

Ala Ser Ser Gly Thr Leu Glu Phe Ile Thr Glu Gly Phe Thr Trp Thr
        115                 120                 125

Gly Val Thr Gln Asn Gly Gly Ser Asn Ala Cys Lys Arg Gly Pro Gly
    130                 135                 140

Ser Gly Phe Phe Ser Arg Leu Asn Trp Leu Thr Lys Ser Gly Ser Thr
145                 150                 155                 160

Tyr Pro Val Leu Asn Val Thr Met Pro Asn Asn Asp Asn Phe Asp Lys
                165                 170                 175

Leu Tyr Ile Trp Gly Ile His His Pro Ser Thr Asn Gln Glu Gln Thr
            180                 185                 190

Ser Leu Tyr Val Gln Ala Ser Gly Arg Val Thr Val Ser Thr Arg Arg
        195                 200                 205

```
Ser Gln Gln Thr Ile Ile Pro Asn Ile Gly Ser Arg Pro Trp Val Arg
    210                 215                 220

Gly Leu Ser Ser Arg Ile Ser Ile Tyr Trp Thr Ile Val Lys Pro Gly
225                 230                 235                 240

Asp Val Leu Val Ile Asn Ser Asn Gly Asn Leu Ile Ala Pro Arg Gly
                245                 250                 255

Tyr Phe Lys Met Arg Thr Gly Lys Ser Ser Ile Met Arg Ser Asp Ala
            260                 265                 270

Pro Ile Asp Thr Cys Ile Ser Glu Cys Ile Thr Pro Asn Gly Ser Ile
        275                 280                 285

Pro Asn Asp Lys Pro Phe Gln Asn Val Asn Lys Ile Thr Tyr Gly Ala
    290                 295                 300

Cys Pro Lys Tyr Val Lys Gln Asn Thr Leu Lys Leu Ala Thr Gly Met
305                 310                 315                 320

Arg Asn Val Pro Glu Lys Gln Thr Arg
                325

<210> SEQ ID NO 174
<211> LENGTH: 175
<212> TYPE: PRT
<213> ORGANISM: Influenza A virus

<400> SEQUENCE: 174

Gly Leu Phe Gly Ala Ile Ala Gly Phe Ile Glu Asn Gly Trp Glu Gly
1               5                   10                  15

Met Ile Asp Gly Trp Tyr Gly Phe Arg His Gln Asn Ser Glu Gly Thr
            20                  25                  30

Gly Gln Ala Ala Asp Leu Lys Ser Thr Gln Ala Ala Ile Asp Gln Ile
        35                  40                  45

Asn Gly Lys Leu Asn Arg Val Ile Glu Lys Thr Asn Glu Lys Phe His
    50                  55                  60

Gln Ile Glu Lys Glu Phe Ser Glu Val Glu Gly Arg Ile Gln Asp Leu
65                  70                  75                  80

Glu Lys Tyr Val Glu Asp Thr Lys Ile Asp Leu Trp Ser Tyr Asn Ala
                85                  90                  95

Glu Leu Leu Val Ala Leu Glu Asn Gln His Thr Ile Asp Leu Thr Asp
            100                 105                 110

Ser Glu Met Asn Lys Leu Phe Glu Lys Thr Arg Arg Gln Leu Arg Glu
        115                 120                 125

Asn Ala Glu Glu Met Gly Asn Gly Cys Phe Lys Ile Tyr His Lys Cys
    130                 135                 140

Asp Asn Ala Cys Ile Glu Ser Ile Arg Asn Gly Thr Tyr Asp His Asp
145                 150                 155                 160

Val Tyr Arg Asp Glu Ala Leu Asn Asn Arg Phe Gln Ile Lys Gly
                165                 170                 175

<210> SEQ ID NO 175
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Gln Val Gln Leu Val Gln Ser Gly Gly Gly Val Val Gln Pro Gly Arg
1               5                   10                  15
```

Ser Leu Arg Leu Ser Cys Val Ala Ser Gly Phe Thr Phe Ser Thr Tyr
            20                  25                  30

Ala Met His Trp Val Arg Gln Ala Pro Gly Arg Gly Leu Glu Trp Val
            35                  40                  45

Ala Val Ile Ser Tyr Asp Gly Asn Tyr Lys Tyr Ala Asp Ser Val
    50                  55                  60

Lys Gly Arg Phe Ser Ile Ser Arg Asp Asn Ser Asn Thr Leu His
65                  70                  75                  80

Leu Glu Met Asn Thr Leu Arg Thr Glu Asp Thr Ala Leu Tyr Tyr Cys
                85                  90                  95

Ala Lys Asp Ser Gln Leu Arg Ser Leu Leu Tyr Phe Glu Trp Leu Ser
            100                 105                 110

Gln Gly Tyr Phe Asp Pro Trp Gly Gln Gly Thr Leu Val Thr Val Thr
            115                 120                 125

Ser

<210> SEQ ID NO 176
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

Gln Val Gln Leu Val Gln Ser Gly Gly Gly Val Val Pro Pro Gly Arg
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
            35                  40                  45

Ala Val Ile Ser Tyr Asp Gly Asn Tyr Lys Tyr Ala Asp Ser Val
    50                  55                  60

Arg Gly Arg Phe Thr Ile Ser Arg Asp Asn Ser Lys Asn Thr Leu Asn
65                  70                  75                  80

Leu Asp Met Asn Ser Leu Arg Thr Glu Asp Thr Ala Leu Tyr Tyr Cys
                85                  90                  95

Ala Lys Asp Ser Gln Leu Arg Ser Leu Leu Tyr Phe Asp Trp Leu Ser
            100                 105                 110

Gln Gly Tyr Phe Asp His Trp Gly Gln Gly Thr Leu Val Thr Val Ser
            115                 120                 125

Ser

<210> SEQ ID NO 177
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val

```
                35                  40                  45
Ala Val Ile Ser Tyr Asp Gly Ser Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Ser Gln Leu Arg Ser Leu Leu Tyr Phe Asp Trp Leu Ser
            100                 105                 110

Gln Gly Tyr Phe Asp Tyr Trp Gly Gln Gly Thr Leu Val Thr Val Ser
        115                 120                 125

Ser

<210> SEQ ID NO 178
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Thr Tyr
                20                  25                  30

Ala Met His Trp Val Arg Gln Ala Pro Gly Lys Gly Leu Glu Trp Val
            35                  40                  45

Ala Val Ile Ser Tyr Asp Ala Asn Tyr Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Ser Gln Leu Arg Ser Leu Leu Tyr Phe Glu Trp Leu Ser
            100                 105                 110

Gln Gly Tyr Phe Asp Tyr Trp Gly Gln Gly Thr Leu Val Thr Val Ser
        115                 120                 125

Ser

<210> SEQ ID NO 179
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

Gln Val Gln Leu Val Gln Ser Gly Gly Gly Val Val Gln Pro Gly Arg
 1               5                  10                  15

Ser Leu Arg Leu Ser Cys Ala Ala Ser Gly Phe Thr Phe Ser Thr Tyr
                20                  25                  30

Gly Met His Trp Val Arg Gln Ala Pro Gly Lys Gly Leu Glu Trp Val
            35                  40                  45

Ala Val Ile Ser Tyr Asp Gly Asn Tyr Lys Tyr Tyr Ala Asp Ser Val
     50                  55                  60
```

```
Lys Gly Arg Phe Thr Ile Ser Arg Asp Asn Ser Lys Asn Thr Leu Tyr
 65                  70                  75                  80

Leu Glu Met Asn Ser Leu Arg Thr Glu Asp Thr Ala Leu Tyr Tyr Cys
                 85                  90                  95

Ala Lys Asp Ser Gln Leu Arg Ser Leu Leu Tyr Phe Asp Trp Leu Ser
            100                 105                 110

Gln Gly Tyr Phe Asp His Trp Gly Gln Gly Thr Leu Val Thr Val Ser
        115                 120                 125

Ser
```

<210> SEQ ID NO 180
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

```
Asp Ile Gln Met Thr Ser Gln Pro Asp Ser Leu Ala Val Ser Leu Gly
  1               5                  10                  15

Ala Arg Ala Thr Ile Asn Cys Lys Ser Ser Gln Ser Val Thr Phe Asn
             20                  25                  30

Tyr Lys Asn Tyr Leu Ala Trp Tyr Gln Gln Lys Pro Gly Gln Pro Pro
         35                  40                  45

Lys Val Leu Ile Tyr Trp Ala Ser Ala Arg Glu Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln His Tyr
                 85                  90                  95

Arg Thr Pro Pro Thr Phe Gly Gln Gly Thr Lys Val Glu Ile Lys
            100                 105                 110
```

<210> SEQ ID NO 181
<211> LENGTH: 329
<212> TYPE: PRT
<213> ORGANISM: Influenza A virus

<400> SEQUENCE: 181

```
Thr Asn Ala Asp Thr Ile Cys Ile Gly Tyr His Ala Asn Asn Ser Thr
  1               5                  10                  15

Asp Thr Val Asp Thr Val Leu Glu Lys Asn Val Thr Val Thr His Ser
             20                  25                  30

Val Asn Leu Leu Glu Asp Ser His Asn Gly Lys Leu Cys Lys Leu Lys
         35                  40                  45

Gly Ile Ala Pro Leu Gln Leu Gly Lys Cys Asn Ile Ala Gly Trp Leu
 50                  55                  60

Leu Gly Asn Pro Glu Cys Asp Leu Leu Leu Thr Ala Ser Ser Trp Ser
 65                  70                  75                  80

Tyr Ile Val Glu Thr Ser Asn Ser Glu Asn Gly Thr Cys Tyr Pro Gly
                 85                  90                  95

Asp Phe Ile Asp Tyr Glu Glu Leu Arg Glu Gln Leu Ser Ser Val Ser
            100                 105                 110

Ser Phe Glu Lys Phe Glu Ile Phe Pro Lys Thr Ser Ser Trp Pro Asn
        115                 120                 125

His Glu Thr Thr Lys Gly Val Thr Ala Ala Cys Ser Tyr Ala Gly Ala
```

```
              130                 135                 140
Ser Ser Phe Tyr Arg Asn Leu Leu Trp Leu Thr Lys Lys Gly Ser Ser
145                 150                 155                 160

Tyr Pro Lys Leu Ser Lys Ser Tyr Val Asn Asn Lys Gly Lys Glu Val
                165                 170                 175

Leu Val Leu Trp Gly Val His His Pro Pro Thr Gly Thr Asp Gln Gln
            180                 185                 190

Ser Leu Tyr Gln Asn Ala Asp Ala Tyr Val Ser Val Gly Ser Ser Lys
        195                 200                 205

Tyr Asn Arg Arg Phe Thr Pro Glu Ile Ala Ala Arg Pro Lys Val Arg
    210                 215                 220

Asp Gln Ala Gly Arg Met Asn Tyr Tyr Trp Thr Leu Leu Glu Pro Gly
225                 230                 235                 240

Asp Thr Ile Thr Phe Glu Ala Thr Gly Asn Leu Ile Ala Pro Trp Tyr
                245                 250                 255

Ala Phe Ala Leu Asn Arg Gly Ser Gly Ser Gly Ile Ile Thr Ser Asp
            260                 265                 270

Ala Pro Val His Asp Cys Asn Thr Lys Cys Gln Thr Pro His Gly Ala
        275                 280                 285

Ile Asn Ser Ser Leu Pro Phe Gln Asn Ile His Pro Val Thr Ile Gly
    290                 295                 300

Glu Cys Pro Lys Tyr Val Arg Ser Thr Lys Leu Arg Met Ala Thr Gly
305                 310                 315                 320

Leu Arg Asn Ile Pro Ser Ile Gln Ser
                325

<210> SEQ ID NO 182
<211> LENGTH: 222
<212> TYPE: PRT
<213> ORGANISM: Influenza A virus

<400> SEQUENCE: 182

Gly Leu Phe Gly Ala Ile Ala Gly Phe Ile Glu Gly Gly Trp Thr Gly
1               5                   10                  15

Met Ile Asp Gly Trp Tyr Gly Tyr His His Gln Asn Glu Gln Gly Ser
            20                  25                  30

Gly Tyr Ala Ala Asp Gln Lys Ser Thr Gln Asn Ala Ile Asp Gly Ile
        35                  40                  45

Thr Asn Lys Val Asn Ser Val Ile Glu Lys Met Asn Thr Gln Phe Thr
    50                  55                  60

Ala Val Gly Lys Glu Phe Asn Asn Leu Glu Arg Arg Ile Glu Asn Leu
65                  70                  75                  80

Asn Lys Lys Val Asp Asp Gly Phe Leu Asp Ile Trp Thr Tyr Asn Ala
                85                  90                  95

Glu Leu Leu Val Leu Leu Glu Asn Glu Arg Thr Leu Asp Phe His Asp
            100                 105                 110

Ser Asn Val Arg Asn Leu Tyr Glu Lys Val Lys Ser Gln Leu Lys Asn
        115                 120                 125

Asn Ala Lys Glu Ile Gly Asn Gly Cys Phe Glu Phe Tyr His Lys Cys
    130                 135                 140

Asp Asp Ala Cys Met Glu Ser Val Arg Asn Gly Thr Tyr Asp Tyr Pro
145                 150                 155                 160

Lys Tyr Ser Glu Glu Ser Lys Leu Asn Arg Glu Glu Ile Asp Gly Val
                165                 170                 175
```

```
Lys Leu Glu Ser Met Gly Val Tyr Gln Ile Leu Ala Ile Tyr Ser Thr
            180                 185                 190

Val Ala Ser Ser Leu Val Leu Val Ser Leu Gly Ala Ile Ser Phe
        195                 200                 205

Trp Met Cys Ser Asn Gly Ser Leu Gln Cys Arg Ile Cys Ile
    210                 215                 220

<210> SEQ ID NO 183
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 183

Glu Val Gln Leu Leu Glu Ser Gly Gly Gly Leu Val Lys Pro Gly Gln
1               5                   10                  15

Ser Leu Lys Leu Ser Cys Ala Ala Ser Gly Phe Thr Phe Thr
            20                  25                  30

<210> SEQ ID NO 184
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(6)
<223> OTHER INFORMATION: Ser or Thr
<220> FEATURE:
<221> NAME/KEY: MOD_RES
<222> LOCATION: (8)..(8)
<223> OTHER INFORMATION: Ala or Gly

<400> SEQUENCE: 184

Gly Phe Thr Phe Xaa Xaa Tyr Xaa Met His
1               5                   10

<210> SEQ ID NO 185
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys or Arg
<220> FEATURE:
<221> NAME/KEY: MOD_RES
<222> LOCATION: (5)..(5)
<223> OTHER INFORMATION: Ser or Thr
<220> FEATURE:
<221> NAME/KEY: MOD_RES
<222> LOCATION: (6)..(6)
<223> OTHER INFORMATION: Val, Leu or Ile
<220> FEATURE:
<221> NAME/KEY: MOD_RES
<222> LOCATION: (7)..(7)
<223> OTHER INFORMATION: Thr or Ser
<220> FEATURE:
<221> NAME/KEY: MOD_RES
<222> LOCATION: (8)..(8)
<223> OTHER INFORMATION: Tyr, Phe or Trp
<220> FEATURE:
<221> NAME/KEY: MOD_RES
<222> LOCATION: (9)..(9)
```

<223> OTHER INFORMATION: Asn, Ser or Asp

<400> SEQUENCE: 185

Xaa Ser Ser Gln Xaa Xaa Xaa Xaa Xaa Tyr Lys Asn Tyr Leu Ala
1               5                   10                  15

<210> SEQ ID NO 186
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys or Arg
<220> FEATURE:
<221> NAME/KEY: MOD_RES
<222> LOCATION: (5)..(5)
<223> OTHER INFORMATION: Ser or Thr
<220> FEATURE:
<221> NAME/KEY: MOD_RES
<222> LOCATION: (6)..(6)
<223> OTHER INFORMATION: Val, Leu or Ile
<220> FEATURE:
<221> NAME/KEY: MOD_RES
<222> LOCATION: (7)..(7)
<223> OTHER INFORMATION: Thr or Ser
<220> FEATURE:
<221> NAME/KEY: MOD_RES
<222> LOCATION: (8)..(8)
<223> OTHER INFORMATION: Tyr, Phe or Trp
<220> FEATURE:
<221> NAME/KEY: MOD_RES
<222> LOCATION: (9)..(9)
<223> OTHER INFORMATION: Asn, Ser, Asp, Gln, Arg or Glu

<400> SEQUENCE: 186

Xaa Ser Ser Gln Xaa Xaa Xaa Xaa Xaa Tyr Lys Asn Tyr Leu Ala
1               5                   10                  15

<210> SEQ ID NO 187
<211> LENGTH: 653
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 187
gaaattgtaa tgacgcagag ccctgatagc cttgccgtgt ccctgggtga gagggcgaca      60
atcaattgta agtcatcaca gtcggtcacg tacaactaca gaactacct ggcgtggtat      120 caacagaaac ccgggcagcc gcccaaattg ctcatctatt gggcttcgac acgggagtcg     180
ggtgtgccag accgcttctc cgggtcagga tcgggaactg acttcacgtt gactatttcg     240
tccctccagg cagaagatgt agccgtctac tattgccaac agtattacag aacgccgcct     300
acatttggag gcgggaccaa acttgacatc aagggatccg tggccgcccc cagcgtcttc     360
atcttcccgc ccagcgacga gcagctgaag tcgggcacgg ccagcgtggt gtgcctcctg     420
aacaacttct accccgcgcga ggcgaaggtc cagtggaagg tggacaacgc cctgcagagc     480
gggaacagcc aggagagcgt gaccgagcag gactcgaagg acagcaccta cagcctcagc     540
agcaccctga cgctgagcaa ggccgactac gagaagcaca aggtctacgc ctgcgaggtg     600
acccaccagg ggctctcgag ccccgtgacc aagagcttca ccggggcga gtg             653

```
<210> SEQ ID NO 188
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 188

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Thr Tyr Asn
            20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Tyr Tyr
                85                  90                  95

Arg Thr Pro Pro Thr Phe Gly Gly Gly Thr Lys Leu Asp Ile Lys Gly
            100                 105                 110

Ser Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu
    210                 215
```

HA BINDING AGENTS

CROSS REFERENCE TO RELATED APPLICATIONS

This application is a continuation application of U.S. application Ser. No. 13/830,367, filed on Mar. 14, 2013, which claims priority to U.S. Application Ser. No. 61/645,554, filed on May 10, 2012, and U.S. Application Ser. No. 61/716,447, filed on Oct. 19, 2012. The disclosures of the prior applications are considered part of (and are incorporated by reference in) the disclosure of this application.

SEQUENCE LISTING

The instant application contains a Sequence Listing which has been submitted in ASCII format via EFS-Web and is hereby incorporated by reference in its entirety. Said ASCII copy, created on Jun. 24, 2013, is named P2029-700110_SL.txt and is 186,454 bytes in size.

FIELD OF INVENTION

This disclosure relates to novel binding agents, e.g., peptide agents, e.g., antibody molecules, e.g., antibodies, and antigen-binding fragments thereof, that bind hemagglutinin protein of influenza viruses, and in embodiments neutralize the virus, and methods of their use.

BACKGROUND

Influenza is an infectious disease caused by RNA viruses of the family Orthomyxoviridae (the influenza viruses). Influenza viruses are classified based on core protein into three genera A, B and C that are further divided into subtypes determined by the viral envelope glycoproteins haemagglutinin (HA) and neuraminidase (NA). Influenza A viruses infect a range of mammalian and avian species, whereas type B and C infections are largely restricted to humans. Only types A and B cause human disease of any concern.

High mutation rates and frequent genetic reassortments of the influenza viruses contribute to great variability of the HA and NA antigens. Minor point mutations causing small changes ("antigenic drift") occur relatively often. Antigenic drift enables the virus to evade immune recognition, resulting in repeated influenza outbreaks during interpandemic years. Major changes in the HA antigen ("antigenic shift") are caused by reassortment of genetic material from different influenza A subtypes. Antigenic shifts resulting in new pandemic strains are rare events, occurring through reassortment between animal and human subtypes, for example in co-infected pigs.

Influenza A spreads around the world in seasonal epidemics, resulting in the deaths of between 250,000 and 500,000 people every year, and up to millions in some pandemic years. On average 41,400 people died each year in the United States between 1979 and 2001 from influenza.

SUMMARY

The disclosure is based, at least in part, on the discovery of human anti-HA antibodies comprising functional and structural properties disclosed herein, e.g., antibodies that bind a conserved region or epitope on influenza virus and uses thereof.

Accordingly, the disclosure features binding agents, e.g., antibody molecules, or preparations, or isolated preparations thereof, that bind hemagglutinin (HA) from influenza viruses. In an embodiment, a binding agent, e.g., an antibody molecule, is broad spectrum, and binds more than one HA, e.g., an HA from one or both of Group 1 or Group 2 strains of influenza A viruses and/or one or more strains of influenza B viruses. Therefore, in some embodiments, a binding agent, e.g., an antibody molecule, featured in the disclosure can treat or prevent infection by a Group 1 influenza virus and a Group 2 influenza virus. In other embodiments, a binding agent, e.g., an antibody molecule, featured in the disclosure can treat or prevent infection by an influenza A virus and an influenza B virus. The binding agents, e.g, antibody molecules, share sufficient structural similarity with antibodies or variable regions disclosed herein such that they possess functional attributes of the antibodies disclosed herein. In embodiments the structural similarity can be in terms of three dimensional structure or linear amino acid sequence or both.

In one aspect, the disclosure features an anti-hemagglutinin (anti-HA) binding agent, e.g., a specific binding agent, e.g., an antibody molecule, or preparation, or isolated preparation thereof, comprising one or more or all of the following properties:

(a) it fails to produce any escape mutants as determined by the failure of a viral titer to recover following at least 10, 9, 8, 7, 6, or 5 rounds of serial infections in cell culture with a mixture of the antibody molecule and an influenza A virus, e.g., a Group 1 strain, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004;

(b) it produces fewer escape mutants than does a reference anti-HA antibody molecule, e.g., Ab 67-11, FI6, FI28, C179, F10, CR9114, or CR6261, e.g., when tested by the method described in (a);

(c) it prevents infection by at least 1, 2, 3, 4 or 5 influenza subtypes of Group 1, and by at least 1, 2, 3, 4 or 5 influenza subtypes of Group 2;

(d) it inhibits fusogenic activity of the targeted HA;

(e) it treats or prevents infection by a Group 1 virus, such as where the virus is an H1, H5, or H9 virus; and it treats or prevents infection by a Group 2 virus, such as where the virus is an H3 or H7 virus;

(f) it treats or prevents infection by influenza A strains H1N1 and H3N2;

(g) it is effective for prevention or treatment of infection, e.g., in humans or mice, with H1N1 and H3N2 when administered at 50 mg/kg, 25 mg/kg, 10 mg/kg, 6 mg/kg, 5 mg/kg, 4 mg/kg, 3 mg/kg, 2 mg/kg, or 1 mg/kg;

(h) it treats or prevents infection by influenza A H5N1 strains;

(i) it is effective for prevention or treatment of infection, e.g., in humans or mice, with H5N1 when administered at 50 mg/kg, 25 mg/kg, 10 mg/kg, 6 mg/kg, 5 mg/kg, 4 mg/kg, 3 mg/kg, 2 mg/kg, or 1 mg/kg;

(j) the concentration of antibody molecule required for 50% neutralization of influenza A virus is less than 10 µg/mL;

(k) it treats or prevents infection by an influenza B virus, e.g., B/Wisconsin/1/2010;

(l) it is effective for prevention or treatment of infection, e.g., in humans or mice, with an influenza B virus, e.g., B/Wisconsin/1/2010, when administered at 10 mg/kg, 6 mg/kg, 4 mg/kg, 3 mg/kg, 2 mg/kg, or 1 mg/kg;

(m) the concentration of antibody molecule required for 50% neutralization of influenza B virus, e.g., B/Wisconsin/1/2010, virus is less than 10 µg/mL;

(n) it prevents or minimizes secondary infection (e.g., secondary bacterial infection) or effects thereof on a subject;

(o) it is effective for preventing or minimizing secondary infection (e.g., secondary bacterial infection) or effects thereof on a subject when administered at 50 mg/kg, 25 mg/kg, 10 mg/kg, 6 mg/kg, 5 mg/kg, 4 mg/kg, 3 mg/kg, 2 mg/kg, or 1 mg/kg;

(p) it binds an epitope which comprises or consists of the hemagglutinin trimer interface; and (q) it binds an epitope other than that bound by a reference anti-HA antibody molecule, e.g., Ab 67-11, FI6, FI28, C179, F10, CR9114, or CR6261, e.g., as determined by structural analysis, e.g., by X-ray crystallography or NMR spectroscopy;

(r) in an embodiment it binds to an epitope, e.g., it has an epitope that overlaps with or is the same as, of an antibody disclosed herein, e.g., as determined by mutational analysis or crystal structure analysis In one embodiment, the binding agent, e.g., an anti-HA antibody molecule, has one or more of the following characteristics: the anti-HA antibody molecule prevents infection by at least 1, 2, 3, 4 or 5 influenza subtypes of Group 1, and by at least 1, 2, 3, 4 or 5 influenza subtypes of Group 2; the concentration of the anti-HA antibody molecule required for 50% neutralization of influenza A virus is less than 10 µg/mL; or the anti-HA antibody molecule binds an epitope that comprises or consists of the hemagglutinin trimer interface.

In one embodiment, the binding agent, e.g., an anti-HA antibody molecule, featured in the disclosure treats or prevents infection by a Group 1 virus, such as where the virus is an H1, H2, H5, H6, H8, H9, H12, H11, H13, H16, or H17 virus; and treats or prevents infection by a Group 2 virus, such as where the virus is an H3, H4, H7, H10 or H15 virus.

In one embodiment, the binding agent, e.g., an anti-HA antibody molecule, featured in the disclosure prevents infection by at least 1, 2, 3, 4, 5, 6, 7, 8, 9, 10 or 11 influenza subtypes of Group 1, and by at least 1, 2, 3, 4, 5 or 6 influenza subtypes of Group 2.

In one embodiment, the binding agent, e.g., an anti-HA antibody molecule, featured in the disclosure treats or prevents infection by one or more of H1N1, H2N2, H5N1, and H9N2, and also treats or prevents infection by one or more of H3N2 and H7N7.

In an embodiment, a binding agent, e.g., antibody molecule, binds, and in embodiments, neutralizes:

at least one strain from the Group 1 H1, e.g., H1 a or H1b, cluster and at least one strain from the Group 2 H3 or H7 cluster.

In an embodiment, a binding agent, e.g., antibody molecule, binds, and in embodiments, neutralizes:

at least one strain from the Group 1 H1, e.g., H1 a or H1b, cluster and at least one influenza B strain, e.g., B/Wisconsin/1/2010.

In an embodiment, a binding agent, e.g., antibody molecule, binds, and in embodiments, neutralizes:

at least one strain from the Group 2 H3 or H7 cluster and at least one influenza B strain, e.g., B/Wisconsin/1/2010.

In an embodiment, a binding agent, e.g., antibody molecule, binds, and in embodiments, neutralizes:

at least one strain from the Group 1 H1, e.g., H1 a or H1b, cluster, at least one strain from the Group 2 H3 or H7 cluster, and at least one influenza B strain, e.g., B/Wisconsin/1/2010.

In one embodiment, the binding agent, e.g., an anti-HA antibody molecule, featured in the disclosure treats or prevents infection by one or more of influenza B viruses, e.g., B/Wisconsin/1/2010.

In one embodiment, the anti-HA antibody molecule is not an anti-HA antibody molecule previously described in the art. For example, the anti-HA antibody molecule is other than one or more or all of Ab 67-11 (U.S. Provisional Application No. 61/645,453), FI6 (FI6, as used herein, refers to any specifically disclosed FI6 sequence in U.S. Published Application No. 2010/0080813, US published application No. 2011/0274702, WO2013/011347 or Corti et al., Science 333:850-856, 2011, published online Jul. 28, 2011; FIGS. 12A to 12C), FI28 (U.S. Published Application No. 2010/0080813), C179 (Okun et al., J. Virol. 67:2552-1558, 1993), F10 (Sui et al., Nat. Struct. Mol. Biol. 16:265, 2009), CR9114 (Dreyfus et al., Science. 2012; 337(6100):1343-1348; published online Aug. 9, 2012), or CR6261 (Ekiert et al., Science 324:246-251, 2009; published online Feb. 26, 2009).

In one embodiment, the binding agent, e.g., an anti-HA antibody molecule, neutralizes infection with H1N1 and H3N2 in vitro. In another embodiment, binding agent, e.g., an anti-HA antibody molecule, neutralizes infection with H1N1 and H3N2 in vivo.

In one embodiment, the binding agent, e.g., an anti-HA antibody molecule, neutralizes infection with H5N1 in vitro. In another embodiment, binding agent, e.g., an anti-HA antibody molecule, neutralizes infection with H5N1 in vivo.

In one embodiment, the binding agent, e.g., an anti-HA antibody molecule, neutralizes infection with an influenza B virus, e.g., B/Wisconsin/1/2010, in vitro. In another embodiment, the binding agent, e.g., an anti-HA antibody molecule neutralizes infection with an influenza B virus, e.g., B/Wisconsin/1/2010, in vivo.

In another embodiment, the concentration of the binding agent, e.g., an anti-HA antibody molecule, required for 50% neutralization of influenza A virus is 10 µg/mL or less, such as 9 µg/mL or less, 8 µg/mL or less, 7 µg/mL or less, 6 µg/mL or less, or 5 µg/mL or less.

In another embodiment, the concentration of the binding agent, e.g., an anti-HA antibody molecule, required for 60% neutralization of influenza A virus, 50% neutralization of influenza A virus, or 40% neutralization of influenza A virus is 10 µg/mL or less, such as 9 µg/mL or less, 8 µg/mL or less, 7 µg/mL or less, 6 µg/mL or less, or 5 µg/mL or less.

In yet another embodiment, the binding agent, e.g., an anti-HA antibody molecule, is effective for prevention or treatment of infection, e.g., in humans or mice, with H1N1 and H3N2, such as when administered at 50 mg/kg, 25 mg/kg, 10 mg/kg, 6.0 mg/kg, 5.0 mg/kg, 4.0 mg/kg, 3.0 mg/kg, 2.0 mg/kg, 1.0 mg/kg or less.

In still another embodiment, the binding agent, e.g., an the anti-HA antibody molecule, is effective for prevention or treatment of infection, e.g., in humans or mice, with H5N1, such as when administered at 50 mg/kg, 25 mg/kg, 10 mg/kg, 6.0 mg/kg, 5.0 mg/kg, 4.0 mg/kg, 3.0 mg/kg, 2.0 mg/kg, 1.0 mg/kg or less.

In another embodiment, a binding agent, e.g., an anti-HA antibody molecule, is effective for the treatment or prevention of a Group 1 virus, where the Group 1 virus is H1, H5, or H9, and in another embodiment, the binding agent, e.g., an anti-HA antibody molecule, is effective for the treatment or prevention of a Group 2 virus, where the Group 2 virus is H3 or H7.

In another embodiment, the concentration of the binding agent, e.g., an anti-HA antibody molecule, required for 50% neutralization of influenza B virus, e.g., B/Wisconsin/1/2010, is 10 µg/mL or less, such as 9 µg/mL or less, 8 µg/mL or less, 7 µg/mL or less, 6 µg/mL or less, or 5 µg/mL or less.

In another embodiment, the concentration of the binding agent, e.g., an anti-HA antibody molecule, required for 60% neutralization of influenza B virus, e.g., B/Wisconsin/1/2010, 50% neutralization of influenza B virus, e.g., B/Wisconsin/1/2010, or 40% neutralization of influenza B virus, e.g., B/Wisconsin/1/2010, is 10 μg/mL or less, such as 9 μg/mL or less, 8 μg/mL or less, 7 μg/mL or less, 6 μg/mL or less, or 5 μg/mL or less.

In another embodiment, the binding agent, e.g., an anti-HA antibody molecule, is a full length tetrameric antibody, a single chain antibody (scFv), a F(ab')$_2$ fragment, a Fab fragment, or an Fd fragment. In another embodiment, the heavy chain of the antibody molecule is a γ1 heavy chain, and in yet another embodiment, the light chain of the antibody molecule is a κ light chain or a λ light chain. In yet another embodiment, the anti-HA antibody molecule featured in the disclosure is an IgG1 antibody.

In an embodiment, the antibody molecule binds an epitope that has one, two, three, four, five, or all of, the following properties a-f:
a) it includes one, two, or all of, H3 HA1 residues N38, I278, and D291;
b) it includes H3 HA2 residue N12;
c) it does not include one, two or all of, H3 HA1 residues Q327, T328, and R329;
d) it does not include one, two, three, four, or all of, H3 HA2 residues G1, L2, F3, G4, and D46;
e) it includes one, two, or all of, H3 HA1 residues T318, R321, and V323; or
f) it includes 1, 2, 3, 4, 5, 6, 7, 8, 9, 10, 11, 12, 13, 14, 15, 16, 17, or all of, H3 HA2 residues A7, E11, I18, D19, G20, W21, L38, K39, T41, Q42, A43, I45, I48, N49, L52, N53, I56, and E57.

In an embodiment the antibody molecule has properties: a; and b.
In an embodiment the antibody molecule has properties: c; and d.
In an embodiment the antibody molecule has properties: a; and c or d.
In an embodiment the antibody molecule has properties: b; and c or d.
In an embodiment the antibody molecule has properties: c; and a or b.
In an embodiment the antibody molecule has properties: d; and a or b.
In an embodiment the antibody molecule has properties: a, b, c and d.
In an embodiment the antibody molecule has properties: a, b, c, d, e, and f.

In an embodiment, the antibody molecule has a $K_D$ for H3 of equal to or less than $10^{-6}$, wherein said $K_D$ is increased by at least 2, 5, 10, or 100 fold, by a mutation or mutations in any of:
a) H3 HA1 residues N38, I278, or D291;
b) H3 HA2 residue N12;
c) H3 HA1 residues T318, R321, or V323; or
d) H3 HA2 residues A7, E11, I18, D19, G20, W21, L38, K39, T41, Q42, A43, I45, I48, N49, L52, N53, I56, or E57.

In an embodiment, the antibody molecule has a $K_D$ for H3 of equal to or less than $10^{-6}$, wherein said $K_D$ is increased by no more than 2, or 5 fold, by a mutation or mutations in any of:
c) H3 HA1 residues Q327, T328, or R329; or
d) H3 HA2 residues G1, L2, F3, G4, or D46.

In an embodiment, the antibody molecule binds an epitope that has one, two, three, four, five, or all of, the following properties a-f:
aa) it includes one, two, or all of, H1 HA1 residues H31, N279, and S292;
bb) it includes H1 HA2 residue G12;
cc) it does not include one or both of H1 HA1 residues Q328 and S329;
dd) it does not include one, two, three, four, or all of, H1 HA2 residues G1, L2, F3, G4, and D46;
ee) it includes one, two, or all of, H1 HA1 residues T319, R322, and I324 are bound by both Ab 044 and FI6; or
ff) it includes 1, 2, 3, 4, 5, 6, 7, 8, 9, 10, 11, 12, 13, 14, 15, 16, 17, or all of, H1 HA2 residues A7, E11, I18, D19, G20, W21, Q38, K39, T41, Q42, N43, I45, I48, T49, V52, N53, I56, and E57

In an embodiment the antibody molecule has properties: aa; and bb.
In an embodiment the antibody molecule has properties: cc; and dd.
In an embodiment the antibody molecule has properties: aa; and cc or dd.
In an embodiment the antibody molecule has properties: bb; and cc or dd.
In an embodiment the antibody molecule has properties: cc; and aa or bb.
In an embodiment the antibody molecule has properties: dd; and aa or bb.
In an embodiment the antibody molecule has properties: aa, bb, cc and dd.
In an embodiment the antibody molecule has properties: aa, bb, cc, dd, ee, and ff.

In an embodiment, the antibody molecule has a $K_D$ for H1 of equal to or less than $10^{-6}$, wherein said $K_D$ is increased by at least 2, 5, 10, or 100 fold, by a mutation or mutations in any of:
aa) H1 HA1 residues H31, N279, and S292;
bb) H1 HA2 residue G12;
cc) H1 HA1 residues T319, R322, and I324; or
dd) H1 HA2 residues A7, E11, I18, D19, G20, W21, Q38, K39, T41, Q42, N43, I45, I48, T49, V52, N53, I56, and E57.

In an embodiment, the antibody molecule has a $K_D$ for H1 of equal to or less than $10^{-6}$, wherein said $K_D$ is increased by no more than 2, or 5 fold, by a mutation or mutations in any of:
cc) H1 HA1 residues Q328 and S329; or
dd) H1 HA2 residues G1, L2, F3, G4, and D46;

In an embodiment the antibody molecule has one, two, three or all of the following properties:
a and aa;
b and bb;
c and cc;
d and dd.

In an embodiment the molecule has properties c, cc, d, and dd.

In an embodiment the binding agent, e.g., a specific binding agent, e.g., an antibody molecule, comprises one or both of:
a heavy chain variable region comprising at least, or more than, 60, 65, 70, 75, 80, 85, 87, 90, 95, 98 or 99 percent homology with a heavy chain variable region from Table 3, Table 4A, Table 4B, FIG. 2, FIG. 13 or FIG. 17; and
a light chain variable region comprising at least, or more than, 60, 65, 70, 75, 80, 85, 87, 90, 95, 98 or 99 percent homology with light chain variable region from Table 3, Table 4A, Table 4B, FIG. 3, FIG. 14 or FIG. 17.

In an embodiment, the antibody molecule comprises a heavy chain variable region 25 (SEQ ID NO:25), or a structurally or functionally related variable heavy chain region as described herein.

In an embodiment, the antibody molecule comprises a light chain variable region 52 (SEQ ID NO:52), 155 (SEQ ID NO:155), or 45 (SEQ ID NO:45), or a structurally or functionally related variable light chain region as described herein.

In an embodiment, the antibody molecule comprises:
a heavy chain variable region 25 (SEQ ID NO:25), or a structurally or functionally related variable heavy chain region as described herein; and
a light chain variable region 52 (SEQ ID NO:52), 155 (SEQ ID NO:155), or 45 (SEQ ID NO:45), or a structurally or functionally related variable light chain region as described herein.

In an embodiment, the antibody molecule comprises a heavy chain variable region comprising one, two, or all of CDR1, CDR2, and CDR3, from heavy chain variable region 25 (SEQ ID NO:25), or a structurally or functionally related variable heavy chain region as described herein.

In an embodiment, the antibody molecule comprises a light chain variable region comprising one, two, or all of CDR1, CDR2, and CDR3, from light chain variable region 52 (SEQ ID NO:52), 155 (SEQ ID NO:155), or 45 (SEQ ID NO:45), or a structurally or functionally related sequence as described herein.

In an embodiment, the antibody molecule comprises:
a heavy chain variable region comprising one, two, or all of CDR1, CDR2, and CDR3, from heavy chain variable region 25 (SEQ ID NO:25), or a structurally or functionally related variable heavy chain region as described herein; and
a light chain variable region comprising one, two, or all of CDR1, CDR2, and CDR3, from light chain variable region 52 (SEQ ID NO:52), 155 (SEQ ID NO:155), or 45 (SEQ ID NO:45), or a structurally or functionally related variable light chain region as described herein.

In an embodiment the antibody molecule comprises a heavy chain variable region from FIG. 2 or FIG. 13 or a structurally or functionally related variable heavy chain region as described herein.

In an embodiment the antibody molecule comprises a light chain variable region from FIG. 3 or FIG. 14 or a structurally or functionally related variable light chain region as described herein.

In an embodiment the antibody molecule comprises one, two, or all of, a CDR1, CDR2, and CDR3 from a heavy chain variable region from FIG. 2 or FIG. 13, or a structurally or functionally related sequences as described herein.

In an embodiment the antibody molecule comprises one, two, or all of, a CDR1, CDR2, and CDR3 from a light chain variable region from FIG. 3 or FIG. 14, or a structurally or functionally related sequences as described herein.

In an embodiment the antibody molecule comprises one, two or all of, HC CDR1, HC CDR2, and HC CDR3 and one, two or all of, LC CDR1, LC CDR2, and LC CDR3 from an antibody disclosed in Table 3, or a structurally or functionally related sequences as described herein.

In another embodiment, the antibody molecule comprises the light chain LC45 (SEQ ID NO: 45). In yet another embodiment, the antibody comprises the light chain LC45, and the heavy chain HC25 (SEQ ID NO: 25) or 24 (SEQ ID NO: 24). In one embodiment, the antibody molecule comprises the light chain Ab032 (SEQ ID NO: 45) and the heavy chain 25 (SEQ ID NO: 25). In yet another embodiment, the antibody molecule comprises light chain LC52 (SEQ ID NO: 52) and heavy chain HC25 (SEQ ID NO: 25).

In an embodiment the antibody molecule comprises one or both of:
a) one or more framework regions (FRs) from heavy chain disclosed herein. E.g., the antibody molecule comprises one or more or all of FR1, FR2, FR3, or FR4, or FR sequences that differ individually, or collectively, by no more than 1, 2, 3, 4, of 5 amino acid residues, e.g., conservative residues, from a heavy chain disclosed herein; and
b) one or more framework regions (FRs) from light chain disclosed herein. E.g., the antibody molecule comprises one or more or all of FR1, FR2, FR3, or FR4, or FR sequences that differ individually, or collectively, by no more than 1, 2, 3, 4, of 5 amino acid residues, e.g., conservative residues, from light chain disclosed herein.

In one aspect, an anti-HA antibody molecule featured in the disclosure, or preparation, or isolated preparation thereof, comprises
(a) a heavy chain immunoglobulin variable domain comprising a sequence at least 60, 70, 80, 85, 87, 90, 95, 97, 98, or 99, e.g., 90%, homologous, to a heavy chain consensus sequence provided herein, e.g., the heavy chain consensus sequence provided in FIG. 2 or FIG. 13, e.g., the heavy chain consensus sequence provided in FIG. 2, SEQ ID NO:161; and
(b) a light chain immunoglobulin variable domain comprising a sequence at least 60, 70, 80, 85, 87, 90, 95, 97, 98, or 99, e.g., 95%, homologous, to a light chain consensus sequence provided herein, e.g., the light chain consensus sequence provided in FIG. 3 or FIG. 14, e.g., the light chain consensus sequence provided in FIG. 3, SEQ ID NO:62.

For example, in one embodiment, the anti-HA antibody molecule featured in the disclosure comprises one or both of:
(a) a heavy chain immunoglobulin variable domain comprising the sequence of SEQ ID NO:161, or a sequence at least 87% identical to SEQ ID NO:161; and
(b) a light chain immunoglobulin variable domain comprising the sequence SEQ ID NO:62, or a sequence at least 95% identical to SEQ ID NO:62.

In another embodiment the antibody molecule comprises:
(a) a heavy chain immunoglobulin variable domain comprising the sequence of SEQ ID NO:161, or a sequence at least 87% identical to SEQ ID NO:161; and
(b) a light chain immunoglobulin variable domain comprising the sequence SEQ ID NO:62, or a sequence at least 95% identical to SEQ ID NO:62, wherein said antibody molecule:
(i) fails to produce any escape mutants as determined by the failure of a viral titer to recover following at least 10, 9, 8, 7, 6, or 5 rounds of serial infections in cell culture with a mixture of the antibody molecule and an influenza virus (e.g., an influenza A virus, e.g., a Group 1 strain, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004, or an influenza B virus, e.g., B/Wisconsin/1/2010); and
(ii) produces fewer escape mutants than does a reference anti-HA antibody molecule, e.g., Ab 67-11, FI6, FI28, C179, F10, CR9114, or CR6261, such as when tested by the method described in (i).

In an embodiment, the disclosure features an antibody molecule comprising one or both of:

(a) a heavy chain immunoglobulin variable region comprising the sequence of SEQ ID NO:161, or a sequence that differs from SEQ ID NO:161 by not more than 1, 2, 3, 4, 5, 6, 8, 10, 11, 12, 13, 14, 15 or 16, e.g., by no more than 2, 3, 4, or 5 amino acids, e.g., conservative amino acids; and (b) a light chain immunoglobulin variable domain comprising the sequence SEQ ID NO:62, or a sequence that differs from SEQ ID NO:62 that differs by no more than 1, 2, 3, 4 or 5 amino acids, e.g., conservative amino acids.

In one embodiment, the 1, 2, 3, 4, 5, 6, 8, 10, 11, 12, 13, 14, 15 or 16 amino acid differences, e.g., conservative amino acid differences, in the heavy chain immunoglobulin variable region are in the FR regions of the heavy chain immunoglobulin variable domain. In another embodiment, the 1, 2, 3, 4 or 5 amino acid differences, e.g., conservative amino acid differences, in the light chain immunoglobulin variable domain are in the FR regions of the light chain immunoglobulin variable domain. In one embodiment, the amino acid differences in the heavy chain immunoglobulin variable region, or in the light chain immunoglobulin variable region, are conservative amino acid changes.

In an embodiment the binding agent, e.g., an antibody molecule, binds to an epitope, e.g., it has an epitope that overlaps with or is the same as, of an antibody disclosed herein, e.g., as determined by mutational analysis or crystal structure analysis.

In an embodiment the antibody molecule comprises one or both of:
a) one or more framework regions (FRs) from heavy chain consensus sequence disclosed herein. e.g., the antibody molecule comprises one or more or all of FR1, FR2, FR3, or FR4, or sequences that differ individually, or collectively, by no more than 1, 2, 3, 4, of 5 amino acid residues, e.g., conservative residues, from heavy chain consensus sequence disclosed herein; and
b) one or more framework regions (FRs) from light chain consensus sequence disclosed herein. e.g., the antibody molecule comprises one or more or all of FR1, FR2, FR3, or FR4, or sequences that differ individually, or collectively, by no more than 1, 2, 3, 4, of 5 amino acid residues, e.g., conservative residues, from light chain consensus disclosed herein.

In an embodiment the binding agent, e.g., an antibody molecule, specifically binds the HA antigen.

In another aspect, the disclosure features, a binding agent, e.g., an antibody molecule, or preparation, or isolated preparation thereof, comprising a structural or functional property of Ab 044.

In an embodiment, the antibody molecule competes with a reference antibody molecule, e.g., an antibody molecule described herein, for binding to a substrate, e.g., an HA. The reference antibody molecule can be:
a) an antibody molecule comprising:
i) a heavy chain immunoglobulin variable region segment comprising
a CDR1 comprising the sequence S-Y-A-M-H (SEQ ID NO:68);
a CDR2 comprising the sequence V-V-S-Y-D-G-N-Y-K-Y-Y-A-D-S-V-Q-G (SEQ ID NO:69); and
a CDR3 comprising the sequence D-S-R-L-R-S-L-L-Y-F-E-W-L-S-Q-G-Y-F-N-P (SEQ ID NO:70); and
ii) a light chain variable region segment comprising:
a CDR1 comprising the sequence Q-S-I-T-F-D-Y-K-N-Y-L-A (SEQ ID NO:145);
a CDR2 comprising the sequence W-G-S-Y-L-E-S (SEQ ID NO:72); and
a CDR3 comprising the sequence Q-Q-H-Y-R-T-P-P-S (SEQ ID NO:73).
b) an antibody molecule comprises one or both of: (i) a heavy chain immunoglobulin variable region segment comprising SEQ ID NO: 25; and (ii) a light chain variable region segment comprising SEQ ID NO:52; or
c) Ab 044.

The HA can be from a Group 1 strain, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004. Competition between the antibody molecule and a reference antibody molecule can be determined by evaluating the ability of one of the antibody molecules or the reference antibody molecule to decrease binding of the other to a substrate, e.g., HA, e.g., HA1 or HA5, e.g. from an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004. Reduction of the ability to bind can be evaluated by methods in the art. Reduction of the ability to bind can be evaluated, e.g., by one or more of:
a) BIAcore analysis;
b) ELISA assay; and
c) flow cytometry.

The antibody molecule can compete with the reference antibody such that binding of the reference antibody is decreased by 50% or more.

In an embodiment the antibody molecule binds to the same epitope, or a portion thereof, which the reference antibody molecule binds. In an embodiment the antibody molecule does not bind to the same epitope, or a portion thereof, which the reference antibody molecule binds.

In an embodiment the antibody molecule binds to the same epitope, or a portion thereof, on HA, as does a reference antibody molecule, e.g. an antibody molecule disclosed herein. The reference antibody molecule can be:
a) an antibody molecule comprising:
i) a heavy chain immunoglobulin variable region segment comprising
a CDR1 comprising the sequence S-Y-A-M-H (SEQ ID NO:68);
a CDR2 comprising the sequence V-V-S-Y-D-G-N-Y-K-Y-Y-A-D-S-V-Q-G (SEQ ID NO:69); and
a CDR3 comprising the sequence D-S-R-L-R-S-L-L-Y-F-E-W-L-S-Q-G-Y-F-N-P (SEQ ID NO:70); and
ii) a light chain variable region segment comprising:
a CDR1 comprising the sequence Q-S-I-T-F-D-Y-K-N-Y-L-A (SEQ ID NO:145);
a CDR2 comprising the sequence W-G-S-Y-L-E-S (SEQ ID NO:72); and
a CDR3 comprising the sequence Q-Q-H-Y-R-T-P-P-S (SEQ ID NO:73).
b) an antibody molecule comprises one or both of: (i) a heavy chain immunoglobulin variable region segment comprising SEQ ID NO: 25; and (ii) a light chain variable region segment comprising SEQ ID NO:52; or
c) Ab 044.

The HA can be HA1 or HA5, e.g., from an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004 Binding to the same epitope, or a portion thereof, can be shown by one or more of:
a) mutational analysis, e.g., binding to HA, or binding affinity for HA, is decreased or abolished if a residue is mutated;
b) analysis, e.g., comparison, of the crystal structure of the antibody molecule and HA and the crystal structure of a reference antibody and HA, e.g., to determine the touch points of each;
c) competition of the two antibodies for binding to HA, e.g., HA1 or HA5, from, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004; and
d) (c) and one or both of (a) and (b).

Competition between the antibody molecule and a reference antibody molecule can be determined by evaluating the ability of one of the antibody molecule or the reference antibody molecule to decrease binding of the other to a substrate, e.g., HA, e.g., HA1 or HA5, from, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004.

Reduction of the ability to bind can be evaluated by methods in the art. Reduction of the ability to bind can be evaluated, e.g., by one or more of:

a) BIAcore analysis;
b) ELISA assay; or
c) flow cytometry.

The antibody molecule can compete with the reference antibody such that binding of the reference antibody is decreased by 50% or more.

In an embodiment the binding agent, e.g., an antibody molecule, comprises one or both of:
a heavy chain variable region comprising at least 60, 70, 80, 85, 90, 95, 98 or 99 percent homology with SEQ ID NO: 25;
and a light chain variable region comprising at least 60, 70, 80, 85, 90, 95, 98 or 99 percent homology with SEQ ID NO: 52.

In an embodiment the binding agent, e.g., an antibody molecule, comprises one or both of:
a heavy chain variable region comprising at least 60, 70, 80, 85, 90, 95, 98 or 99 percent homology with SEQ ID NO: 25;
and a light chain variable region comprising at least 60, 70, 80, 85, 90, 95, 98 or 99 percent homology with SEQ ID NO: 52,
wherein, each HC CDR differs by no more than 1, 2, 3, 4 or 5 amino acids, e.g., 1 or 2, e.g., conservative amino acids, from the corresponding CDR of SEQ ID NO: 25 and each LC CDR differs by no more than 1, 2, 3, 4 or 5 amino acids, e.g., 1 or 2, e.g., conservative amino acids, from the corresponding CDR of SEQ ID NO: 52.

In an embodiment the binding agent, e.g., an antibody molecule, comprises one or both of:
a heavy chain variable region comprising at least 60, 70, 80, 85, 90, 95, 98 or 99 percent homology with SEQ ID NO: 25;
and a light chain variable region comprising at least 60, 70, 80, 85, 90, 95, 98 or 99 percent homology with SEQ ID NO: 52,
wherein the antibody molecule comprises 1, 2, 3, 4, 5, or all of:
(i) a HC CDR1 comprising: S at the 1st position and A at the 3rd position in HC CDR1;
(ii) a HC CDR2 comprising one or both, e.g., one of: V at the $2^{nd}$ position; or N at the $7^{th}$ position and Q at the $16^{th}$ position in HC CDR2;
(iii) a HC CDR3 comprising: R at the 3rd position (and optionally, L at the $3^{rd}$ position);
(iv) a LC CDR1 comprising one or both of, e.g., one of: I at the 3rd position; or D at the 6th position in LC CDR1;
(v) a LC CDR2 comprising one, two, or three of, e.g., one of: G at the $2^{nd}$ position; Y at the $4^{th}$ position; or L at the $5^{th}$ position in LC CDR2;
(vi) a LC CDR3 comprising: S at the $9^{th}$ position in LC CDR3;

In an embodiment, the binding agent, e.g., an antibody molecule, comprises:
(a) a heavy chain immunoglobulin variable region segment comprising SEQ ID NO:25 (or a sequence that differs by no more than 1, 2, 3, 4 or 5 amino acids, e.g., conservative amino acids, therefrom); and (b) a light chain variable region segment comprising SEQ ID NO:52 (or a sequence that differs by no more than 1, 2, 3, 4 or 5 amino acids, e.g., conservative amino acids, therefrom).

In an embodiment, the binding agent, e.g., an antibody molecule, comprises one or both of:
(a) a heavy chain immunoglobulin variable region segment comprising
  a CDR1 comprising the sequence S-Y-A-M-H (SEQ ID NO:68) (or a sequence that differs by no more than, 1, 2, 3, 4, or 5, e.g., 1 or 2 amino acids, e.g., conservative amino acids, therefrom);
  a CDR2 comprising the sequence V-V-S-Y-D-G-N-Y-K-Y-Y-A-D-S-V-Q-G (SEQ ID NO:69) (or a sequence that differs by no more than, 1, 2, 3, 4, or 5, e.g., 1 or 2 amino acids, e.g., conservative amino acids, therefrom);
  a CDR3 comprising the sequence D-S-R-L-R-S-L-L-Y-F-E-W-L-S-Q-G-Y-F-N-P (SEQ ID NO:70) (or a sequence that differs by no more than, 1, 2, 3, 4, or 5, e.g., 1 or 2 amino acids, e.g., conservative amino acids, therefrom); and
(b) a light chain variable region segment comprising
  a CDR1 comprising the sequence:
    Q-S-I-T-F-D-Y-K-N-Y-L-A (SEQ ID NO:145) (or a sequence that differs by no more than, 1, 2, 3, 4, or 5, e.g., 1 or 2 amino acids, e.g., conservative amino acids, therefrom);
  a CDR2 comprising the sequence W-G-S-Y-L-E-S (SEQ ID NO:72) (or a sequence that differs by no more than, 1, 2, 3, 4, or 5, e.g., 1 or 2 amino acids, e.g., conservative amino acids, therefrom);
  a CDR3 comprising the sequence Q-Q-H-Y-R-T-P-P-S (SEQ ID NO:73) (or a sequence that differs by no more than, 1, 2, 3, 4, or 5, e.g., 1 or 2 amino acids, e.g., conservative amino acids, therefrom).

In an embodiment the binding agent, e.g., an antibody molecule, comprises one or both of:
a) LC CDR1-3, that collectively, differ from the AB 044 LC CDR1-3 by no more than, 1, 2, 3, 4, 5, 6, 7, 8, 9, or 10, e.g., 1, 2, 3, or 4, amino acids, e.g., conservative amino acids; and
b) HC CDR1-3, that collectively, differ from the AB 044 HC CDR1-3 by no more than, 1, 2, 3, 4, 5, 6, 7, 8, 9, or 10, e.g., 1, 2, 3, or 4, amino acids, e.g., conservative amino acids.

In one embodiment, the antibody molecule comprises one or both of:
(a) a heavy chain immunoglobulin variable region segment comprising SEQ ID NO: 25; and (b) a light chain variable region segment comprising SEQ ID NO:52.

In an embodiment, the binding agent is an antibody molecule comprising one or both of:
(a) a heavy chain immunoglobulin variable region segment comprising
  a CDR1 comprising the sequence S̲-Y-A̲-M-H (SEQ ID NO:68) (or a sequence that differs by no more than, 1, 2, or 3, e.g., 1 or 2, amino acids, e.g., conservative amino acids, there from, optionally provided that at least 1 or 2 of the highlighted residue are not changed, e.g., both S and A̲ are not changed);
  a CDR2 comprising the sequence V-V̲-S-Y-D-G-N̲-Y-K-Y-Y-A-D-S-V-Q̲-G (SEQ ID NO:69) (or a sequence that differs by no more than, 1, 2, 3, 4, or 5, e.g., 1 or 2 amino acids, e.g., conservative amino acids, therefrom, optionally provided that at least 1, 2, or 3 of the highlighted residues are not changed, e.g., V̲ or both N̲ and Q̲ or all three of V̲, N̲, and Q̲ are not changed);
  a CDR3 comprising the sequence D-S-R̲-L-R-S-L-L-Y-F-E-W-L-S-Q-G-Y-F-N-P (SEQ ID NO:70) (or a sequence that differs by no more than, 1, 2, 3, 4, or 5, e.g., 1 or 2 amino acids, e.g., conservative amino acids, therefrom, optionally provided that R is not changed); and (b) a light chain variable region segment comprising
a CDR1 comprising the sequence:
Q-S-I-T-F-D-Y-K-N-Y-L-A (SEQ ID NO:145) (or a sequence that differs by no more than, 1, 2, 3, 4, or 5, e.g., 1 or 2, amino acids, e.g., conservative amino acids, therefrom, optionally provided that at least 1 or 2 of the highlighted residues are not changed, e.g., I or D is not changed);
a CDR2 comprising the sequence W-G-S-Y-L-E-S (SEQ ID NO:72) (or a sequence that differs by no more than, 1, 2, 3, 4, or 5, e.g., 1 or 2, amino acids, e.g., conservative amino acids, therefrom, optionally provided that at least 1, 2 or 3 of the highlighted residues are not changed, e.g., 1, 2 or all of G, Y, and L are not changed);
a CDR3 comprising the sequence Q-Q-H-Y-R-T-P-P-S (SEQ ID NO:73) (or a sequence that differs by no more than, 1, 2, 3, 4, or 5, e.g., 1 or 2, amino acids, e.g., conservative amino acids, therefrom, optionally provided that at least 1 or both of the highlighted residues are not changed, e.g., S is not changed).

In an embodiment a CDR of the light or heavy chain includes one of the highlighted residues, or one of the highlighted combinations of residues, for that CDR, (i.e., while other residues in that CDR might be changed, the highlighted residue or combination of residues, are not changed). E.g., in an embodiment, V or both N and Q, for heavy chain CDR2 are not changed.

In an embodiment a CDR of the light and a CDR of the heavy chain each includes one of the highlighted residues, or one of the highlighted combinations of residues, for that CDR.

In an embodiment each of two CDRs in the antibody molecule includes one of the highlighted residues, or one of the highlighted combinations of residues, for that CDR. In embodiments both are in the light chain. In embodiments both are in the heavy chain.

In an embodiment each of the three CDRs in the heavy chain includes one of the highlighted residues, or one of the highlighted combinations of residues, for that CDR.

In an embodiment each of the three CDRs in the light chain includes one of the highlighted residues, or one of the highlighted combinations of residues, for that CDR.

In an embodiment each of the six CDRs in the heavy and light chain includes one of the highlighted residues, or one of the highlighted combinations of residues, for that CDR.

In one embodiment, the binding agent is an antibody molecule that comprises one or more or all of the following properties:
(a) both S and A in HC CDR1 are unchanged;
(b) V or both N and Q or all three of V, N, and Q in HC CDR2 are unchanged;
(c) R in HC CDR3 is unchanged;
(d) One or both of I and D in LC CDR1 are unchanged.
(e) 1, 2 or 3 of G, Y, and L in LC CDR2 are unchanged; OR
(f) S in LC CDR3 is unchanged.

In an embodiment the antibody molecule comprises 1, 2, 3, 4, 5, or all 6 properties selected from (a) to (f).

In an embodiment, the antibody molecule comprises a heavy chain having a one or more properties selected from (a), (b), and (c) and a light chain having one or more properties selected from (d), (e), and (f).

In one embodiment, the binding agent, e.g., an antibody molecule, comprises one or both of:

(a) a heavy chain immunoglobulin variable region segment comprising:
a CDR1 comprising the sequence S-Y-A-M-H (SEQ ID NO:68);
a CDR2 comprising the sequence V-V-S-Y-D-G-N-Y-K-Y-Y-A-D-S-V-Q-G (SEQ ID NO:69);
a CDR3 comprising the sequence D-S-R-L-R-S-L-L-Y-F-E-W-L-S-Q-G-Y-F-N-P (SEQ ID NO:70); and
(b) a light chain variable region segment comprising
a CDR1 comprising the sequence Q-S-I-T-F-D-Y-K-N-Y-L-A (SEQ ID NO:145);
a CDR2 comprising the sequence W-G-S-Y-L-E-S (SEQ ID NO:72); and
a CDR3 comprising the sequence Q-Q-H-Y-R-T-P-P-S (SEQ ID NO:73).

In some embodiments, the antibody molecule comprises one or more or all of the following properties: (i) it fails to produce any escape mutants as determined by the failure of a viral titer to recover following at least 10, 9, 8, 7, 6, or 5 rounds of serial infections in cell culture with a mixture of the antibody molecule and an influenza virus (e.g., an influenza A virus, e.g., a Group 1 strain, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004, or an influenza B virus, e.g., B/Wisconsin/1/2010); and (ii) it produces fewer escape mutants than does a reference anti-HA antibody molecule, such as Ab 67-11, FI6, FI28, C179, F10, CR9114, or CR6261, such as when tested by the method described in (i).

In an embodiment the antibody molecule comprises one or both of:

a) one or more framework regions (FRs) from SEQ ID NO: 25 e.g., the antibody molecule comprises one or more or all of FR1, FR2, FR3, or FR4, or sequences that differ individually, or collectively, by no more than 1, 2, 3, 4, of 5 amino acid residues, e.g., conservative residues, from SEQ ID NO: 25; and b) one or more framework regions (FRs) from SEQ ID NO: 52. E.g., the antibody molecule comprises one or more or all of FR1, FR2, FR3, or FR4, or sequences that differ individually, or collectively, by no more than 1, 2, 3, 4, of 5 amino acid residues, e.g., conservative residues, from SEQ ID NO: 52.

In one embodiment, the antibody molecule comprises:

(a) a heavy chain immunoglobulin variable region segment that further comprises one or more or all of:

an FR1 comprising the sequence Q-V-Q-L-L-E-T-G-G-G-L-V-K-P-G-Q-S-L-K-L-S-C-A-A-S-G-F-T-F-T (SEQ ID NO:74) (or a sequence that differs by no more than, 1, 2, 3, 4, or 5, e.g., 1 or 2, amino acids, e.g., conservative amino acids, therefrom, optionally provided that T is not changed);

an FR2 comprising the sequence W-V-R-Q-P-P-G-K-G-L-E-W-V-A (SEQ ID NO:75) (or a sequence that differs by no more than, 1, 2, 3, 4, or 5, e.g., 1 or 2, amino acids, e.g., conservative amino acids, therefrom, optionally provided that W is not changed, or that if changed, is other than R);

an FR3 comprising the sequence R-F-T-I-S-R-D-N-S-K-N-T-L-Y-L-Q-M-N-S-L-R-A-E-D-T-A-V-Y-Y-C-A-K (SEQ ID NO:76) (or a sequence that differs by no more than, 1, 2, 3, 4, or 5, e.g., 1 or 2, amino acids, e.g., conservative amino acids, therefrom, optionally provided that one, two or three of I, R, or L is not changed, or that if I is changed it is other than G, if R is changed it is other than P. or if L is changed it is other than A); and an FR4 comprising the sequence W-G-Q-G-T-T-L-T-V-S-S (SEQ ID NO:77) (or a sequence that differs by no more than, 1, 2, 3, 4, or 5, e.g., 1 or 2, amino acids, e.g., conservative amino acids, therefrom) or W-G-Q-G-T-T-V-T-V-S-S(SEQ ID NO:171) (or a sequence that differs by no more than, 1, 2, 3, 4, or 5, e.g., 1 or 2, amino acids, e.g., conservative amino acids, therefrom); and (b) a light chain immunoglobulin variable region segment comprising one or more or all of:

an FR1 comprising the sequence D-I-Q-M-T-Q-S-P-S-S-L-S-A-S-V-G-D-R-V-T-I-T-C-R-S-S (SEQ ID NO:78) (or a sequence that differs by no more than, 1, 2, 3, 4, or 5, e.g., 1 or 2, amino acids, e.g., conservative amino acids, therefrom, optionally provided that R is not changed);

an FR2 comprising the sequence W-Y-Q-Q-K-P-G-K-A-P-K-L-L-I-Y (SEQ ID NO:79) (or a sequence that differs by no more than, 1, 2, 3, 4, or 5, e.g., 1 or 2 amino acids, e.g., conservative amino acids, therefrom);

an FR3 comprising the sequence G-V-P-S-R-F-S-G-S-G-S-G-T-D-F-T-L-T-I-S-S-L-Q-P-E-D-F-A-T-Y-Y-C (SEQ ID NO:80) (or a sequence that differs by no more than, 1, 2, 3, 4, or 5, e.g., 1 or 2 amino acids, e.g., conservative amino acids, therefrom, optionally provided that C is not changed, or if changed, is other than P); and an FR4 comprising the sequence F-G-Q-G-T-K-V-E-I-K (SEQ ID NO:81) (or a sequence that differs by no more than, 1, 2, 3, 4, or 5, e.g., 1 or 2 amino acids, e.g., conservative amino acids, therefrom).

In an embodiment a FR of the light or heavy chain includes one of the highlighted residues, or one of the highlighted combinations of residues, for that FR, (i.e., while other residues in that FR might be changed, the highlighted residue or combination of residues, are not changed). E.g., in an embodiment, one, two or three of I, R, or L for heavy chain FR3 is not changed.

In an embodiment a FR of the light and a FR of the heavy chain each includes one of the highlighted residues, or one of the highlighted combinations of residues, for that FR.

In an embodiment each of two FRs in the antibody molecule includes one of the highlighted residues, or one of the highlighted combinations of residues, for that FR. In embodiments both are in the light chain. In embodiments both are in the heavy chain.

In an embodiment each of FR2 and FR3 in the heavy chain includes one of the highlighted residues, or one of the highlighted combinations of residues, for that FR.

In an embodiment each of FR1 and FR2 in the heavy and light chain includes one of the highlighted residues for that FR.

In an embodiment all of the highlighted residues in heavy chain FR1-4 are unchanged.

In an embodiment all of the highlighted residues in light chain FR1-4 are unchanged.

In an embodiment all of the highlighted residues in both heavy and light chain FR1-4 are unchanged.

In an embodiment, sequence of FR1 of the heavy chain variable region segment is Q-V-Q-L-L-E-T-G-G-G-L-V-K-P-G-Q-S-L-K-L-S-C-A-A-S-G-F-T-F-T (SEQ ID NO:74).

In an embodiment, sequence of FR1 of the heavy chain variable region segment is E-V-Q-L-L-E-S-G-G-G-L-V-K-P-G-Q-S-L-K-L-S-C-A-A-S-G-F-T-F-T (SEQ ID NO:183).

In another embodiment, the binding agent, e.g., an antibody molecule, comprises one or more or all of the following properties: (a) it fails to produce any escape mutants as determined by the failure of a viral titer to recover following at least 10, 9, 8, 7, 6, or 5 rounds of serial infections in cell culture with a mixture of the antibody molecule and an influenza virus (e.g., an influenza A virus, e.g., a Group 1 strain, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004, or an influenza B virus, e.g., B/Wisconsin/1/2010); (b) it produces fewer escape mutants than does a reference anti-HA antibody molecule, e.g., Ab 67-11, FI6, FI28, C179, or CR6261, e.g., when tested by the method described in (a); (c) it binds with high affinity to a hemagglutinin (HA) of at least 1, 2, 3, 4 or 5 influenza subtypes of Group 1 and at least 1, 2, 3, 4 or 5 influenza subtypes of Group 2; (d) it treats or prevents infection by at least 1, 2, 3, 4 or 5 influenza subtypes of Group 1, and by at least 1, 2, 3, 4 or 5 influenza subtypes of Group 2; (e) it inhibits fusogenic activity of the targeted HA; (f) it treats or prevents infection by a Group 1 virus, wherein the virus is an H1, H5, or H9 virus; and treats or prevents infection by a Group 2 virus, wherein the virus is an H3 or H7 virus; (g) it treats or prevents infection by influenza A strains H1N1 and H3N2; (h) it is effective for prevention or treatment of infection, e.g., in humans or mice, with H1N1 and H3N2 when administered at 50 mg/kg, 25 mg/kg, 10 mg/kg, 6 mg/kg, 5 mg/kg, 4 mg/kg, 3 mg/kg, 2 mg/kg or 1 mg/kg; (i) it treats or prevents infection by influenza A strains H5N1; (j) it is effective for prevention or treatment of infection, e.g., in humans or mice, with H5N1 when administered at 50 mg/kg, 25 mg/kg, 10 mg/kg, 6 mg/kg, 5 mg/kg, 4 mg/kg, 3 mg/kg, 2 mg/kg or 1 mg/kg; (k) it binds with high affinity to a hemagglutinin (HA) of an influenza B virus, e.g., B/Wisconsin/1/2010; (l) it treats or prevents infection by an influenza B virus, e.g., B/Wisconsin/1/2010; (m) it is effective for prevention or treatment of infection, e.g., in humans or mice, with an influenza B virus, e.g., B/Wisconsin/1/2010 when administered at 50 mg/kg, 25 mg/kg, 10 mg/kg, 6 mg/kg, 5 mg/kg, 4 mg/kg, 3 mg/kg, 2 mg/kg or 1 mg/kg; (n) the concentration of antibody molecule required for 50% neutralization of influenza A virus is less than 10 µg/mL; (o) the concentration of antibody molecule required for 50% neutralization of influenza B virus, e.g., B/Wisconsin/1/2010, is less than 10 µg/mL; (p) it prevents or minimizes secondary infection (e.g., secondary bacterial infection) or effects thereof on a subject; (q) it is effective for preventing or minimizing secondary infection (e.g., secondary bacterial infection) or effects thereof on a subject when administered at 50 mg/kg, 25 mg/kg, 10 mg/kg, 6 mg/kg, 5 mg/kg, 4 mg/kg, 3 mg/kg, 2 mg/kg or 1 mg/kg; (r) it binds an epitope which comprises or consists of the hemagglutinin trimer interface; and (s) it binds an epitope other than that bound by a reference anti-HA antibody molecule, e.g., Ab 67-11, FI6, FI28, C179, F10, CR9114, or CR6261, e.g., when tested by a method disclosed herein, e.g., by competition in an ELISA assay.

In an embodiment the binding agent, e.g., an antibody molecule, specifically binds the HA antigen.

In an embodiment, the antibody molecule binds an epitope that has one, two, three, four, five, or all of, the following properties a-f:
a) it includes one, two, or all of, H3 HA1 residues N38, I278, and D291;
b) it includes H3 HA2 residue N12;
c) it does not include one, two or all of, H3 HA1 residues Q327, T328, and R329;
d) it does not include one, two, three, four, or all of, H3 HA2 residues G1, L2, F3, G4, and D46;
e) it includes one, two, or all of, H3 HA1 residues T318, R321, and V323; or
f) it includes 1, 2, 3, 4, 5, 6, 7, 8, 9, 10, 11, 12, 13, 14, 15, 16, 17, or all of, H3 HA2 residues A7, E11, I18, D19, G20, W21, L38, K39, T41, Q42, A43, I45, I48, N49, L52, N53, I56, and E57.

In an embodiment the antibody molecule has properties: a; and b.

In an embodiment the antibody molecule has properties: c; and d.
In an embodiment the antibody molecule has properties: a; and c or d.
In an embodiment the antibody molecule has properties: b; and c or d.
In an embodiment the antibody molecule has properties: c; and a or b.
In an embodiment the antibody molecule has properties: d; and a or b.
In an embodiment the antibody molecule has properties: a, b, c and d.
In an embodiment the antibody molecule has properties: a, b, c, d, e, and f.
In an embodiment, the antibody molecule has a $K_D$ for H3 of equal to or less than $10^{-6}$, wherein said $K_D$ is increased by at least 2, 5, 10, or 100 fold, by a mutation or mutations in any of:
a) H3 HA1 residues N38, I278, or D291;
b) H3 HA2 residue N12;
c) H3 HA1 residues T318, R321, or V323; or
d) H3 HA2 residues A7, E11, I18, D19, G20, W21, L38, K39, T41, Q42, A43, I45, I48, N49, L52, N53, I56, or E57.
In an embodiment, the antibody molecule has a $K_D$ for H3 of equal to or less than $10^{-6}$, wherein said $K_D$ is increased by no more than 2, or 5 fold, by a mutation or mutations in any of:
c) H3 HA1 residues Q327, T328, or R329; or
d) H3 HA2 residues G1, L2, F3, G4, or D46.
In an embodiment, the antibody molecule binds an epitope that has one, two, three, four, five, or all of, the following properties a-f:
aa) it includes one, two, or all of, H1 HA1 residues H31, N279, and S292;
bb) it includes H1 HA2 residue G12;
cc) it does not include one or both of H1 HA1 residues Q328 and S329;
dd) it does not include one, two, three, four, or all of, H1 HA2 residues G1, L2, F3, G4, and D46;
ee) it includes one, two, or all of, H1 HA1 residues T319, R322, and I324 are bound by both Ab 044 and FI6; or
ff) it includes 1, 2, 3, 4, 5, 6, 7, 8, 9, 10, 11, 12, 13, 14, 15, 16, 17, or all of, H1 HA2 residues A7, E11, I18, D19, G20, W21, Q38, K39, T41, Q42, N43, I45, I48, T49, V52, N53, I56, and E57.
In an embodiment the antibody molecule has properties: aa; and bb.
In an embodiment the antibody molecule has properties: cc; and dd.
In an embodiment the antibody molecule has properties: aa; and cc or dd.
In an embodiment the antibody molecule has properties: bb; and cc or dd.
In an embodiment the antibody molecule has properties: cc; and aa or bb.
In an embodiment the antibody molecule has properties: dd; and aa or bb.
In an embodiment the antibody molecule has properties: aa, bb, cc and dd.
In an embodiment the antibody molecule has properties: aa, bb, cc, dd, ee, and ff.
In an embodiment, the antibody molecule has a $K_D$ for H1 of equal to or less than $10^{-6}$, wherein said $K_D$ is increased by at least 2, 5, 10, or 100 fold, by a mutation or mutations in any of:

aa) H1 HA1 residues H31, N279, and S292;
bb) H1 HA2 residue G12;
cc) H1 HA1 residues T319, R322, and I324; or
dd) H1 HA2 residues A7, E11, I18, D19, G20, W21, Q38, K39, T41, Q42, N43, I45, I48, T49, V52, N53, I56, and E57.
In an embodiment, the antibody molecule has a $K_D$ for H1 of equal to or less than $10^{-6}$, wherein said $K_D$ is increased by no more than 2, or 5 fold, by a mutation or mutations in any of:
cc) H1 HA1 residues Q328 and S329; or
dd) H1 HA2 residues G1, L2, F3, G4, and D46;
In an embodiment the antibody molecule has one, two, three or all of the following properties:
a and aa;
b and bb;
c and cc;
d and dd.
In an embodiment the molecule has properties c, cc, d, and dd.
In another aspect, the disclosure features, a binding agent, e.g., an antibody molecule, or preparation, or isolated preparation thereof, comprising a structural or functional property of Ab 069.
In an embodiment, the antibody molecule competes with a reference antibody molecule, e.g., an antibody molecule described herein, for binding to a substrate, e.g., an HA. The reference antibody molecule can be:
a) an antibody molecule comprising:
i) a heavy chain immunoglobulin variable region segment comprising
a CDR1 comprising the sequence S-Y-A-M-H (SEQ ID NO:68);
a CDR2 comprising the sequence V-V-S-Y-D-G-N-Y-K-Y-Y-A-D-S-V-Q-G
(SEQ ID NO:69); and
a CDR3 comprising the sequence D-S-R-L-R-S-L-L-Y-F-E-W-L-S-Q-G-Y-F-N-P (SEQ ID NO:70); and
ii) a light chain variable region segment comprising:
a CDR1 comprising the sequence Q-S-I-T-F-E-Y-K-N-Y-L-A (SEQ ID NO:172);
a CDR2 comprising the sequence W-G-S-Y-L-E-S (SEQ ID NO:72); and
a CDR3 comprising the sequence Q-Q-H-Y-R-T-P-P-S (SEQ ID NO:73).
b) an antibody molecule comprises one or both of: (i) a heavy chain immunoglobulin variable region segment comprising SEQ ID NO: 25; and (ii) a light chain variable region segment comprising SEQ ID NO:155; or
c) Ab 069.
The HA can be HA1 or HA 5, e.g. from an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004. Competition between the antibody molecule and a reference antibody molecule can be determined by evaluating the ability of one of the antibody molecule or the reference antibody molecule to decrease binding of the other to a substrate, e.g., HA, e.g., HA1 or HA5, e.g. from an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004. Reduction of the ability to bind can be evaluated by methods in the art. Reduction of the ability to bind can be evaluated, e.g., by one or more of:
a) BIAcore analysis;
b) ELISA assay;
c) flow cytometry.

The antibody molecule can compete with the reference antibody such that binding of the reference antibody is decreased by 50% or more. In an embodiment the antibody molecule binds to the same epitope, or a portion thereof, which the reference antibody molecule binds. In an embodiment the antibody molecule does not bind to the same epitope, or a portion thereof, which the reference antibody molecule binds.

In an embodiment the antibody molecule binds to the same epitope, or a portion thereof, on HA, as does a reference antibody molecule, e.g. an antibody molecule disclosed herein. The reference antibody molecule can be:
  a) an antibody molecule comprising:
    i) a heavy chain immunoglobulin variable region segment comprising
      a CDR1 comprising the sequence S-Y-A-M-H (SEQ ID NO:68);
      a CDR2 comprising the sequence V-V-S-Y-D-G-N-Y-K-Y-Y-A-D-S-V-Q-G
      (SEQ ID NO:69); and
      a CDR3 comprising the sequence D-S-R-L-R-S-L-L-Y-F-E-W-L-S-Q-G-Y-F-N-P (SEQ ID NO:70); and
    ii) a light chain variable region segment comprising:
      a CDR1 comprising the sequence Q-S-I-T-F-E-Y-K-N-Y-L-A (SEQ ID NO:172);
      a CDR2 comprising the sequence W-G-S-Y-L-E-S (SEQ ID NO:72); and
      a CDR3 comprising the sequence Q-Q-H-Y-R-T-P-P-S (SEQ ID NO:73).
  b) an antibody molecule comprises one or both of: (i) a heavy chain immunoglobulin variable region segment comprising SEQ ID NO: 25; and (ii) a light chain variable region segment comprising SEQ ID NO:155; or
  c) Ab 069.

The HA can be HA1 or HA5, e.g. from an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004. Binding to the same epitope, or a portion thereof, can be shown by one or more of:
  a) mutational analysis, e.g., binding or lack thereof to mutant HA, e.g., if a residue is mutated;
  b) analysis, e.g., comparison, of the crystal structure of the antibody molecule and HA and the crystal structure of a reference antibody and HA, e.g., to determine the touch points of each;
  c) competition of the two antibodies for binding to HA, e.g., HA1 or HA5, from, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004; or
  d) (c) and one or both of (a) and (b);

Competition between the antibody molecule and a reference antibody molecule can be determined by evaluating the ability of one of the antibody molecule or the reference antibody molecule to decrease binding of the other to a substrate, e.g., HA, e.g., HA1 or HA5, e.g. from an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004. Reduction of the ability to bind can be evaluated by methods in the art. Reduction of the ability to bind can be evaluated, e.g., by one or more of:
  a) BIAcore analysis;
  b) ELISA assay;
  c) flow cytometry. The antibody molecule can compete with the reference antibody such that binding of the reference antibody is decreased by 50% or more.

In an embodiment the binding agent, e.g., an antibody molecule, comprises one or both of:
  a heavy chain variable region comprising at least 60, 70, 80, 85, 90, 95, 98 or 99 percent homology with SEQ ID NO: 25;
  and a light chain variable region comprising at least 60, 70, 80, 85, 90, 95, 98 or 99 percent homology with SEQ ID NO: 155.

In an embodiment the binding agent, e.g., an antibody molecule, comprises one or both of:
  a heavy chain variable region comprising at least 60, 70, 80, 85, 90, 95, 98 or 99 percent homology with SEQ ID NO: 25;
  and a light chain variable region comprising at least 60, 70, 80, 85, 90, 95, 98 or 99 percent homology with SEQ ID NO: 155,
  wherein each HC CDR differs by no more than 1, 2, 3, 4 or 5 amino acids, e.g., 1 or 2, e.g., conservative amino acids, from the corresponding CDR of SEQ ID NO: 25 and each LC CDR differs by no more than 1, 2, 3, 4 or 5 amino acids, e.g., 1 or 2, e.g., conservative amino acids, from the corresponding CDR of SEQ ID NO: 155.

In an embodiment the binding agent, e.g., an antibody molecule, comprises one or both of:
  a heavy chain variable region comprising at least 60, 70, 80, 85, 90, 95, 98 or 99 percent homology with SEQ ID NO: 25;
  and a light chain variable region comprising at least 60, 70, 80, 85, 90, 95, 98 or 99 percent homology with SEQ ID NO: 155,
  wherein the antibody molecule comprises 1, 2, 3, 4, 5, or all of:
    (i) a HC CDR1 comprising: S at the 1st position and A at the 3rd position in HC CDR1;
    (ii) a HC CDR2 comprising one or both, e.g., one of: V at the 2nd position; or N at the $7^{th}$ position and Q at the $16^{th}$ position in HC CDR2;
    (iii) a HC CDR3 comprising: R at the 3rd position (and optionally, L at the $3^{rd}$ position);
    (iv) a LC CDR1 comprising one or both of, e.g., one of: I at the 3rd position; or E at the 6th position in LC CDR1;
    (v) a LC CDR2 comprising one, two or three of, e.g., one of: G at the 2nd position; Y at the $4^{th}$ position; or L at the $5^{th}$ position in LC CDR2;
    (vi) a LC CDR3 comprising: S at the $9^{th}$ position in LC CDR3;

In an embodiment, the binding agent, e.g., an antibody molecule, comprises one or both of:
  (a) a heavy chain immunoglobulin variable region segment comprising SEQ ID NO:25 (or a sequence that differs by no more than 1, 2, 3, 4 or 5 amino acids, e.g., conservative amino acids, therefrom); and
  (b) a light chain variable region segment comprising SEQ ID NO:155 (or a sequence that differs by no more than 1, 2, 3, 4 or 5 amino acids, e.g., conservative amino acids, therefrom).

In one embodiment, the antibody molecule comprises one or both of:
  (a) a heavy chain immunoglobulin variable region segment comprising SEQ ID NO: 25; and
  (b) a light chain variable region segment comprising SEQ ID NO:155.

In an embodiment, the binding agent, e.g., an antibody molecule, comprises one or both of:
  (a) a heavy chain immunoglobulin variable region segment comprising a CDR1 comprising the sequence S-Y-A-M-H (SEQ ID NO:68) (or a sequence that differs by no more than, 1, 2, 3, 4, or 5, e.g., 1 or 2 amino acids, e.g., conservative amino acids, therefrom);
a CDR2 comprising the sequence V-V-S-Y-D-G-N-Y-K-Y-Y-A-D-S-V-Q-G (SEQ ID NO:69) (or a sequence that differs by no more than, 1, 2, 3, 4, or 5, e.g., 1 or 2 amino acids, e.g., conservative amino acids, therefrom);
a CDR3 comprising the sequence D-S-R-L-R-S-L-L-Y-F-E-W-L-S-Q-G-Y-F-N-P (SEQ ID NO:70) (or a sequence that differs by no more than, 1, 2, 3, 4, or 5, e.g., 1 or 2 amino acids, e.g., conservative amino acids, therefrom); and
(b) a light chain variable region segment comprising
a CDR1 comprising the sequence:
Q-S-I-T-F-E-Y-K-N-Y-L-A (SEQ ID NO: 172) or a sequence that differs by no more than, 1, 2, 3, 4, or 5, e.g., 1 or 2 amino acids, e.g., conservative amino acids, therefrom);
a CDR2 comprising the sequence W-G-S-Y-L-E-S (SEQ ID NO:72) (or a sequence that differs by no more than, 1, 2, 3, 4, or 5, e.g., 1 or 2 amino acids, e.g., conservative amino acids, therefrom);
a CDR3 comprising the sequence Q-Q-H-Y-R-T-P-P-S (SEQ ID NO:73) (or a sequence that differs by no more than, 1, 2, 3, 4, or 5, e.g., 1 or 2 amino acids, e.g., conservative amino acids, therefrom).

In an embodiment the binding agent, e.g., an antibody molecule, comprises one or both of:
a) LC CDR1-3, that collectively, differ from the AB 069 LC CDR1-3 by no more than, 1, 2, 3, 4, 5, 6, 7, 8, 9, or 10, e.g., 1, 2, 3, or 4, amino acids, e.g., conservative amino acids; and
b) HC CDR1-3, that collectively, differ from the AB 069 HC CDR1-3 by no more than, 1, 2, 3, 4, 5, 6, 7, 8, 9, or 10, e.g., 1, 2, 3, or 4, amino acids, e.g., conservative amino acids.

In an embodiment, the binding agent is an antibody molecule comprising one or both of:
(a) a heavy chain immunoglobulin variable region segment comprising
a CDR1 comprising the sequence S-Y-A-M-H (SEQ ID NO:68) (or a sequence that differs by no more than, 1, 2, or 3, e.g., 1 or 2 amino acids, e.g., conservative amino acids, therefrom, optionally provided that at least 1 or 2 of the highlighted residues are not changed, e.g., both S and A are not changed);
a CDR2 comprising the sequence V-V-S-Y-D-G-N-Y-K-Y-Y-A-D-S-V-Q-G (SEQ ID NO:69) (or a sequence that differs by no more than, 1, 2, 3, 4, or 5, e.g., 1 or 2 amino acids, e.g., conservative amino acids, therefrom, optionally provided that at least 1, 2, or 3 of the highlighted residues are not changed, e.g., V or both N and Q or all three of V, N, and Q are not changed);
a CDR3 comprising the sequence D-S-R-L-R-S-L-L-Y-F-E-W-L-S-Q-G-Y-F-N-P (SEQ ID NO:70) (or a sequence that differs by no more than, 1, 2, 3, 4, or 5, e.g., 1 or 2 amino acids, e.g., conservative amino acids, therefrom optionally provided that, R is not changed); and
(b) a light chain variable region segment comprising
a CDR1 comprising the sequence:
Q-S-I-T-F-E-Y-K-N-Y-L-A (SEQ ID NO: 172) or a sequence that differs by no more than, 1, 2, 3, 4, or 5, e.g., 1 or 2 amino acids, e.g., conservative amino acids, therefrom, optionally provided that at least 1 or 2 of the highlighted residues are not changed, e.g., I or E is not changed);
a CDR2 comprising the sequence W-G-S-Y-L-E-S (SEQ ID NO:72) (or a sequence that differs by no more than, 1, 2, 3, 4, or 5, e.g., 1 or 2 amino acids, e.g., conservative amino acids, therefrom, optionally provided that at least 1, 2, or 3 of the highlighted residues are not changed, e.g., 1, 2 or all of G, Y, and L are not changed);
a CDR3 comprising the sequence Q-Q-H-Y-R-T-P-P-S (SEQ ID NO:73) (or a sequence that differs by no more than, 1, 2, 3, 4, or 5, e.g., 1 or 2 amino acids, e.g., conservative amino acids, therefrom, optionally provided that, at least one or both of the highlighted residues are not changed, e.g., S is not changed).

In an embodiment a CDR of the light or heavy chain includes one of the highlighted residues, or one of the highlighted combinations of residues, for that CDR, (i.e., while other residues in that CDR might be changed, the highlighted residue or combination of residues, are not changed).

In an embodiment a CDR of the light and a CDR of the heavy chain each includes one of the highlighted residues, or one of the highlighted combinations of residues, for that CDR.

In an embodiment each of two CDRs in the antibody molecule includes one of the highlighted residues, or one of the highlighted combinations of residues, for that CDR. In embodiments both are in the light chain. In embodiments both are in the heavy chain.

In an embodiment each of the three CDRs in the heavy chain includes one of the highlighted residues, or one of the highlighted combinations of residues, for that CDR.

In an embodiment each of the three CDRs in the light chain includes one of the highlighted residues, or one of the highlighted combinations of residues, for that CDR.

In an embodiment each of the six CDRs in the heavy and light chain includes one of the highlighted residues, or one of the highlighted combinations of residues, for that CDR.

In one embodiment, the binding agent is an antibody molecule that comprises one or more or all of the following properties:
(a) both S and A in HC CDR1 are unchanged.
(b) V or both N and Q or all three of V, N, and Q in HC CDR2 are unchanged.
(c) R in HC CDR3 is unchanged.
(d) one or both of I and E in LC CDR1 are unchanged.
(e) 1, 2 or 3 of G, Y, and L in LC CDR2 are unchanged;
(f) S in LC CDR3 is unchanged.

In an embodiment the antibody molecule comprises 1, 2, 3, 4, 5, or all 6 properties selected from (a) to (f).

In an embodiment, the antibody molecule comprises a heavy chain having a one or more properties selected from (a), (b), and (c) and a light chain having one or more properties selected from (d), (e), and (f).

In one embodiment, the antibody molecule comprises one or both of:
(a) a heavy chain immunoglobulin variable region segment comprising:
a CDR1 comprising the sequence S-Y-A-M-H (SEQ ID NO:68);
a CDR2 comprising the sequence V-V-S-Y-D-G-N-Y-K-Y-Y-A-D-S-V-Q-G (SEQ ID NO:69);
a CDR3 comprising the sequence D-S-R-L-R-S-L-L-Y-F-E-W-L-S-Q-G-Y-F-N-P (SEQ ID NO:70); and
(b) a light chain variable region segment comprising
a CDR1 comprising the sequence Q-S-I-T-F-E-Y-K-N-Y-L-A (SEQ ID NO:172);
a CDR2 comprising the sequence W-G-S-Y-L-E-S (SEQ ID NO:72); and a CDR3 comprising the sequence Q-Q-H-Y-R-T-P-P-S (SEQ ID NO:73).

In some embodiments, the antibody molecule comprises one or more or all of the following properties: (i) it fails to produce any escape mutants as determined by the failure of a viral titer to recover following at least 10, 9, 8, 7, 6, or 5 rounds of serial infections in cell culture with a mixture of the antibody molecule and an influenza virus (e.g., an influenza A virus, e.g., a Group 1 strain, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004, or an influenza B virus, e.g., B/Wisconsin/1/2010); and (ii) it produces fewer escape mutants than does a reference anti-HA antibody molecule, such as Ab 67-11, FI6, FI28, C179, F10, CR9114, or CR6261, such as when tested by the method described in (i).

In an embodiment the antibody molecule comprises one or both of:

a) one or more framework regions (FRs) from SEQ ID NO: 25. E.g., the antibody molecule comprises one or more or all of FR1, FR2, FR3, or FR4, or sequences that differ individually, or collectively, by no more than 1, 2, 3, 4, of 5 amino acid residues, e.g., conservative residues, from SEQ ID NO: 25; and b) one or more framework regions (FRs) from SEQ ID NO: 155. E.g., the antibody molecule comprises one or more or all of FR1, FR2, FR3, or FR4, or sequences that differ individually, or collectively, by no more than 1, 2, 3, 4, of 5 amino acid residues, e.g., conservative residues, from SEQ ID NO: 155.

In one embodiment, the antibody molecule comprises:

(a) a heavy chain immunoglobulin variable region segment that further comprises one or more or all of:

an FR1 comprising the sequence Q-V-Q-L-L-E-T-G-G-G-L-V-K-P-G-Q-S-L-K-L-S-C-A-A-S-G-F-T-F-T̲ (SEQ ID NO:74) (or a sequence that differs by no more than, 1, 2, 3, 4, or 5, e.g., 1 or 2, amino acids, e.g., conservative amino acids, therefrom, optionally provided that T̲ is not changed);

an FR2 comprising the sequence W-V-R-Q-P-P-G-K-G-L-E-W̲-V-A (SEQ ID NO:75) (or a sequence that differs by no more than, 1, 2, 3, 4, or 5, e.g., 1 or 2, amino acids, e.g., conservative amino acids, therefrom, optionally provided that W̲ is not changed, or that if changed, is other than R);

an FR3 comprising the sequence R-F-T-I̲-S-R-D-N-S-K-N-T-L̲-Y-L-Q-M-N-S-L-R-A-E-D-T-A-V-Y-Y-C-A-K (SEQ ID NO:76) (or a sequence that differs by no more than, 1, 2, 3, 4, or 5, e.g., 1 or 2, amino acids, e.g., conservative amino acids, therefrom, optionally provided that one, two or three of I̲, R̲, or L̲ is not changed, or that if I̲ is changed it is other than G, if R is changed it is other than P. or if L̲ is changed it is other than A); and (b) the light chain immunoglobulin variable region segment comprises one or more or all of an FR1 comprising the sequence D-I-Q-M-T-Q-S-P-S-S-L-S-A-S-V-G-D-R-V-T-I-T-C-R̲-S-S (SEQ ID NO:78) (or a sequence that differs by no more than, 1, 2, 3, 4, or 5, e.g., 1 or 2 amino acids, e.g., conservative amino acids, therefrom, optionally provided that R̲ is not changed);

an FR2 comprising the sequence W-Y-Q-Q-K-P-G-K-A-P-K-L-L-1-Y (SEQ ID NO:79) (or a sequence that differs by no more than, 1, 2, 3, 4, or 5, e.g., 1 or 2 amino acids, e.g., conservative amino acids, therefrom);

an FR3 comprising the sequence G-V-P-S-R-F-S-G-S-G-S-G-T-D-F-T-L-T-I-S-S-L-Q-P-E-D-F-A-T-Y-Y-C̲ (SEQ ID NO:80) (or a sequence that differs by no more than, 1, 2, 3, 4, or 5, e.g., 1 or 2 amino acids, e.g., conservative amino acids, therefrom, optionally provided that C̲ is not changed, or if changed, is other than P); and an FR4 comprising the sequence F-G-Q-G-T-K-V-E-I-K (SEQ ID NO:81) (or a sequence that differs by no more than, 1, 2, 3, 4, or 5, e.g., 1 or 2 amino acids, e.g., conservative amino acids, therefrom).

In an embodiment a FR of the light or heavy chain includes one of the highlighted residues, or one of the highlighted combinations of residues, for that FR, (i.e., while other residues in that FR might be changed, the highlighted residue or combination of residues, are not changed). E.g., in an embodiment, one, two or three of I̲, R̲, or L̲ for heavy chain FR3 is not changed.

In an embodiment a FR of the light and a FR of the heavy chain each includes one of the highlighted residues, or one of the highlighted combinations of residues, for that FR.

In an embodiment each of two FRs in the antibody molecule includes one of the highlighted residues, or one of the highlighted combinations of residues, for that FR. In embodiments both are in the light chain. In embodiments both are in the heavy chain.

In an embodiment each of FR2 and FR3 in the heavy chain includes one of the highlighted residues, or one of the highlighted combinations of residues, for that FR.

In an embodiment each of FR1 and FR2 in the heavy and light chain includes one of the highlighted residues for that FR.

In an embodiment all of the highlighted residues in heavy chain FR1-4 are unchanged.

In an embodiment all of the highlighted residues in light chain FR1-4 are unchanged.

In an embodiment all of the highlighted residues in both heavy and light chain FR1-4 are unchanged.

In another embodiment, the binding agent, e.g., an antibody molecule, comprises one or more or all of the following properties: (a) it fails to produce any escape mutants as determined by the failure of a viral titer to recover following at least 10, 9, 8, 7, 6, or 5 rounds of serial infections in cell culture with a mixture of the antibody molecule and an influenza virus (e.g., an influenza A virus, e.g., a Group 1 strain, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004, or an influenza B virus, e.g., B/Wisconsin/1/2010); (b) it produces fewer escape mutants than does a reference anti-HA antibody molecule, e.g., Ab 67-11, FI6, FI28, C179, or CR6261, e.g., when tested by the method described in (a); (c) it binds with high affinity to a hemagglutinin (HA) of at least 1, 2, 3, 4 or 5 influenza subtypes of Group 1 and at least 1, 2, 3, 4 or 5 influenza subtypes of Group 2; (d) it treats or prevents infection by at least 1, 2, 3, 4 or 5 influenza subtypes of Group 1, and by at least 1, 2, 3, 4 or 5 influenza subtypes of Group 2; (e) it inhibits fusogenic activity of the targeted HA; (f) it treats or prevents infection by a Group 1 virus, wherein the virus is an H1, H5, or H9 virus; and treats or prevents infection by a Group 2 virus, wherein the virus is an H3 or H7 virus; (g) it treats or prevents infection by influenza A strains H1N1 and H3N2; (h) it is effective for prevention or treatment of infection, e.g., in humans or mice, with H1N1 and H3N2 when administered at 50 mg/kg, 25 mg/kg, 10 mg/kg, 6 mg/kg, 5 mg/kg, 4 mg/kg, 3 mg/kg, 2 mg/kg or 1 mg/kg; (i) it treats or prevents infection by influenza A strains H5N1; (j) it is effective for prevention or treatment of infection, e.g., in humans or mice, with H5N1 when administered at 50 mg/kg, 25 mg/kg, 10 mg/kg, 6 mg/kg, 5 mg/kg, 4 mg/kg, 3 mg/kg, 2 mg/kg or 1 mg/kg; (k) it binds with high affinity to a hemagglutinin (HA) of an influenza B virus, e.g., B/Wisconsin/1/2010; (l) it treats or prevents infection by an influenza B virus, e.g., B/Wisconsin/1/2010; (m) it is effective for prevention or treatment of infection, e.g., in humans or mice, with an influenza B virus, e.g., B/Wisconsin/1/2010 when administered at 50 mg/kg, 25 mg/kg, 10 mg/kg, 6 mg/kg, 5 mg/kg, 4 mg/kg, 3 mg/kg, 2 mg/kg or 1 mg/kg; (n) the concentration of antibody molecule required for 50% neutralization of influenza A virus is less than 10 µg/mL; (o) the concentration of antibody molecule required for 50% neutralization of influenza B virus, e.g., B/Wisconsin/1/2010, is less than 10 µg/mL; (p) it prevents or minimizes secondary infection (e.g., secondary bacterial infection) or effects thereof on a subject; (q) it is effective for preventing or minimizing secondary infection (e.g., secondary bacterial infection) or effects thereof on a subject when administered at 50 mg/kg, 25 mg/kg, 10 mg/kg, 6 mg/kg, 5 mg/kg, 4 mg/kg, 3 mg/kg, 2 mg/kg or 1 mg/kg; (r) it binds an epitope which comprises or consists of the hemagglutinin trimer interface; and (s) it binds an epitope other than that bound by a reference anti-HA antibody molecule, e.g., Ab 67-11, FI6, FI28, C179, F10, CR9114, or CR6261, e.g., when tested by a method disclosed herein, e.g., by competition in an ELISA assay.

In an embodiment the binding agent, e.g., an antibody molecule, specifically binds the HA antigen.

In an embodiment, the antibody molecule binds an epitope that has one, two, three, four, five, or all of, the following properties a-f:
a) it includes one, two, or all of, H3 HA1 residues N38, I278, and D291;
b) it includes H3 HA2 residue N12;
c) it does not include one, two or all of, H3 HA1 residues Q327, T328, and R329;
d) it does not include one, two, three, four, or all of, H3 HA2 residues G1, L2, F3, G4, and D46;
e) it includes one, two, or all of, H3 HA1 residues T318, R321, and V323; or
f) it includes 1, 2, 3, 4, 5, 6, 7, 8, 9, 10, 11, 12, 13, 14, 15, 16, 17, or all of, H3 HA2 residues A7, E11, I18, D19, G20, W21, L38, K39, T41, Q42, A43, I45, I48, N49, L52, N53, I56, and E57.

In an embodiment the antibody molecule has properties: a; and b.
In an embodiment the antibody molecule has properties: c; and d.
In an embodiment the antibody molecule has properties: a; and c or d.
In an embodiment the antibody molecule has properties: b; and c or d.
In an embodiment the antibody molecule has properties: c; and a or b.
In an embodiment the antibody molecule has properties: d; and a or b.
In an embodiment the antibody molecule has properties: a, b, c and d.
In an embodiment the antibody molecule has properties: a, b, c, d, e, and f.

In an embodiment, the antibody molecule has a $K_D$ for H3 of equal to or less than $10^{-6}$, wherein said $K_D$ is increased by at least 2, 5, 10, or 100 fold, by a mutation or mutations in any of:
a) H3 HA1 residues N38, I278, or D291;
b) H3 HA2 residue N12;
c) H3 HA1 residues T318, R321, or V323; or
d) H3 HA2 residues A7, E11, I18, D19, G20, W21, L38, K39, T41, Q42, A43, I45, I48, N49, L52, N53, I56, or E57.

In an embodiment, the antibody molecule has a $K_D$ for H3 of equal to or less than $10^{-6}$, wherein said $K_D$ is increased by no more than 2, or 5 fold, by a mutation or mutations in any of:
c) H3 HA1 residues Q327, T328, or R329; or
d) H3 HA2 residues G1, L2, F3, G4, or D46.

In an embodiment, the antibody molecule binds an epitope that has one, two, three, four, five, or all of, the following properties a-f:
aa) it includes one, two, or all of, H1 HA1 residues H31, N279, and S292;
bb) it includes H1 HA2 residue G12;
cc) it does not include one or both of H1 HA1 residues Q328 and S329;
dd) it does not include one, two, three, four, or all of, H1 HA2 residues G1, L2, F3, G4, and D46;
ee) it includes one, two, or all of, H1 HA1 residues T319, R322, and I324 are bound by both Ab 044 and FI6; or
ff) it includes 1, 2, 3, 4, 5, 6, 7, 8, 9, 10, 11, 12, 13, 14, 15, 16, 17, or all of, H1 HA2 residues A7, E11, I18, D19, G20, W21, Q38, K39, T41, Q42, N43, I45, I48, T49, V52, N53, I56, and E57.

In an embodiment the antibody molecule has properties: aa; and bb.
In an embodiment the antibody molecule has properties: cc; and dd.
In an embodiment the antibody molecule has properties: aa; and cc or dd.
In an embodiment the antibody molecule has properties: bb; and cc or dd.
In an embodiment the antibody molecule has properties: cc; and aa or bb.
In an embodiment the antibody molecule has properties: dd; and aa or bb.
In an embodiment the antibody molecule has properties: aa, bb, cc and dd.
In an embodiment the antibody molecule has properties: aa, bb, cc, dd, ee, and ff.

In an embodiment, the antibody molecule has a $K_D$ for H1 of equal to or less than $10^{-6}$, wherein said $K_D$ is increased by at least 2, 5, 10, or 100 fold, by a mutation or mutations in any of:
aa) H1 HA1 residues H31, N279, and S292;
bb) H1 HA2 residue G12;
cc) H1 HA1 residues T319, R322, and I324; or
dd) H1 HA2 residues A7, E11, I18, D19, G20, W21, Q38, K39, T41, Q42, N43, I45, I48, T49, V52, N53, I56, and E57.

In an embodiment, the antibody molecule has a $K_D$ for H1 of equal to or less than $10^{-6}$, wherein said $K_D$ is increased by no more than 2, or 5 fold, by a mutation or mutations in any of:
cc) H1 HA1 residues Q328 and S329; or
dd) H1 HA2 residues G1, L2, F3, G4, and D46;

In an embodiment the antibody molecule has one, two, three or all of the following properties:
a and aa;
b and bb;
c and cc;
d and dd.

In an embodiment the molecule has properties c, cc, d, and dd.

In an embodiment the molecule has properties c, cc, d, and dd.

In another aspect, the disclosure features, a binding agent, e.g., an antibody molecule, or preparation, or isolated preparation thereof, comprising a structural or functional property of Ab 032.

In an embodiment, the antibody molecule competes with a reference antibody molecule, e.g., an antibody molecule described herein, for binding to a substrate, e.g., an HA. The reference antibody molecule can be:

a) an antibody molecule comprising:
  i) a heavy chain immunoglobulin variable region segment comprising
    a CDR1 comprising the sequence S-Y-A-M-H (SEQ ID NO:68);
    a CDR2 comprising the sequence V-V-S-Y-D-G-N-Y-K-Y-Y-A-D-S-V-Q-G (SEQ ID NO:69); and
    a CDR3 comprising the sequence D-S-R-L-R-S-L-L-Y-F-E-W-L-S-Q-G-Y-F-N-P (SEQ ID NO:70); and
  ii) a light chain variable region segment comprising:
    a CDR1 comprising the sequence Q-S-I-T-F-N-Y-K-N-Y-L-A (SEQ ID NO: 71);
    a CDR2 comprising the sequence W-G-S-Y-L-E-S (SEQ ID NO:72); and
    a CDR3 comprising the sequence Q-Q-H-Y-R-T-P-P-S (SEQ ID NO:73).
b) an antibody molecule comprises one or both of: (i) a heavy chain immunoglobulin variable region segment comprising SEQ ID NO: 25; and (ii) a light chain variable region segment comprising SEQ ID NO:45; or
c) Ab 032.

The HA can be HA1 or HA5, e.g. from an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004. Competition between the antibody molecule and a reference antibody molecule can be determined by evaluating the ability of one of the antibody molecule or the reference antibody molecule to decrease binding of the other to a substrate, e.g., HA, e.g., HA1 or HA5, e.g. from an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004. Reduction of the ability to bind can be evaluated by methods in the art. Reduction of the ability to bind can be evaluated, e.g., by one or more of:

a) BIAcore analysis;
b) ELISA assay; and
c) flow cytometry.

The antibody molecule can compete with the reference antibody such that binding of the reference antibody is decreased by 50% or more.

In an embodiment the antibody molecule binds to the same epitope, or a portion thereof, which the reference antibody molecule binds. In an embodiment the antibody molecule does not bind to the same epitope, or a portion thereof, which the reference antibody molecule binds.

In an embodiment the antibody molecule binds to the same epitope, or a portion thereof, on HA, as does a reference antibody molecule, e.g. an antibody molecule disclosed herein. The reference antibody molecule can be:

a) an antibody molecule comprising:
  i) a heavy chain immunoglobulin variable region segment comprising
    a CDR1 comprising the sequence S-Y-A-M-H (SEQ ID NO:68);
    a CDR2 comprising the sequence V-V-S-Y-D-G-N-Y-K-Y-Y-A-D-S-V-Q-G (SEQ ID NO:69); and
    a CDR3 comprising the sequence D-S-R-L-R-S-L-L-Y-F-E-W-L-S-Q-G-Y-F-N-P (SEQ ID NO:70); and
  ii) a light chain variable region segment comprising:
    a CDR1 comprising the sequence Q-S-I-T-F-N-Y-K-N-Y-L-A (SEQ ID NO: 71);
    a CDR2 comprising the sequence W-G-S-Y-L-E-S (SEQ ID NO:72); and
    a CDR3 comprising the sequence Q-Q-H-Y-R-T-P-P-S (SEQ ID NO:73).
b) an antibody molecule comprises one or both of: (i) a heavy chain immunoglobulin variable region segment comprising SEQ ID NO: 25; and (ii) a light chain variable region segment comprising SEQ ID NO:45; or
c) Ab 32.

The HA can be HA1 or HA5, e.g. from an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004. Binding to the same epitope, or a portion thereof, can be shown by one or more of:

a) mutational analysis, e.g., binding to HA, or binding affinity for HA, is decreased or abolished if a residue is mutated;
b) analysis, e.g., comparison, of the crystal structure of the antibody molecule and HA and the crystal structure of a reference antibody and HA, e.g., to determine the touch points of each;
c) competition of the two antibodies for binding to HA, e.g., HA1 or HA5, from, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004; and
d) (c) and one or both of (a) and (b);

Competition between the antibody molecule and a reference antibody molecule can be determined by evaluating the ability of one of the antibody molecule or the reference antibody molecule to decrease binding of the other to a substrate, e.g., HA, e.g., HA1 or HA5, from, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004. Reduction of the ability to bind can be evaluated by methods in the art. Reduction of the ability to bind can be evaluated, e.g., by one or more of:

a) BIAcore analysis;
b) ELISA assay; and
c) flow cytometry.

The antibody molecule can compete with the reference antibody such that binding of the reference antibody is decreased by 50% or more.

In an embodiment the binding agent, e.g., an antibody molecule, comprises one or both of:
a heavy chain variable region comprising least 60, 70, 80, 85, 90, 95, 98 or 99 percent homology with SEQ ID NO: 25; and a light chain variable region comprising least 60, 70, 80, 85, 90, 95, 98 or 99 percent homology with SEQ ID NO: 45.

In an embodiment the binding agent, e.g., an antibody molecule, comprises one or both of:
a heavy chain variable region comprising least 60, 70, 80, 85, 90, 95, 98 or 99 percent homology with SEQ ID NO: 25; and a light chain variable region comprising least 60, 70, 80, 85, 90, 95, 98 or 99 percent homology with SEQ ID NO: 45,
wherein each HC CDR differs by no more than 1, 2, 3, 4 or 5 amino acids, e.g., 1 or 2, e.g., conservative amino acids, from the corresponding CDR of SEQ ID NO: 25 and each LC CDR differs by no more than 1, 2, 3, 4 or 5 amino acids, e.g., 1 or 2, e.g., conservative amino acids, from the corresponding CDR of SEQ ID NO: 45.

In an embodiment the binding agent, e.g., an antibody molecule, comprises one or both of:
a heavy chain variable region comprising least 60, 70, 80, 85, 90, 95, 98 or 99 percent homology with SEQ ID NO: 25;
and a light chain variable region comprising least 60, 70, 80, 85, 90, 95, 98 or 99 percent homology with SEQ ID NO: 45,
wherein the antibody molecule comprises 1, 2, 3, 4, 5, or all of:
(i) a HC CDR1 comprising: S at the 1st position and A at the 3rd position in HC CDR1;
(ii) a HC CDR2 comprising one or both, e.g., one of: V at the $2^{nd}$ position; or N at the $7^{th}$ position and Q at the $16^{th}$ position in HC CDR2;
(iii) a HC CDR3 comprising: R at the 3rd position (and optionally, L at the $3^{rd}$ position);
(iv) a LC CDR1 comprising: I at the 3rd position;
(v) a LC CDR2 comprising one, two, or three of, e.g., one of: G at the $2^{nd}$ position; Y at the $4^{th}$ position; or L at the $5^{th}$ position in LC CDR2;
(vi) a LC CDR3 comprising: S at the $9^{th}$ position in LC CDR3;

In an embodiment, the binding agent, e.g., an antibody molecule, comprises one or both of:
(a) a heavy chain immunoglobulin variable region segment comprising SEQ ID NO:25 (or a sequence that differs by no more than 1, 2, 3, 4 or 5 amino acids, e.g., conservative amino acids, therefrom); and
(b) a light chain variable region segment comprising SEQ ID NO:155 (or a sequence that differs by no more than 1, 2, 3, 4 or 5 amino acids, e.g., conservative amino acids, therefrom).

In one embodiment, the antibody molecule comprises one or both of:
(a) a heavy chain immunoglobulin variable region segment comprising SEQ ID NO: 25; and
(b) a light chain variable region segment comprising SEQ ID NO:155.

In an embodiment, the binding agent, e.g., an antibody molecule, comprises one or both of:
(a) a heavy chain immunoglobulin variable region segment comprising
a CDR1 comprising the sequence S-Y-A-M-H (SEQ ID NO:68) (or a sequence that differs by no more than, 1, 2, 3, 4, or 5, e.g., 1 or 2 amino acids, e.g., conservative amino acids, therefrom);
a CDR2 comprising the sequence V-V-S-Y-D-G-N-Y-K-Y-Y-A-D-S-V-Q-G (SEQ ID NO:69) (or a sequence that differs by no more than, 1, 2, 3, 4, or 5, e.g., 1 or 2 amino acids, e.g., conservative amino acids, therefrom);
a CDR3 comprising the sequence D-S-R-L-R-S-L-L-Y-F-E-W-L-S-Q-G-Y-F-N-P (SEQ ID NO:70) (or a sequence that differs by no more than, 1, 2, 3, 4, or 5, e.g., 1 or 2 amino acids, e.g., conservative amino acids, therefrom); and
(b) a light chain variable region segment comprising
a CDR1 comprising the sequence:
Q-S-I-T-F N-Y-K-N-Y-L-A (SEQ ID NO:71) (or a sequence that differs by no more than, 1, 2, 3, 4, or 5, e.g., 1 or 2 amino acids, e.g., conservative amino acids, therefrom);
a CDR2 comprising the sequence W-G-S-Y-L-E-S (SEQ ID NO:72) (or a sequence that differs by no more than, 1, 2, 3, 4, or 5, e.g., 1 or 2 amino acids, e.g., conservative amino acids, therefrom);
a CDR3 comprising the sequence Q-Q-H-Y-R-T-P-P-S (SEQ ID NO:73) (or a sequence that differs by no more than, 1, 2, 3, 4, or 5, e.g., 1 or 2 amino acids, e.g., conservative amino acids, therefrom).

In an embodiment the binding agent, e.g., an antibody molecule, comprises one or both of:
a) LC CDR1-3, that collectively, differ from the AB 032 LC CDR1-3 by no more than, 1, 2, 3, 4, 5, 6, 7, 8, 9, or 10, e.g., 1, 2, 3, or 4, amino acids, e.g., conservative amino acids; and
b) HC CDR1-3, that collectively, differ from the AB 032 HC CDR1-3 by no more than, 1, 2, 3, 4, 5, 6, 7, 8, 9, or 10, e.g., 1, 2, 3, or 4, amino acids, e.g., conservative amino acids.

In an embodiment, the binding agent is an antibody molecule comprising one or both of:
(a) a heavy chain immunoglobulin variable region segment comprising
a CDR1 comprising the sequence S̲-Y-A̲-M-H (SEQ ID NO:68) (or a sequence that differs by no more than, 1, 2, or 3, e.g., 1 or 2 amino acids, e.g., conservative amino acids, therefrom, optionally provided that at least 1 or 2 of the highlighted residues are not changed, e.g., both S̲ and A̲ are not changed);
a CDR2 comprising the sequence V-V̲-S-Y-D-G-N̲-Y-K-Y-Y-A-D-S-V-Q̲-G (SEQ ID NO:69) (or a sequence that differs by no more than, 1, 2, 3, 4, or 5, e.g., 1 or 2 amino acids, e.g., conservative amino acids, therefrom, provided that, e,g., at least 1, 2, or 3 of the highlighted residues are not changed, e.g., V̲ or both N̲ and Q̲ or all three of V̲, N̲, and Q̲ are not changed);
a CDR3 comprising the sequence D-S-R̲-L-R-S-L-L-Y-F-E-W-L-S-Q-G-Y-F-N-P (SEQ ID NO:70) (or a sequence that differs by no more than, 1, 2, 3, 4, or 5, e.g., 1 or 2 amino acids, e.g., conservative amino acids, therefrom, optionally provided that R̲ is not changed); and
(b) a light chain variable region segment comprising
a CDR1 comprising the sequence: Q-S-I̲-T-F-N-Y-K-N-Y-L-A (SEQ ID NO: 71) or a sequence that differs by no more than, 1, 2, 3, 4, or 5, e.g., 1 or 2 amino acids, e.g., conservative amino acids, therefrom, optionally provided that at least 1 or 2 of the highlighted residues are not changed, e.g., I̲ is not changed);
a CDR2 comprising the sequence W-G̲-S-Y̲-L̲-E-S (SEQ ID NO:72) (or a sequence that differs by no more than, 1, 2, 3, 4, or 5, e.g., 1 or 2 amino acids, e.g., conservative amino acids, therefrom, optionally provided that at least 1, 2, or 3 of the highlighted residues are not changed, e.g., 1, 2 or all of G̲, Y̲, and L̲ are not changed);
a CDR3 comprising the sequence Q-Q-H̲-Y-R-T-P-P-S̲ (SEQ ID NO:73) (or a sequence that differs by no more than, 1, 2, 3, 4, or 5, e.g., 1 or 2 amino acids, e.g., conservative amino acids, therefrom, optionally provided that at least one or both of the highlighted residues are not changed, e.g., S̲ is not changed).

In an embodiment a CDR of the light or heavy chain includes one of the highlighted residues, or one of the highlighted combinations of residues, for that CDR, (i.e., while other residues in that CDR might be changed, the highlighted residue or combination of residues, are not changed).

In an embodiment a CDR of the light and a CDR of the heavy chain each includes one of the highlighted residues, or one of the highlighted combinations of residues, for that CDR.

In an embodiment each of two CDRs in the antibody molecule includes one of the highlighted residues, or one of the highlighted combinations of residues, for that CDR. In embodiments both are in the light chain. In embodiments both are in the heavy chain.

In an embodiment each of the three CDRs in the heavy chain includes one of the highlighted residues, or one of the highlighted combinations of residues, for that CDR.

In an embodiment each of the three CDRs in the light chain includes one of the highlighted residues, or one of the highlighted combinations of residues, for that CDR.

In an embodiment each of the six CDRs in the heavy and light chain includes one of the highlighted residues, or one of the highlighted combinations of residues, for that CDR.

In one embodiment, the binding agent is an antibody molecule that comprises one or more or all of the following properties:
  (a) both S and A in HC CDR1 are unchanged.
  (b) V or both N and Q or all three of V, N, and Q in HC CDR2 are unchanged.
  (c) R in HC CDR3 is unchanged.
  (d) I in LC CDR1 is unchanged.
  (e) 1, 2 or 3 of G, Y, and L in LC CDR2 are unchanged;
  (f) S in LC CDR3 is unchanged.

In an embodiment the antibody molecule comprises 1, 2, 3, 4, 5, or all 6 properties selected from (a) to (f).

In an embodiment, the antibody molecule comprises a heavy chain having a one or more properties selected from (a), (b), and (c) and a light chain having one or more properties selected from (d), (e), and (f).

In one embodiment, the antibody molecule comprises one or both of:
  (a) a heavy chain immunoglobulin variable region segment comprising:
    a CDR1 comprising the sequence S-Y-A-M-H (SEQ ID NO:68);
    a CDR2 comprising the sequence V-V-S-Y-D-G-N-Y-K-Y-Y-A-D-S-V-Q-G (SEQ ID NO:69);
    a CDR3 comprising the sequence D-S-R-L-R-S-L-L-Y-F-E-W-L-S-Q-G-Y-F-N-P (SEQ ID NO:70); and
  (b) a light chain variable region segment comprising
    a CDR1 comprising the sequence Q-S-I-T-F-N-Y-K-N-Y-L-A (SEQ ID NO: 71);
    a CDR2 comprising the sequence W-G-S-Y-L-E-S (SEQ ID NO:72); and
    a CDR3 comprising the sequence Q-Q-H-Y-R-T-P-P-S (SEQ ID NO:73).

In some embodiments, the antibody molecule comprises one or more or all of the following properties: (i) it fails to produce any escape mutants as determined by the failure of a viral titer to recover following at least 10, 9, 8, 7, 6, or 5 rounds of serial infections in cell culture with a mixture of the antibody molecule and an influenza virus (e.g., an influenza A virus, e.g., a Group 1 strain, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004, or an influenza B virus, e.g., B/Wisconsin/1/2010); and (ii) it produces fewer escape mutants than does a reference anti-HA antibody molecule, such as Ab 67-11, FI6, FI28, C179, F10, CR9114, or CR6261, such as when tested by the method described in (i).

In an embodiment the antibody molecule comprises one or both of:

a) one or more framework regions (FRs) from SEQ ID NO: 25. E.g., the antibody molecule comprises one or more or all of FR1, FR2, FR3, or FR4, or sequences that differ individually, or collectively, by no more than 1, 2, 3, 4, of 5 amino acid residues, e.g., conservative residues, from SEQ ID NO: 25; and b) one or more framework regions (FRs) from SEQ ID NO: 45. E.g., the antibody molecule comprises one or more or all of FR1, FR2, FR3, or FR4, or sequences that differ individually, or collectively, by no more than 1, 2, 3, 4, of 5 amino acid residues, e.g., conservative residues, from SEQ ID NO: 45.

In one embodiment, the antibody molecule comprises:

(a) a heavy chain immunoglobulin variable region segment that further comprises one or more or all of:

an FR1 comprising the sequence Q-V-Q-L-L-E-T-G-G-G-L-V-K-P-G-Q-S-L-K-L-S-C-A-A-S-G-F-T-F-T (SEQ ID NO:74) (or a sequence that differs by no more than, 1, 2, 3, 4, or 5, e.g., 1 or 2, amino acids, e.g., conservative amino acids, therefrom, optionally provided that T is not changed);

an FR2 comprising the sequence W-V-R-Q-P-P-G-K-G-L-E-W-V-A (SEQ ID NO:75) (or a sequence that differs by no more than, 1, 2, 3, 4, or 5, e.g., 1 or 2, amino acids, e.g., conservative amino acids, therefrom, optionally provided that W is not changed, or that if changed, is other than R);

an FR3 comprising the sequence R-F-T-I-S-R-D-N-S-K-N-T-L-Y-L-Q-M-N-S-L-R-A-E-D-T-A-V-Y-Y-C-A-K (SEQ ID NO:76) (or a sequence that differs by no more than, 1, 2, 3, 4, or 5, e.g., 1 or 2, amino acids, e.g., conservative amino acids, therefrom, optionally provided that one, two or three of I, R, or L is not changed, or that if I is changed it is other than G, if R is changed it is other than P. or if L is changed it is other than A); and an FR4 comprising the sequence W-G-Q-G-T-T-L-T-V-S-S (SEQ ID NO:77) (or a sequence that differs by no more than, 1, 2, 3, 4, or 5, e.g., 1 or 2 amino acids, e.g., conservative amino acids, therefrom) or W-G-Q-G-T-T-V-T-V-S-S (SEQ ID NO:171) (or a sequence that differs by no more than, 1, 2, 3, 4, or 5, e.g., 1 or 2 amino acids, e.g., conservative amino acids, therefrom); and (b) the light chain immunoglobulin variable region segment comprises one or more or all of an FR1 comprising the sequence D-I-Q-M-T-Q-S-P-S-S-L-S-A-S-V-G-D-R-V-T-I-T-C-R-S-S (SEQ ID NO:78) (or a sequence that differs by no more than, 1, 2, 3, 4, or 5, e.g., 1 or 2 amino acids, e.g., conservative amino acids, therefrom, optionally provided that R is not changed);

an FR2 comprising the sequence W-Y-Q-Q-K-P-G-K-A-P-K-L-L-I-Y (SEQ ID NO:79) (or a sequence that differs by no more than, 1, 2, 3, 4, or 5, e.g., 1 or 2 amino acids, e.g., conservative amino acids, therefrom);

an FR3 comprising the sequence G-V-P-S-R-F-S-G-S-G-S-G-T-D-F-T-L-T-I-S-S-L-Q-P-E-D-F-A-T-Y-Y-C (SEQ ID NO:80) (or a sequence that differs by no more than, 1, 2, 3, 4, or 5, e.g., 1 or 2 amino acids, e.g., conservative amino acids, therefrom, optionally provided that C is not changed, or if changed, is other than P); and an FR4 comprising the sequence F-G-Q-G-T-K-V-E-I-K (SEQ ID NO:81) (or a sequence that differs by no more than, 1, 2, 3, 4, or 5, e.g., 1 or 2 amino acids, e.g., conservative amino acids, therefrom).

In an embodiment a FR of the light or heavy chain includes one of the highlighted residues, or one of the highlighted combinations of residues, for that FR, (i.e., while other residues in that FR might be changed, the highlighted residue or combination of residues, are not changed). E.g., in an embodiment, one, two or three of I, R, or L for heavy chain FR3 is not changed.

In an embodiment a FR of the light and a FR of the heavy chain each includes one of the highlighted residues, or one of the highlighted combinations of residues, for that FR.

In an embodiment each of two FRs in the antibody molecule includes one of the highlighted residues, or one of the highlighted combinations of residues, for that FR. In embodiments both are in the light chain. In embodiments both are in the heavy chain.

In an embodiment each of FR2 and FR3 in the heavy chain includes one of the highlighted residues, or one of the highlighted combinations of residues, for that FR.

In an embodiment each of FR1 and FR2 in the heavy and light chain includes one of the highlighted residues for that FR.

In an embodiment all of the highlighted residues in heavy chain FR1-4 are unchanged.

In an embodiment all of the highlighted residues in light chain FR1-4 are unchanged.

In an embodiment all of the highlighted residues in both heavy and light chain FR1-4 are unchanged.

In another embodiment, the binding agent, e.g., an antibody molecule, comprises one or more or all of the following properties: (a) it fails to produce any escape mutants as determined by the failure of a viral titer to recover following at least 10, 9, 8, 7, 6, or 5 rounds of serial infections in cell culture with a mixture of the antibody molecule and an influenza virus (e.g., an influenza A virus, e.g., a Group 1 strain, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004, or an influenza B virus, e.g., B/Wisconsin/1/2010); (b) it produces fewer escape mutants than does a reference anti-HA antibody molecule, e.g., Ab 67-11, FI6, FI28, C179, or CR6261, e.g., when tested by the method described in (a); (c) it binds with high affinity to a hemagglutinin (HA) of at least 1, 2, 3, 4 or 5 influenza subtypes of Group 1 and at least 1, 2, 3, 4 or 5 influenza subtypes of Group 2; (d) it treats or prevents infection by at least 1, 2, 3, 4 or 5 influenza subtypes of Group 1, and by at least 1, 2, 3, 4 or 5 influenza subtypes of Group 2; (e) it inhibits fusogenic activity of the targeted HA; (f) it treats or prevents infection by a Group 1 virus, wherein the virus is an H1, H5, or H9 virus; and treats or prevents infection by a Group 2 virus, wherein the virus is an H3 or H7 virus; (g) it treats or prevents infection by influenza A strains H1N1 and H3N2; (h) it is effective for prevention or treatment of infection, e.g., in humans or mice, with H1N1 and H3N2 when administered at 50 mg/kg, 25 mg/kg, 10 mg/kg, 6 mg/kg, 5 mg/kg, 4 mg/kg, 3 mg/kg, 2 mg/kg or 1 mg/kg; (i) it treats or prevents infection by influenza A strains H5N1; (j) it is effective for prevention or treatment of infection, e.g., in humans or mice, with H5N1 when administered at 50 mg/kg, 25 mg/kg, 10 mg/kg, 6 mg/kg, 5 mg/kg, 4 mg/kg, 3 mg/kg, 2 mg/kg or 1 mg/kg; (k) it binds with high affinity to a hemagglutinin (HA) of an influenza B virus, e.g., B/Wisconsin/1/2010; (l) it treats or prevents infection by an influenza B virus, e.g., B/Wisconsin/1/2010; (m) it is effective for prevention or treatment of infection, e.g., in humans or mice, with an influenza B virus, e.g., B/Wisconsin/1/2010 when administered at 50 mg/kg, 25 mg/kg, 10 mg/kg, 6 mg/kg, 5 mg/kg, 4 mg/kg, 3 mg/kg, 2 mg/kg or 1 mg/kg; (n) the concentration of antibody molecule required for 50% neutralization of influenza A virus is less than 10 µg/mL; (o) the concentration of antibody molecule required for 50% neutralization of influenza B virus, e.g., B/Wisconsin/1/2010, is less than 10 µg/mL; (p) it prevents or minimizes secondary infection (e.g., secondary bacterial infection) or effects thereof on a subject; (q) it is effective for preventing or minimizing secondary infection (e.g., secondary bacterial infection) or effects thereof on a subject when administered at 50 mg/kg, 25 mg/kg, 10 mg/kg, 6 mg/kg, 5 mg/kg, 4 mg/kg, 3 mg/kg, 2 mg/kg or 1 mg/kg; (r) it binds an epitope which comprises or consists of the hemagglutinin trimer interface; and (s) it binds an epitope other than that bound by a reference anti-HA antibody molecule, e.g., Ab 67-11, FI6, FI28, C179, F10, CR9114, or CR6261, e.g., when tested by a method disclosed herein, e.g., by competition in an ELISA assay.

In an embodiment the binding agent, e.g., an antibody molecule, specifically binds the HA antigen.

In an embodiment, the antibody molecule binds an epitope that has one, two, three, four, five, or all of, the following properties a-f:
a) it includes one, two, or all of, H3 HA1 residues N38, I278, and D291;
b) it includes H3 HA2 residue N12;
c) it does not include one, two or all of, H3 HA1 residues Q327, T328, and R329;
d) it does not include one, two, three, four, or all of, H3 HA2 residues G1, L2, F3, G4, and D46;
e) it includes one, two, or all of, H3 HA1 residues T318, R321, and V323; or
f) it includes 1, 2, 3, 4, 5, 6, 7, 8, 9, 10, 11, 12, 13, 14, 15, 16, 17, or all of, H3 HA2 residues A7, E11, I18, D19, G20, W21, L38, K39, T41, Q42, A43, I45, I48, N49, L52, N53, I56, and E57.

In an embodiment the antibody molecule has properties: a; and b.

In an embodiment the antibody molecule has properties: c; and d.

In an embodiment the antibody molecule has properties: a; and c or d.

In an embodiment the antibody molecule has properties: b; and c or d.

In an embodiment the antibody molecule has properties: c; and a or b.

In an embodiment the antibody molecule has properties: d; and a or b.

In an embodiment the antibody molecule has properties: a, b, c and d.

In an embodiment the antibody molecule has properties: a, b, c, d, e, and f.

In an embodiment, the antibody molecule has a $K_D$ for H3 of equal to or less than $10^{-6}$, wherein said $K_D$ is increased by at least 2, 5, 10, or 100 fold, by a mutation or mutations in any of:
a) H3 HA1 residues N38, I278, or D291;
b) H3 HA2 residue N12;
c) H3 HA1 residues T318, R321, or V323; or
d) H3 HA2 residues A7, E11, I18, D19, G20, W21, L38, K39, T41, Q42, A43, I45, I48, N49, L52, N53, I56, or E57.

In an embodiment, the antibody molecule has a $K_D$ for H3 of equal to or less than $10^{-6}$, wherein said $K_D$ is increased by no more than 2, or 5 fold, by a mutation or mutations in any of:
c) H3 HA1 residues Q327, T328, or R329; or
d) H3 HA2 residues G1, L2, F3, G4, or D46.

In an embodiment, the antibody molecule binds an epitope that has one, two, three, four, five, or all of, the following properties a-f:
aa) it includes one, two, or all of, H1 HA1 residues H31, N279, and S292;
bb) it includes H1 HA2 residue G12;
cc) it does not include one or both of H1 HA1 residues Q328 and S329;
dd) it does not include one, two, three, four, or all of, H1 HA2 residues G1, L2, F3, G4, and D46;
ee) it includes one, two, or all of, H1 HA1 residues T319, R322, and I324 are bound by both Ab 044 and FI6; or ff) it includes 1, 2, 3, 4, 5, 6, 7, 8, 9, 10, 11, 12, 13, 14, 15, 16, 17, or all of, H1 HA2 residues A7, E11, I18, D19, G20, W21, Q38, K39, T41, Q42, N43, I45, I48, T49, V52, N53, I56, and E57.

In an embodiment the antibody molecule has properties: aa; and bb.

In an embodiment the antibody molecule has properties: cc; and dd.

In an embodiment the antibody molecule has properties: aa; and cc or dd.

In an embodiment the antibody molecule has properties: bb; and cc or dd.

In an embodiment the antibody molecule has properties: cc; and aa or bb.

In an embodiment the antibody molecule has properties: dd; and aa or bb.

In an embodiment the antibody molecule has properties: aa, bb, cc and dd.

In an embodiment the antibody molecule has properties: aa, bb, cc, dd, ee, and ff.

In an embodiment, the antibody molecule has a $K_D$ for H1 of equal to or less than $10^{-6}$, wherein said $K_D$ is increased by at least 2, 5, 10, or 100 fold, by a mutation or mutations in any of:
aa) H1 HA1 residues H31, N279, and S292;
bb) H1 HA2 residue G12;
cc) H1 HA1 residues T319, R322, and I324; or
dd) H1 HA2 residues A7, E11, I18, D19, G20, W21, Q38, K39, T41, Q42, N43, I45, I48, T49, V52, N53, I56, and E57.

In an embodiment, the antibody molecule has a $K_D$ for H1 of equal to or less than $10^{-6}$, wherein said $K_D$ is increased by no more than 2, or 5 fold, by a mutation or mutations in any of:
cc) H1 HA1 residues Q328 and S329; or
dd) H1 HA2 residues G1, L2, F3, G4, and D46;

In an embodiment the antibody molecule has one, two, three or all of the following properties:
a and aa;
b and bb;
c and cc;
d and dd.

In the molecule has properties c, cc, d, and dd.

In another aspect, the disclosure features, a binding agent, e.g., an antibody molecule, or preparation, or isolated preparation thereof, comprising a structural or functional property of Ab 031.

In an embodiment, the antibody molecule competes with a reference antibody molecule, e.g., an antibody molecule described herein, for binding to a substrate, e.g., an HA. The reference antibody molecule can be:

a) an antibody molecule comprising:
i) a heavy chain immunoglobulin variable region segment comprising
a CDR1 comprising the sequence S-Y-A-M-H (SEQ ID NO:68);
a CDR2 comprising the sequence V-V-S-Y-D-G-N-Y-K-Y-Y-A-D-S-V-Q-G
(SEQ ID NO:69); and
a CDR3 comprising the sequence D-S-R-L-R-S-L-L-Y-F-E-W-L-S-Q-G-Y-F-N-P (SEQ ID NO:70); and
ii) a light chain variable region segment comprising:
a CDR1 comprising the sequence Q-S-I-T-F-N-Y-K-N-Y-L-A (SEQ ID NO:71);
a CDR2 comprising the sequence W-G-S-Y-L-E-S (SEQ ID NO:72); and
a CDR3 comprising the sequence Q-Q-H-Y-R-T-P-P-S (SEQ ID NO:73).

b) an antibody molecule comprises one or both of: (i) a heavy chain immunoglobulin variable region segment comprising SEQ ID NO: 24; and (ii) a light chain variable region segment comprising SEQ ID NO:45; or c) Ab 031.

The HA can be HA1 or HA5, e.g. from an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004. Competition between the antibody molecule and a reference antibody molecule can be determined by evaluating the ability of one of the antibody molecule or the reference antibody molecule to decrease binding of the other to a substrate, e.g., HA, e.g., HA1 or HA5, e.g. from an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004. Reduction of the ability to bind can be evaluated by methods in the art. Reduction of the ability to bind can be evaluated, e.g., by one or more of:
a) BIAcore analysis;
b) ELISA assay; and
c) flow cytometry.

The antibody molecule can compete with the reference antibody such that binding of the reference antibody is decreased by 50% or more.

In an embodiment the antibody molecule binds to the same epitope, or a portion thereof, which the reference antibody molecule binds.

In an embodiment the antibody molecule does not bind to the same epitope, or a portion thereof, which the reference antibody molecule binds.

In an embodiment the antibody molecule binds to the same epitope, or a portion thereof, on HA, as does a reference antibody molecule, e.g. an antibody molecule disclosed herein. The reference antibody molecule can be:

a) an antibody molecule comprising:
i) a heavy chain immunoglobulin variable region segment comprising
a CDR1 comprising the sequence S-Y-A-M-H (SEQ ID NO:68);
a CDR2 comprising the sequence V-V-S-Y-D-G-N-Y-K-Y-Y-A-D-S-V-Q-G
(SEQ ID NO:69); and
a CDR3 comprising the sequence D-S-R-L-R-S-L-L-Y-F-E-W-L-S-Q-G-Y-F-N-P (SEQ ID NO:70); and
ii) a light chain variable region segment comprising:
a CDR1 comprising the sequence Q-S-I-T-F-N-Y-K-N-Y-L-A (SEQ ID NO:71);
a CDR2 comprising the sequence W-G-S-Y-L-E-S (SEQ ID NO:72); and
a CDR3 comprising the sequence Q-Q-H-Y-R-T-P-P-S (SEQ ID NO:73).

b) an antibody molecule comprises one or both of: (i) a heavy chain immunoglobulin variable region segment comprising SEQ ID NO: 24; and (ii) a light chain variable region segment comprising SEQ ID NO:45; or c) Ab 031.

The HA can be HA1 or HA5, e.g. from an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004. Binding to the same epitope, or a portion thereof, can be shown by one or more of:
a) mutational analysis, e.g., binding to HA, or binding affinity for HA, is decreased or abolished if a residue is mutated;

b) analysis, e.g., comparison, of the crystal structure of the antibody molecule and HA and the crystal structure of a reference antibody and HA, e.g., to determine the touch points of each;

c) competition of the two antibodies for binding to HA, e.g., HA1 or HA5, from, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004;

d) (c) and one or both of (a) and (b).

Competition between the antibody molecule and a reference antibody molecule can be determined by evaluating the ability of one of the antibody molecule or the reference antibody molecule to decrease binding of the other to a substrate, e.g., HA, e.g., HA1 or HA5, from, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004. Reduction of the ability to bind can be evaluated by methods in the art. Reduction of the ability to bind can be evaluated, e.g., by one or more of:

a) BIAcore analysis;

b) ELISA assay; and c) flow cytometry.

The antibody molecule can compete with the reference antibody such that binding of the reference antibody is decreased by 50% or more.

In an embodiment the binding agent, e.g., an antibody molecule, comprises one or both of:

a heavy chain variable region comprising least 60, 70, 80, 85, 90, 95, 98 or 99 percent homology with SEQ ID NO: 24;

and a light chain variable region comprising least 60, 70, 80, 85, 90, 95, 98 or 99 percent homology with SEQ ID NO: 45.

In an embodiment the binding agent, e.g., an antibody molecule, comprises one or both of:

a heavy chain variable region comprising least 60, 70, 80, 85, 90, 95, 98 or 99 percent homology with SEQ ID NO: 24;

and a light chain variable region comprising least 60, 70, 80, 85, 90, 95, 98 or 99 percent homology with SEQ ID NO: 45, wherein, optionally, each HC CDR differs by no more than 1, 2, 3, 4 or 5 amino acids, e.g., 1 or 2, e.g., conservative amino acids, from the corresponding CDR of SEQ ID NO: 24 and each LC CDR differs by no more than 1, 2, 3, 4 or 5 amino acids, e.g., 1 or 2, e.g., conservative amino acids, from the corresponding CDR of SEQ ID NO: 45.

In an embodiment the binding agent, e.g., an antibody molecule, comprises one or both of:

a heavy chain variable region comprising least 60, 70, 80, 85, 90, 95, 98 or 99 percent homology with SEQ ID NO: 25;

and a light chain variable region comprising least 60, 70, 80, 85, 90, 95, 98 or 99 percent homology with SEQ ID NO: 45, wherein the antibody molecule comprises 1, 2, 3, 4, 5, or all of:

(i) a HC CDR1 comprising: S at the 1st position and A at the 3rd position in HC CDR1;

(ii) a HC CDR2 comprising one or both, e.g., one of: V at the 2nd position; or N at the $7^{th}$ position and Q at the $16^{th}$ position in HC CDR2;

(iii) a HC CDR3 comprising: R at the 3rd position (and optionally, L at the $3^{rd}$ position);

(iv) a LC CDR1 comprising: I at the 3rd position;

(v) a LC CDR2 comprising one, two, or three of, e.g., one of: G at the 2nd position; Y at the $4^{th}$ position; or L at the $5^{th}$ position in LC CDR2;

(vi) a LC CDR3 comprising: S at the $9^{th}$ position in LC CDR3;

In an embodiment, the binding agent comprises an antibody molecule comprising:

(a) a heavy chain immunoglobulin variable region segment comprising SEQ ID NO:24 (or a sequence that differs by no more than 1, 2, 3, 4 or 5 amino acids, e.g., conservative amino acids, therefrom); and (b) a light chain variable region segment comprising SEQ ID NO:45 (or a sequence that differs by no more than 1, 2, 3, 4 or 5 amino acids, e.g., conservative amino acids, therefrom).

In one embodiment, the antibody molecule comprises one or both of:

(a) a heavy chain immunoglobulin variable region segment comprising SEQ ID NO: 24; and (b) a light chain variable region segment comprising SEQ ID NO:45.

In an embodiment, the binding agent, e.g., an antibody molecule, comprises one or both of:

(a) a heavy chain immunoglobulin variable region segment comprising a CDR1 comprising the sequence S-Y-A-M-H (SEQ ID NO:68) (or a sequence that differs by no more than, 1, 2, 3, 4, or 5, e.g., 1 or 2 amino acids, e.g., conservative amino acids, therefrom);

a CDR2 comprising the sequence V-V-S-Y-D-G-N-Y-K-Y-Y-A-D-S-V-Q-G (SEQ ID NO:69) (or a sequence that differs by no more than, 1, 2, 3, 4, or 5, e.g., 1 or 2 amino acids, e.g., conservative amino acids, therefrom); and a CDR3 comprising the sequence D-S-R-L-R-S-L-L-Y-F-E-W-L-S-Q-G-Y-F-N-P (SEQ ID NO:70) (or a sequence that differs by no more than, 1, 2, 3, 4, or 5, e.g., 1 or 2 amino acids, e.g., conservative amino acids, therefrom); and (b) a light chain variable region segment comprising a CDR1 comprising the sequence Q-S-I-T-F-N-Y-K-N-Y-L-A (SEQ ID NO:71) (or a sequence that differs by no more than, 1, 2, 3, 4, or 5, e.g., 1 or 2 amino acids, e.g., conservative amino acids, therefrom);

a CDR2 comprising the sequence W-G-S-Y-L-E-S (SEQ ID NO: 72) (or a sequence that differs by no more than, 1, 2, 3, 4, or 5, e.g., 1 or 2 amino acids, e.g., conservative amino acids, therefrom); and a CDR3 comprising the sequence Q-Q-H-Y-R-T-P-P-S (SEQ ID NO:73) (or a sequence that differs by no more than, 1, 2, 3, 4, or 5, e.g., 1 or 2 amino acids, e.g., conservative amino acids, therefrom).

In an embodiment the binding agent, e.g., an antibody molecule, comprises one or both of:

a) LC CDR1-3, that collectively, differ from the AB 031 LC CDR1-3 by no more than, 1, 2, 3, 4, 5, 6, 7, 8, 9, or 10, e.g., 1, 2, 3, or 4, amino acids, e.g., conservative amino acids; and b) HC CDR1-3, that collectively, differ from the AB 031 HC CDR1-3 by no more than, 1, 2, 3, 4, 5, 6, 7, 8, 9, or 10, e.g., 1, 2, 3, or 4, amino acids, e.g., conservative amino acids.

In an embodiment, the binding agent, e.g., an antibody molecule, comprises one or both of:

(a) a heavy chain immunoglobulin variable region segment comprising a CDR1 comprising the sequence <u>S</u>-Y-<u>A</u>-M-H (SEQ ID NO:68) (or a sequence that differs by no more than, 1, 2, or 3, e.g., 1 or 2 amino acids, e.g., conservative amino acids, therefrom, optionally provided that at least 1 or 2 of the highlighted residues are not changed, e.g., both <u>S</u> and <u>A</u> are not changed);

a CDR2 comprising the sequence V-<u>V</u>-S-Y-D-G-<u>N</u>-Y-K-Y-Y-A-D-S-V-<u>Q</u>-G (SEQ ID NO:69) (or a sequence that differs by no more than, 1, 2, 3, 4, or 5, e.g., 1 or 2 amino acids, e.g., conservative amino acids, therefrom, provided that, e.g., at least 1, 2, or 3 of the highlighted residues are not changed, e.g., V or both N and Q or all three of V, N, and Q are not changed);
a CDR3 comprising the sequence D-S-R-L-R-S-L-L-Y-F-E-W-L-S-Q-G-Y-F-N-P (SEQ ID NO:70) (or a sequence that differs by no more than, 1, 2, 3, 4, or 5, e.g., 1 or 2 amino acids, e.g., conservative amino acids, therefrom optionally provided that, e.g., R is not changed); and (b) a light chain variable region segment comprising
a CDR1 comprising the sequence Q-S-I-T-F-N-Y-K-N-Y-L-A (SEQ ID NO: 71) or a sequence that differs by no more than, 1, 2, 3, 4, or 5, e.g., 1 or 2 amino acids, e.g., conservative amino acids, therefrom, optionally provided that at least 1 or 2 of the highlighted residues are not changed, e.g., I is not changed);
a CDR2 comprising the sequence W-G-S-Y-L-E-S (SEQ ID NO:72) (or a sequence that differs by no more than, 1, 2, 3, 4, or 5, e.g., 1 or 2 amino acids, e.g., conservative amino acids, therefrom, optionally provided that at least 1, 2, or 3 of the highlighted residues are not changed, e.g., 1, 2 or all of G, Y, and L are not changed);
a CDR3 comprising the sequence Q-Q-H-Y-R-T-P-P-S (SEQ ID NO:73) (or a sequence that differs by no more than, 1, 2, 3, 4, or 5, e.g., 1 or 2 amino acids, e.g., conservative amino acids, therefrom, optionally provided that at least one or both of the highlighted residues are not changed, e.g., S is not changed).

In an embodiment a CDR of the light or heavy chain includes one of the highlighted residues, or one of the highlighted combinations of residues, for that CDR, (i.e., while other residues in that CDR might be changed, the highlighted residue or combination of residues, are not changed).

In an embodiment a CDR of the light and a CDR of the heavy chain each includes one of the highlighted residues, or one of the highlighted combinations of residues, for that CDR.

In an embodiment each of two CDRs in the antibody molecule includes one of the highlighted residues, or one of the highlighted combinations of residues, for that CDR. In embodiments both are in the light chain. In embodiments both are in the heavy chain.

In an embodiment each of the three CDRs in the heavy chain includes one of the highlighted residues, or one of the highlighted combinations of residues, for that CDR.

In an embodiment each of the three CDRs in the light chain includes one of the highlighted residues, or one of the highlighted combinations of residues, for that CDR.

In an embodiment each of the six CDRs in the heavy and light chain includes one of the highlighted residues, or one of the highlighted combinations of residues, for that CDR.

In one embodiment, the binding agent is an antibody molecule that comprises one or more or all of the following properties:
(a) both S and A in HC CDR1 are unchanged.
(b) V or both N and Q or all three of V, N, and Q in HC CDR2 are unchanged.
(c) R in HC CDR3 is unchanged.
(d) I in LC CDR1 is unchanged.
(e) 1, 2 or 3 of G, Y, and L in LC CDR2 are unchanged;
(f) S in LC CDR3 is unchanged.

In an embodiment the antibody molecule comprises 1, 2, 3, 4, 5, or all 6 properties selected from (a) to (f).

In an embodiment, the antibody molecule comprises a heavy chain having a one or more properties selected from (a), (b), and (c) and a light chain having one or more properties selected from (d), (e), and (f).

In the embodiment, the antibody molecule comprises one or both of:
(a) a heavy chain immunoglobulin variable region segment comprising
a CDR1 comprising the sequence S-Y-A-M-H (SEQ ID NO:68);
a CDR2 comprising the sequence V-V-S-Y-D-G-N-Y-K-Y-Y-A-D-S-V-Q-G (SEQ ID NO:69); and
a CDR3 comprising the sequence D-S-R-L-R-S-L-L-Y-F-E-W-L-S-Q-G-Y-F-N-P (SEQ ID NO:70); and (b) a light chain variable region segment comprising
a CDR1 comprising the sequence Q-S-I-T-F-N-Y-K-N-Y-L-A (SEQ ID NO:71);
a CDR2 comprising the sequence W-G-S-Y-L-E-S (SEQ ID NO:72); and
a CDR3 comprising the sequence Q-Q-H-Y-R-T-P-P-S (SEQ ID NO:73).

In some embodiments, the antibody molecule comprises one or more or all of the following properties: (i) it fails to produce any escape mutants as determined by the failure of a viral titer to recover following at least 10, 9, 8, 7, 6, or 5 rounds of serial infections in cell culture with a mixture of the antibody molecule and an influenza virus (e.g., an influenza A virus, e.g., a Group 1 strain, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004, or an influenza B virus, e.g., B/Wisconsin/1/2010); and (ii) it produces fewer escape mutants than does a reference anti-HA antibody molecule, e.g., Ab 67-11, FI6, FI28, C179, F10, CR9114, or CR6261, e.g., when tested by the method described in (i).

In an embodiment the antibody molecule comprises one or both of:

a) one or more framework regions (FRs) from SEQ ID NO: 24. E.g., the antibody molecule comprises one or more or all of FR1, FR2, FR3, or FR4, or sequences that differ individually, or collectively, by no more than 1, 2, 3, 4, of 5 amino acid residues, e.g., conservative residues, from SEQ ID NO: 24; and b) one or more framework regions (FRs) from SEQ ID NO: 45. E.g., the antibody molecule comprises one or more or all of FR1, FR2, FR3, or FR4, or sequences that differ individually, or collectively, by no more than 1, 2, 3, 4, of 5 amino acid residues, e.g., conservative residues, from SEQ ID NO: 45.

In one embodiment, the antibody molecule comprises:

(a) a heavy chain immunoglobulin variable region segment that further comprises one or more or all of:

an FR1 comprising the sequence E-V-Q-L-L-E-S-G-G-G-L-V-K-P-G-Q-S-L-K-L-S-C-A-A-S-G-F-T-F-T (SEQ ID NO:82) (or a sequence that differs by no more than, 1, 2, 3, 4, or 5, e.g., 1 or 2 amino acids, e.g., conservative amino acids, therefrom, optionally provided that T is not changed);

an FR2 comprising the sequence W-V-R-Q-P-P-G-K-G-L-E-W-V-A (SEQ ID NO:75) (or a sequence that differs by no more than, 1, 2, 3, 4, or 5, e.g., 1 or 2 amino acids, e.g., conservative amino acids, therefrom, optionally provided that W is not changed, or that if changed, is other than R);

an FR3 comprising the sequence R-F-T-I-S-R-D-N-S-K-N-T-L-Y-L-Q-M-N-S-L-R-A-E-D-T-A-V-Y-Y-C-A-K (SEQ ID NO:76) (or a sequence that differs by no more than, 1, 2, 3, 4, or 5, e.g., 1 or 2 amino acids, e.g., conservative amino acids, therefrom, optionally provided that one, two or three of I, R, or L is not changed, or that if I is changed it is other than G, if R is changed it is other than P. or if L is changed it is other than A); and an FR4 comprising the sequence W-G-Q-G-T-T-L-T-V-S-S (SEQ ID NO:77) (or a sequence that differs by no more than, 1, 2, 3, 4, or 5, e.g., 1 or 2 amino acids, e.g., conservative amino acids, therefrom) or W-G-Q-G-T-T-V-T-V-S-S (SEQ ID NO:171) (or a sequence that differs by no more than, 1, 2, 3, 4, or 5, e.g., 1 or 2 amino acids, e.g., conservative amino acids, therefrom); and (a) a light chain immunoglobulin variable region segment further comprises one or more or all of:

an FR1 comprising the sequence D-I-Q-M-T-Q-S-P-S-S-L-S-A-S-V-G-D-R-V-T-I-T-C-R-S-S (SEQ ID NO:78) (or a sequence that differs by no more than, 1, 2, 3, 4, or 5, e.g., 1 or 2 amino acids, e.g., conservative amino acids, therefrom, optionally provided that R is not changed);

an FR2 comprising the sequence W-Y-Q-Q-K-P-G-K-A-P-K-L-L-I-Y (SEQ ID NO:79) (or a sequence that differs by no more than, 1, 2, 3, 4, or 5, e.g., 1 or 2 amino acids, e.g., conservative amino acids, therefrom);

an FR3 comprising the sequence G-V-P-S-R-F-S-G-S-G-S-G-T-D-F-T-L-T-I-S-S-L-Q-P-E-D-F-A-T-Y-Y-C (SEQ ID NO:80) (or a sequence that differs by no more than, 1, 2, 3, 4, or 5, e.g., 1 or 2 amino acids, e.g., conservative amino acids, therefrom, optionally provided that C is not changed, or if changed, is other than P); and an FR4 comprising the sequence F-G-Q-G-T-K-V-E-I-K (SEQ ID NO:81) (or a sequence that differs by no more than, 1, 2, 3, 4, or 5, e.g., 1 or 2 amino acids, e.g., conservative amino acids, therefrom).

In an embodiment a FR of the light or heavy chain includes one of the highlighted residues, or one of the highlighted combinations of residues, for that FR, (i.e., while other residues in that FR might be changed, the highlighted residue or combination of residues, are not changed). E.g., in an embodiment, one, two or three of I, R, or L for heavy chain FR3 is not changed.

In an embodiment a FR of the light and a FR of the heavy chain each includes one of the highlighted residues, or one of the highlighted combinations of residues, for that FR.

In an embodiment each of two FRs in the antibody molecule includes one of the highlighted residues, or one of the highlighted combinations of residues, for that FR. In embodiments both are in the light chain. In embodiments both are in the heavy chain.

In an embodiment each of FR2 and FR3 in the heavy chain includes one of the highlighted residues, or one of the highlighted combinations of residues, for that FR.

In an embodiment each of FR1 and FR2 in the heavy and light chain includes one of the highlighted residues for that FR.

In an embodiment all of the highlighted residues in heavy chain FR1-4 are unchanged.

In an embodiment all of the highlighted residues in light chain FR1-4 are unchanged.

In an embodiment all of the highlighted residues in both heavy and light chain FR1-4 are unchanged.

In one embodiment, the antibody molecule comprises:

(a) the heavy chain immunoglobulin variable region segment comprises one or more or all of an FR1 comprising the sequence E-V-Q-L-L-E-S-G-G-G-L-V-K-P-G-Q-S-L-K-L-S-C-A-A-S-G-F-T-F-T (SEQ ID NO:82);

an FR2 comprising the sequence W-V-R-Q-P-P-G-K-G-L-E-W-V-A (SEQ ID NO:75);

an FR3 comprising the sequence R-F-T-I-S-R-D-N-S-K-N-T-L-Y-L-Q-M-N-S-L-R-A-E-D-T-A-V-Y-Y-C-A-K (SEQ ID NO:76); and an FR4 comprising the sequence W-G-Q-G-T-T-L-T-V-S-S (SEQ ID NO:77) or W-G-Q-G-T-T-V-T-V-S-S (SEQ ID NO:171); and (b) the light chain immunoglobulin variable region segment comprising one or more or all of an FR1 comprising the sequence D-I-Q-M-T-Q-S-P-S-S-L-S-A-S-V-G-D-R-V-T-I-T-C-R-S-S (SEQ ID NO:78);

an FR2 comprising the sequence W-Y-Q-Q-K-P-G-K-A-P-K-L-L-I-Y (SEQ ID NO:79);

an FR3 comprising the sequence G-V-P-S-R-F-S-G-S-G-S-G-T-D-F-T-L-T-I-S-S-L-Q-P-E-D-F-A-T-Y-Y-C (SEQ ID NO:80); and an FR4 comprising the sequence F-G-Q-G-T-K-V-E-I-K (SEQ ID NO:81).

In another embodiment, the antibody molecule comprises one or more or all of the following properties: (a) it fails to produce any escape mutants as determined by the failure of a viral titer to recover following at least 10, 9, 8, 7, 6, or 5 rounds of serial infections in cell culture with a mixture of the antibody molecule and an influenza virus (e.g., an influenza A virus, e.g., a Group 1 strain, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004, or an influenza B virus, e.g., B/Wisconsin/1/2010); (b) it produces fewer escape mutants than does a reference anti-HA antibody molecule, e.g., Ab 67-11, FI6, FI28, C179, F10, CR9114, or CR6261, e.g., when tested by the method described in (a); (c) it binds with high affinity to a hemagglutinin (HA) of at least 1, 2, 3, 4 or 5 influenza subtypes of Group 1 and at least 1, 2, 3, 4 or 5 influenza subtypes of Group 2; (d) it treats or prevents infection by at least 1, 2, 3, 4 or 5 influenza subtypes of Group 1, and by at least 1, 2, 3, 4 or 5 influenza subtypes of Group 2; (e) it inhibits fusogenic activity of the targeted HA; (f) it treats or prevents infection by a Group 1 virus, wherein the virus is an H1, H5, or H9 virus; and treats or prevents infection by a Group 2 virus, wherein the virus is an H3 or H7 virus; (g) it treats or prevents infection by influenza A strains H1N1 and H3N2; (h) it is effective for prevention or treatment of infection, e.g., in humans or mice, with H1N1 and H3N2 when administered at 50 mg/kg, 25 mg/kg, 10 mg/kg, 6 mg/kg, 5 mg/kg, 4 mg/kg, 3 mg/kg, 2 mg/kg, or 1 mg/kg; (i) it treats or prevents infection by influenza A strains H5N1; (j) it is effective for prevention or treatment of infection, e.g., in humans or mice, with H5N1 when administered at 50 mg/kg, 25 mg/kg, 10 mg/kg, 6 mg/kg, 5 mg/kg, 4 mg/kg, 3 mg/kg, 2 mg/kg, or 1 mg/kg; (k) it binds with high affinity to a hemagglutinin (HA) of an influenza B virus, e.g., B/Wisconsin/1/2010; (l) it treats or prevents infection by an influenza B virus, e.g., B/Wisconsin/1/2010; (m) it is effective for prevention or treatment of infection, e.g., in humans or mice, with an influenza B virus, e.g., B/Wisconsin/1/2010 when administered at 50 mg/kg, 25 mg/kg, 10 mg/kg, 6 mg/kg, 5 mg/kg, 4 mg/kg, 3 mg/kg, 2 mg/kg, or 1 mg/kg; (n) the concentration of antibody molecule required for 50% neutralization of influenza A virus is less than 10 μg/mL; (o) the concentration of antibody molecule required for 50% neutralization of influenza B virus, e.g., B/Wisconsin/1/2010, is less than 10 μg/mL; (p) it prevents or minimizes secondary infection (e.g., secondary bacterial infection) or effects thereof on a subject; (q) it is effective for preventing or minimizing secondary infection (e.g., secondary bacterial infection) or effects thereof on a subject when administered at 50 mg/kg, 25 mg/kg, 10 mg/kg, 6 mg/kg, 5 mg/kg, 4 mg/kg, 3 mg/kg, 2 mg/kg, or 1 mg/kg; (r)

it binds an epitope which comprises or consists of the hemagglutinin trimer interface; and (s) it binds an epitope other than that bound by a reference anti-HA antibody molecule, e.g., Ab 67-11, FI6, FI28, C179, F10, CR9114, or CR6261, e.g., when tested by a method disclosed herein, e.g., by competition in an ELISA assay.

In another aspect, the disclosure features an antibody molecule comprising: (a) a heavy chain immunoglobulin variable region segment comprising SEQ ID NO:24 (or a sequence that differs by no more than 1, 2, 3, 4 or 5 amino acids, e.g., conservative amino acids, therefrom); and (b) a light chain variable region segment comprising SEQ ID NO:45 (or a sequence that differs by no more than 1, 2, 3, 4 or 5 amino acids, e.g., conservative amino acids, therefrom). In some embodiments, the antibody molecule comprises one or more or all of the following properties: (i) it fails to produce any escape mutants as determined by the failure of a viral titer to recover following at least 10, 9, 8, 7, 6, or 5 rounds of serial infections in cell culture with a mixture of the antibody molecule and an influenza a virus, e.g., a Group 1 strain, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004; and (ii) it produces fewer escape mutants than does a reference anti-HA antibody molecule, such as Ab 67-11, FI6, FI28, C179, F10, CR9114, or CR6261, such as when tested by the method described in (i).

In an embodiment the binding agent, e.g., an antibody molecule, specifically binds the HA antigen.

In an embodiment, the antibody molecule binds an epitope that has one, two, three, four, five, or all of, the following properties a-f:
 a) it includes one, two, or all of, H3 HA1 residues N38, I278, and D291;
 b) it includes H3 HA2 residue N12;
 c) it does not include one, two or all of, H3 HA1 residues Q327, T328, and R329;
 d) it does not include one, two, three, four, or all of, H3 HA2 residues G1, L2, F3, G4, and D46;
 e) it includes one, two, or all of, H3 HA1 residues T318, R321, and V323; or
 f) it includes 1, 2, 3, 4, 5, 6, 7, 8, 9, 10, 11, 12, 13, 14, 15, 16, 17, or all of, H3 HA2 residues A7, E11, I18, D19, G20, W21, L38, K39, T41, Q42, A43, I45, I48, N49, L52, N53, I56, and E57.

In an embodiment the antibody molecule has properties: a; and b.
In an embodiment the antibody molecule has properties: c; and d.
In an embodiment the antibody molecule has properties: a; and c or d.
In an embodiment the antibody molecule has properties: b; and c or d.
In an embodiment the antibody molecule has properties: c; and a or b.
In an embodiment the antibody molecule has properties: d; and a or b.
In an embodiment the antibody molecule has properties: a, b, c and d.
In an embodiment the antibody molecule has properties: a, b, c, d, e, and f.

In an embodiment, the antibody molecule has a $K_D$ for H3 of equal to or less than $10^{-6}$, wherein said $K_D$ is increased by at least 2, 5, 10, or 100 fold, by a mutation or mutations in any of:
 a) H3 HA1 residues N38, I278, or D291;
 b) H3 HA2 residue N12;
 c) H3 HA1 residues T318, R321, or V323; or
 d) H3 HA2 residues A7, E11, I18, D19, G20, W21, L38, K39, T41, Q42, A43, I45, I48, N49, L52, N53, I56, or E57.

In an embodiment, the antibody molecule has a $K_D$ for H3 of equal to or less than $10^{-6}$, wherein said $K_D$ is increased by no more than 2, or 5 fold, by a mutation or mutations in any of:
 c) H3 HA1 residues Q327, T328, or R329; or
 d) H3 HA2 residues G1, L2, F3, G4, or D46.

In an embodiment, the antibody molecule binds an epitope that has one, two, three, four, five, or all of, the following properties a-f:
 aa) it includes one, two, or all of, H1 HA1 residues H31, N279, and S292;
 bb) it includes H1 HA2 residue G12;
 cc) it does not include one or both of H1 HA1 residues Q328 and S329;
 dd) it does not include one, two, three, four, or all of, H1 HA2 residues G1, L2, F3, G4, and D46;
 ee) it includes one, two, or all of, H1 HA1 residues T319, R322, and I324 are bound by both Ab 044 and FI6; or
 ff) it includes 1, 2, 3, 4, 5, 6, 7, 8, 9, 10, 11, 12, 13, 14, 15, 16, 17, or all of, H1 HA2 residues A7, E11, I18, D19, G20, W21, Q38, K39, T41, Q42, N43, I45, I48, T49, V52, N53, I56, and E57.

In an embodiment the antibody molecule has properties: aa; and bb.
In an embodiment the antibody molecule has properties: cc; and dd.
In an embodiment the antibody molecule has properties: aa; and cc or dd.
In an embodiment the antibody molecule has properties: bb; and cc or dd.
In an embodiment the antibody molecule has properties: cc; and aa or bb.
In an embodiment the antibody molecule has properties: dd; and aa or bb.
In an embodiment the antibody molecule has properties: aa, bb, cc and dd.
In an embodiment the antibody molecule has properties: aa, bb, cc, dd, ee, and ff.

In an embodiment, the antibody molecule has a $K_D$ for H1 of equal to or less than $10^{-6}$, wherein said $K_D$ is increased by at least 2, 5, 10, or 100 fold, by a mutation or mutations in any of:
 aa) H1 HA1 residues H31, N279, and S292;
 bb) H1 HA2 residue G12;
 cc) H1 HA1 residues T319, R322, and I324; or
 dd) H1 HA2 residues A7, E11, I18, D19, G20, W21, Q38, K39, T41, Q42, N43, I45, I48, T49, V52, N53, I56, and E57.

In an embodiment, the antibody molecule has a $K_D$ for H1 of equal to or less than $10^{-6}$, wherein said $K_D$ is increased by no more than 2, or 5 fold, by a mutation or mutations in any of:
 cc) H1 HA1 residues Q328 and S329; or
 dd) H1 HA2 residues G1, L2, F3, G4, and D46;

In an embodiment the antibody molecule has one, two, three or all of the following properties:
a and aa;
b and bb;
c and cc;
d and dd.

In an embodiment the molecule has properties c, cc, d, and dd.

In another aspect, the disclosure features, a binding agent, e.g., an antibody molecule, or preparation, or isolated preparation thereof, comprising a structural or functional property of one or both a heavy chain variable region and a light chain variable region disclosed herein.

In an embodiment, the antibody molecule competes with a reference antibody molecule, e.g., an antibody molecule described herein, for binding to a substrate, e.g., an HA. The reference antibody molecule can be:
  a) an antibody molecule comprising the heavy and light CDRs from
    a heavy chain variable region from Table 3, Table 4A, Table 4B, FIG. 2, FIG. 13, or FIG. 17; and
    a light chain variable region from Table 3, Table 4A, Table 4B, FIG. 3, FIG. 14, or FIG. 17.
  b) an antibody molecule that comprises: (i) a heavy chain immunoglobulin variable region segment from Table 3, Table 4A, Table 4B, FIG. 2, FIG. 13, or FIG. 17; and (ii) a light chain variable region segment from Table 3, Table 4A, Table 4B, FIG. 3, FIG. 14, or FIG. 17; or
  c) an antibody disclosed herein.

The HA can be HA1 or HA5, e.g. from an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004. Competition between the antibody molecule and a reference antibody molecule can be determined by evaluating the ability of one of the antibody molecule or the reference antibody molecule to decrease binding of the other to a substrate, e.g., HA, e.g., HA1 or HA5, e.g. from an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004. Reduction of the ability to bind can be evaluated by methods in the art. Reduction of the ability to bind can be evaluated, e.g., by one or more of:
  a) BIAcore analysis;
  b) ELISA assay; and
  c) flow cytometry. The antibody molecule can compete with the reference antibody such that binding of the reference antibody is decreased by 50% or more. In an embodiment the antibody molecule binds to the same epitope, or a portion thereof, which the reference antibody molecule binds. In an embodiment the antibody molecule does not bind to the same epitope, or a portion thereof, which the reference antibody molecule binds.

In an embodiment the antibody molecule binds to the same epitope, or a portion thereof, on HA, as does a reference antibody molecule, e.g. an antibody molecule disclosed herein. The reference antibody molecule can be:
  a) an antibody molecule comprising the heavy and light CDRs from:
    a heavy chain variable region from Table 3, Table 4A, Table 4B, FIG. 2, FIG. 13, or FIG. 17; and
    a light chain variable region from Table 3, Table 4A, Table 4B, FIG. 3, FIG. 14, or FIG. 17.
  b) an antibody molecule that comprises: (i) a heavy chain immunoglobulin variable region segment from Table 3, Table 4A, Table 4B, FIG. 2, FIG. 13, or FIG. 17; and (ii) a light chain variable region segment from Table 3, Table 4A, Table 4B, FIG. 3, FIG. 14, or FIG. 17; or
  c) an antibody disclosed herein.

The HA can be HA1 or HA5, e.g. from an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004. Binding to the same epitope, or a portion thereof, can be shown by one or more of:
  a) mutational analysis, e.g., binding to HA, or binding affinity for HA, is decreased or abolished if a residue is mutated;
  b) analysis, e.g., comparison, of the crystal structure of the antibody molecule and HA and the crystal structure of a reference antibody and HA, e.g., to determine the touch points of each;
  c) competition of the two antibodies for binding to HA, e.g., HA1 or HA5, e.g. from an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004; and
  d) (c) and one or both of (a) and (b);

Competition between the antibody molecule and a reference antibody molecule can be determined by evaluating the ability of one of the antibody molecule or the reference antibody molecule to decrease binding of the other to a substrate, e.g., HA, e.g., HA1 or HA5, from, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004. Reduction of the ability to bind can be evaluated by methods in the art. Reduction of the ability to bind can be evaluated, e.g., by one or more of:
  a) BIAcore analysis;
  b) ELISA assay; and
  c) flow cytometry. The antibody molecule can compete with the reference antibody such that binding of the reference antibody is decreased by 50% or more.
  d) competition of the two antibodies for binding to HA, e.g., HA1 or HA5, from, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004; and
  e) (c) and one or both of (a) and (b).

Competition between the antibody molecule and a reference antibody molecule can be determined by evaluating the ability of one of the antibody molecule or the reference antibody molecule to decrease binding of the other to a substrate, e.g., HA, e.g., HA1 or HA5, from, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004. Reduction of the ability to bind can be evaluated by methods in the art.

In an embodiment the binding agent, e.g., an antibody molecule, comprises one or both of:
  a heavy chain variable region comprising least 60, 70, 80, 85, 90, 95, 98 or 99 percent homology with a reference heavy chain from Table 3, Table 4A, Table 4B, FIG. 2, FIG. 13 or FIG. 17; and
  a light chain variable region comprising least 60, 70, 80, 85, 90, 95, 98 or 99 percent homology with reference light chain from Table 3, Table 4A, Table 4B, FIG. 3, FIG. 14 or FIG. 17,
  wherein, optionally, each HC CDR differs by no more than 1, 2, 3, 4 or 5 amino acids, e.g., 1 or 2, e.g., conservative amino acids, from the corresponding HC CDR from its reference heavy chain and each LC CDR differs by no more than 1, 2, 3, 4 or 5 amino acids, e.g., 1 or 2, e.g., conservative amino acids, from the corresponding CDR in its reference light chain.

In an embodiment the binding agent, e.g., an antibody molecule, comprises: a heavy chain variable region comprising least 60, 70, 80, 85, 90, 95, 98 or 99 percent homology with a heavy chain from Table 3 and a light chain variable region comprising least 60, 70, 80, 85, 90, 95, 98 or 99 percent homology with the corresponding light chain from Table 3.

In an embodiment the binding agent, e.g., an antibody molecule, comprises: a heavy chain variable region comprising least 60, 70, 80, 85, 90, 95, 98 or 99 percent homology with a heavy chain from Table 4A and a light chain variable region comprising least 60, 70, 80, 85, 90, 95, 98 or 99 percent homology with the corresponding light chain from Table 4A.

In an embodiment the binding agent, e.g., an antibody molecule, comprises: a heavy chain variable region comprising least 60, 70, 80, 85, 90, 95, 98 or 99 percent homology with a heavy chain from Table 4B and a light chain variable region comprising least 60, 70, 80, 85, 90, 95, 98 or 99 percent homology with the corresponding light chain from Table 4B.

In an embodiment the binding agent, e.g., an antibody molecule, comprises one or both of:
a heavy chain variable region from Table 3, Table 4A, Table 4B, FIG. 2, FIG. 13, or FIG. 17; and
a light chain variable region from Table 3, Table 4A, Table 4B, FIG. 3, FIG. 14, or FIG. 17.

In an embodiment the binding agent, e.g., an antibody molecule, comprises:
a heavy chain variable region from Table 3 and the corresponding light chain from Table 3;
a heavy chain from Table 4A and the corresponding light chain from Table 4A; or
a heavy chain from Table 4B and the corresponding light chain from Table 4B.

In an embodiment, the binding agent, e.g., an antibody molecule, comprises one or both of:
(a) a heavy chain immunoglobulin variable region segment comprising a CDR1, a CDR2 and a CDR3 from a heavy chain sequence of Table 3, Table 4A, Table 4B, FIG. 2, FIG. 13, or FIG. 17 (or CDRs that, individually or collectively, differ therefrom by no more than, 1, 2, 3, 4, or 5, e.g., 1 or 2 amino acids, e.g., conservative amino acids)); and
(b) a light chain immunoglobulin variable region segment comprising a CDR1, a CDR2 and a CDR3 from a light chain sequence of Table 3, Table 4A, Table 4B, FIG. 3, FIG. 14, or FIG. 17 (or CDRs that, individually or collectively, differ therefrom by no more than, 1, 2, 3, 4, or 5, e.g., 1 or 2 amino acids, e.g., conservative amino acids).

In an embodiment the binding agent, e.g., an antibody molecule, comprises one or both of:
CDRs from a heavy chain of Table 3 and the light chain CDRs from the corresponding light chain from Table 3.

In an embodiment the binding agent, e.g., an antibody molecule, comprises one or both of:
CDRs from a heavy chain of Table 4A and the light chain CDRs from the corresponding light chain from Table 4A.

In an embodiment the binding agent, e.g., an antibody molecule, comprises one or both of:
CDRs from a heavy chain of Table 4B and the light chain CDRs from the corresponding light chain from Table 4B.

In some embodiments, the binding agent, e.g., an antibody molecule, comprises one or more or all of the following properties: (i) it fails to produce any escape mutants as determined by the failure of a viral titer to recover following at least 10, 9, 8, 7, 6, or 5 rounds of serial infections in cell culture with a mixture of the antibody molecule and an influenza virus (e.g., an influenza A virus, e.g., a Group 1 strain, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004, or an influenza B virus, e.g., B/Wisconsin/1/2010); (ii) it produces fewer escape mutants than does a reference anti-HA antibody molecule, e.g., Ab 67-11, FI6, FI28, C179, F10, CR9114, or CR6261, e.g., when tested by the method described in (i); and (iii) it is other than Ab 67-11 and FI6.

In one embodiment, the antibody molecule comprises one or both of:
(a) a heavy chain immunoglobulin variable region segment comprising a CDR1, a CDR2; and a CDR3 from a heavy chain sequence of FIG. 2, FIG. 13, or FIG. 17; and
(b) a light chain immunoglobulin variable region segment comprising a CDR1, a CDR2 and a CDR3 from a light chain sequence of FIG. 3, FIG. 14, or FIG. 17.

In one embodiment, the antibody molecule comprises:
(a) a heavy chain immunoglobulin variable region segment from FIG. 2 or FIG. 17; and
(b) a light chain immunoglobulin variable region segment from FIG. 3 or FIG. 17.

In one embodiment, the heavy chain immunoglobulin variable region further comprises an Isoleucine-Aspartate (Ile-Asp) dipeptide at the N-terminus. In another embodiment, the light chain immunoglobulin variable region further comprises an Ile-Asp dipeptide at the N-terminus. In yet another embodiment, both the heavy chain immunoglobulin variable region and the light chain immunoglobulin variable region or an antibody featured in the disclosure further comprises an Ile-Asp dipeptide at the N-terminus. In other embodiment the Ile-Asp dipeptide is absent from one or both the heavy and light chain.

In one embodiment, the binding agent, e.g., an antibody molecule, further comprises one or more or all of the following: (a) it treats or prevents infection by at least 1, 2, 3, 4 or 5 influenza subtypes of Group 1, and by at least 1, 2, 3, 4 or 5 influenza subtypes of Group 2; (b) it inhibits fusogenic activity of the targeted HA; (c) it treats or prevents infection by a Group 1 virus, wherein the virus is an H1, H5, or H9 virus; and treats or prevents infection by a Group 2 virus, wherein the virus is an H3 or H7 virus; (d) it treats or prevents infection by influenza A strains H1N1 and H3N2; (e) it is effective for prevention or treatment of infection, e.g., in humans or mice, with H1N1 and H3N2 when administered at 50 mg/kg, 25 mg/kg, 10 mg/kg, 6 mg/kg, 5 mg/kg, 4 mg/kg, 3 mg/kg, 2 mg/kg, or 1 mg/kg; (0 it treats or prevents infection by influenza A strains H5N1; (g) it is effective for prevention or treatment of infection, e.g., in humans or mice, with H5N1 when administered at 50 mg/kg, 25 mg/kg, 10 mg/kg, 6 mg/kg, 5 mg/kg, 4 mg/kg, 3 mg/kg, 2 mg/kg, or 1 mg/kg; (h) it binds with high affinity to a hemagglutinin (HA) of an influenza B virus, e.g., B/Wisconsin/1/2010; (i) it treats or prevents infection by an influenza B virus, e.g., B/Wisconsin/1/2010; (j) it is effective for prevention or treatment of infection, e.g., in humans or mice, with an influenza B virus, e.g., B/Wisconsin/1/2010 when administered at 50 mg/kg, 25 mg/kg, 10 mg/kg, 6 mg/kg, 5 mg/kg, 4 mg/kg, 3 mg/kg, 2 mg/kg, or 1 mg/kg; (k) the concentration of antibody molecule required for 50% neutralization of influenza A virus is less than 10 µg/mL; (l) the concentration of antibody molecule required for 50% neutralization of influenza B virus, e.g., B/Wisconsin/1/2010, is less than 10 µg/mL; (m) it prevents or minimizes secondary infection (e.g., secondary bacterial infection) or effects thereof on a subject; (n) it is effective for preventing or minimizing secondary infection (e.g., secondary bacterial infection) or effects thereof on a subject when administered at 50 mg/kg, 25 mg/kg, 10 mg/kg, 6 mg/kg, 5 mg/kg, 4 mg/kg, 3 mg/kg, 2 mg/kg, or 1 mg/kg; (o) it binds an epitope which comprises or consists of the hemagglutinin trimer interface; and (p) it binds an epitope other than that bound by a reference anti-HA antibody molecule, e.g., Ab 67-11, FI6, FI28, C179, F10, CR9114, or CR6261, e.g., when tested by a method disclosed herein, e.g., by competition in an ELISA assay.

In an embodiment the antibody molecule comprises one or both of:
a) one or more framework regions (FRs) from heavy chain disclosed herein. E.g., the antibody molecule comprises one or more or all of FR1, FR2, FR3, or FR4, or sequences that differ individually, or collectively, by no more than 1, 2, 3, 4, of 5 amino acid residues, e.g., conservative residues, from heavy chain disclosed herein; and
b) one or more framework regions (FRs) from light chain disclosed herein. E.g., the antibody molecule comprises one or more or all of FR1, FR2, FR3, or FR4, or sequences that differ individually, or collectively, by no more than 1, 2, 3, 4, of 5 amino acid residues, e.g., conservative residues, from light chain disclosed herein.

In an embodiment the binding agent, e.g., an antibody molecule, specifically binds the HA antigen.

In an embodiment, the antibody molecule binds an epitope that has one, two, three, four, five, or all of, the following properties a-f:
a) it includes one, two, or all of, H3 HA1 residues N38, I278, and D291;
b) it includes H3 HA2 residue N12;
c) it does not include one, two or all of, H3 HA1 residues Q327, T328, and R329;
d) it does not include one, two, three, four, or all of, H3 HA2 residues G1, L2, F3, G4, and D46;
e) it includes one, two, or all of, H3 HA1 residues T318, R321, and V323; or
f) it includes 1, 2, 3, 4, 5, 6, 7, 8, 9, 10, 11, 12, 13, 14, 15, 16, 17, or all of, H3 HA2 residues A7, E11, I18, D19, G20, W21, L38, K39, T41, Q42, A43, I45, I48, N49, L52, N53, I56, and E57.

In an embodiment the antibody molecule has properties: a; and b.

In an embodiment the antibody molecule has properties: c; and d.

In an embodiment the antibody molecule has properties: a; and c or d.

In an embodiment the antibody molecule has properties: b; and c or d.

In an embodiment the antibody molecule has properties: c; and a or b.

In an embodiment the antibody molecule has properties: d; and a or b.

In an embodiment the antibody molecule has properties: a, b, c and d.

In an embodiment the antibody molecule has properties: a, b, c, d, e, and f.

In an embodiment, the antibody molecule has a $K_D$ for H3 of equal to or less than $10^{-6}$, wherein said $K_D$ is increased by at least 2, 5, 10, or 100 fold, by a mutation or mutations in any of:

a) H3 HA1 residues N38, I278, or D291;

b) H3 HA2 residue N12;

c) H3 HA1 residues T318, R321, or V323; or d) H3 HA2 residues A7, E11, I18, D19, G20, W21, L38, K39, T41, Q42, A43, I45, I48, N49, L52, N53, I56, or E57.

In an embodiment, the antibody molecule has a $K_D$ for H3 of equal to or less than $10^{-6}$, wherein said $K_D$ is increased by no more than 2, or 5 fold, by a mutation or mutations in any of:

c) H3 HA1 residues Q327, T328, or R329; or d) H3 HA2 residues G1, L2, F3, G4, or D46.

In an embodiment, the antibody molecule binds an epitope that has one, two, three, four, five, or all of, the following properties a-f:

aa) it includes one, two, or all of, H1 HA1 residues H31, N279, and S292;

bb) it includes H1 HA2 residue G12;

cc) it does not include one or both of H1 HA1 residues Q328 and S329;

dd) it does not include one, two, three, four, or all of, H1 HA2 residues G1, L2, F3, G4, and D46;

ee) it includes one, two, or all of, H1 HA1 residues T319, R322, and I324 are bound by both Ab 044 and FI6; or ff) it includes 1, 2, 3, 4, 5, 6, 7, 8, 9, 10, 11, 12, 13, 14, 15, 16, 17, or all of, H1 HA2 residues A7, E11, I18, D19, G20, W21, Q38, K39, T41, Q42, N43, I45, I48, T49, V52, N53, I56, and E57.

In an embodiment the antibody molecule has properties: aa; and bb.

In an embodiment the antibody molecule has properties: cc; and dd.

In an embodiment the antibody molecule has properties: aa; and cc or dd.

In an embodiment the antibody molecule has properties: bb; and cc or dd.

In an embodiment the antibody molecule has properties: cc; and aa or bb.

In an embodiment the antibody molecule has properties: dd; and aa or bb.

In an embodiment the antibody molecule has properties: aa, bb, cc and dd.

In an embodiment the antibody molecule has properties: aa, bb, cc, dd, ee, and ff.

In an embodiment, the antibody molecule has a $K_D$ for H1 of equal to or less than $10^{-6}$, wherein said $K_D$ is increased by at least 2, 5, 10, or 100 fold, by a mutation or mutations in any of:

aa) H1 HA1 residues H31, N279, and S292;

bb) H1 HA2 residue G12;

cc) H1 HA1 residues T319, R322, and I324; or dd) H1 HA2 residues A7, E11, I18, D19, G20, W21, Q38, K39, T41, Q42, N43, I45, I48, T49, V52, N53, I56, and E57.

In an embodiment, the antibody molecule has a $K_D$ for H1 of equal to or less than $10^{-6}$, wherein said $K_D$ is increased by no more than 2, or 5 fold, by a mutation or mutations in any of:

cc) H1 HA1 residues Q328 and S329; or dd) H1 HA2 residues G1, L2, F3, G4, and D46;

In an embodiment the antibody molecule has one, two, three or all of the following properties:

a and aa;

b and bb;

c and cc;

d and dd.

In an embodiment the molecule has properties c, cc, d, and dd.

In one aspect, the disclosure features an anti-hemagglutinin (anti-HA) binding agent, e.g., antibody molecule, or preparation, or isolated preparation thereof, comprising:

(a) a heavy chain immunoglobulin variable region segment comprising one or more or all of a CDR1 comprising the sequence G-F-T-F-[S/T]-[S/T]-Y-[A/G]-M-H (SEQ ID NO:184), or a sequence that differs from SEQ ID NO:184 by no more than 1 or 2 residues;

a CDR2 comprising the sequence V-[I/V/L]-S-[Y/F]-D-G-[S/N]-[Y/N]-[K/R]-Y-Y-A-D-S-V-Q-G (SEQ ID NO:2) or a sequence that differs from SEQ ID NO:2 by no more than 1 or 2 residues; and a CDR3 comprising the sequence D-[S/T]-[R/K/Q]-L-R-[S/T]-L-L-Y-F-E-W-L-S-[Q/S]-G-[Y/L/V]-[F/L]-[N/D]-[P/

Y] (SEQ ID NO:3), or a sequence that differs from SEQ ID NO:3 by no more than 1 or 2 residues; and (b) a light chain variable region segment comprising one or more or all of a CDR1 comprising the sequence [K/R]-S-S-Q-[S/I]-[V/L/I]-[T/S]-[Y/F/W]-[N/S/D]-Y-K-N-Y-L-A (SEQ ID NO:185) or a sequence that differs from SEQ ID NO:185 by no more than 1 or 2 residues, or comprising the sequence [K/R]-S-S-Q-[S/T]-[V/L/I]-[T/S]-[Y/F/W]-[N/S/D/Q/R/E]-Y-K-N-Y-L-A (SEQ ID NO:186) or a sequence that differs from SEQ ID NO:186 by no more than 1 or 2 residues or [K/R]-S-S-Q-[S/T]-[V/L/I]-[T/S]-[Y/F/W]-[N/S/D/E]-Y-K-N-Y-L-A (SEQ ID NO:185) or a sequence that differs from SEQ ID NO:185 by no more than 1 or 2 residues;

a CDR2 comprising the sequence W-[A/G]-S-[T/A/Y/H/K/D]-[R/L]-E-[S/T] (SEQ ID NO:5) or a sequence that differs from SEQ ID NO:5 by no more than 1 or 2 residues;

a CDR3 comprising the sequence Q-Q-[Y/H]-Y-R-T-P-P-[T/S] (SEQ ID NO:6) or a sequence that differs from SEQ ID NO:6 by no more than 1 or 2 residues; optionally, provided that, if the light chain variable region segment comprises: a CDR 1 comprising the sequence K-S-S-Q-S-V-T-Y-N-Y-K-N-Y-L-A (SEQ ID NO:83); a CDR2 comprising the sequence W-A-S-T-R-E-S (SEQ ID NO:84); and a CDR3 comprising the sequence Q-Q-Y-Y-R-T-P-P-T (SEQ ID NO:85);

then the heavy chain variable region segment comprises one or more of the following: (a) CDRs other than the following: a CDR1 comprising the sequence S-Y-G-M-H (SEQ ID NO:86); a CDR2 comprising the sequence V-I-S-Y-D-G-S-Y-K-Y-Y-A-D-S-V-Q-G (SEQ ID NO:87); or a CDR3 comprising the sequence D-S-E-L-R-S-L-L-Y-F-E-W-L-S-Q-G-Y-F-N-P (SEQ ID NO:88); or (b) FRs other than the following: an FR1 other than E-V-Q-L-L-E-S-G-G-G-L-V-K-P-G-Q-S-L-K-L-S-C-A-A-S-G-F-T-F-T (SEQ ID NO:82); an FR2 other than W-V-R-Q-P-P-G-K-G-L-E-W-V-A (SEQ ID NO:75); an FR3 other than R-F-T-I-S-R-D-N-S-K-N-T-L-Y-L-Q-M-N-S-L-R-A-E-D-T-A-V-Y-Y-C-A-K (SEQ ID NO:76); or an FR4 other than W-G-A-G-T-T-L-T-V-S-S (SEQ ID NO:89); (c) a CDR1 where the amino residue at position 5 of SEQ ID NO:184 is an S, the amino acid residue at position 6 of SEQ ID NO:184 is a T, or the amino acid residue at position 8 of SEQ ID NO:184 is an A; (d) a CDR2 wherein the amino acid residue at position 2 of SEQ ID NO:2 is a V or an L, the amino acid at position 4 is an F, the amino acid at position 7 is an N, the amino acid at position 8 is a Y, or the amino acid at position 9 is a R; (e) a CDR3 wherein the amino acid residue at position 2 of SEQ ID NO:3 is a T, the amino acid residue at position 3 of SEQ ID NO:3 is an R, a K, or a Q, the amino acid residue at position 6 of SEQ ID NO:3 is a T, the amino acid residue at position 15 of SEQ ID NO:3 is an S, the amino acid residue at position 17 of SEQ ID NO:3 is an L, or a V, the amino acid residue at position 18 of SEQ ID NO:3 is an L, the amino acid residue at position 19 of SEQ ID NO:3 is a D, or the amino acid residue at position 20 of SEQ ID NO:3 is a Y; (f) an FR1 wherein the amino residue at position 11 of SEQ ID NO:7 is a Q, or the amino acid residue at position 7 of SEQ ID NO:7 is a T; (g) an FR4 wherein the amino residue at position 3 of SEQ ID NO:10 is a Q, the amino acid residue at position 5 of SEQ ID NO:10 is an A; the amino acid residue at position 6 of SEQ ID NO:10 is an M, or the amino acid residue at position 7 of SEQ ID NO:10 is a V; or (h) it produces fewer escape mutants than does a reference anti-HA antibody molecule, e.g., Ab 67-11, FI6, FI28, C179, F10, CR9114, or CR6261, e.g., when tested by a method disclosed herein, and also provided that, if the heavy chain immunoglobulin variable region segment comprises: a CDR1 comprising the sequence S-Y-G-M-H (SEQ ID NO:86); a CDR2 comprising the sequence V-1-S-Y-D-G-S-Y-K-Y-Y-A-D-S-V-Q-G (SEQ ID NO:87); and a CDR3 comprising the sequence D-S-E-L-R-S-L-L-Y-F-E-W-L-S-Q-G-Y-F-N-P (SEQ ID NO:88), then the light chain variable region segment comprises one of more of the following: (a) CDRs other than the following: CDR1 KSSQSVTYNYKNYLA (SEQ ID NO:83); CDR2 WASTRES (SEQ ID NO:84); or CDR3 QQYYRTPPT (SEQ ID NO:85); (b) FRs other than the following: FR1 comprising the sequence EIVMTQSPDSLAVSLGERATINC (SEQ ID NO:90); FR2 comprising the sequence WYQQKPGQPPKLLIY (SEQ ID NO:91); FR3 comprising the sequence GVPDRFSGSGSGTDFTLTISSLQAEDVAVYYC (SEQ ID NO:92); or FR4 comprising the sequence FGGGTKLDIK (SEQ ID NO:93); (c) a CDR1 wherein the amino residue at position 1 of SEQ ID NO:185 is an R, the amino residue at position 5 of SEQ ID NO:185 is a T, the amino residue at position 6 of SEQ ID NO:185 is an L or an I, the amino residue at position 7 of SEQ ID NO:185 is an S, the amino residue at position 8 of SEQ ID NO:185 is an F or a W, or the amino residue at position 9 of SEQ ID NO:185 is an S or a D; (d) a CDR2 wherein the amino residue at position 2 of SEQ ID NO:5 is a G, the amino residue at position 4 of SEQ ID NO:5 is an A, a Y, an H, a K, or a D, the amino residue at position 5 of SEQ ID NO:5 is an L, the amino residue at position 7 of SEQ ID NO:5 is a T; (e) a CDR3 wherein the amino residue at position 3 of SEQ ID NO:6 is an H; the amino acid residue at position 9 of SEQ ID NO:6 is an S; (f) an FR1 wherein the amino residue at position 1 of SEQ ID NO:11 is a D; the amino residue at position 3 of SEQ ID NO:11 is a Q, the amino residue at position 9 of SEQ ID NO:11 is an S, the amino residue at position 10 of SEQ ID NO:11 is a T, the amino residue at position 11 of SEQ ID NO:11 is a V, the amino residue at position 12 of SEQ ID NO:11 is an S, the amino residue at position 13 of SEQ ID NO:11 is an A, the amino residue at position 14 of SEQ ID NO:11 is a T, the amino residue at position 15 of SEQ ID NO:11 is a V or an R, the amino residue at position 17 of SEQ ID NO:11 is a D, the amino residue at position 20 of SEQ ID NO:11 is an S, the amino residue at position 22 of SEQ ID NO:11 is a T, a Q, a D, or an R; (g) an FR2 wherein the amino residue at position 8 of SEQ ID NO:12 is a K; or the amino residue at position 9 of SEQ ID NO: 12 is an A; (h) an FR3 wherein the amino residue at position 4 of SEQ ID NO: 13 is an E or an S; the amino residue at position 24 of SEQ ID NO: 13 is a P, the amino residue at position 27 of SEQ ID NO: 13 is an F, a K, or a D, the amino residue at position 29 of SEQ ID NO: 13 is a T; (i) an FR4 wherein the amino residue at position 3 of SEQ ID NO:14 is a Q, a T, an S, or an N, the amino residue at position 7 of SEQ ID NO:14 is a V, or the amino residue at position 8 of SEQ ID NO:14 is an E; or (j) it produces fewer escape mutants than does a reference anti-HA antibody molecule, e.g., Ab 67-11, FI6, FI28, C179, F10, CR9114, or CR6261, e.g., when tested by a method disclosed herein; and further provided that if the light chain variable region segment comprises: a CDR 1 comprising the sequence K-S-S-Q-S-V-T-F-N-Y-K-N-Y-L-A (SEQ ID NO:146); a CDR2 comprising the sequence W-A-S-A-R-E-S (SEQ ID NO:147); and a CDR3 comprising the sequence Q-Q-H-Y-R-T-P-P-T (SEQ ID NO:148); then the heavy chain variable region segment comprises one or more of the following: CDRs other than the CDR's described at FIG. 12B; or FRs other than the FRs described at FIG. 12C.

In one embodiment, the heavy chain CDR sequences, collectively, differ from the recited sequences by no more than 5, 4, 3, 2 or 1 amino acid residues; and the light chain CDR sequences, collectively, differ from the recited sequences by no more than 5, 4, 3, 2 or 1 amino acid residues.

In one aspect, the disclosure features an isolated nucleic acid molecule comprising a nucleotide sequence that encodes a heavy chain immunoglobulin variable region segment featured in the disclosure.

In another aspect, the disclosure features an isolated nucleic acid molecule that comprises a nucleotide sequence encoding a light chain immunoglobulin variable region segment featured in the disclosure.

In yet another aspect, the disclosure features an isolated nucleic acid molecule that comprises a nucleotide sequence that encodes a heavy chain immunoglobulin variable region segment featured in the disclosure and a light chain immunoglobulin variable region segment featured in the disclosure.

In yet another aspect, the disclosure features a recombinant vector, such as an expression vector, that comprises a nucleic acid molecule that comprises a nucleotide sequence that encodes a heavy chain immunoglobulin variable region segment or nucleotide sequence that encodes a light chain immunoglobulin variable region segment featured in the disclosure.

In one aspect, the disclosure features a recombinant vector, such as an expression vector, that comprises a nucleotide sequence that encodes a heavy chain immunoglobulin variable region segment and a nucleotide sequence that encodes a light chain immunoglobulin variable region segment featured in the disclosure.

In one embodiment, the nucleic acid molecules in the recombinant vector include a nucleotide sequence encoding (a) a heavy chain immunoglobulin variable region segment comprising the amino acid sequence of: S-Y-A-M-H (SEQ ID NO:68) in CDR1; V-V-S-Y-D-G-N-Y-K-Y-Y-A-D-S-V-Q-G (SEQ ID NO:69) in CDR2; and D-S-R-L-R-S-L-L-Y-F-E-W-L-S-Q-G-Y-F-N-P (SEQ ID NO:70) in CDR3; and (b) a light chain immunoglobulin variable region segment comprising the amino acid sequence of: Q-S-I-T-F-D-Y-K-N-Y-L-A (SEQ ID NO:145) in CDR1; W-G-S-Y-L-E-S (SEQ ID NO:72) in CDR2; and Q-Q-H-Y-R-T-P-P-S (SEQ ID NO:73) in CDR3.

In one aspect, the disclosure features a cell containing a recombinant vector featured in the disclosure, such as a recombinant vector comprising a nucleic acid sequence that encodes a heavy chain immunoglobulin variable region, or a recombinant vector comprising a nucleic acid sequence that encodes a light chain immunoglobulin variable region. In one embodiment, the cell contains a recombinant vector comprising a nucleic acid sequence that encodes a heavy chain immunoglobulin variable region, and a recombinant vector comprising a nucleic acid sequence that encodes a light chain immunoglobulin variable region. In yet another embodiment, the cell contains a recombinant vector comprising a nucleic acid sequence that encodes a heavy chain immunoglobulin variable region, and a nucleic acid sequence that encodes a light chain immunoglobulin variable region.

In one aspect, the disclosure features a method of making an antibody molecule featured in the invention, such as by providing a host cell comprising a nucleic acid sequence expressing a heavy chain segment and a nucleic acid sequence expressing a light chain segment, and expressing the nucleic acids in the host cell.

In one embodiment, the nucleic acid sequence expressing the heavy chain segment and the nucleic acid sequence expressing the light chain segment are on the same recombinant expression vector. In another embodiment, the nucleic acid sequence expressing the heavy chain segment and the nucleic acid sequence expressing the light chain segment are on separate recombinant expression vectors.

In one aspect, the disclosure features a pharmaceutical composition containing an antibody molecule featured in the disclosure, and a pharmaceutically acceptable carrier.

In another aspect, the disclosure features a method of treating or preventing infection with an influenza virus (e.g., an influenza A virus, e.g., a Group 1 strain, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004, or an influenza B virus, e.g., B/Wisconsin/1/2010), in a subject, e.g., a human subject, that comprises:

administering a binding agent, e.g., an antibody molecule, featured in the disclosure to a subject, e.g., human subject, in need thereof.

In one embodiment, the influenza A virus is an H1, H5, H9, H3 or H7 strain, such as an H1N1 strain, an H3N2 strain, or an H5N1 strain of influenza A virus.

In an embodiment the administration results in, or correlates with, one or more of a reduction in the incidence or severity of a symptom or manifestation of an influenza infection, or the delay or onset of a symptom or manifestation of an influenza infection.

In an embodiment the administration results in, or correlates with, one or more of a reduction in the incidence or severity of a symptom or manifestation of a secondary infection, or the delay or onset of a symptom or manifestation of a secondary infection.

In embodiments the subject, e.g., a human subject, has been administered, or the method comprises, administering, or recommending the administration of, a second or additional therapy.

In embodiments the antibody molecule is administered in combination with a second or additional agent or therapy.

In embodiments the second or additional therapy comprises administration of a vaccine or an anti-viral therapy, e.g., an anti-NA or an anti-M2 therapy.

In an embodiment the second or additional therapy comprises a administration of a vaccine, e.g., a vaccine described herein or a mixture (a.k.a. a cocktail) of influenza peptides to stimulate the patient's immune system to prevent infection with particular strains of influenza A.

In an embodiment the second or additional agent comprises administering an anti-viral agent, a pain reliever, an anti-inflammatory, an antibiotic, a steroidal agent, a second therapeutic antibody molecule (e.g., an anti-HA antibody), an adjuvant, a protease or glycosidase (e.g., sialidase).

In an embodiment the second or additional agent comprises, acyclovir, ribavirin, amantadine, remantidine, a neuraminidase inhibitor (e.g., zanamivir (Relenza®), oseltamivir (Tamiflu®), laninamivir, peramivir), or rimantadine.

In an embodiment the second or additional agent comprises a second antibody molecule, e.g., Ab 67-11 (U.S. Provisional application No. 61/645,453, FI6 (U.S. Published Application No. 2010/0080813), FI28 (U.S. Published Application No. 2010/0080813), C179 (Okuno et al., J. Virol. 67:2552-8, 1993), F10 (Sui et al., Nat. Struct. Mol. Biol. 16:265, 2009), CR9114 (Dreyfus et al., Science 337:1343, 2012), or CR6261 (see, e.g., Ekiert et al., Science 324:246, 2009). Thus, Ab 044 can be used in combination of any of those antibodies.

In an embodiment the second or additional agent comprises a second or additional binding agent, e.g., antibody molecule, e.g., an anti-HA antibody, e.g., an disclosed herein. E.g., two or more of Ab 044, Ab 069, Ab 032, and Ab 031 can be administered. E.g., Ab 044 can be administered in combination with Ab 069 or Ab 032

In the case of combinations, two agents can be administered as part of the same dosage unit or administered separately. Other exemplary agents useful for treating the symptoms associated with influenza infection are acetaminophen, ibuprofen, aspirin, and naproxen.

In an embodiment the binding agent, e.g., an antibody molecule, is administered to a human subject suffering from or susceptible to an influenza infection.

In an embodiment the binding agent, e.g., an antibody molecule, is administered prior to known exposure to influenza, or to particular influenza subtypes or strains.

In an embodiment the binding agent, e.g., an antibody molecule, is administered prior to manifestation of effects or symptoms of influenza infection, or to one or more particular effects manifestation of effects or symptoms of influenza infection.

In an embodiment the binding agent, e.g., an antibody molecule, is administered after known exposure to influenza, or to particular influenza subtypes or strains.

In an embodiment the binding agent, e.g., an antibody molecule, is administered after manifestation of effects or symptoms of influenza infection, or after observation of one or more particular effects manifestation of effects or symptoms of influenza infection.

In an embodiment the binding agent, e.g., an antibody molecule, is administered in response to, or to treat or prevent, a manifestation of an effect or a symptom of influenza infection, e.g., inflammation, fever, nausea, weight loss, loss of appetite, rapid breathing, increase heart rate, high blood pressure, body aches, muscle pain, eye pain, fatigue, malaise, dry cough, runny nose, and/or sore throat.

In an embodiment, the method further comprises, testing the human subject for the influenza virus, e.g., with a method disclosed herein. In embodiments, the administration is responsive to a positive test for influenza.

In yet another aspect, the disclosure features a method of treating a subject, e.g., a human subject, infected with an influenza virus (e.g., an influenza A virus, e.g., a Group 1 strain, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004, or an influenza B virus, e.g., B/Wisconsin/1/2010) by administering a binding agent, e.g., an antibody molecule, featured in the disclosure. For example, the influenza A virus is an H1, H5, H9, H3 or H7 strain, such as an H1N1 strain, an H3N2 strain, or an H5N1 strain of influenza A virus.

In one embodiment, a binding agent, e.g., an anti-HA antibody, described herein is administered instead of a vaccine for prevention of influenza. In another embodiment, the binding agent, e.g., anti-HA antibody molecule, is administered in combination with (simultaneously or sequentially with) a vaccine for prevention of the flu.

In yet another aspect, the disclosure features a method of detecting influenza (e.g., influenza A or influenza B) virions in a biological sample, such as by contacting the sample with a binding agent, e.g., an antibody molecule, featured in the disclosure, and then detecting the binding of the antibody molecule to the sample. In one embodiment, the method of detecting the influenza virus (e.g., influenza A or influenza B virus) is performed in vitro.

In one aspect, the disclosure features a method of (a) providing a sample from a patient; (b) contacting the sample with a binding agent, e.g., an antibody molecule, featured in the disclosure, and (c) determining whether the binding agent, e.g., an antibody molecule, featured in the disclosure binds a polypeptide in the sample, where if the binding agent, e.g., an antibody molecule, binds a polypeptide in the sample, then the patient is determined to be infected with an influenza virus (e.g., an influenza A virus, e.g., a Group 1 strain, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004, or an influenza B virus, e.g., e.g., B/Wisconsin/1/2010). In one embodiment, the patient is determined to be infected with an influenza virus (e.g., an influenza A virus, e.g., a Group 1 strain, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004, or an influenza B virus, e.g., B/Wisconsin/1/2010), and the patient is further administered a binding agent, e.g., an antibody molecule, disclosed herein, e.g., the binding agent, e.g., an antibody molecule, with which the test was performed.

In another aspect, the invention features, a method of inducing immunity to one or more influenza strains, or preventing, delaying or reducing infection with an influenza strain, or symptom thereof, in a vertebrate, e.g., a human. The method comprises administering to the vertebrate, e.g., a human, a broad range vaccine, or broad range immunogen, described herein.

In an embodiment the broad range vaccine, or broad range immunogen, induces an immune response against, or confers protection against, one or more influenza strains.

In an embodiment the broad range vaccine, or broad range immunogen, induces an immune response against, or confers protection against, two influenza strains.

In an embodiment the broad range vaccine, or broad range immunogen, induces an immune response against, or confers protection against, two Group 1 influenza strains.

In an embodiment the broad range vaccine induces, or broad range immunogen, an immune response against, or confers protection against, at least one Group 1 strain, and a second strain from Group 1, Group 2 or an influenza B strain.

In one embodiment, the influenza A virus is an H1, H5, H9, H3 or H7 strain, such as an H1N1 strain, an H3N2 strain, or an H5N1 strain of influenza A virus.

In an embodiment the administration results in, or correlates with, one or more of: a reduction in the chance of an infection, a reduction in the incidence or severity of a symptom or manifestation of an influenza infection, or the delay or onset of a symptom or manifestation of an influenza infection.

In an embodiment the administration results in, or correlates with, one or more of: a reduction in the incidence or severity of a symptom or manifestation of a secondary infection, or the delay or onset of a symptom or manifestation of a secondary infection.

In embodiments the subject, e.g., a human subject, has been administered, or the method comprises, administering, or recommending the administration of, a second or additional therapy.

In embodiments the broad range vaccine is administered in combination with a second or additional agent or therapy.

In embodiments the second or additional agent comprises administration of another vaccine or another anti-viral therapy, e.g., an anti-NA or an anti-M2 therapy.

In an embodiment the second or additional agent comprises administration of a vaccine comprising a mixture (a.k.a. a cocktail) of influenza peptides to stimulate the patient's immune system to prevent infection with particular strains of influenza A.

In an embodiment the second or additional agent comprises administering an anti-viral agent, a pain reliever, an anti-inflammatory, an antibiotic, a steroidal agent, a second therapeutic antibody molecule (e.g., an anti-HA antibody), an adjuvant, a protease or glycosidase (e.g., sialidase).

In an embodiment the second or additional agent comprises, acyclovir, ribavirin, amantadine, remantidine, a neuraminidase inhibitor (e.g., zanamivir (Relenza®), oseltamivir (Tamiflu®), laninamivir, peramivir), or rimantadine.

In an embodiment the second or additional agent comprises an antibody molecule, e.g., Ab 67-11 (U.S. Provisional application No. 61/645,453, FI6 (U.S. Published Application No. 2010/0080813), FI28 (U.S. Published Application No. 2010/0080813), C179 (Okuno et al., J. Virol. 67:2552-8, 1993), F10 (Sui et al., Nat. Struct. Mol. Biol. 16:265, 2009), CR9114 (Dreyfus et al., Science 337:1343, 2012), or CR6261 (see, e.g., Ekiert et al., Science 324:246, 2009).

In an embodiment the second or additional agent comprises an antibody molecule disclosed herein, e.g., an antibody molecule selected from Ab-044, Ab 069, Ab 032, and Ab 031 antibody molecules.

In the case of combinations, two agents can be administered as part of the same dosage unit or administered separately.

Other exemplary second or additional agents useful for treating the symptoms associated with influenza infection are acetaminophen, ibuprofen, aspirin, and naproxen.

In an embodiment the broad range vaccine, or broad range immunogen, is administered to a human subject suffering from or susceptible to an influenza infection.

In an embodiment the broad range vaccine, or broad range immunogen, is administered prior to known exposure to influenza, or to particular influenza substypes or strains.

In an embodiment the broad range vaccine, or broad range immunogen, is administered prior to manifestation of effects or symptoms of influenza infection, or to one or more particular effects manifestation of effects or symptoms of influenza infection.

In an embodiment the broad range vaccine, or broad range immunogen, is administered after known exposure to influenza, or to particular influenza substypes or strains.

In an embodiment the broad range vaccine is administered after manifestation of effects or symptoms of influenza infection, or after observation of one or more particular effects manifestation of effects or symptoms of influenza infection.

In an embodiment the broad range vaccine, or broad range immunogen, is administered in response to, or to treat or prevent, a manifestation of an effect or a symptom of influenza infection, e.g., inflammation, fever, nausea, weight loss, loss of appetite, rapid breathing, increase heart rate, high blood pressure, body aches, muscle pain, eye pain, fatigue, malaise, dry cough, runny nose, and/or sore throat.

In an embodiment, the method further comprises, testing the human subject for the influenza virus, e.g., with a method disclosed herein. In embodiments, the administration is responsive to a positive test for influenza.

In yet another aspect, the disclosure features a method of treating a subject, e.g., a human subject, infected with an influenza virus (e.g., an influenza A virus, e.g., a Group 1 strain, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004, or an influenza B virus, e.g., B/Wisconsin/1/2010) by administering a broad range vaccine featured in the disclosure. For example, the influenza A virus is an H1, H5, H9, H3 or H7 strain, such as an H1N1 strain, an H3N2 strain, or an H5N1 strain of influenza A virus.

In another aspect, the invention features, a method of reducing the severity of influenza in a population. The method includes administering a broad range vaccine, or broad range immunogen, to sufficient individuals in the population to prevent or decrease the chance of influenza virus transmission to another individual in the population.

In another aspect, the invention features, a kit comprising one or more containers having disposed therein a broad range immunogen, a nucleic acid encoding the broad range epitope, or a broad range vaccine described herein. In an embodiment the kit includes a container having adjuvant disposed therein. In an embodiment the kit comprises a delivery device, e.g., an injection device or inhaler. In an embodiment the broad range epitope described herein, or a nucleic acid encoding the broad range epitope or broad range vaccine, is disposed in a delivery device.

In an embodiment the kit comprises a delivery device, e.g., an injection device or inhaler. In an embodiment the vaccine is disposed in a delivery device.

In another aspect, the invention features, a composition, e.g., a vaccine, comprising a broad range epitope described herein, packaged in a hermetically sealed container such as an ampoule. In an embodiment, the composition a liquid. In an embodiment, the composition is liquid a dry sterilized lyophilized powder or water free concentrate.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments featured in the disclosure are set forth in the accompanying drawings and the description below. Other features, objects, and advantages featured in the disclosure will be apparent from the description and drawings, and from the claims.

BRIEF DESCRIPTION OF DRAWINGS

FIG. 1 is the heavy and light chain amino acid sequences (SEQ ID NOs:94 and 95, respectively) of the anti-HA antibody A18. The constant domain sequence is indicated by italics. The CDRs are indicated by underlining FIG. 2 is the variable heavy chain domain sequence of exemplary anti-HA antibodies. The SEQ ID NOs. for sequences shown are as follows: VH15 is SEQ ID NO: 15; VH16 is SEQ ID NO: 16; VH17 is SEQ ID NO: 17; VH18 is SEQ ID NO: 18; VH19 is SEQ ID NO: 19; VH21 is SEQ ID NO: 21; VH22 is SEQ ID NO: 22; VH20 is SEQ ID NO: 20; VH23 is SEQ ID NO: 23; VH24 is SEQ ID NO: 24; VH25 is SEQ ID NO: 25; VH26 is SEQ ID NO: 26; VH27 is SEQ ID NO: 27; and VH161 is SEQ ID NO: 161.

FIG. 3 is the variable light chain domain sequence of exemplary anti-HA antibodies. The SEQ ID NOs. for sequences shown are as follows: VL28 is SEQ ID NO: 28; VL29 is SEQ ID NO: 29; VL30 is SEQ ID NO: 30; VL35 is SEQ ID NO: 35; VL31 is SEQ ID NO: 31; VL32 is SEQ ID NO: 32; VL33 is SEQ ID NO: 33; VL34-ID is SEQ ID NO: 34; VL36 is SEQ ID NO: 36; VL45 is SEQ ID NO: 45; VL46 is SEQ ID NO: 46; VL37 is SEQ ID NO: 37; VL38 is SEQ ID NO: 38; VL39 is SEQ ID NO: 39; VL40 is SEQ ID NO: 40; VL41 is SEQ ID NO: 41; VL42 is SEQ ID NO: 42; VL43 is SEQ ID NO: 43; VL44 is SEQ ID NO: 44; VL47 is SEQ ID NO: 47; VL48 is SEQ ID NO: 48; VL49 is SEQ ID NO: 49; VL50 is SEQ ID NO: 50; VL51 is SEQ ID NO: 51; VL52 is SEQ ID NO: 52; VL53 is SEQ ID NO: 53; VL54 is SEQ ID NO: 54; VL55 is SEQ ID NO: 55; VL56 is SEQ ID NO: 56; VL57 is SEQ ID NO: 57; VL58 is SEQ ID NO: 58; VL59 is SEQ ID NO: 59; VL60 is SEQ ID NO: 60; VL61 is SEQ ID NO: 61; VL153 is SEQ ID NO: 153; VL154 is SEQ ID NO: 154; VL155 is SEQ ID NO: 155; VL156 is SEQ ID NO: 156; and VL62 is SEQ ID NO: 62.

FIG. 12 shows the amino acid sequences of the heavy chain variable regions of FI6 (SEQ ID NO: 175), FI370 (SEQ ID NO: 176), FI6 variant 1 (SEQ ID NO: 177), FI6 variant 3 (SEQ ID NO: 178), FI6/370 (SEQ ID NO: 179) and the amino acid sequence of kappa light chain variable region of FI6 (SEQ ID NO: 180).

FIG. 13 is the variable heavy chain domain sequence of exemplary anti-HA antibodies as shown in FIG. 2 and including an N-terminal ID dipeptide. The SEQ ID NOs. for sequences shown are as follows: VH15-ID is SEQ ID NO: 96; VH16-ID is SEQ ID NO: 97; VH17-ID is SEQ ID NO: 98; VH18-ID is SEQ ID NO: 99; VH19-ID is SEQ ID NO: 100; VH21-ID is SEQ ID NO: 101; VH22-ID is SEQ ID NO: 102; VH20-ID is SEQ ID NO: 103; VH23-ID is SEQ ID NO: 104; VH24-ID is SEQ ID NO: 105; VH25-ID is SEQ ID NO: 106; VH26-ID is SEQ ID NO: 107; VH27-ID is SEQ ID NO: 108; and VH161-ID is SEQ ID NO: 109.

FIG. 14 is the variable light chain domain sequence of exemplary anti-HA antibodies as shown in FIG. 3 and including an N-terminal ID dipeptide. The SEQ ID NOs. for sequences shown are as follows: VL28-ID is SEQ ID NO: 110; VL29-ID is SEQ ID NO: 111; VL30-ID is SEQ ID NO: 112; VL35-ID is SEQ ID NO: 113; VL31-ID is SEQ ID NO: 114; VL32-ID is SEQ ID NO: 115; VL33-ID is SEQ ID NO: 116; VL34-ID is SEQ ID NO: 117; VL36-ID is SEQ ID NO: 118; VL45-ID is SEQ ID NO: 119; VL46-ID is SEQ ID NO: 120; VL37-ID is SEQ ID NO: 121; VL38-ID is SEQ ID NO: 122; VL39-ID is SEQ ID NO: 123; VL40-ID is SEQ ID NO: 124; VL41-ID is SEQ ID NO: 125; VL42-ID is SEQ ID NO: 126; VL43-ID is SEQ ID NO: 127; VL44-ID is SEQ ID NO: 128; VL47-ID is SEQ ID NO: 129; VL48-ID is SEQ ID NO: 130; VL49-ID is SEQ ID NO: 131; VL50-ID is SEQ ID NO: 132; VL51-ID is SEQ ID NO: 133; VL52-ID is SEQ ID NO: 134; VL53-ID is SEQ ID NO: 135; VL54-ID is SEQ ID NO: 136; VL55-ID is SEQ ID NO: 137; VL56-ID is SEQ ID NO: 138; VL57-ID is SEQ ID NO: 139; VL58-ID is SEQ ID NO: 140; VL59-ID is SEQ ID NO: 141; VL60-ID is SEQ ID NO: 142; VL61-ID is SEQ ID NO: 143; VL153-ID is SEQ ID NO: 157; VL154-ID is SEQ ID NO: 158; VL155-ID is SEQ ID NO: 159; VL156-ID is SEQ ID NO: 160; and VL62-ID is SEQ ID NO: 144.

FIG. 17 shows the variable light and heavy chain sequences of additional exemplary anti-HA antibodies. The SEQ ID NOs. for sequences shown are as follows: VL165 is SEQ ID NO: 165; VL166 is SEQ ID NO: 166; VL167 is SEQ ID NO: 167; VL168 is SEQ ID NO: 168; VL169 is SEQ ID NO: 169; VH164 is SEQ ID NO: 164; VH162 is SEQ ID NO: 162; VH163 is SEQ ID NO: 163.

FIG. 21A shows lung viral load in mice four days after viral challenge with H1N1, as measured by plaque assay. Infected mice were treated with vehicle, ribavirin, Ab 044 prophylaxis at 10 mg/kg, Ab 044 prophylaxis at 2.5 mg/kg, Ab 044 prophylaxis at 0.6 mg/kg, Ab 044 therapy at 10 mg/kg, Ab 044 therapy at 2.5 mg/kg, Ab 044 therapy at 0.6 mg/kg, or Ab 044 therapy at 72 h.

FIG. 21B shows lung viral load in mice four days after viral challenge with H3N2. Infected mice were treated with vehicle, ribavirin, Ab 044 prophylaxis at 10 mg/kg, Ab 044 therapy at 10 mg/kg, Ab 044 therapy at 2.5 mg/kg, Ab 044 therapy at 0.6 mg/kg, or Ab 044 therapy at 72 h. Asterisk, p<0.05.

DETAILED DESCRIPTION

Figure 4:
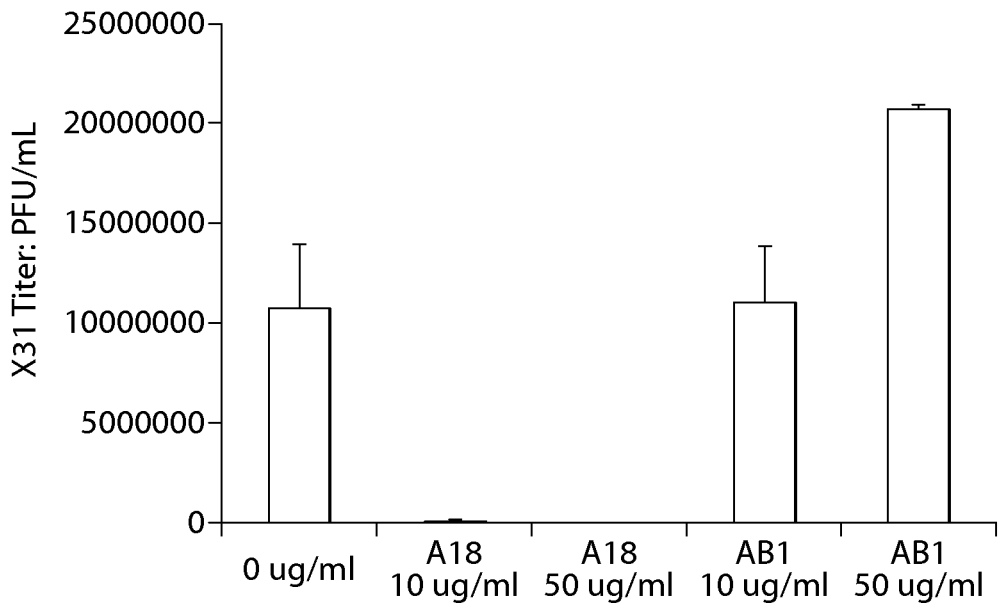
FIG. 4 is a graph depicting neutralization of the H3N2 strain X-31 by A18 antibodies. In contrast, strain X-31 was not neutralized by AB1 antibodies.

The disclosure is based, at least in part, on the design and synthesis of antibody molecules that can bind an epitope that is conserved across multiple hemagglutinin subtypes of influenza viruses (e.g., influenza A and influenza B viruses). For example, the antibody molecules described herein are useful as broad spectrum therapy against disease caused by at least one influenza A strain belonging to Group 1 and one influenza A strain belonging to Group 2 to neutralize infectivity of viruses belonging to both Group 1 and Group 2 (at least one subtype of each).

The antibody molecules were designed by a rational structure-based approach to target a region on the virus that is not fully accessible to the human immune system and, therefore, not amenable to antibody selection through more classical screening approaches. This rational-based approach to the design and development of broad-spectrum antibody molecules allows for the development of more efficacious vaccines for pandemic and seasonal influenza. This approach also allows for the advance preparation of pandemic vaccines so that they are ready to be employed against specific virus subtypes (e.g., avian virus subtypes) that may mutate to become human-adapted and highly transmissible. Vaccines (e.g., seasonal vaccines) that utilize the antibody molecules described herein can generate a more potent immune response without the use of adjuvants and provide broad protection against viral strain variation.

DEFINITIONS

As used herein, the term "antibody molecule" refers to a polypeptide that comprises sufficient sequence from an immunoglobulin heavy chain variable region and/or sufficient sequence from an immunoglobulin light chain variable region, to provide antigen specific binding. It comprises full length antibodies as well as fragments thereof, e.g., Fab fragments, that support antigen binding. Typically an antibody molecule will comprise heavy chain CDR1, CDR2, and CDR3 and light chain CDR1, CDR2, and CDR3 sequence. Antibody molecules include human, humanized, CDR-grafted antibodies and antigen binding fragments thereof. In embodiments an antibody molecule comprises a protein that comprises at least one immunoglobulin variable region segment, e.g., an amino acid sequence that provides an immunoglobulin variable domain or immunoglobulin variable domain sequence.

The VH or VL chain of the antibody molecule can further include all or part of a heavy or light chain constant region, to thereby form a heavy or light immunoglobulin chain, respectively. In one embodiment, the antibody molecule is a tetramer of two heavy immunoglobulin chains and two light immunoglobulin chains.

An antibody molecule can comprise one or both of a heavy (or light) chain immunoglobulin variable region segment. As used herein, the term "heavy (or light) chain immunoglobulin variable region segment," refers to an entire heavy (or light) chain immunoglobulin variable region, or a fragment thereof, that is capable of binding antigen. The ability of a heavy or light chain segment to bind antigen is measured with the segment paired with a light or heavy chain, respectively. In some embodiment, a heavy or light chain segment that is less than a full length variable region will, when paired with the appropriate chain, bind with an affinity that is at least 20, 30, 40, 50, 60, 70, 80, 90, or 95% of what is seen when the full length chain is paired with a light chain or heavy chain, respectively.

An immunoglobulin variable region segment may differ from a reference or consensus sequence. As used herein, to "differ," means that a residue in the reference sequence or consensus sequence is replaced with either a different residue or an absent or inserted residue.

An antibody molecule can comprise a heavy (H) chain variable region (abbreviated herein as VH), and a light (L) chain variable region (abbreviated herein as VL). In another example, an antibody comprises two heavy (H) chain variable regions and two light (L) chain variable regions or antibody binding fragments thereof. The light chains of the immunoglobulin may be of types kappa or lambda. In one embodiment, the antibody molecule is glycosylated. An antibody molecule can be functional for antibody dependent cytotoxicity and/or complement-mediated cytotoxicity, or may be non-functional for one or both of these activities. An antibody molecule can be an intact antibody or an antigen-binding fragment thereof.

Antibody molecules include "antigen-binding fragments" of a full length antibody, e.g., one or more fragments of a full-length antibody that retain the ability to specifically bind to an HA target of interest. Examples of binding fragments encompassed within the term "antigen-binding fragment" of a full length antibody include (i) a Fab fragment, a monovalent fragment consisting of the VL, VH, CL and CH1 domains; (ii) a F(ab') or F(ab')$_2$ fragment, a bivalent fragment including two Fab fragments linked by a disulfide bridge at the hinge region; (iii) an Fd fragment consisting of the VH and CH1 domains; (iv) an Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR) that retains functionality. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules known as single chain Fv (scFv). See e.g., Bird et al. (1988) Science 242:423-426; and Huston et al. (1988) Proc. Natl. Acad. Sci. USA 85:5879-5883. Antibody molecules include diabodies.

As used herein, an antibody refers to a polypeptide, e.g., a tetrameric or single chain polypeptide, comprising the structural and functional characteristics, particularly the antigen binding characteristics, of an immunoglobulin. Typically, a human antibody comprises two identical light chains and two identical heavy chains. Each chain comprises a variable region.

The variable heavy (VH) and variable light (VL) regions can be further subdivided into regions of hypervariability, termed "complementarity determining regions" ("CDR"), interspersed with regions that are more conserved, termed "framework regions" (FR). Human antibodies have three VH CDRs and three VL CDRs, separated by framework regions FR1-FR4. The extent of the FRs and CDRs has been precisely defined (see, Kabat, E. A., et al. (1991) *Sequences of Proteins of Immunological Interest, Fifth Edition*, U.S. Department of Health and Human Services, NIH Publication No. 91-3242; and Chothia, C. et al. (1987) J. Mol. Biol. 196:901-917). Kabat definitions are used herein. Each VH and VL is typically composed of three CDRs and four FRs, arranged from amino-terminus to carboxyl-terminus in the following order: FR1, CDR1, FR2, CDR2, FR3, CDR3, FR4.

The heavy and light immunoglobulin chains can be connected by disulfide bonds. The heavy chain constant region typically comprises three constant domains, CH1, CH2 and CH3. The light chain constant region typically comprises a CL domain. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system.

The term "immunoglobulin" comprises various broad classes of polypeptides that can be distinguished biochemically. Those skilled in the art will appreciate that heavy chains are classified as gamma, mu, alpha, delta, or epsilon ($\gamma$, $\mu$, $\alpha$, $\delta$, $\epsilon$) with some subclasses among them (e.g., $\gamma1$-$\gamma4$). It is the nature of this chain that determines the "class" of the antibody as IgG, IgM, IgA IgD, or IgE, respectively. The immunoglobulin subclasses (isotypes) e.g., IgG1, IgG2, IgG3, IgG4, IgA1, etc. are well characterized and are known to confer functional specialization. Modified versions of each of these classes and isotypes are readily discernable to the skilled artisan in view of the instant disclosure and, accordingly, are within the scope of the instant disclosure. All immunoglobulin classes are clearly within the scope of the present disclosure. Light chains are classified as either kappa or lambda ($\kappa$, $\lambda$). Each heavy chain class may be bound with either a kappa or lambda light chain.

Suitable antibodies include, but are not limited to, monoclonal, monospecific, polyclonal, polyspecific, human antibodies, primatized antibodies, chimeric antibodies, bi-specific antibodies, humanized antibodies, conjugated antibodies (i.e., antibodies conjugated or fused to other proteins, radiolabels, cytotoxins), Small Modular ImmunoPharmaceuticals ("SMIPs™"), single chain antibodies, cameloid antibodies, and antibody fragments.

In embodiments, an antibody is a humanized antibody. A humanized antibody refers to an immunoglobulin comprising a human framework region and one or more CDR's from a non-human, e.g., mouse or rat, immunoglobulin. The immunoglobulin providing the CDR's is often referred to as the "donor" and the human immunoglobulin providing the framework often called the "acceptor," though in embodiments, no source or no process limitation is implied. Typically a humanized antibody comprises a humanized light chain and a humanized heavy chain immunoglobulin.

An "immunoglobulin domain" refers to a domain from the variable or constant domain of immunoglobulin molecules Immunoglobulin domains typically contain two $\beta$-sheets formed of about seven $\beta$-strands, and a conserved disulphide bond (see, e.g., A. F. Williams and A. N. Barclay (1988) Ann Rev. Immunol. 6:381-405).

As used herein, an "immunoglobulin variable domain sequence" refers to an amino acid sequence that can form the structure of an immunoglobulin variable domain. For example, the sequence may include all or part of the amino acid sequence of a naturally-occurring variable domain. For example, the sequence may omit one, two or more N- or C-terminal amino acids, internal amino acids, may include one or more insertions or additional terminal amino acids, or may include other alterations. In one embodiment, a polypeptide that comprises an immunoglobulin variable domain sequence can associate with another immunoglobulin variable domain sequence to form a target binding structure (or "antigen binding site"), e.g., a structure that interacts with the target antigen.

As used herein, the term antibodies comprises intact monoclonal antibodies, polyclonal antibodies, single domain antibodies (e.g., shark single domain antibodies (e.g., IgNAR or fragments thereof)), multispecific antibodies (e.g., bi-specific antibodies) formed from at least two intact antibodies, and antibody fragments so long as they exhibit the desired biological activity. Antibodies for use herein may be of any type (e.g., IgA, IgD, IgE, IgG, IgM).

The antibody or antibody molecule can be derived from a mammal, e.g., a rodent, e.g., a mouse or rat, horse, pig, or goat. In embodiments, an antibody or antibody molecule is produced using a recombinant cell. In some embodiments an antibody or antibody molecule is a chimeric antibody, for example, from mouse, rat, horse, pig, or other species, bearing human constant and/or variable regions domains.

A binding agent, as used herein, is an agent that bind, e.g., specifically binds, a target antigen, e.g., HA. Binding agents of the invention share sufficient structural relationship with anti-HA antibody molecules disclosed herein to support specific binding to HA, and in embodiments, other functional properties of an anti-HA antibody molecule disclosed herein. In embodiments a binding agent will exhibit a binding affinity at of at least 10, 20, 30, 40, 50, 60, 70, 80, or 90% of an antibody molecule disclosed herein, e.g., an antibody molecule with which it shares, significant structural homology, e.g., CDR sequences. Binding agents can be naturally occurring, e.g., as are some antibodies, or synthetic. In an embodiment a binding agents is a polypeptide, e.g., an antibody molecule, e.g., an antibody. While some binding agents are antibody molecules, other molecules, e.g., other polypeptides, can also function as binding agents. Polypeptide binding agents can be monomeric or multimeric, e.g., dimeric, trimeric, or tetrameric and can be stabilized by intra- or interchain bonds, e.g., disulfide bonds. They can contain natural or non-naturally occurring amino acid residues. In embodiments, binding agents are antibody molecules, or other polypeptides, that present one or more CDRs of antibody molecules disclosed herein or that otherwise mimic the structure of an antibody molecule disclosed herein. Binding agents can also comprise aptomers, nucleic acids or other molecular entities. A binding agent can be developed in a variety of ways, e.g., by innumization, by rational design, screening of random structures, or a combination of those or other approaches. Typically a binding agent will act by making contact with substantially the same epitope as an antibody molecule disclosed herein, e.g., an antibody molecule with which it shares, significant structural homology, e.g., CDR sequences. A binding agent can interact with amino acids, saccharides, or combinations thereof. Polypeptides other than antibodies can be used as a scaffold to present sequence, e.g., one or more, or a complete set of heavy chain and/or light chain CDRs, disclosed herein. Exemplary scaffolds include adnectin, zinc finger DNA-binding proteins. protein A, lipoclins, ankryin consensus repeat domain, thioredoxin, anticalins, centyrin, avimer domains, ubiquitin, peptidomimetics, stapled peptides, cystine-knot miniproteins, and IgNARs. In some embodiments, a binding agent is or comprises a nucleic acid, e.g., DNA, RNA or mixtures thereof. In embodiments a binding agent, e.g., a nucleic acid, shows secondary, tertiary, or quaternary structure. In some embodiments a binding agent, e.g., a nucleic acid, forms a structure that mimics the structure of an antibody molecule disclosed herein.

A broad spectrum binding agent, e.g., antibody molecule, as used herein, binds, a plurality of different HA molecules, and optionally neutralizes viruses comprising the different HA molecules. In an embodiment it binds a first HA and binds a second HA from influenza A Group 1, and optionally neutralizes viruses comprising the first or second HA molecules. In an embodiments it binds a first HA from an influenza A Group 1 virus, and binds a second HA from an influenza A Group 2 virus, and optionally neutralizes viruses comprising the different HA molecules. In an embodiment it binds a first HA from an influenza A Group 1 or 2 virus and binds a HA from an influenza B virus, and optionally neutralizes viruses comprising the different HA molecules. In an embodiments it binds, and in embodiments neutralizes, at least two different clades or clusters of virus, e.g., from different Groups. In embodiments it binds, and in embodiments neutralizes, all or substantially all strains of Group 1 an/or Group 2 disclosed herein. In an embodiment, a binding agent, e.g., antibody molecule, binds, and in embodiments, neutralizes: at least one strain from the Group 1 H1, e.g., H1a or H1b, cluster and at least one strain from the Group 2 H3 or H7 cluster. In an embodiment, a binding agent, e.g., antibody molecule, binds, and in embodiments, neutralizes: at least one strain from the Group 1 H1, e.g., H1a or H1b, cluster and at least one influenza B strain. In an embodiment, a binding agent, e.g., antibody molecule, binds, and in embodiments, neutralizes: at least one strain from the Group 2 H3 or H7 cluster and at least one influenza B strain. In an embodiment, a binding agent, e.g., antibody molecule, binds, and in embodiments, neutralizes: at least one strain from the Group 1 H1, e.g., H1a or H1b, cluster, at least one strain from the Group 2 H3 or H7 cluster, and at least one influenza B strain. In some embodiments, binding agent, e.g., antibody molecule, binds, and optionally neutralizes or mediate infection of particular hosts, e.g., avian, camel, canine, cat, civet, equine, human, mouse, swine, tiger, or other mammal or bird.

The term "combination therapy", as used herein, refers to administration of a plurality of agents, e.g., wherein at least one binding agent, e.g., antibody molecule, disclosed herein is administered to a subject, e.g., a human subject. The introduction of the agents into the subject can be at different times. In embodiments the agents are administered in overlapping regimens, or such that the subject is simultaneously exposed to both agents, or such that the response of the subject is better than would be seen with either agent administered alone.

As used herein, an "escape mutant" is a mutated influenza strain that is resistant to neutralization by an anti-HA antibody molecule described herein. In embodiments an escape mutant is resistant to neutralization with a binding agent, e.g., antibody molecule, but its parent strain is neutralized by the binding agent, e.g., antibody molecule.

As used herein, "pandemic influenza" refers to a new viral strain that arises due to human adaptation of an influenza strain by mutation or by emergence of a strain by reassortment of different strains of influenza A. The resulting pandemic strain is significantly different from previous strains and most people will have little or no pre-existing immunity. Symptoms and complications may be more severe and more frequent than those typical of seasonal influenza. Examples of past pandemic flu viruses include, e.g., the 2009 H1N1 'swine flu,' the 1957-58 H2N2 'Asian flu' and the 1968 H3N2 influenza strains.

The terms "purified" and "isolated" as used herein in the context of an antibody molecule, e.g., a antibody, a immunogen, or generally a polypeptide, obtained from a natural source, refers to a molecule which is substantially free of contaminating materials from the natural source, e.g., cellular materials from the natural source, e.g., cell debris, membranes, organelles, the bulk of the nucleic acids, or proteins, present in cells. Thus, a polypeptide, e.g., an antibody molecule, that is isolated includes preparations of a polypeptide having less than about 30%, 20%, 10%, 5%, 2%, or 1% (by dry weight) of cellular materials and/or contaminating materials. The terms "purified" and "isolated" when used in the context of a chemically synthesized species, e.g., an antibody molecule, or immunogen, refers to the species which is substantially free of chemical precursors or other chemicals which are involved in the syntheses of the molecule.

A preparation of binding agents, e.g., antibody molecules, as used herein, comprises a plurality of molecules of a binding agent, e.g., antibody molecule, described herein. In embodiments that binding agent, e.g., antibody molecule, makes up at least 60, 70, 80, 90, 95, 98, 99, 99.5 or 99.9%, of the preparation, or of the active ingredients of the preparation, by weight or number. In embodiments that binding agent is an antibody molecule which makes up at least 60, 70, 80, 90, 95, 98, 99, 99.5 or 99.9%, of the preparation, or of the active ingredients, or polypeptide ingredients, or antibody molecules, of the preparation, by weight or number. In embodiments the binding agent is an antibody molecule and the preparation contains no more than 30, 20, 10, 5, 2, 1, or 0.5%, by weight or number, of a contaminant, e.g., a reactant, solvent, precursor or other species, from the source, or used in the preparation, of the antibody molecule, e.g., a species from a cell, reaction mixture, or other system used to produce the antibody molecule.

As used herein, the term "prevent infection" means that a subject (e.g., a human) is less likely to be infected by influenza if the subject receives the antibody prior to (e.g., 1 day, 2 days, 1 week, 2 weeks, 3 weeks, or 1 month of more) before being exposed to influenza.

As used herein, "seasonal influenza" is a strain that is identical or closely related to strains that have been circulating in the human population in recent years and therefore most people are at least partially immune to it. Such a strain is not likely to cause severe disease. Symptoms can include fever, cough, runny nose, and muscle pain, and in rare cases, death can result from complications, such as pneumonia. Outbreaks follow predictable seasonal patterns, annually, and usually in fall and winter and in temperate climates. Infection due to seasonal influenza is commonly referred to as the flu.

As used herein, specific binding, means that a binding agent, e.g., an antibody molecule, binds its antigen with a $K_D$ of equal to or less than $10^{-5}$. In embodiments, the antibody binds it's antigen with a $K_D$ of equal to or less than $10^{-6}$, $10^{-7}$, $10^{-8}$, $10^{-9}$, $10^{-10}$, $10^{-11}$, or $10^{-12}$.

As used herein, the term "therapeutically effective amount" refers to an amount of a therapeutic agent, e.g., a binding agent, e.g., an antibody molecule, which results in a positive outcome for the subject. In embodiments, it can be statistically correlated with therapeutic effect or benefit, e.g., the lessening or prevention of a manifestation of an effect or a symptom, when administered to a population of subjects. In embodiments it is an amount that also provides a preselected, or reasonable, benefit/risk ratio. In embodiments it is an amount effective to reduce the incidence and/or severity of and/or to delay onset of one or more features, symptoms, or characteristics of a disease, disorder, or condition. A therapeutically effective amount is can be administered in a dosing regimen that may comprise one or multiple unit doses.

As used herein, the term "treat infection" means that a subject (e.g., a human) who has been infected with an influenza and experiences symptoms of the influenza (e.g., the flu), will in embodiments, suffer less severe symptoms and/or will recover faster when the antibody molecule is administered than if the antibody is never administered. In embodiments, when an infection is treated, an assay to detect virus in the subject will detect less virus after effective treatment for the infection. For example, a diagnostic assay using an antibody molecule, such as an antibody molecule described herein, will detect less or no virus in a biological sample of a patient after administration of an antibody molecule for the effective treatment of the viral infection. Other assays, such as PCR (e.g., qPCR) can also be used to monitor treatment in a patient, to detect the presence, e.g., decreased presence (or absence) after treatment of viral infection in the patient. Treatment can, e.g., partially or completely alleviate, ameliorate, relive, inhibit, reduce the severity of, and/or reduces incidence and optionally, delay onset of, one or more manifestations of the effects or symptoms, features, and/or causes of a particular disease, disorder, and/or condition (e.g., influenza. In embodiments treatment is of a subject who does not exhibit signs of the relevant disease, disorder and/or condition and/or of a subject who exhibits only early signs of the disease, disorder, and/or condition. In embodiments treatment is of a subject who exhibits one or more established signs of the relevant disease, disorder and/or condition. In embodiments, treatment is of a subject diagnosed as suffering from influenza.

Calculations of "homology" or "sequence identity" or "identity" between two sequences (the terms are used interchangeably herein) can be performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). The optimal alignment is determined as the best score using the GAP program in the GCG software package with a Blossum 62 scoring matrix with a gap penalty of 12, a gap extend penalty of 4, and a frameshift gap penalty of 5. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences.

Hemagglutinin (HA) Polypeptides and Influenza

Influenza viruses are negative sense, single-stranded, segmented RNA envelope viruses. Two glycoproteins, a hemagglutinin (HA) polypeptide and a neuraminidase (NA) polypeptide, are displayed on the outer surface of the viral envelope. There are several Influenza A subtypes, labeled according to an H number (for the type of hemagglutinin) and an N number (for the type of neuraminidase). There are 17 different H antigens (H1 to H17) and nine different N antigens (N1 to N9). Influenza strains are identified by a nomenclature based on the number of the strain's HA polypeptide and NA polypeptide subtypes, for example, H1N1, H1N2, H1N3, H1N4, H1N5, and the like.

HA is the major viral surface glycoprotein that mediates binding and entry of the virus into host cells and is a primary target of neutralizing antibody responses. HA is a trimer of three identical monomers. Each monomer is synthesized as a precursor, $HA_0$, that is proteolytically processed into two disulfide-bonded polypeptide chains, $HA_1$ and $HA_2$. The ectodomain of this protein has (i) a globular head domain possessing receptor binding activity and major antigenic determinants, (ii) a hinge region, and (iii) a stem region where a sequence critical for fusion, the fusion peptide, is located. The viral replication cycle is initiated when the virion attaches via its surface hemagglutinin proteins to sialylated glycan receptors on the host cell and enters the cell by endocytosis. The acidic environment in the endosome induces conformational changes in HA that expose the fusion peptide hidden within the stem region of the trimer. The exposed fusion peptide mediates the fusion of the viral and target cell membranes resulting in the release of the viral ribonucleoprotein into the cell cytoplasm.

Influenza A hemagglutinin subtypes have been divided into two main groups and four smaller clades, and these are further divided into clusters. Group 1 influenza A strains are divided into 3 clades: (i) H8, H9 and H12 ("the H9 cluster"); (ii) H1, H2, H5, H6 and H17 ("the H1a cluster"); and (iii) H11, H13 and H16 ("the H1b cluster"). Group 2 strains are divided into 2 clades: (i) H3, H4 and H14 ("the H3 cluster"); and (ii) H7, H10 and H15 ("the H7 cluster"). The H1b and the H1a clusters are classified together as the H1 cluster. The different HA subtypes do not necessarily share strong amino acid sequence identity, but their overall 3D structures are similar.

Of the 17 HA polypeptide subtypes, only 3 (H1, H2 and H3) have adapted for human infection. These subtypes have in common an ability to bind alpha 2,6 sialylated glycans. In contrast, their avian counterparts preferentially bind to alpha 2,3 sialylated glycans. HA polypeptides that have adapted to infect humans (e.g., of HA polypeptides from the pandemic H1N1 (1918) and H3N2 (1967-68) influenza subtypes) have been characterized by an ability to preferentially bind to α2,6 sialylated glycans in comparison with their avian progenitors that preferentially bind to α2,3 sialylated glycans (see, e.g., Skehel & Wiley, Annu Rev Biochem, 69:531, 2000; Rogers, & Paulson, Virology, 127:361, 1983; Rogers et al., Nature, 304:76, 1983; Sauter et al., Biochemistry, 31:9609, 1992

Further, HA polypeptides that mediate infection of humans preferentially bind to umbrella topology glycans over cone topology glycans (see, e.g., U.S. 2011/0201547). Without wishing to be bound by any particular theory, it has been proposed that the ability to infect human hosts correlates less with binding to glycans of a particular linkage, and more with binding to glycans of a particular topology, even though cone-topology glycans may be α2,6 sialylated glycans. In has been demonstrated that HA polypeptides that mediate infection of humans bind to umbrella topology glycans, often showing preference for umbrella topology glycans over cone topology glycans (See, for example, U.S. Ser. No. 12/348,266 filed Jan. 2, 2009, U.S. Ser. No. 12/301,126, filed Nov. 17, 2008, U.S. Ser. No. 61/018,783, filed Jan. 3, 2008, U.S. Ser. No. 11/969,040, filed Jan. 3, 2008, U.S. Ser. No. 11/893,171, filed Aug. 14, 2007, U.S. Ser. No. 60/837,868, filed on Aug. 14, 2006, U.S. Ser. No. 60/837,869, filed on August 14, and to PCT application PCT/US07/18160, filed Aug. 14, 2007.

Mature HA polypeptides include three domains, (i) a globular domain (a.k.a., the head domain) consists mainly of the HA1 peptide and contains the receptor (sialylated glycoproteins)-binding region, (ii) a stalk domain (HA1 and HA2) where the membrane fusion peptide resides, and (iii) a transmembrane domain (HA2) that anchors hemagglutinin to the viral envelope. A set of amino acids in the interface of the HA1 and HA2 peptides is highly conserved across all influenza subtypes. The HA1/HA2 membrane proximal region (MPER), including a canonical alpha-helix, is also highly conserved across influenza subtypes.

HA polypeptides interact with the surface of cells by binding to a glycoprotein receptor, known as the HA receptor. Binding of an HA polypeptide to an HA receptor is predominantly mediated by N-linked glycans on the HA receptors. HA polypeptides on the surface of flu virus particles recognize sialylated glycans that are associated with HA receptors on the surface of the cellular host. Following replication of viral proteins and genome by the cellular machinery, new viral particles bud from the host to infect neighboring cells.

Currently, vaccines are administered to subjects, e.g., humans, to prevent the flu, e.g., to prevent infection or to minimize the effects of an infection with influenza virus. Traditional vaccines contain a cocktail of antigens from various strains of influenza and are administered to humans to prevent the human from getting infected with the virus. HA is the main target of influenza A-neutralizing antibodies, and HA undergoes continuous evolution driven by the selective pressure of the antibody response, which is primarily directed against the membrane-distal receptor-binding subdomain of the HA polypeptide. The subject, however, is protected only from strains that are identical to, or closely related to, the strains from which the antigens in the cocktail were derived. The human is still most vulnerable to infection by other strains of the flu that were not included in the cocktail. One of the advantages of the antibodies provided herein is their ability to bind an epitope of HA that is conserved across multiple strains of influenza A, and in embodiments influenza B. Thus, administration of an anti-HA antibody described herein will be more effective to protect an individual from infection from a broader spectrum of influenza (e.g., influenza A and, in embodiments, influenza B) and conditions associate thereof (e.g., secondary infections, e.g., secondary bacterial infections). Further, the antibodies are effective in treating a subject after infection has occurred.

Anti-HA Antibody Molecules

Binding agents, and in particular, the antibody molecules described herein, can bind to influenza A viruses from both Group 1 and Group 2, and in embodiments also bind influenza B viruses. For example, the antibody molecules described herein can bind to an HA polypeptide on at least 1, 2, 3, 4, 5, 6, 7, 8, 9, 10 or 11 strains from Group 1, and can also bind to an HA polypeptide on at least 1, 2, 3, 4, 5, or 6 strains from Group 2. In another example, the antibody molecules described herein can bind to an HA polypeptide on an influenza strain from at least 1, 2 or 3 clades from Group 1, and can also bind to an HA polypeptide on an influenza strain from one or both clades of Group 2. The antibody molecules described herein inhibit cell entry and thus targeting an early step in the infection process.

The binding agents, and in particular, the antibody molecules featured in the disclosure, can be effective to treat or prevent infection by seasonal or pandemic influenza strains. The binding agents, and in particular the antibody molecules described herein, can be characterized by their ability to prevent or treat a Group 1 or a Group 2 strain of influenza A viruses or, in embodiments, a strain of influenza B viruses. The binding agents, and in particular the antibody molecules featured in the disclosure, are effective to prevent or treat infection by one or more strains of Group 1, one or more strains of Group 2, and also one or more strains of influenza B viruses.

The binding agents, and in particular the antibody molecules can be effective to treat the infection when administered the same day as the subject is exposed, or when administered, e.g., 1 day, 2 days, 3 days, 4 days or later after infection, or upon a first symptom experienced by the patient.

Strains

The antibody molecules described herein are effective to treat one or more influenza strains of Group 1, one or more influenza strains of Group 2, and also one or more influenza B strains, and specific isolates within these strains. Certain antibody molecules may be more effective for treatment of certain isolates than other isolates. Exemplary influenza strains and isolates are described in the below Table 1.

TABLE 1

Exemplary influenza strains and Isolates

| Type | Group | HA type | Isolate |
|---|---|---|---|
| A | 1 | H1N1 | A/PR/8/34 (aka PR-8) |
| | | | A/Solomon Islands/03/06 |
| | | | A/Solomon Islands/20/1999 |
| | | | A/California/07/2009 |
| | | | A/New Caledonia/20/99 |
| | | | A/Bangkok/10/83 |
| | | | A/Yamagata/120/86 |
| | | | A/Osaka/930/88 |
| | | | A/Suita/1/89 |
| | | | A/California/04/2009 |
| A | 1 | H2N2 | A/Okuda/57 |
| | | | A/Adachi/2/57 |
| | | | A/Kumamoto/1/65 |
| | | | A/Kaizuka/2/65 |
| | | | A/Izumi/5/65 |
| | | | A/Chicken/PA/2004 |
| A | 1 | H5N1 | A/Vietnam/1203/04 |
| | | | A/Duck/Singapore/3/97 |
| | | | A/Duck/MN/1525/81 |
| A | 1 | H9N2 | A/Hong Kong/1073/2004 |
| | | | A/Swine/Hong Kong/9/98 |
| | | | A/Guinea fowl/HK/WF10/99 |
| A | 1 | H16N3 | A/black headed gull/Mongolia/1756/2006 |
| A | 2 | H3N2 | X-31 |
| | | | A/Victoria/3/75 |
| | | | A/Wyoming/03/2003 |
| | | | A/Wisconsin/67/2005 |
| | | | A/Brisbane/10/2007 |
| | | | A/California/7/2004 |
| | | | A/New York/55/2004 |
| | | | A/Moscow/10/1999 |
| | | | A/Aichi/2/68 |
| | | | A/Beijing/32/92/X-117 |
| | | | A/Fukuoka/C29/85 |
| | | | A/Sichuan/2/87 |
| | | | A/Ibaraki/1/90 |
| | | | A/Suita/1/90 |
| | | | A/Perth/16/2009 |
| | | | A/Uruguay/716/2007 |
| | | | A/Fujian/411/2003 |
| | | | A/Panama/2007/99 |
| | | | A/Shangdong/09/93 |

TABLE 1-continued

Exemplary influenza strains and Isolates

| Type | Group | HA type | Isolate |
|---|---|---|---|
| A | 2 | H7N7 | A/Netherlands/219/2003 |
| B | | | B/Wisconsin/1/2010 |

Affinity can also be in reference to a particular isolate of a given Group 1 or Group 2 strain for influenza A viruses or a strain for influenza B viruses. Exemplary isolates are as provided in the above Table 1.

Mechanisms of Inhibition

While not being limited by a specific mechanism, HA specific antibodies can inhibit infection by numerous methods, such as by blocking viral attachment to sialic acid residues on surface proteins on host cells, by interfering with the structural transition of HA that triggers fusion activity in the endosome, or by simultaneously inhibiting attachment and virus-cell fusion.

In embodiments, antibody molecules featured herein bind an epitope at the HA trimer interface. Structural changes at the trimer interface are important for fusion of the viral membrane and the endocytic membrane, and the antibody molecules described herein interfere with this critical step of infection. Assays to measure fusogenic activity of HA are known in the art. For example, one fusion assay measures syncytia formation, which occurs in cell-cell fusion events. Cells that express and display an influenza viral strain HA can be used in the assay. Membrane-anchored hemagglutinin in these cells is induced to convert to the fusion conformation by a brief (e.g., 3 minute) exposure to low pH (e.g., pH 5). A 2-3-hour incubation period follows to allow the cells to recover and fuse to form syncytia. A nuclear stain can be used to aid in the visualization of these fusion products, and their count is used as a gauge of fusion activity. A candidate anti-HA antibody can be added either before or after the low pH treatment to determine at which stage of the fusion process the antibody interferes.

Another type of fusion assay monitors content mixing. To measure content mixing, host cells (e.g., erythrocytes) are loaded with a dye (e.g., Lucifer yellow) to determine whether the contents of HA-bound host cells could be delivered to HA-expressing cells after exposure to fusion-inducing conditions (e.g., low pH, such as pH less than 6 or pH less than 5). If the dye fails to mix with the contents of the host cells, then the conclusion can be made that fusion is inhibited. See, e.g., Kemble et al., J. Virol. 66:4940-4950, 1992.

In another example, a fusion assay is performed by monitoring lipid mixing. The lipid mixing assay can be performed by labeling host cells (e.g., erythrocytes) with a fluorescent dye (e.g., R18 (octadecylrhodamine)) or dye pairs (e.g., CPT-PC/DABS-PC) (for fluorescence resonance energy transfer), exposing the host cells and HA-expressing cells to fusion-inducing conditions, and assaying for fluorescence dequenching (FDQ). Lipid mixing leads to dilution of the label into the viral envelope and a consequent dequenching. A lag in dequenching or the absence of dequenching is indicative of membrane fusion inhibition. See, e.g., Kemble et al., J. Virol. 66:4940-4950, 1992; and Carr et al., Proc. Natl. Acad. Sci. 94:14306-14313, 1997.

Escape Mutants

In embodiments, influenza strains will rarely if ever produce escape mutants when contacted with the featured antibody molecules.

Escape mutants can be identified by methods known in the art. For example, an antibody featured in the disclosure will not produce an escape mutant when the cells are infected with the virus under prolonged or repeated exposure to anti-HA antibodies featured in the disclosure.

One exemplary method includes infection of cells (e.g. MDCK cells) with a fixed amount of influenza A viral particles in the presence of the antibody at a concentration known to attenuate infection rates by 50%. Viral progeny collected after each passaging is used to infect a fresh cell culture in the presence of the same or greater concentration of the antibody. After multiple cycles of infection, e.g., after 15 cycles, 12 cycles, 11 cycles, 10 cycles, 9 cycles, 8 cycles, 7 cycles, 6 cycles, or 5 cycles, of infection under these conditions, the HA nucleotide sequence extracted from 20 viral plaque picks is evaluated for enrichment for mutations that renders the viral isolate resistant to neutralization by the antibody (an escape mutant). If no mutants with reduced sensitivity to the antibody are detected after the multiple rounds of selection, e.g., after 11 rounds, 10 rounds, or 9 rounds of selection, the antibody is determined to be resistant to escape mutations (see, e.g., Throsby et al. (2008) PLoS One, volume 3, e3942).

In another example, an assay that measures minimum inhibitory concentration (MIC) of the neutralizing antibody can be used to identify escape mutants. The MIC of an antibody molecule is the lowest concentration of an antibody molecule that can be mixed with virus to prevent infection of cell culture with influenza. If escape mutants arise within a viral population, then the MIC of a particular antibody will be observed to increase with increased rounds of propagation under the antibody selective pressure, as the proportion of the viral particles that carry the resistance mutation within the population increased. Influenza escape mutants rarely if ever evolve in response to an anti-HA antibody molecule described herein, and therefore the MIC will stay the same over time.

Another assay suitable for monitoring for the development of escape mutants is a Cytopathic Effect (CPE) assay. A CPE assay monitors the ability of an antibody to neutralize (i.e., prevent infection by) an influenza strain. A CPE assay provides the minimal concentration of antibody required in cell culture to neutralize the virus. If escape mutants arise, than the CPE of a particular antibody will increase over time, as the antibody becomes less effective at neutralizing the virus. Viral strains rarely if ever produce escape mutants in response to an anti-HA antibody molecule described herein, and therefore the CPE will stay essentially the same over time.

Quantitative polymerase chain reaction (qPCR) can also be used to monitor for the development of escape mutants. qPCR is useful to monitor the ability of an antibody to neutralize (i.e., prevent infection by) an influenza strain. If an antibody effectively neutralizes a virus, then qPCR performed on cell culture samples will not detect presence of viral genomic nucleic acid. If escape mutants arise, than over time, qPCR will amplify more and more viral genomic nucleic acid. Escape mutants rarely if ever develop in response to an anti-HA antibody molecule described herein, and therefore qPCR will rarely if ever detect viral genomic nucleic acid, even after the passage of time.

Binding and Affinity

In embodiments, the binding agents, particularly antibody molecules, featured herein bind to two or more of the following:

at least one HA polypeptide from a Group 1 influenza strain (e.g., an H1, H2, H5, H6, H8, H9 H12, H11, H13, H16 or H17 polypeptide);

at least one HA polypeptide from a Group 2 influenza strain (e.g., an H3, H4, H14, H7, H10, or H15 polypeptide); and at least one HA polypeptide from a influenza B strain.

In an embodiment, a binding agent, e.g., an antibody molecule, will have a $K_D$ for an HA from a Group 1 influenza strain (e.g., an H1, H2, H5, H6, H8, H9 H12, H11, H13, H16 or H17 polypeptide) of equal to or less than $10^{-6}$, $10^{-7}$, $10^{-8}$, $10^{-9}$, $10^{-10}$, $10^{-11}$, or $10^{-12}$.

In an embodiment, a binding agent, e.g., an antibody molecule, will have a $K_D$ for an HA from a Group 2 influenza strain (e.g., an H3, H4, H14, H7, H10, or H15 polypeptide) of equal to or less than $10^{-6}$, $10^{-7}$, $10^{-8}$, $10^{-9}$, $10^{-10}$, $10^{-11}$, or $10^{-12}$.

In an embodiment, a binding agent, e.g., an antibody molecule, will have a $K_D$ for an influenza B HA of equal to or less than $10^{-6}$, $10^{-7}$, $10^{-8}$, $10^{-9}$, $10^{-10}$, $10^{-11}$, or $10^{-12}$.

In an embodiment, a binding agent, e.g., an antibody molecule, will have:

a) a first $K_D$ (representing an affinity for an HA from a Group 1 influenza strain, e.g., an H1, H2, H5, H6, H8, H9 H12, H11, H13, H16 or H17 polypeptide); and b) a second $K_D$ (representing an affinity for an HA from a Group 2 influenza strain, e.g., an H3, H4, H14, H7, H10, or H15 polypeptide), wherein the first and second $K_D$ are one or both of:
both equal to or less than $10^{-8}$; and
within 10 or 100 fold of each other;

In an embodiment, a binding agent, e.g., an antibody molecule, will have a) a first $K_D$ (representing an affinity for an H1, e.g., the H1 from an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004); and b) a second $K_D$ (representing an affinity for an H3 polypeptide, e.g., the H3 from an H3N2 strain, e.g., from A/Brisbane/59/2007), wherein the first and second $K_D$ are one or both of:
both equal to or less than $10^{-8}$; and
within 10 or 100 fold of each other;

In an embodiment, a binding agent, e.g., an antibody molecule, will have a) a first $K_D$ (representing an affinity for an H1, e.g., the H1 from an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004); and b) a second $K_D$ (representing an affinity for an H3 polypeptide, e.g., the H3 from an H3N2 strain, e.g., A/Brisbane/59/2007), wherein the first and second $K_D$ are one or both of:
both equal to or less than $10^{-8}$; and
within 10 or 100 fold of each other.

In an embodiment, a binding agent, e.g., an antibody molecule, will have:

a) a first $K_D$ (representing an affinity for an HA from a Group 1 influenza strain, e.g., an H1, H2, H5, H6, H8, H9 H12, H11, H13, H16 or H17 polypeptide and/or an affinity for an HA from a Group 2 influenza strain, e.g., an H3, H4, H14, H7, H10, or H15 polypeptide); and b) a second $K_D$ (representing an affinity for an influenza B HA, e.g., from B/Wisconsin/1/2010);

wherein the first and second $K_D$ are one or both of:
both equal to or less than $10^{-8}$; and
within 10 or 100 fold of each other.

In an embodiment, a binding agent, e.g., an antibody molecule, will have:

a) a first $K_D$ (representing an affinity for an HA from a Group 1 influenza strain, e.g., an H1, e.g., the H1 from an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004, and/or an affinity for an HA from a Group 2 influenza strain, e.g., an H3 polypeptide, from an H3N2 strain, e.g., from A/Brisbane/59/2007); and b) a second $K_D$ (an affinity for an influenza B HA);

wherein the first and second $K_D$ are: one or both of:
both equal to or less than $10^{-8}$; and
within 10 or 100 fold of each other.

In one embodiment, the antibody molecule binds to at least one HA polypeptide from a Group 1 influenza strain with a higher affinity than a reference anti-HA antibody, and to at least one HA polypeptide from a Group 2 influenza strain with a higher affinity than a reference anti-HA antibody. In another embodiment, the antibody molecule binds to at least one HA polypeptide from an influenza A strain with a higher affinity than a reference anti-HA antibody, and to at least one HA polypeptide from an influenza B strain with a higher affinity than a reference anti-HA antibody. Exemplary reference HA antibodies include Ab 67-11 (U.S. Provisional application No. 61/645,453, filed on the same date as the present application), FI6 (FI6, as used herein, refers to any specifically disclosed FI6 sequence in U.S. Published Application No. 2010/0080813, US published application No. 2011/0274702, WO2013/011347 or Corti et al., Science 333: 850-856, 2011, published online Jul. 28, 2011; FIGS. 12A to 12C), FI28 (U.S. Published Application No. 2010/0080813), and C179 (Okuno et al., J. Virol. 67:2552-1558, 1993), F10 (Sui et al., Nat. Struct. Mol. Biol. 16:265, 2009), CR9114 (Dreyfus et al., Science. 2012; 337(6100):1343-1348; published online Aug. 9, 2012), and CR6261 (Ekiert et al., Science 324:246-251, 2009; published online Feb. 26, 2009).

Affinity, or relative affinity or aviditiy, can be measured by methods known in the art, such as by ELISA assay (Enzyme Linked Immunosorbent Assay), Surface Plasmon Resonance (SPR, e.g., by a Biacore™ Assay), or KinExA® assay (Sapidyne, Inc.). Relative binding affinity is expressed herein according to ELISA assay. As used herein, an anti-HA antibody that binds with "high affinity" to a Group 1 HA, to a Group 2 HA, and to a influenza B HA, can bind a Group 1 HA with a Kd less than or equal to 200 pM, e.g., less than or equal to 100 pM, as measured by ELISA, can bind a Group 2 HA with a Kd less than or equal to 200 pM, e.g., less than or equal to 100 pM, as measured by ELISA, and can bind an influenza B HA with a Kd less than or equal to 200 pM, e.g., less than or equal to 100 pM, as measured by ELISA.

Exemplary Anti-HA Antibody Molecules

Provided herein are antibodies that have one or more CDR sequences and one or more framework (FR) sequences as shown in Table 2.

TABLE 2

Heavy and Light Chain CDR and FR Sequences for Anti-HA Antibodies.

| CDR/FR Region | Amino Acid Sequence | SEQ ID NO: |
|---|---|---|
| HC CDR1 | [S/T]Y[A/G]MH | 1 |
| HC CDR2 | V[I/V/L]S[Y/F]DG[S/N][Y/N][K/R]YYADSVQG | 2 |
| HC CDR3 | D[S/T][R/K/Q]LR[S/T]LLYFEWLS[Q/S]G[Y/L/V][F/L][N/D][P/Y] | 3 |
| LC CDR1 | Q[S/T][V/L/I][T/S][Y/F/W][N/S/D]YKNYLA | 4 |
| LC CDR1 | Q[S/T][V/L/I][T/S][Y/F/W][N/S/D/Q/R/E]YKNYLA | 170 |
| LC CDR2 | W[A/G]S[T/A/Y/H/K/D][R/L]E[S/T] | 5 |
| LC CDR3 | QQ[Y/H]YRTP TABLE 3-continued Heavy and Light Chain Amino Acid Sequence Designations for Anti-HA Antibodies

|  | Antibody | HC | SEQ ID NO: | LC | SEQ ID NO: |
|---|---|---|---|---|---|
| 62. | Ab C18 | 27 | 27 | 49 | 49 |
| 63. | Ab A019 | 27 | 27 | 50 | 50 |
| 64. | Ab 031 | 24 | 24 | 45 | 45 |
| 65. | Ab 032 | 25 | 25 | 45 | 45 |
| 66. | Ab 033 | 26 | 26 | 45 | 45 |
| 67. | Ab 034 | 27 | 27 | 45 | 45 |
| 68. | Ab 037 | 24 | 24 | 46 | 46 |
| 69. | Ab 038 | 25 | 25 | 46 | 46 |
| 70. | Ab 039 | 26 | 26 | 46 | 46 |
| 71. | Ab 040 | 27 | 27 | 46 | 46 |
| 72. | Ab 043 | 25 | 25 | 60 | 60 |
| 73. | Ab 044 | 25 | 25 | 52 | 52 |
| 74. | Ab 045 | 25 | 25 | 57 | 57 |
| 75. | Ab 046 | 25 | 25 | 59 | 59 |
| 76. | Ab 047 | 25 | 25 | 55 | 55 |
| 77. | Ab 048 | 25 | 25 | 58 | 58 |
| 78. | Ab 049 | 25 | 25 | 54 | 54 |
| 79. | Ab 050 | 25 | 25 | 56 | 56 |
| 80. | Ab 051 | 25 | 25 | 53 | 53 |
| 81. | Ab 052 | 25 | 25 | 61 | 61 |
| 82. | Ab 067 | 25 | 25 | 153 | 153 |
| 83. | Ab 068 | 25 | 25 | 154 | 154 |
| 84. | Ab 069 | 25 | 25 | 155 | 155 |
| 85. | Ab 070 | 25 | 25 | 156 | 156 |
| 86. | Ab 071 | 162 | 162 | 52 | 52 |
| 87. | Ab 072 | 163 | 163 | 52 | 52 |
| 88. | Ab 073 | 25 | 25 | 165 | 165 |
| 89. | Ab 074 | 25 | 25 | 166 | 166 |
| 90. | Ab 075 | 25 | 25 | 167 | 167 |
| 91. | Ab 076 | 25 | 25 | 168 | 168 |
| 92. | Ab 077 | 25 | 25 | 169 | 169 |
| 93. | Ab 078 | 164 | 164 | 52 | 52 |
| 94. | Ab 079 | 164 | 164 | 155 | 155 |
| 95. | Ab 080 | 164 | 164 | 166 | 166 |
| 96. | Ab 081 | 164 | 164 | 169 | 169 |

In one embodiment, the anti-HA antibody comprises a heavy chain as defined in Table 4A below, and/or a light chain as defined in Table 4A below.

TABLE 4A

Heavy and Light Chain Amino Acid Sequence Designations

| HC | SEQ ID NO: | LC | SEQ ID NO: |
|---|---|---|---|
| 15 | 15 | 28 | 28 |
| 16 | 16 | 29 | 29 |
| 17 | 17 | 30 | 30 |
| 18 | 18 | 35 | 35 |
| 19 | 19 | 31 | 31 |
| 21 | 21 | 32 | 32 |
| 22 | 22 | 33 | 33 |
| 20 | 20 | 34 | 34 |
| 23 | 23 | 36 | 36 |
| 24 | 24 | 45 | 45 |
| 25 | 25 | 46 | 46 |
| 26 | 26 | 37 | 37 |
| 27 | 27 | 38 | 38 |
| Hc consensus (HC161) | 161 | 39 | 39 |
| 162 | 162 | 40 | 40 |
| 163 | 163 | 41 | 41 |
| 164 | 164 | 42 | 42 |
|  |  | 43 | 43 |
|  |  | 44 | 44 |
|  |  | 47 | 47 |
|  |  | 48 | 48 |
|  |  | 49 | 49 |
|  |  | 50 | 50 |
|  |  | 51 | 51 |
|  |  | 52 | 52 |
|  |  | 53 | 53 |

TABLE 4A-continued

Heavy and Light Chain Amino Acid Sequence Designations

| HC | SEQ ID NO: | LC | SEQ ID NO: |
|---|---|---|---|
|  |  | 54 | 54 |
|  |  | 55 | 55 |
|  |  | 56 | 56 |
|  |  | 57 | 57 |
|  |  | 58 | 58 |
|  |  | 59 | 59 |
|  |  | 60 | 60 |
|  |  | 61 | 61 |
|  |  | 153 | 153 |
|  |  | 154 | 154 |
|  |  | 155 | 155 |
|  |  | 156 | 156 |
|  |  | LC consensus (LC62) | 62 |
|  |  | 165 | 165 |
|  |  | 166 | 166 |
|  |  | 167 | 167 |
|  |  | 168 | 168 |
|  |  | 169 | 169 |

In one embodiment, an antibody featured in the disclosure comprises a heavy chain sequence as defined in Table 4A and a light chain sequence as defined in Table 4A.

In one embodiment, an antibody featured in the disclosure comprises a heavy chain sequence as defined herein, e.g., in Table 4A, where a dipeptide is fused to the N-terminus. Typically, the dipeptide is isoleucine-aspartic acid (Ile-Asp). In another embodiment, an antibody featured in the disclosure comprises a light chain sequence as defined herein, e.g., in Table 4A, where a dipeptide is fused to the N-terminus. Typically, the dipeptide is Ile-Asp. In yet another embodiment, an antibody featured in the disclosure comprises a heavy chain comprising an N-terminal Ile-Asp dipeptide and a light chain comprising an Ile-Asp dipeptide. In the propeptide sequence of the heavy chain or light chain polypeptide, the Ile-Asp dipeptide occurs between the signal sequence and FR1. Heavy chain and light chain variable sequences comprising an Ile-Asp dipeptide at the N-terminus are identified in Table 4B.

TABLE 4B

Heavy and Light Chain Amino Acid Sequence Designations, where the Sequence Includes an N-terminal Ile-Asp Dipeptide

| HC | SEQ ID NO: | LC | SEQ ID NO: |
|---|---|---|---|
| 15-ID | 96 | 28-ID | 110 |
| 16-ID | 97 | 29-ID | 111 |
| 17-ID | 98 | 30-ID | 112 |
| 18-ID | 99 | 35-ID | 113 |
| 19-ID | 100 | 31-ID | 114 |
| 21-ID | 101 | 32-ID | 115 |
| 22-ID | 102 | 33-ID | 116 |
| 20-ID | 103 | 34-ID | 117 |
| 23-ID | 104 | 36-ID | 118 |
| 24-ID | 105 | 45-ID | 119 |
| 25-ID | 106 | 46-ID | 120 |
| 26-ID | 107 | 37-ID | 121 |
| 27-ID | 108 | 38-ID | 122 |
| Hc consensus ID (161-ID) | 109 | 39-ID | 123 |
|  |  | 40-ID | 124 |
|  |  | 41-ID | 125 |
|  |  | 42-ID | 126 |
|  |  | 43-ID | 127 |
|  |  | 44-ID | 128 |
|  |  | 47-ID | 129 |
|  |  | 48-ID | 130 |
|  |  | 49-ID | 131 |

TABLE 4B-continued

Heavy and Light Chain Amino Acid Sequence Designations, where the Sequence Includes an N-terminal Ile-Asp Dipeptide

| HC SEQ ID NO: | LC SEQ ID NO: |
|---|---|
| 50-ID | 132 |
| 51-ID | 133 |
| 52-ID | 134 |
| 53-ID | 135 |
| 54-ID | 136 |
| 55-ID | 137 |
| 56-ID | 138 |
| 57-ID | 139 |
| 58-ID | 140 |
| 59-ID | 141 |
| 60-ID | 142 |
| 61ID | 143 |
| 153-ID | 157 |
| 154-ID | 158 |
| 155-ID | 159 |
| 156-ID | 160 |
| LC consensus ID (62-ID) | 144 |

In another embodiment, an antibody featured in the disclosure is other than an antibody known in the art. For example, the antibody is not Ab 67-11 (U.S. Provisional application No. 61/645,453) FI6 (FI6, as used herein, refers to any specifically disclosed FI6 sequence in U.S. Published Application No. 2010/0080813, US published application No. 2011/0274702, WO2013/011347 or Corti et al., Science 333:850-856, 2011, published online Jul. 28, 2011; FIGS. 12A to 12C) FI28 (U.S. Published Application No. 2010/0080813), C179 (Okuno et al., J. Virol. 67:2552, 1993), F10 (Sui et al., Nat. Struct. Mol. Biol. 16:265, 2009), CR9114 (Dreyfus et al., Science 337:1343, 2012), or CR6261 (Ekiert et al., Science 324:246, 2009).

In one embodiment, an antibody featured in the disclosure is other than Ab 67-11 (U.S. Provisional application No. 61/645,453, filed on the same date as the present application).

Variants

In an embodiment, an antibody molecule, e.g., an antibody featured in the disclosure has a variable heavy chain immunoglobulin domain that is at least 85%, 87%, 88%, 89%, 90%, 92%, 94%, 95%, 96%, 97%, 98%, or 99% homologous, or at least 85%, 87%, 88%, 89%, 90%, 92%, 94%, 95%, 96%, 97%, 98%, or 99% identical, to a heavy chain disclosed herein, e.g., from Table 3, Table 4A, Table 4B, FIG. 2, FIG. 13 or FIG. 17, e.g. consensus sequence of SEQ ID NO:161, and has a variable light chain immunoglobulin domain that is at least 85%, 87%, 88%, 89%, 90%, 92%, 94%, 95%, 96%, 97%, 98%, or 99% homologous, or at least 85%, 87%, 88%, 89%, 90%, 92%, 94%, 95%, 96%, 97%, 98%, or 99% identical, to a light chain disclosed herein, e.g., from Table 3, Table 4A, Table 4B, FIG. 3, FIG. 14 or FIG. 17, e.g., the consensus sequence of SEQ ID NO:62. The consensus sequences were determined through the analysis of biochemical and biophysical properties of several hundred computationally designed VH/VL combinations. The consensus sequences represent the amino acid sequences in which each amino acid is the one that occurs most frequently at that site when multiple sequences comprising desirable biochemical and biophysical data are aligned.

An exemplary anti-HA binding antibody has one or more CDRs, e.g., all three HC CDRs and/or all three LC CDRs of a particular antibody disclosed herein, or CDRs that are, in sum, at least 85%, 87%, 88%, 89%, 90%, 92%, 94%, 95%, 96%, 97%, 98%, or 99% homologous, or at least 85%, 87%, 88%, 89%, 90%, 92%, 94%, 95%, 96%, 97%, 98%, or 99% identical, to such an antibody.

In one embodiment, the H1 and H2 hypervariable loops have the same canonical structure as those of an antibody described herein. In one embodiment, the L1 and L2 hypervariable loops have the same canonical structure as those of an antibody described herein.

In one embodiment, the amino acid sequence of the HC and/or LC variable domain sequence is at least 85%, 87%, 88%, 89%, 90%, 92%, 94%, 95%, 96%, 97%, 98%, or 99% homologous, or at least 85%, 87%, 88%, 89%, 90%, 92%, 94%, 95%, 96%, 97%, 98%, or 99% identical, to the amino acid sequence of the HC and/or LC variable domain of an antibody described herein. The amino acid sequence of the HC and/or LC variable domain sequence can differ by at least one amino acid, but no more than ten, eight, six, five, four, three, or two amino acids from the corresponding sequence of an antibody described herein. For example, the differences may be primarily or entirely in the framework regions.

In certain embodiments, the amino acid differences are conservative amino acid differences (e.g., conservative amino acid substitutions). A "conservative" amino acid substitution is one in which the amino acid residue is replaced with an amino acid residue comprising a similar side chain. Families of amino acid residues comprising similar side chains have been defined in the art. These families include, e.g., amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The amino acid sequences of the HC and LC variable domain sequences can be encoded by a nucleic acid sequence that hybridizes under high stringency conditions to a nucleic acid sequence described herein or one that encodes a variable domain or an amino acid sequence described herein. In one embodiment, the amino acid sequences of one or more framework regions (e.g., FR1, FR2, FR3, and/or FR4) of the HC and/or LC variable domain are at least 85%, 87%, 88%, 89%, 90%, 92%, 94%, 95%, 96%, 97%, 98%, or 99% homologous, or at least 85%, 87%, 88%, 89%, 90%, 92%, 94%, 95%, 96%, 97%, 98%, or 99% identical, to corresponding framework regions of the HC and LC variable domains of an antibody described herein. In one embodiment, one or more heavy or light chain framework regions (e.g., HC FR1, FR2, and FR3) are at least 85%, 87%, 88%, 89%, 90%, 92%, 94%, 95%, 96%, 97%, 98%, or 99% homologous, or at least 85%, 87%, 88%, 89%, 90%, 92%, 94%, 95%, 96%, 97%, 98%, or 99% identical, to the sequence of corresponding framework regions from a human germline antibody.

Validation of Epitopes

In one embodiment, the antibodies featured in the disclosure are useful for validating a vaccine based on a particular epitope. For example, an epitope that is the target of an antibody featured in the disclosure can be assessed by computation methods to identify a peptide framework suitable for supporting the epitope conformation, such as to stabilize an epitope that is transient or minimally accessible in nature. Computational abstraction of the epitope and framework properties allows automated screening of databases to identify candidate acceptor peptide scaffolds. The acceptor scaffold can have a particular tertiary structure that includes, for example, one or more of a beta sheet, a beta sandwich, a loop, or an alpha or beta helix. The candidate epitope-scaffold antigens can be assayed in vitro, such as to identify binding properties with an antibody featured in the disclosure, e.g., binding affinity or structure analysis of the epitope-scaffold/antibody complex, or in vitro neutralization. The ability of the epitope-scaffold to generate an immune response (e.g., to generate antibodies) can be tested by administering the epitope-scaffold to an animal (e.g., in a mammal, such as a rat, a mouse, a guinea pig, or a rabbit), and then testing sera for the presence of anti-epitope-scaffold antibodies, e.g., by ELISA assay. The ability of the epitope-scaffold to elicit protection against infection by an influenza A Group 1 or Group 2 strain, or by both types of influenza strains, or an influenza B strain, can be assessed in vivo, such as in an animal (e.g., in a mammal). Thus, an antibody featured in the disclosure can provide validation that the epitope is functionally important and that targeting the epitope will provide protection from infection with a Group 1 or Group 2 influenza strain, or both types of strains, or an influenza B strain.

Production of Antibody Molecules

The nucleic acids (e.g., the genes) encoding an antibody molecule generated by a method described herein can be sequenced, and all or part of the nucleic acids can be cloned into a vector that expresses all or part of the nucleic acids. For example, the nucleic acids can include a fragment of the gene encoding the antibody, such as a single chain antibody (scFv), a $F(ab')_2$ fragment, a Fab fragment, or an Fd fragment.

The disclosure also provides host cells comprising the nucleic acids encoding an antibody or fragment thereof as described herein. The host cells can be, for example, prokaryotic or eukaryotic cells, e.g., mammalian cells, or yeast cells, e.g., *Pichia* (see, e.g., Powers et al. (2001) J. Immunol. Methods 251:123-35), Hanseula, or *Saccharomyces.*

Antibody molecules, particularly full length antibody molecules, e.g., IgGs, can be produced in mammalian cells. Exemplary mammalian host cells for recombinant expression include Chinese Hamster Ovary (CHO) cells (including $dhfr^-$ CHO cells, described in Urlaub and Chasin (1980) Proc. Natl. Acad. Sci. USA 77:4216-4220, used with a DHFR selectable marker, e.g., as described in Kaufman and Sharp (1982) Mol. Biol. 159:601-621), lymphocytic cell lines, e.g., NS0 myeloma cells and SP2 cells, COS cells, K562, and a cell from a transgenic animal, e.g., a transgenic mammal. For example, the cell is a mammary epithelial cell.

In addition to the nucleic acid sequence encoding the immunoglobulin domain, the recombinant expression vectors may carry additional nucleic acid sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216; 4,634,665; and 5,179,017). Exemplary selectable marker genes include the dihydrofolate reductase (DHFR) gene (for use in $dhfr^-$ host cells with methotrexate selection/amplification) and the neo gene (for G418 selection).

In an exemplary system for recombinant expression of an antibody molecule (e.g., a full length antibody or an antigen-binding portion thereof), a recombinant expression vector encoding both the antibody heavy chain and the antibody light chain is introduced into dhfr– CHO cells by calcium phosphate-mediated transfection. Within the recombinant expression vector, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody molecule is recovered from the culture medium. Standard molecular biology techniques are used to prepare the recombinant expression vector, to transfect the host cells, to select for transformants, culture the host cells, and to recover the antibody from the culture medium. For example, some antibodies can be isolated by affinity chromatography with a Protein A or Protein G. For example, purified antibodies can be concentrated to about 100 mg/mL to about 200 mg/mL using protein concentration techniques that are known in the art.

Antibody molecules can also be produced by a transgenic animal. For example, U.S. Pat. No. 5,849,992 describes a method for expressing an antibody molecule in the mammary gland of a transgenic mammal. A transgene is constructed that includes a milk-specific promoter and nucleic acid sequences encoding the antibody molecule of interest, e.g., an antibody described herein, and a signal sequence for secretion. The milk produced by females of such transgenic mammals includes, secreted therein, the antibody of interest, e.g., an antibody described herein. The antibody molecule can be purified from the milk, or for some applications, used directly.

Antibody molecules can also be expressed in vivo, following administration of a vector containing nucleic acids encoding the antibody heavy chain and the antibody light chain. Vector mediated gene-transfer is then used to engineer secretion of the anti-HA antibody into circulation. For example, an anti-HA antibody heavy chain and an anti-HA antibody light chain as described herein are cloned into an adeno-associated virus (AAV)-based vector, and each of the anti-HA antibody heavy chain and the anti-HA antibody light chain are under control of a promoter, such as a cytomegalovirus (CMV) promoter. Administration of the vector to a subject, such as to a patient, e.g., a human patient, such as by intramuscular injection, results in expression of an anti-HA antibody, and secretion into the circulation.

Modifications of Binding Agents

Binding, agents, e.g., antibody molecules can be modified to have numerous properties, e.g., to have altered, e.g., extended half life, to be associated with, e.g., covalently bound to detectable moieties, e.g., labels, to be associated with, e.g., covalently bound to toxins, or to have other properties, e.g., altered immune functions.

Antibody molecules may include modifications, e.g., modifications that alter Fc function, e.g., to decrease or remove interaction with an Fc receptor or with C1q, or both. In one example, the human IgG1 constant region can be mutated at one or more residues.

For some antibody molecules that include an Fc domain, the antibody production system may be designed to synthesize antibody molecules in which the Fc region is glycosylated. The Fc domain can be produced in a mammalian expression system that appropriately glycosylates the residue corresponding to asparagine 297. The Fc domain can also include other eukaryotic post-translational modifications.

Other suitable Fc domain modifications include those described in WO2004/029207. For example, the Fc domain can be an XmAb® Fc (Xencor, Monrovia, Calif.). The Fc domain, or a fragment thereof, can have a substitution in an Fcγ Receptor (FcγR) binding region, such as the domains and fragments described in WO05/063815. In some embodiments, the Fc domain, or a fragment thereof, has a substitution in a neonatal Fc Receptor (FcRn) binding region, such as the domains and fragments described in WO05047327. In other embodiments, the Fc domain is a single chain, or fragment thereof, or modified version thereof, such as those described in WO2008143954. Other suitable Fc modifications are known and described in the art.

Antibody molecules can be modified, e.g., with a moiety that improves its stabilization and/or retention in circulation, e.g., in blood, serum, lymph, bronchoalveolar lavage, or other tissues, e.g., by at least 1.5, 2, 5, 10, or 50 fold.

For example, an antibody molecule generated by a method described herein can be associated with a polymer, e.g., a substantially non-antigenic polymer, such as a polyalkylene oxide or a polyethylene oxide. Suitable polymers will vary substantially by weight. Polymers comprising molecular number average weights ranging from about 200 to about 35,000 daltons (or about 1,000 to about 15,000, and 2,000 to about 12,500) can be used.

For example, an antibody molecule generated by a method described herein can be conjugated to a water soluble polymer, e.g., a hydrophilic polyvinyl polymer, e.g. polyvinylalcohol or polyvinylpyrrolidone. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained. Additional useful polymers include polyoxyalkylenes such as polyoxyethylene, polyoxypropylene, and block copolymers of polyoxyethylene and polyoxypropylene (Pluronics); polymethacrylates; carbomers; branched or unbranched polysaccharides that comprise the saccharide monomers D-mannose, D- and L-galactose, fucose, fructose, D-xylose, L-arabinose, D-glucuronic acid, sialic acid, D-galacturonic acid, D-mannuronic acid (e.g. polymannuronic acid, or alginic acid), D-glucosamine, D-galactosamine, D-glucose and neuraminic acid including homopolysaccharides and heteropolysaccharides such as lactose, amylopectin, starch, hydroxyethyl starch, amylose, dextrane sulfate, dextran, dextrins, glycogen, or the polysaccharide subunit of acid mucopolysaccharides, e.g. hyaluronic acid; polymers of sugar alcohols such as polysorbitol and polymannitol; heparin or heparan.

Binding agents, e.g., antibody molecules, as disclosed herein, can by conjugated to another entity or moiety (e.g., to a cytotoxic or cytostatic moiety, a label or detectable moiety, or a therapeutic moiety). Exemplary moieties include: a cytotoxic or cytostatic agent, e.g., a therapeutic agent, a drug, a compound emitting radiation, molecules of plant, fungal, or bacterial origin, or a biological protein (e.g., a protein toxin) or particle (e.g., a recombinant viral particle, e.g., via a viral coat protein), a detectable agent; a pharmaceutical agent, and/or a protein or peptide that can mediate association of the antibody or antibody portion with another molecule (such as a streptavidin core region or a polyhistidine tag). A binding agent, e.g., an antibody molecule, as disclosed herein, can be functionally linked by any suitable method (e.g., chemical coupling, genetic fusion, covalent binding, noncovalent association or otherwise) to one or more other molecular entities.

Binding agents, e.g., antibody molecules, disclosed herein can be conjugated with a detectable moiety, e.g., a label or imaging agent. Such moieties can include enzymes (e.g., horseradish peroxidase, beta-galactosidase, luciferase, alkaline phosphatase, acetylcholinesterase, glucose oxidase and the like), radiolabels (e.g., $^3$H, $^{14}$C, $^{15}$N, $^{35}$S, $^{90}$Y, $^{99}$Tc, $^{111}$In, $^{125}$I, $^{131}$I and the like), haptens, fluorescent labels (e.g., FITC, rhodamine, lanthanide phosphors, fluorescein, fluorescein isothiocyanate, rhodamine, 5-dimethylamine-1-napthalenesulfonyl chloride, phycoerythrin and the like), phosphorescent molecules, chemiluminescent molecules, chromophores, luminescent molecules, photoaffinity molecules, colored particles or affinity ligands, such as biotin, predetermined polypeptide epitopes recognized by a secondary reporter (e.g., leucine zipper pair sequences, or binding sites for secondary antibodies, metal binding domains, epitope tags). In some embodiments, a moiety, e.g., a detectable moiety, e.g., a label, is attached by spacer arms of various lengths to reduce potential steric hindrance.

In embodiments a binding agent, e.g., antibody molecule, disclosed herein, is derivatized with a detectable enzyme and is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. A binding agent, e.g., antibody molecule, disclosed herein, may also be derivatized with a prosthetic group (e.g., streptavidin/biotin and avidin/biotin). For example, an antibody may be derivatized with biotin, and detected through indirect measurement of avidin or streptavidin binding.

In embodiments the moiety comprises paramagnetic ions and NMR-detectable substances, among others. For example, in some embodiments, a paramagnetic ion is one or more of chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III), erbium (III), lanthanum (III), gold (III), lead (II), and/or bismuth (III).

Binding agents, e.g., antibody molecules, as disclosed herein, can be modified to be associated with, e.g., conjugated to, a therapeutic agent, e.g., an agent comprising anti-viral activity, anti-inflammatory activity, or cytotoxic activity, etc. In some embodiments, therapeutic agents can treat symptoms or causes of influenza infection (e.g., for example, anti-viral, pain-relief, antiinflammatory, immunomodulatory, sleep-inducing activities, etc).

Treatment Methods and Administration

The binding agents, e.g., antibody molecules, featured in the disclosure, can be used to treat a subject, e.g., a subject, e.g., a human subject, infected with, or at risk for becoming infected with, an influenza virus.

Any human is candidate to receive an antibody molecule featured in the disclosure for treatment or prevention of an infection by an influenza virus. Humans at high risk of infection, such as immunocompromised individuals, and humans who are at high risk of exposure to influenza virus are particularly suited to receive treatment with the antibody molecule. Immunocompromised individuals include the elderly (65 years and older) and children (e.g., 6 months to 18 years old), and people with chronic medical conditions. People at high risk of exposure include heath care workers, teachers and emergency responders (e.g., firefighters, policemen).

The antibody molecules described herein can also be used to prevent or reduce (e.g., minimize) secondary infection (e.g., secondary bacterial infection) or a risk of comprising secondary infection associated with influenza, or any effects (e.g., symptoms or complications) thereof on a subject. Opportunistic secondary bacterial infections (e.g., secondary bacterial pneumonia, e.g., primarily with *Streptococcus pneumonia*) contribute significantly to the overall morbidity and mortality associated with seasonal and pandemic influenza infections. The antibody molecules described herein can be used to prevent or reduce (e.g., minimize) the complications from secondary, opportunistic infections (e.g., bacterial infections) in a subject.

An antibody molecule can be administered to a subject, e.g., a human subject, by a variety of methods. For many applications, the route of administration is one of: intravenous injection or infusion, subcutaneous injection, or intramuscular injection. An antibody molecule can be administered as a fixed dose, or in a mg/kg dose. The antibody molecule can be administered intravenously (IV) or subcutaneously (SC). For example, the antibody molecule can be administered at a fixed unit dose of between about 50-600 mg IV, e.g., every 4 weeks, or between about 50-100 mg SC (e.g., 75 mg), e.g., at least once a week (e.g., twice a week). In one embodiment, the antibody molecule is administered IV at a fixed unit dose of 50 mg, 60 mg, 80 mg, 100 mg, 120 mg, 130 mg, 140 mg, 150 mg, 160 mg, 180 mg, 200 mg, 300 mg, 400 mg, 500 mg, or 600 mg or more. Administration of the IV dose can be once or twice or three times or more per week, or once every two, three, four, or five weeks, or less frequently.

In one embodiment, the antibody molecule is administered SC at a fixed unit dose of 50 mg, 60 mg, 70 mg, 75 mg, 80 mg, 100 mg, or 120 mg or more. Administration of the SC dose can be once or twice or three times or more per week, or once every two, three, four, or five weeks, or less frequently.

An anti-HA antibody featured in the disclosure can also be administered by inhalation, such as by intranasal or by oral inhalation, such as at a fixed unit dose of 50 mg, 60 mg, 80 mg, 100 mg, 120 mg, 130 mg, 140 mg, 150 mg, 160 mg, 180 mg, 200 mg, 300 mg, 400 mg, 500 mg, or 600 mg or more.

In one embodiment, an anti-HA antibody is administered to a subject via vector-mediated gene transfer, such as through the delivery of a vector encoding the heavy chain and the light chain of an anti-HA antibody, and the antibody is expressed from the heavy chain and light chain genes in the body. For example, nucleic acids encoding a heavy chain and a light chain can be cloned in a AAV vector, such as a self-complementary AAV vector, the scAAV vector administered to a human by injection, such as by IM injection, and the antibody is expressed and secreted into the circulation of the human.

An antibody molecule can also be administered in a bolus at a dose of between about 1 and 50 mg/kg, e.g., between about 1 and 10 mg/kg, between about 1 and 25 mg/kg or about 25 and 50 mg/kg, e.g., about 50 mg/kg, 25 mg/kg, 10 mg/kg, 6.0 mg/kg, 5.0 mg/kg, 4.0 mg/kg, 3.0 mg/kg, 2.0 mg/kg, 1.0 mg/kg, or less. Modified dose ranges include a dose that is less than about 3000 mg/subject, about 1500 mg/subject, about 1000 mg/subject, about 600 mg/subject, about 500 mg/subject, about 400 mg/subject, about 300 mg/subject, about 250 mg/subject, about 200 mg/subject, or about 150 mg/subject, typically for administration every fourth week or once a month. The antibody molecule can be administered, for example, every three to five weeks, e.g., every fourth week, or monthly.

Dosing can be adjusted according to a patient's rate of clearance of a prior administration of the antibody. For example, a patient may not be administered a second or follow-on dose before the level of antibodies in the patient's system has dropped below a pre-determined level. In one embodiment, a sample from a patient (e.g., plasma, serum, blood, urine, or cerebrospinal fluid (CSF)) is assayed for the presence of antibodies, and if the level of antibodies is above a pre-determined level, the patient will not be administered a second or follow-on dose. If the level of antibodies in the patient's system is below a pre-determined level, then the patient is administered a second or follow-on dose. A patient whose antibody levels are determined to be too high (above the pre-determined level) can be tested again after one or two or three days, or a week, and if the level of antibody in the patient samples has dropped below the pre-determined level, the patient may be administered a second or follow-on dose of antibody.

In certain embodiments, the antibody may be prepared with a carrier that will protect the drug against rapid release, such as a controlled release formulation, including implants, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known. See, e.g., *Controlled Drug Delivery* (*Drugs and the Pharmaceutical Sciences*), Second Edition, J. Robinson and V. H. L. Lee, eds., Marcel Dekker, Inc., New York, 1987.

Pharmaceutical compositions can be administered with a medical device. For example, pharmaceutical compositions can be administered with a needleless hypodermic injection device, such as the devices disclosed in U.S. Pat. No. 5,399,163; 5,383,851; 5,312,335; 5,064,413; 4,941,880; 4,790,824; or 4,596,556. Examples of well-known implants and modules are discussed in, e.g., U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system comprising multi-chamber compartments; and U.S. Pat. No. 4,475,196, which discloses an osmotic drug delivery system. Of course, many other such implants, delivery systems, and modules are also known.

In embodiments the binding agent, e.g., an antibody molecule, is administered buccally, orally, or by nasal delivery, e.g., as a liquid, spray, or aerosol, e.g., by topical application, e.g., by a liquid or drops, or by inhalation.

An antibody molecule described herein can be administered with one or more additional therapeutic agents, e.g., a second drug, for treatment of a viral infection, or a symptom of the infection. The antibody molecule and the one or more second or additional agents can be formulated together, in the same formulation, or they can be in separate formulations, and administered to a patient simultaneously or sequentially, in either order.

Dosage regimens are adjusted to provide the desired response, such as a therapeutic response or a combinatorial therapeutic effect. Generally, any combination of doses (either separate or co-formulated) of an antibody molecule and a second or additional agent can be used in order to provide a subject with both agents in bioavailable quantities.

Dosage unit form or "fixed dose" as used herein refers to physically discrete units suited as unitary dosages for the subjects to be treated; each unit contains a predetermined quantity of active compound calculated to produce the desired therapeutic effect in association with the required pharmaceutical carrier and optionally in association with another agent.

A pharmaceutical composition may include a "therapeutically effective amount" of an agent described herein. In embodiments where the antibody molecule is administered in combination with a second or additional agent, such effective amounts can be determined based on the combinatorial effect of the administered first and second or additional agent. A therapeutically effective amount of an agent may also vary according to factors such as the disease state, age, sex, and weight of the individual, and the ability of the compound to elicit a desired response in the individual, such as amelioration of at least one infection parameter, or amelioration of at least one symptom of the infection, such as chills, fever, sore throat, muscle pain, headache, coughing, weakness, fatigue and general discomfort. A therapeutically effective amount is also one in which any toxic or detrimental effects of the composition are outweighed by the therapeutically beneficial effects.

In an embodiment, administration of a binding agent, e.g., antibody molecule, provided, e.g., as a pharmaceutical preparation, is by one of the following routes: oral, intravenous, intramuscular, intra-arterial, subcutaneous, intraventricular, transdermal, interdermal, rectal, intravaginal, intraperitoneal, topical (as by liquids, powders, ointments, creams, sprays, or drops), mucosal, nasal, buccal, enteral, sublingual; intratracheal instillation, bronchial instillation, and/or inhalation; and/or as an oral spray, nasal spray, and/or aerosol.

Combination Treatments and Exemplary Second or Additional Agents

Binding agents, e.g., antibody molecules, provided e.g., as pharmaceutical compositions, can be administered either alone or in combination with one or more other therapy, e.g., the administration of a second or additional therapeutic agent.

In embodiments the combination can result in a lower dose of the antibody molecule or of the other therapy being needed, which, in embodiments can reduce side effects. In embodiments the combination can result in enhanced delivery or efficacy of one or both agents. The agents or therapies can be administered at the same time (e.g., as a single formulation that is administered to a patient or as two separate formulations administered concurrently) or sequentially in any order.

Such second or additional agents include vaccines, antiviral agents, and/or additional antibodies. In typical embodiments the second or additional agent is not co-formulated with the binding agent, e.g., antibody molecule, though in others it is.

In embodiments the binding agent, e.g., antibody molecule, and the second or additional agent are administered such that one or more of the following is achieved: therapeutic levels, or therapeutic effects, of one overlap the other; detectable levels of both are present at the same time; or the therapeutic effect is greater than what would be seen in the absence of either the binding agent, e.g., antibody molecule, or the second or additional agent. In embodiments each agent will be administered at a dose and on a time schedule determined for that agent.

The second or additional agent can be, for example, for treatment or prevention of influenza. For example, the binding agents, e.g., antibody molecules, e.g., therapeutic antibodies, provided herein can be administered in combination with a vaccine, e.g., a vaccine described herein or a mixture (a.k.a. a cocktail) of influenza peptides to stimulate the patient's immune system to prevent infection with particular strains of influenza A. In other examples, the second or additional agent is an anti-viral agent (e.g., an anti-NA or anti-M2 agent), a pain reliever, an anti-inflammatory, an antibiotic, a steroidal agent, a second therapeutic antibody molecule (e.g., an anti-HA antibody), an adjuvant, a protease or glycosidase (e.g., sialidase), etc.

Exemplary anti-viral agents include, e.g., vaccines, neuraminidase inhibitors or nucleoside analogs. Exemplary anti-viral agents can include, e.g., zidovudine, gangcyclovir, vidarabine, idoxuridine, trifluridine, foscarnet, acyclovir, ribavirin, amantadine, remantidine, saquinavir, indinavir, ritonavir, alpha-interferons and other interferons, a neuraminidase inhibitor (e.g., zanamivir (Relenza®), oseltamivir (Tamiflu®), laninamivir, peramivir), rimantadine. Exemplary second antibody molecules include, for example Ab 67-11 (U.S. Provisional application No. 61/645,453, FI6 (U.S. Published Application No. 2010/0080813), FI28 (U.S. Published Application No. 2010/0080813), C179 (Okuno et al., J. Virol. 67:2552-8, 1993), F10 (Sui et al., Nat. Struct. Mol. Biol. 16:265, 2009), CR9114 (Dreyfus et al., Science 337:1343, 2012), or CR6261 (see, e.g., Ekiert et al., Science 324:246, 2009). Thus, Ab 044 can be used in combination of any of those antibodies. In other embodiments, two or more binding agents, e.g., antibody molecules disclosed herein, can be administered in combination, e.g., Ab 044 can be administered in combination with Ab 032. In the case of combinations, two agents can be administered as part of the same dosage unit or administered separately. Other exemplary agents useful for treating the symptoms associated with influenza infection are acetaminophen, ibuprofen, aspirin, and naproxen.

In one embodiment, the antibody molecule and the second or additional agent are provided as a co-formulation, and the co-formulation is administered to the subject. It is further possible, e.g., at least 24 hours before or after administering the co-formulation, to administer separately one dose of the antibody formulation and then one dose of a formulation containing a second or additional agent. In another implementation, the antibody molecule and the second or additional agent are provided as separate formulations, and the step of administering includes sequentially administering the antibody molecule and the second or additional agent. The sequential administrations can be provided on the same day (e.g., within one hour of one another or at least 3, 6, or 12 hours apart) or on different days.

In embodiments the antibody molecule and the second or additional agent are each administered as a plurality of doses separated in time. The antibody molecule and the second or additional agent are generally each administered according to a regimen. The regimen for one or both may have a regular periodicity. The regimen for the antibody molecule can have a different periodicity from the regimen for the second or additional agent, e.g., one can be administered more frequently than the other. In one implementation, one of the antibody molecule and the second or additional agent is administered once weekly and the other once monthly. In another implementation, one of the antibody molecule and the second or additional agent is administered continuously, e.g., over a period of more than 30 minutes but less than 1, 2, 4, or 12 hours, and the other is administered as a bolus. In embodiments sequential administrations are administered. The time between administration of the one agent and another agent can be minutes, hours, days, or weeks. The use of an antibody molecule described herein can also be used to reduce the dosage of another therapy, e.g., to reduce the side-effects associated with another agent that is being administered. Accordingly, a combination can include administering a second or additional agent at a dosage at least 10, 20, 30, or 50% lower than would be used in the absence of the antibody molecule. The antibody molecule and the second or additional agent can be administered by any appropriate method, e.g., subcutaneously, intramuscularly, or intravenously.

In some embodiments, each of the antibody molecule and the second or additional agent is administered at the same dose as each is prescribed for monotherapy. In other embodiments, the antibody molecule is administered at a dosage that is equal to or less than an amount required for efficacy if administered alone. Likewise, the second or additional agent can be administered at a dosage that is equal to or less than an amount required for efficacy if administered alone.

In some cases, the formulations described herein, e.g., formulations containing an antibody molecule featured in the disclosure, include one or more second or additional agents, or are administered in combination with a formulation containing one or more second or additional agents.

In an embodiment a binding agent, e.g., antibody molecule, provided, e.g., as a pharmaceutical preparation, is administered by inhalation or aerosol delivery of a plurality of particles, e.g., particles comprising a mean particle size of 4, 5, 6, 7, 8, 9, 10, 11, 12, or 13 microns.

Pharmaceutical Compositions

The binding agents, e.g., antibody molecules, featured in the disclosure can be formulated as pharmaceutical compositions, such as for the treatment or prevention of influenza.

Typically, a pharmaceutical composition includes a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible.

A "pharmaceutically acceptable salt" refers to a salt that retains the desired biological activity of the parent compound and does not impart any undesired toxicological effects (see e.g., Berge, S. M., et al. (1977) J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

The compositions comprising antibody molecules can be formulated according to methods known in the art. Pharmaceutical formulation is a well-established art, and is further described in Gennaro (ed.), *Remington: The Science and Practice of Pharmacy*, 20$^{th}$ ed., Lippincott, Williams & Wilkins (2000) (ISBN: 0683306472); Ansel et al., *Pharmaceutical Dosage Forms and Drug Delivery Systems*, 7$^{th}$ Ed., Lippincott Williams & Wilkins Publishers (1999) (ISBN: 0683305727); and Kibbe (ed.), *Handbook of Pharmaceutical Excipients American Pharmaceutical Association*, 3$^{rd}$ ed. (2000) (ISBN: 091733096X).

Pharmaceutical compositions may be in a variety of forms. These include, for example, liquid, semi-solid and solid dosage forms, such as liquid solutions (e.g., injectable and infusible solutions), dispersions or suspensions, tablets, pills, powders, liposomes and suppositories. The form can depend on the intended mode of administration and therapeutic application. Typically, compositions for the agents described herein are in the form of injectable or infusible solutions.

Such compositions can be administered by a parenteral mode (e.g., intravenous, subcutaneous, intraperitoneal, or intramuscular injection). The phrases "parenteral administration" and "administered parenterally" as used herein mean modes of administration other than enteral and topical administration, usually by injection, and include, without limitation, intravenous, intramuscular (IM), intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and by intrasternal injection or by infusion.

Pharmaceutical compositions may be provided in a sterile indictable form (e.g., a form that is suitable for subcutaneous injection or intravenous infusion). In some embodiments, pharmaceutical compositions are provided in a liquid dosage form that is suitable for injection or topical application. In some embodiments, pharmaceutical compositions are provided as in dry form, e.g., as powders (e.g. lyophilized and/or sterilized preparations). The Pharmaceutical composition can be provided under conditions that enhance stability, e.g., under nitrogen or under vacuum. Dry material can be reconstituted with an aqueous diluent (e.g., water, buffer, salt solution, etc.) prior to injection.

In one embodiment, the pharmaceutical composition containing an anti-HA antibody is administered intranasally. In another embodiment, the pharmaceutical composition containing an anti-HA antibody is administered by inhalation, such as by oral or by nasal inhalation.

In embodiments the pharmaceutical composition is suitable for buccal, oral or nasal delivery, e.g., as a liquid, spray, or aerosol, e.g., by topical application, e.g., by a liquid or drops, or by inhalation). In embodiments a pharmaceutical preparation comprises a plurality of particles, suitable, e.g., for inhaled or aerosol delivery. In embodiments the mean particle size of 4, 5, 6, 7, 8, 9, 10, 11, 12, or 13 microns. In embodiments a pharmaceutical preparation is formulated as a dry powder, suitable, e.g., for inhaled or aerosol delivery. In embodiments a pharmaceutical preparation is formulated as a wet powder, through inclusion of a wetting agent, e.g., water, saline, or other liquid of physiological pH. In embodiments a pharmaceutical preparation is provided as drops, suitable, e.g., for delivery to the nasal or buccal cavity.

In embodiments the pharmaceutical composition is disposed in a delivery device, e.g., a syringe, a dropper or dropper bottle, an inhaler, or a metered dose device, e.g., an inhaler.

In one embodiment, a pharmaceutical composition contains a vector, such as an adenovirus-associated virus (AAV)-based vector, that encodes a heavy chain of an anti-HA antibody molecule, and a light chain of an anti-HA antibody molecule featured in the disclosure. The composition containing the vector can be administered to a subject, such as a patient, such as by injection, e.g., IM injection. Genes encoding the anti-HA antibody under control of, for example, cytomegalovirus (CMV) promoters, are expressed in the body, and the recombinant anti-HA antibody molecule is introduced into the circulation. See, e.g., Balazs et al., Nature 30:481:81-84, 2011.

Pharmaceutical compositions typically should be sterile and stable under the conditions of manufacture and storage. A pharmaceutical composition can also be tested to insure it meets regulatory and industry standards for administration.

The composition can be formulated as a solution, microemulsion, dispersion, liposome, or other ordered structure suitable to high drug concentration. Sterile injectable solutions can be prepared by incorporating an agent described herein in the required amount in an appropriate solvent with one or a combination of ingredients enumerated above, as required, followed by filtered sterilization. Generally, dispersions are prepared by incorporating an agent described herein into a sterile vehicle that contains a basic dispersion medium and the required other ingredients from those enumerated above. In the case of sterile powders for the preparation of sterile injectable solutions, typical methods of preparation are vacuum drying and freeze-drying that yields a powder of an agent described herein plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

A pharmaceutical composition may be provided, prepared, packaged, and/or sold in bulk, as a single unit dose, and/or as a plurality of single unit doses. Typically a bulk preparation will contain at least 2, 5, 10, 20, 50, or 100 unit doses. A unit dose is typically the amount introduced into the patient in a single administration. In embodiments only a portion of a unit dose is introduced. In embodiments a small multiple, e.g., as much as 1.5, 2, 3, 5, or 10 times a unit dose is administered. The amount of the active ingredient is generally equal to a dose which would be administered to a subject and/or a convenient fraction of such a dose such as, for example, one-half or one-third of such a dose.

Immunogens and Vaccines

Antibodies of the invention have elucidated epitopes that are useful for inducing immunity to, and in embodiments, provide protection from, one or more, e.g., at least two, influenza strains. These epitopes are referred to herein as "broad range immunogens." In an embodiment the broad range immunogen induces immunity, and in embodiments, confers protection against at least one Group 1 strain, and a second strain selected from a Group 1 strain, a Group 2 strain, and an influenza B strain. A broad range immunogen, as the term is used herein, comprises a polypeptide having sufficient sequence and three dimensional structure of an HA, e.g., a HA from a Group 1 strain, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004, to allow binding of an antibody of the invention, e.g., one of Ab 044, Ab 069, Ab 032 and Ab 031, to the broad range immunogen. In embodiments the broad range immunogen comprises the epitope of an antibody described herein e.g., one of Ab 044, Ab 069, Ab 032, and Ab 031. In embodiments, a broad range immunogen does not bind one or more of Ab 67-11, FI6, FI28, C179, or CR6261. In an embodiment Ab 044 binds the broad range immunogen with at least 50, 60, 70, 80, 90, 95, or 99% of the affinity with which it binds a native HA, e.g., a HA from a Group 1 strain, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004. In an embodiment CR6261 binds the broad range immunogen with less than 60, 50, 40, 30, 20, or 10% of the affinity with which it binds a native HA, e.g., a HA from a Group 1 strain, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004. In an embodiment the broad range immunogen differs from wildtype by at least 1, 2, 3, 4, 5, 6, 7, 8, 9, 10, 20, 30, or 40 residues. In an embodiment the broad range immunogen binds to one or more of Ab 67-11, FI6, FI28, C179, or CR6261 with less than 60, 50, 40, 30, 20, or 10% of the affinity with which it binds a native HA, e.g., a HA from a Group 1 strain, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004. In an embodiment the broad range immunogen binds to Ab 044 with an affinity that is at least 10, 30, 50, 100, or 200% greater than its affinity for CR626. In an embodiment the epitope of one of Ab 044, Ab 069, Ab 032, and Ab 031, e.g, Ab 044, is the immunodominant epitople on the broad range immunogen.

As used herein, the term "broad range vaccine" refers to a preparation comprising a broad range immunogen, or a nucleic acid encoding a broad range immunogen, that can induce formation of antibodies or immunity against the broad range immunogen or an organism, e.g., an influenza virus. The broad range immunogen can include dead or weakened virus or antigenic determinants from the organism, e.g., an influenza virus. Typically the broad range vaccine will include one or more additional components, e.g., carriers, adjuvants and the like.

In an embodiment a broad range vaccine comprises two broad range immunogens, or nucleic acid encoding two broad range immunogens.

A broad range immunogen disclosed here, and vaccines including a broad range immunogen or a nucleic acid encoding a broad range immunogen (broad range vaccines), can be used to elicit an immune response, in a subject, e.g., a human subject, against one or more influenza viruses described herein. In embodiments the broad range vaccine confers protection against one or more of the influenza viruses described herein, e.g., it decreases the chance of developing an infection or the symptom of an infection, or moderates the severity of an infection. Broad range vaccines of the invention can comprise an HA polypeptide comprising a broad range immunogen, a nucleic acid encoding a HA polypeptide comprising a broad range immunogen, a particle, e.g., a VLP, liposome, nanoparticle, or microparticle, comprising a broad range immunogen or an nucleic acid that encodes a broad range immunogen. Vaccines can comprise live or inactivated, e.g., replication deficient, viruses. Influenza, as well as other viruses can be used in broad range vaccines.

As used herein, the term "immunogen" or "antigenic formulation" or "antigenic composition" refers to a preparation which, when administered to a vertebrate, e.g., a mammal, e.g., a human, can induce an immune response.

Vaccine Formulation

A broad range immunogen, e.g., a polypeptide, or VLP, liposome, nanoparticle, or microparticle comprising a broad range immunogen, can be formulated into compositions that further comprise a pharmaceutically acceptable carrier or excipient. A nucleic acid that encodes a broad range immunogen can be formulated into a composition that further comprises a pharmaceutically acceptable carrier or excipient. A carrier or excipient is a pharmaceutical agent that does not itself induce the production of an immune response harmful to the animal receiving the composition and which may be administered as a vaccine component without causing undue toxicity. As used herein, the term "pharmaceutically acceptable vaccine component" includes components, e.g., a carrier, that have been approved by a regulatory agency of the Federal or a state government or listed in the U.S. Pharmacopia, European Pharmacopia, or other generally recognized pharmacopia for use in mammals, e.g., in humans. Non-limiting examples of pharmaceutically acceptable carriers are saline, buffered saline, dextrose, water, glycerol, sterile isotonic aqueous buffer, mannitol, lactose, starch, magnesium stearate, sodium saccharine, cellulose, magnesium carbonate, and combinations thereof. In one embodiment, the formulation can be used for administration of the vaccine to humans. In some embodiments, the formulation is sterile, free from particulate matter, and/or non-pyrogenic. The vaccine may also include one or more of: a wetting agent, an emulsifying agent, and a buffering agent. The vaccine can be in solid form, e.g., a lyophilized powder, liquid solution, suspension, emulsion, tablet, pill, capsule, sustained release formulation, or powder.

In some embodiments, broad range vaccines may include one or more adjuvants. Adjuvants are agents that enhance immune responses, and their use is known in the art (see, e.g., "Vaccine Design: The Subunit and Adjuvant Approach", Pharmaceutical Biotechnology, Volume 6, Eds. Powell and Newman, Plenum Press, New York and London, 1995). Non-limiting examples of adjuvants are complete Freund's adjuvant (CFA), incomplete Freund's adjuvant (IFA), squalene, squalane, aluminum hydroxide, aluminum salts, calcium salts, and saponin fractions derived from the bark of the South American tree Quillaja *Saponaria* Molina (e.g., QS21). In some embodiments the adjuvant may be an emulsion comprising oil and water. The oil phase may comprise squalene, squalane, and/or a surfactant. The surfactant may be a nonionic surfactant, e.g., a mono- or di-Ci2-C24-fatty acid ester of sorbitan or mannide.

Synthetic variants of molecules recognized by Toll-Like Receptors (TLRs) may also be used as adjuvants. TLRs help the body to distinguish between self and non-self molecules by recognizing molecular patterns associated with pathogens. Molecules recognized by TLRs include double-stranded RNA, lipopolysaccharides, single-stranded RNA with viral-specific or bacterial-specific modifications, and DNA with viral-specific or bacterial-specific modifications. Synthetic molecules that mimic the properties of these naturally-occurring molecules recognized by TLRs help to trigger an immune response and therefore can be used as adjuvants. Non-limiting examples of such synthetic molecules include polyriboinosinic:polyribocytidylic acid (poly (I:C)), double-stranded nucleic acids with at least one locked nucleic acid nucleoside, attenuated lipid A derivatives (ALDs) (e.g., monophosphoryl lipid A and 3-deacyl monophosphoryl lipid A), and imiquimod.

Vaccines may be formulated with or administered in combination with the administration of immune stimulators. Immune stimulators are molecules that increase the response of the immune system. Non-limiting examples of immune stimulators are cytokines, lymphokines, and chemokines that have immunostimulatory, immunopotentiating, and pro-inflammatory activities, such as interleukins (e.g., IL-1, IL-2, IL-3, IL-4, IL-12, IL-13), growth factors (e.g., granulocyte-macrophage (GM)-colony stimulating factor (CSF)); and other immunostimulatory molecules, such as macrophage inflammatory factor, Flt3 ligand, B7.1; B7.2, etc Immune stimulators may be administered in the same formulation as the VLPs or may be administered separately Immune stimulators may be administered as proteins or as nucleic acids from which the immunostimulatory protein can be expressed.

Administration

Generally, broad range vaccines will be administered in an effective amount or quantity sufficient to stimulate an immune response against one or more strains of influenza. Vaccine dosage can be adjusted within this range based on clinical factors, e.g., age, physical condition, body weight, sex, diet, and time of administration.

Methods of administering a broad range immunogen or broad range vaccine include enteral and parenteral administration. They can also be provided by epidural or mucosal administration (e.g., intranasal and oral or pulmonary routes or by suppositories). They can be provided by inhalation or direct contact with the buccal or nasal cavities. In embodiments a broad range immunogen or broad range vaccine is administered intramuscularly, intravenously, subcutaneously, transdermally, or intradermally. The compositions may be administered by any convenient route, for example by infusion or bolus injection, by absorption through epithelial or mucocutaneous linings (e.g., oral mucous, colon, conjunctiva, nasopharynx, oropharynx, vagina, urethra, urinary bladder and intestinal mucosa, etc.) and by any convenient means, for example, by injection using a needle and syringe or a needleless injection device, by drops, via an aerosol comprising large particles, or by spray into the upper respiratory tract. A broad range immunogen or vaccine may be administered together with other biologically active agents, for example, immunogenic agents, for example, antivirals and/or antibiotics.

In some embodiments a broad range immunogen or broad range vaccine is administered so as to target mucosal tissues in order to elicit an immune response at the site of immunization. For example, mucosal tissues can be targeted for immunization by using oral administration of compositions which contain adjuvants with particular mucosal targeting properties. Examples of mucosal tissues that can be targeted include, but are not limited to, gut-associated lymphoid tissue (GALT), nasopharyngeal lymphoid tissue (NALT), and bronchial-associated lymphoid tissue (BALT).

A broad range immunogen or broad range vaccine may be administered on a dosage schedule, for example, by sequential administrations to subject. In some embodiments a first dose of the composition is followed after a period of time by a second dose. The period of time between the first and second doses may be anywhere from two weeks to one year, for example, about 1, about 2, about 3, about 4, about 5 to about 6 months. In some embodiments the second dose of the composition is followed by a third dose administered a period of time after the first dose. The period of time between the first and third doses may be anywhere from about three months to about two years or more, for example, about 4, about 5, or about 6 months, or about 7 months to about one year. In some embodiments the second, third, or higher dose is administered when the levels of specific immunoglobulins in the serum, urine, and/or mucosal secretions of the subject drop below a threshold. In one embodiment the period of time between the first and second doses is about one month and the period of time between the first and third doses is about six months. In another embodiment the period of time between the first and second doses is about six months. In some embodiments, for example, when the subject is a neonate or infant, doses can be administered throughout childhood. Other factors that put the subject at increased risk of infection, for example, subjects who are health care workers, day care workers, family members of young children, the elderly, and/or individuals with compromised cardiopulmonary function, may influence the dosage schedule, for example, may require the subject to have more doses or more frequent doses. When multiple doses are required, the doses may be administered by the same or different routes.

One skilled in the art can readily determine the dosage of the broad range immunogen or broad range vaccine. For example, the dosage may be determined by identifying doses that elicit a protective or therapeutic immune response, for example, by measuring the level of specific immunoglobulins in the serum or measuring the inhibitory ratio of antibodies in samples of serum, urine, or mucosal secretions from a subject. Dosages can be determined from studies in animals, for example, in guinea pigs, hamsters, ferrets, chinchillas, mice, or rats. An animal need not be a natural host to a particular infectious agent to serve as a subject in studies of the disease caused by said infection agent. Dosages can also be determined from clinical studies in humans, which are routine in the art. The skilled artisan will understand that the route of administration will affect the dosage. Dosages can also be calculated from dose-response curves obtained from in vitro studies or studies using animal models.

A broad range immunogen or vaccine can be administered a subject that does not have a disease caused by influenza virus infection or has not been and is not currently infected with an influenza virus infection, e.g., a broad range immunogen or vaccine can be administered to a subject at risk for infection. A broad range immunogen or vaccine can be administered to a subject infected with a first influenza strain, e.g., to protect against infection with a second strain. In embodiments the broad range immunogen or vaccine is protective against the first strain. In embodiments the broad range immunogen or vaccine is not protective against the first strain.

In embodiments the subject is an adult, an adult over 50 years of age, a person less than 18 years of age, a person less than 2 years of age, or a person less than 6 months of age.

In an embodiment the subject is at risk for a disorder of the lung, e.g., cystic fibrosis, emphysema, asthma, or bacterial infections, or cardiovascular disease. In an embodiment the subject is immune-compromised. In an embodiment the subject is a health care provider, e.g., a physician, nurse, or aid. In an embodiment the subject works at or regularly visits, or lives in a hospital, nursing home, assisted care facility, clinic, or doctor's office.

Broad range immunogens and broad range vaccines can be administered either alone or in combination with one or more other therapy or agent, e.g., the administration of a second or additional agent, e.g., to prevent or delay or minimize one or more symptoms or effects of an influenza infection.

In embodiments the combination can result in a lower dose of the broad range vaccine or of the other therapy being needed, which, in embodiments can reduce side effects. In embodiments the combination can result in enhanced delivery or efficacy of one or both agents. The agents or therapies can be administered at the same time (e.g., as a single formulation that is administered to a patient or as two separate formulations administered concurrently) or sequentially in any order.

Such second or additional agents include other vaccines, anti-viral agents, and/or antibodies. In typical embodiments the second or additional agent is not co-formulated with the binding agent, e.g., antibody molecule, though in others it is.

In embodiments the broad range vaccine and the second or additional agent are administered such that one or more of the following is achieved: therapeutic levels, or therapeutic effects, of one overlap the other; detectable levels of both are present at the same time; or the therapeutic effect is greater than what would be seen in the absence of either the broad range vaccine, or the second or additional agent. In embodiments each agent will be administered at a dose and on a time schedule determined for that agent.

The second or additional agent can be, for example, for treatment or prevention of influenza. For example, a broad range vaccine provided herein can be administered in combination with another vaccine, e.g., a mixture (a.k.a. a cocktail) of influenza peptides to stimulate the patient's immune system to prevent infection with particular strains of influenza A. In other examples, the second or additional agent is an anti-viral agent (e.g., an anti-NA or anti-M2 agent), a pain reliever, an anti-inflammatory, an antibiotic, a steroidal agent, a second therapeutic antibody molecule (e.g., an anti-HA antibody), an adjuvant, a protease or glycosidase (e.g., sialidase), etc.

Exemplary anti-viral agents include, e.g., vaccines, neuraminidase inhibitors or nucleoside analogs. Exemplary anti-viral agents can include, e.g., zidovudine, gangcyclovir, vidarabine, idoxuridine, trifluridine, foscarnet, acyclovir, ribavirin, amantadine, remantidine, saquinavir, indinavir, ritonavir, alpha-interferons and other interferons, a neuraminidase inhibitor (e.g., zanamivir (Relenza®), oseltamivir (Tamiflu®), laninamivir, peramivir), rimantadine. Exemplary antibody molecules include, for example, Ab 67-11 (U.S. Provisional application No. 61/645,453), FI6 (U.S. Published Application No. 2010/0080813), FI28 (U.S. Published Application No. 2010/0080813), C179 (Okuno et al., J. Virol. 67:2552-8, 1993), F10 (Sui et al., Nat. Struct. Mol. Biol. 16:265, 2009), CR9114 (Dreyfus et al., Science 337:1343, 2012), or CR6261 (see, e.g., Ekiert et al., Science 324:246, 2009). Other exemplary antibodies include those described herein, e.g., Ab 044, Ab 069, Ab 032, or Ab 031. In the case of combinations, two agents can be administered as part of the same dosage unit or administered separately. Other exemplary agents useful for treating the symptoms associated with influenza infection are acetaminophen, ibuprofen, aspirin, and naproxen.

In an embodiment the broad range vaccine and the second or additional agent are provided as separate formulations, and the step of administering includes sequentially administering the broad range vaccine and the second or additional agent. The sequential administrations can be provided on the same day (e.g., within one hour of one another or at least 3, 6, or 12 hours apart) or on different days.

In embodiments the broad range vaccine and the second or additional agent are each administered as a plurality of doses separated in time. The broad range vaccine and the second or additional agent are generally each administered according to a regimen. The regimen for one or both may have a regular periodicity. The regimen for the broad range vaccine can have a different periodicity from the regimen for the second or additional agent, e.g., one can be administered more frequently than the other. In one implementation, one of the broad range vaccine and the second or additional agent is administered once weekly and the other once monthly. In another implementation, one of the broad range vaccine and the second or additional agent is administered continuously, e.g., over a period of more than 30 minutes but less than 1, 2, 4, or 12 hours, and the other is administered as a bolus. In embodiments sequential administrations are administered. The time between administration of the one agent and another agent can be minutes, hours, days, or weeks. The use of a broad range vaccine described herein can also be used to reduce the dosage of another therapy, e.g., to reduce the side-effects associated with another agent that is being administered. Accordingly, a combination can include administering a second or additional agent at a dosage at least 10, 20, 30, or 50% lower than would be used in the absence of the broad range vaccine. The broad range vaccine and the second or additional agent can be administered by any appropriate method, e.g., subcutaneously, intramuscularly, or intravenously.

In some embodiments, each of the broad range vaccine and the second or additional agent is administered at the same dose as each is prescribed for monotherapy. In other embodiments, the broad range vaccine is administered at a dosage that is equal to or less than an amount required for efficacy if administered alone. Likewise, the second or additional agent can be administered at a dosage that is equal to or less than an amount required for efficacy if administered alone.

In some cases, the formulations described herein, e.g., formulations containing an broad range vaccine featured in the disclosure, include one or more second or second or additional agents, e.g., a second or additional agent, or are administered in combination with a formulation containing one or more second or additional agents.

In an embodiment, administration of a broad range vaccine is by one of the following routes: oral, intravenous, intramuscular, intra-arterial, subcutaneous, intraventricular, transdermal, interdermal, rectal, intravaginal, intraperitoneal, topical (as by liquids, powders, ointments, creams, sprays, or drops), mucosal, nasal, buccal, enteral, sublingual; intratracheal instillation, bronchial instillation, and/or inhalation; and/or as an oral spray, nasal spray, and/or aerosol.

In an embodiment a broad range vaccine is administered by inhalation or aerosol delivery of a plurality of particles, e.g., particles comprising a mean particle size of 4, 5, 6, 7, 8, 9, 10, 11, 12, or 13 microns.

Vaccines of the invention can be combined with the secondary agents and treatments discussed in the context of treatment with antibodies of the invention elsewhere herein.

Virus-Like Particles

A broad range immunogen can be provided in a virus-like particle (VLP). A VLP is a structure that shares some component and structural similarity to a virus but generally is not infectious. VLPs typically lack a viral genome and therefore cannot reproduce. VLPs can be produced by cloning and co-expressing one or more viral proteins, typically including an antigenic protein of interest, in a cell, and recovering from the cells VLPs that include the antigenic protein of interest. This is described in more detail below.

Cloning

Methods of molecular cloning are known in the art (see, e.g., Berger and Kimmel, Guide to Molecular Cloning Techniques, Methods in Enzymology, Vol. 152 Academic Press, Inc., San Diego, Calif., and Sambrook et al, Molecular Cloning—A Laboratory Manual (3rd Ed.), Vol. 1-3, Cold Spring Harbor Laboratory, Cold Spring Harbor, N.Y., 2000). Methods of molecular cloning include techniques for polypeptide engineering and mutagenesis, which allow for the deletion, insertion, substitution, and other alterations of amino acids within a polypeptide. Methods of molecular cloning also include techniques for isolation and manipulation of nucleic acids that encode polypeptides or that increase, decrease, regulate, or otherwise alter the expression of polypeptides. Methods of molecular cloning further comprise vectors that facilitate the genetic manipulation and expression of polypeptides and nucleic acids.

A vector is a vehicle through which a nucleic acid can be reproduced or transmitted between cells or living organisms. A vector may be, but is not limited to, a plasmid, virus, bacteriophage, provirus, phagemid, transposon, or artificial chromosome. A vector may replicate autonomously or via the machinery of a host cell or organism. A vector may comprise DNA and/or RNA, which may exist in an isolated form or in a complex with other components, e.g., proteins. Molecular cloning methods may be used to insert exogenous nucleic acids into vectors to create constructs for the expression of nucleic acids and/or polypeptides, e.g., influenza HA.

Expression

Methods of expressing exogenous nucleic acids and/or polypeptides are known in the art (see, e.g., Sambrook). Typically, exogenous expression entails introducing an expression construct, created using the methods described above, into a host cell or organism and allowing the biochemical machinery of the host cell to produce one or more of the foreign nucleic acids and/or polypeptides. The host cell may be, but is not limited to, a prokaryotic cell, e.g., a bacterium, or a eukaryotic cell, e.g., a fungal, plant, avian, amphibian, nematode, insect, or mammalian, e.g., a mouse, hamster, monkey, or human, cell. Examples of insect cells include Sf9, SfZl, High Five cells, and *Drosophila* S2 cells. Examples of fungi (including yeast) host cells are *S. cerevisiae, Kluyveromyces lactis*, species of *Candida albicans, Candida glabrata, Aspergillus nidulans, Schizosaccharomyces pombe, Pichia pastoris*, and *Yarrowia lipolytica*. Examples of mammalian cells include COS cells, baby hamster kidney cells, mouse L cells, LNCaP cells, Chinese hamster ovary (CHO) cells, human embryonic kidney (HEK) cells, African green monkey cells, CV1 cells, HeLa cells, MDCK cells, Vero, and Hep-2 cells. An example of an amphibian cell is an oocyte from *Xenopus laevis*. Examples of prokaryotic cells include *E. coli, B. subtilis*, and mycobacteria. The host cell may be part of a multicellular organism or may be grown in vitro, e.g., in a culture of a tissue, organ, a mixed population of cells, or a clonal population of cells. The expression construct may be introduced into the host cell by, e.g., transfection, transduction, transformation, electroporation, microinjection, lipofection, or infection.

VLPs can be produced by culturing host cells into which one or more constructs that enable the expression of exogenous polypeptides have been introduced. The exogenous proteins may be polypeptides identical to or derived from the polypeptides of the influenza virus, e.g., M1, HA, or NA, fragments of M1, HA, or NA, or variants of M1, HA, or NA. The expression construct may contain one or more additional elements, e.g., a marker, e.g., a selectable marker, or an origin of replication. Methods to grow cells for production of VLPs include, but are not limited to, batch, batch-fed, continuous and perfusion cell culture techniques. Methods and reagents may be used to increase efficiency of VLP production. For example, a leader sequence, e.g., a signal sequence, may be added to one or more exogenous polypeptides, e.g., M1, HA, and/or NA, to facilitate transport of the exogenous polypeptide(s) within the host cell.

Isolation and Purification of VLPs

VLPs can be isolated and purified using methods known in the art, such as density gradient centrifugation, filtration, ion exchange chromatography, and gel filtration chromatography. Using the methods described above, VLPs are produced by host cells and secreted into the culture medium. A typical stepwise procedure for isolating and purifying VLPs from the culture medium involves (1) ultrafiltration of the culture medium to concentrate VLPs, (2) diafiltration of VLPs to remove components of the culture medium, (3) centrifugation of VLPs on a sucrose density gradient to remove cellular debris and particulate matter, and (4) anion exchange chromatography of VLPs to remove nucleic acids.

Vesicles

A broad range immunogen may be incorporated into, or packaged in, a vesicle. Typically, vesicles have an aqueous compartment enclosed by one or more bilayers comprising amphipathic molecules (e.g., fatty acids, lipids, steroids, etc.). A broad range immunogen may be contained within the aqueous core of the vesicle or may be localized to the amphipathic bilayer.

In some embodiments the amphipathic molecules of the vesicle are nonionic, e.g., a nonionic surfactant. For example, the nonionic amphipathic molecule may be a glyercol-based, ester-linked surfactant. Such glycerol esters may comprise one of two higher aliphatic acyl groups, e.g., an acyl group containing at least ten carbon atoms in each acyl moiety. Surfactants based on such glycerol esters may comprise more than one glycerol unit, e.g., 2, 3, 4, or 5 glycerol units. Glycerol monoesters may be used, e.g., those containing a C12-C20 alkanoyl or alkenoyl moiety, for example caproyl, lauroyl, myristoyl, palmitoyl, oleyl or stearoyl. An exemplary ester linked surfactant based on glycerol is 1-monopalmitoyl glycerol.

The nonionic amphipathic molecule of the vesicle bilayer may also be an ether-linked surfactant. For example, ether-linked surfactants based on glycerol or a glycol having a lower aliphatic glycol of up to 4 carbon atoms, such as ethylene glycol, may be used. Surfactants based on such glycols may comprise more than one glycol unit, e.g., 2, 3, 4, or 5 glycol units (e.g., diglycolcetyl ether and/or polyoxyethylene-3-lauryl ether). Glycol or glycerol monoethers may be used, including those containing a C12-C20 alkanyl or alkenyl moiety, for example capryl, lauryl, myristyl, cetyl, oleyl or stearyl. For examples of ethylene oxide condensation products that can be used as amphipathic molecules, see PCT Publication No. WO88/06882 (e.g., polyoxyethylene higher aliphatic ether and amine surfactants). Non-limiting examples of ether-linked surfactants are 1-monocetyl glycerol ether and diglycolcetyl ether.

In some embodiments the vesicle comprising a nonionic surfactant may also comprise an ionic amphipathic molecule. For example, an ionic amphiphile may cause the vesicles become negatively charged, which may help stabilize the vesicles and promote dispersion. Ionic amphipathic molecules that can be incorporated into vesicles include, but are not limited to, higher alkanoic and alkenoic acids (e.g., palmitic acid, oleic acid) and other compounds containing acidic groups, for example, phosphates, (e.g., dialkyl phosphates, e.g., dicetylphosphate, or phosphatidic acid or phosphatidyl serine) and sulphate monoesters (e.g., higher alkyl sulphates, e.g., cetylsulphate). The ionic amphiphile may be present at between 1% and 30%, between 2% and 20%, or between 5% and 15% the amount, by weight, of nonionic surfactant.

In some embodiments the vesicle may further comprise a high-molecular weight hydrophobic molecule capable of forming a bilayer, for example, a steroid, for example, cholesterol. The presence of the steroid may facilitate formation of the bilayer, for example, by conferring physical properties on the bilayer. The steroid may be present at between 20% and 120%, between 25% and 90%, or between 35% and 75% amount, by weight, of nonionic surfactant In some embodiments, the vesicle may be a bilosome (see, e.g., U.S. Pat. No. 5,876,721). As used herein, "bilosomes" are vesicles that comprise non-ionic surfactants and transport enhancing molecules which facilitate the transport of lipid-like molecules across mucosal membranes.

Methods for preparing vesicles comprising nonionic surfactants are known in the art. The skilled artisan will understand that such methods may be used to prepare vesicles comprising a broad range immunogen.

Viral Vectors

A broad range immunogen can be provided in an influenza virus. In an embodiment the broad range immunogen is incorporated in an HA polypeptide, e.g., an HA polypeptide that differs from wildtype. In embodiments the HA polypeptide that comprises the broad range immunogen is other than a wild type sequence, e.g., an engineered sequence. It can be incorporated into a virion by supplying the polypeptide in trans during production of the virion or the genome of the virus can be engineered to produce it. In either case, viral particles comprising the broad range immunogen are produced. In an embodiment the virus is engineered to have an attenuated phenotype, e.g., the virus can have no, or only very low levels of, replication in human cells. In embodiments the virus is inactivated. Inactivation methods include contact with denaturants, e.g., formalin, heat, or detergent. A broad range immunogen can be provided in a non-influenza virus, e.g., the non-influenza virus vector can be a Newcastle disease virus, a vaccinia virus, an adenovirus, adeno-associated virus (AAV), retrovirus, or lentivirus.

Kits

In one embodiment, the broad range immunogen or vaccine is packaged in a kit. In some embodiments, the kit comprises two containers, one of which contains the broad range immunogen and the other of which contains an adjuvant. In some embodiments the kit comprises two containers, one of which contains broad range immunogen as a lyophilized powder and the other of which contains a liquid for resuspending the broad range immunogen. The kit may contain a notice as required by governmental agency regulating the manufacture, use, and sale of pharmaceuticals or biological products, the notice indicating that the composition has been approved for manufacture, use, and/or sale for administration to humans.

The vaccine may be supplied in a hermetically-sealed container. The vaccine may be provided as a liquid or as a lyophilized powder that can be reconstituted by the addition, e.g., of water or saline, to a concentration suitable for administration to a subject.

Epitope

HAs exist in nature as homotrimers of proteolytically processed mature subunits. Each subunit of the trimer is synthesized as a precursor. A precursor molecule is proteolytically processed into two disulfide bonded polypeptide chains to form a mature HA polypeptide. The mature HA polypeptide includes two domains: (1) a core HA-1 domain that extends from the base of the molecule through the fibrous stem to the membrane distal head region that contains the glycan receptor binding domain, returning to fibrous region ending in the cleavage site, and (2) HA-2 domain that includes the stem region and the transmembrane domain of HA. HA-1 includes a glycan binding site. The glycan binding site may be responsible for mediating binding of HA to the HA-receptor. The HA-2 domain acts to present the HA-1 domain. The HA trimer can be stabilized by polar and non-polar interactions between the three long HA alpha-helices of the stem of HA monomers.

HA sequences from all influenza subtypes share a set of amino acids in the interface of the HA-1 and HA-2 domains that are well conserved. The HA-1/HA-2 interface membrane proximal epitope region (MPER) that includes the canonical α-helix and residues in its vicinity are also conserved across a broad spectrum of subtypes. (Ekiert et al., *Science*, 324 (5924):246, 2009; Sui et al., *Nat Struct Mol Biol.* 16(3):265, 2009).

Ab 044 has high affinity for HA's from Group 1 and Group 2. It binds a conformational epitope that is broadly conserved across a plurality of influenza strains. Numerous amino acid residues distributed along the linear sequences of HA from different strains/subtypes contribute the Ab 044 conformational epitope. The interaction of Ab044 with H3 was analyzed by docking studies and residues bound by (or not bound by) Ab044 were identified.

The Fv of Ab 044 was docked against HA of group I and II strains using ZDOCK. The structure of the HA antigen was modeled using the SWISS MODEL homology modeling server keeping the solved crystal structure of H1N1 as the template. ZDOCK uses shape complementarity along with desolvation and electrostatic energy terms ('ZRANK') to rank docked poses. To ensure the docked poses do not deviate significantly from the native complex, mapped epitope and paratope residues by alanine scanning are forced to be included in the binding interface.

For comparison studies, amino acids that bind (or do not bind) FI6 were taken from published US patent application US 2011/0274702 A1, Neutralizing Anti-Influenza A Virus Antibodies and Uses Thereof, filed Jul. 18, 2011.

ZDOCK is a Fast Fourier Transform based protein docking program. It was developed by Zhiping Weng at the University of Massachusetts Medical School. In ZDOCK, two PDB files are input and the output is the predicted structure of their complex. The program searches all possible binding modes in the translational and rotational space between the two proteins and evaluates each by an energy scoring function. The protein's structure is converted to a digital signal and a Fast Fourier Transform technique used to reduce computational time. ZDOCK is discussed in Pierce B G, Hourai Y, Weng Z. (2011) Accelerating Protein Docking in ZDOCK Using an Advanced 3D Convolution Library. PLoS One 6(9): e24657, Pierce B, Tong W, Weng Z. (2005) M-ZDOCK: A Grid-based Approach for C_n Symmetric Multimer Docking. Bioinformatics 21(8): 1472-1476; Mintseris J, Pierce B, Wiehe K, Anderson R, Chen R, Weng Z. (2007) Integrating Statistical Pair Potentials into Protein Complex Prediction. Proteins 69(3): 511-520; and Chen R, Li L, Weng Z. (2003) ZDOCK: An Initial-stage Protein Docking Algorithm. Proteins 52(1): 80-7.

SWISS-MODEL is a fully automated protein structure homology-modeling server. It is accessible via the ExPASy web server, or from the program DeepView (Swiss Pdb-Viewer). Swiss-Model is discussed in Arnold K., Bordoli L., Kopp J., and Schwede T. (2006). The SWISS-MODEL Workspace: A web-based environment for protein structure homology modelling. Bioinformatics, 22, 195-201; Kiefer F, Arnold K, Künzli M, Bordoli L, Schwede T (2009). The SWISS-MODEL Repository and associated resources. Nucleic Acids Research. 37, D387-D392; and Peitsch, M. C. (1995) Protein modeling by E-mail Bio/Technology 13: 658-660.

H3 residues that bind Ab 044 and H3 residues that bind FI6 are discussed below.

H3 HA1

The amino acid sequence of H3 HA1 is provided below, as SEQ ID NO: 173. Residues N38, I278, and D291 shown in dashed boxes, are bound by Ab 044 but not by FI6; Residues Q327, T328, and R329 shown in dotted boxes, are bound by FI6 but not by Ab 044; residues T318, R321, and V323 shown in solid boxes, are bound by both Ab 044 and FI6.

(SEQ ID NO: 173)

```
QDLPGNDNST ATLCLGHHAV PNGTLVKTIT DDQIEVTNAT ELVQSSSTGK

ICNNPHRILD GIDCTLIDAL LGDPHCDVFQ NETWDLFVER SKAFSNCYPY DVPDYASLRS

LVASSGTLEF ITEGFTWTGV TQNGGSNACK RGPGSGFFSR LNWLTKSGST YPVLNVTMPN

NDNFDKLYIW GIHHPSTNQE QTSLYVQASG RVTVSTRRSQ QTIIPNIGSR PWVRGLSSRI

SIYWTIVKPG DVLVINSNGN LIAPRGYFKM RTGKSSIMRS DAPIDTCISE CITPNGSIPN

DKPFQNVNKI TYGACPKYVK QNTLKLATGM RNVPEKQTR
```

H3 HA2

The amino acid sequence of H3 HA21 is provided below, as SEQ ID NO: 174 Residue N12 shown in a dash box, is bound by Ab 044 but not by FI6; Residues G1, L2, F3, G4, and D46 shown in dotted boxes, are bound by FI6 but not by Ab 044; residues A7, E11, I18, D19, G20, W21, L38, K39, T41, Q42, A43, I45, I48, N49, L52, N53, I56, and E57, shown in solid boxes, are bound by both Ab 044 and FI6.

(SEQ ID NO: 174)

```
GLFGAIAGFI ENGWEGMIDG WYGFRHQNSE GTGQAADLKS TQAAIDQING

KLNRVIEKTN EKFHQIEKEF SEVEGRIQDL EKYVEDTKID LWSYNAELLV ALENQHTIDL

TDSEMNKLFE KTRRQLRENA EEMGNGCFKI YHKCDNACIE SIRNGTYDHD VYRDEALNNR

FQIKG
```

H1 residues that bind Ab 044 and H1 residues that bind FI6 are discussed below.

H1 HA1

The amino acid sequence of H1 HA1 is provided below, as SEQ ID NO: 181. Residues H31, N279, and 5292 shown in dashed boxes, are bound by Ab 044 but not by FI6. Residues Q328 and S329 shown in dotted boxes, are bound by FI6 but not by Ab 044. Residues T319, R322, and I324 shown in solid boxes, are bound by both Ab 044 and FI6.

(SEQ ID NO: 181)

```
TNADTI CIGYHANNST DTVDTVLEKN VTVTHSVNLL

EDSHNGKLCK LKGIAPLQLG KCNIAGWLLG NPECDLLLTA SSWSYIVETS

NSENGTCYPG DFIDYEELRE QLSSVSSFEK FEIFPKTSSW PNHETTKGVT
```

```
AACSYAGASS FYRNLLWLTK KGSSYPKLSK SYVNNKGKEV LVLWGVHHPP

TGTDQQSLYQ NADAYVSVGS SKYNRRFTPE IAARPKVRDQ AGRMNYYWTL

LEPGDTITFE ATGNLIAPWY AFALNRGSGS GIITSDAPVH DCNTKCQTPH

GAINSSLPFQ NIHPVTIGEC PKYVRSTKLR MATGLRNIPS IQS
```

H1 HA2

The amino acid sequence of H1 HA2 is provided below, as SEQ ID NO: 182. Residues G12 shown in a dashed box, is bound by Ab 044 but not by FI6. Residues G1, L2, F3, G4, and D46 shown in dotted boxes, are bound by FI6 but not by Ab 044. Residues A7, E11, I18, D19, G20, W21, Q38, K39, T41, Q42, N43, I45, I48, T49, V52, N53, I56, and E57 shown in solid boxes, are bound by both Ab 044 and FI6.

(SEQ ID NO: 182)

GLFGAIAGF IEGGWTGMID GWYGYHHQNE QGSGYAADQK STQNAIDGIT

NKVNSVIEKM NTQFTAVGKE FNNLERRIEN LNKKVDDGFL DIWTYNAELL

VLLENERTLD FHDSNVRNLY EKVKSQLKNN AKEIGNGCFE FYHKCDDACM

ESVRNGTYDY PKYSEESKLN REEIDGVKLE SMGVYQILAI YSTVASSLVL

LVSLGAISFW MCSNGSLQCR ICI

FIG. 26 is a three dimensional representation of H3 HA with the amino acids residues that are predicted to be part of Ab044 epitope but not part of FI6's epitope highlighted. That is, the highlighted amino acids are unique to Ab044's epitope.

FIG. 27 is a three dimensional representation of H3 HA with the amino acid residues that are part of FI6's epitope but not predicted to be part of Ab044's epitope highlighted. indicated.

Diagnostic Methods

The binding agents, e.g., antibody molecules, provided herein are useful for identifying the presence of influenza in a biological sample, e.g., a patient sample, such as a fluid sample, e.g., a blood, serum, saliva, mucous, or urine sample, or a tissue sample, such as a biopsy.

In one embodiment, a patient sample is contacted with a binding agent, e.g., an antibody molecule, featured in the disclosure, and binding is detected. Binding can be detected with a number of formats and means of detection, e.g., with an antigen capture assay, such as an ELISA assay or Western blot, or an immunohistochemistry assay. In embodiments the binding agent, e.g., an antibody molecule, is provided, e.g., coupled to an insoluble matrix, e.g., a bead or other substrate, and a detection molecule used to detect binding of HA.

Binding of binding agent, e.g, antibody molecule, to HA, can be detected with a reagent comprising a detectable moiety, e.g., a reagent, e.g., an antibody, which binds the binding agent, e.g., antibody molecule. In embodiments the binding agent, e.g, antibody molecule, has a detectable moiety. Suitable detectable moieties include enzymes (e.g., horseradish peroxidase, beta-galactosidase, luciferase, alkaline phosphatase, acetylcholinesterase, glucose oxidase and the like), radiolabels (e.g., $^{3}H$, $^{14}C$, $^{15}N$, $^{35}S$, $^{90}Y$, $^{99}Tc$, $^{111}In$, $^{125}I$, $^{131}I$), haptens, fluorescent labels (e.g., FITC, rhodamine, lanthanide phosphors, fluorescein, fluorescein isothiocyanate, rhodamine, 5-dimethylamine-1-napthalenesulfonyl chloride, phycoerythrin and the like), phosphorescent molecules, chemiluminescent molecules, chromophores, luminescent molecules, photoaffinity molecules, colored particles or affinity ligands, such as biotin, predetermined polypeptide epitopes recognized by a secondary reporter (e.g., leucine zipper pair sequences, or binding sites for secondary antibodies, metal binding domains, epitope tags). In some embodiments, labels are attached by spacer arms of various lengths to reduce potential steric hindrance.

In embodiments, a human is tested for presence of influenza virus be a method described herein, and if the test is positive, a binding agents, e.g., antibody molecules, e.g., an antibody, provided herein, is administered.

The binding agents, e.g., antibody molecules, e.g., an antibody, provided herein can be used for cytology assays, such as to identify an HA in a cell. The assay can be a colorimetric assay. A biological sample from a normal (non-infected) individual is used as a control. The diagnostic assay can be performed in vitro.

The diagnostic assay can also be performed to determine infection of cells in culture, e.g., of mammalian cells in culture. The antibody molecules can be used in in vitro assays.

Because the antibody molecules featured herein bind a broad spectrum of HA subtypes, the diagnostic assays featured in the disclosure can detect the presence of influenza virus in patients infected with a variety of distinct strains of influenza. A patient sample can be further tested with subtype specific antibodies, or other assays (e.g., RFLP (Restriction Fragment Length Polymorphism), PCR (Polymerase Chain Reaction), RT-PCR (Reverse Transcription coupled to Polymerase Chain Reaction), Northern blot, Southern blot or DNA sequencing) to further determine the particular strain of virus.

In one embodiment, a patient determined to be infected with influenza A can be further administered an antibody molecule featured in the disclosure, to treat the infection.

Also provided are solid substrates, e.g., beads, dipsticks, arrays, and the like, on which is disposed a binding agent, e.g., antibody molecule.

Kits

A binding agent, e.g., an antibody molecule, disclosed herein, e.g., generated by the methods described herein, can be provided in a kit. The kit can include one or more other components, e.g., containers, buffers or other diluents, delivery devices, and the like.

In one embodiment, the kit includes materials for administering an antibody molecule to a subject, such as for treatment or prevention of infection by influenza viruses. For example, the kit can include one or more or all of: (a) a container that contains a composition that includes an antibody molecule, optionally (b) a container that contains a composition that includes a second therapeutic agent, and optionally (c) informational material.

In another embodiment, the kit includes materials for using an antibody molecule in a diagnostic assay, such as for detection of HA in a biological sample. For example, the kit can include one or more or all of: (a) a container that contains a composition that includes an antibody molecule, optionally (b) a container that contains a reagents, e.g., labeled with a detectable moiety, to detect the antibody, e.g., for use in an ELISA or immunohistochemistry assay, and optionally (c) informational material. In other embodiments, the kit comprises a binding agent, e.g., antibody molecule, comprising a detectable moiety.

In an embodiment, the kit comprises a solid substrate, e.g., bead, dipstick, array, and the like, on which is disposed a binding agent, e.g., antibody molecule.

The informational material can be descriptive, instructional, marketing or other material that relates to the methods described herein and/or the use of the agents for therapeutic benefit, or for a diagnostic assay.

The informational material of the kits is not limited in its form. In one embodiment, the informational material can include information about production of the antibody, concentration, date of expiration, batch or production site information, and so forth. In one embodiment, the informational material relates to methods of administering the antibody, e.g., in a suitable dose, dosage form, or mode of administration (e.g., a dose, dosage form, or mode of administration described herein), to treat a subject who has an infection, e.g., viral infection or secondary infection (e.g., secondary bacterial infection).

In another embodiment, the informational material relates to methods for using the antibody molecule for a diagnostic assay, e.g., to detect the presence of influenza viruses in a biological sample.

The information can be provided in a variety of formats, including printed text, computer readable material, video recording, or audio recording, or information that provides a link or address to substantive material.

In addition to the agent, the composition in the kit can include other ingredients, such as a solvent or buffer, a stabilizer, or a preservative. The agent can be provided in any form, e.g., a liquid, dried or lyophilized form, and substantially pure and/or sterile. When the agents are provided in a liquid solution, the liquid solution typically is an aqueous solution. When the agents are provided as a dried form, reconstitution generally is by the addition of a suitable solvent. The solvent, e.g., sterile water or buffer, can optionally be provided in the kit.

The kit can include one or more containers for the composition or compositions containing the agents. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of the agents. The containers can include a combination unit dosage, e.g., a unit that includes both the antibody molecule and the second or additional agent, such as in a desired ratio. For example, the kit can include a plurality of syringes, ampoules, foil packets, blister packs, or medical devices each containing, for example, a single combination unit dose. The containers of the kits can be air tight, waterproof (e.g., impermeable to changes in moisture or evaporation), and/or light-tight.

The kit optionally includes a device suitable for administering the composition, e.g., a syringe or device for delivering particles or aerosols, e.g., an inhaler, a spray device, or a dropper or other suitable delivery device. The device can be provided pre-loaded with one or both of the agents or can be empty but suitable for loading.

The invention is further illustrated by the following examples, which should not be construed as further limiting.

TABLE 4C

Nucleic acid and amino acid sequences

| SEQ ID NO. | Lab no. | Source | Comment | Sequence |
|---|---|---|---|---|
| 1 | n.a. | Table 2 | Consensus AA sequence of HC CDR1 | [S/T]Y[A/G]MH |
| 2 | n.a. | Table 2 | Consensus AA sequence of HC CDR2 | V[I/V/I]S[Y/F]DG[S/N][Y/N][K/R]YYADSVQG |
| 3 | n.a. | Table 2 | Consensus AA sequence of HC CDR3 | D[S/T][R/K/Q]LR[S/T]LLYFEWLS[Q/S]G[Y/L/V][F/L][N/D][P/Y] |
| 4 | n.a. | Table 2 | Consensus AA sequence of LC CDR1 | Q[S/T][V/L/I][VS][Y/F/W][N/S/D]YKNYLA |
| 170 | n.a. | Table 2 | Consensus AA sequence of LC CDR1 | Q[S/T][V/L/I][VS][Y/F/W][N/S/D/Q/R/E]YKNYLA |
| 5 | n.a. | Table 2 | Consensus AA sequence of LC CDR2 | W[A/G]S[T/A/Y/H/K/D][R/L]E[S/T] |
| 6 | n.a. | Table 2 | Consensus AA sequence of LC CDR3 | QQ[Y/H]YRTPP[T/S] |
| 7 | n.a. | Table 2 | Consensus AA sequence of HC FR1 | [E/Q]VQLLE[S/T]GGGLVKPGQSLKLSCAASGFTF[S/T] |
| 8 | n.a. | Table 2 | Consensus AA sequence of HC FR2 | WVRQPPGKGLEWVA |

TABLE 4C-continued

Nucleic acid and amino acid sequences

| SEQ ID NO. | Lab no. | Source | Comment | Sequence |
|---|---|---|---|---|
| 9 | n.a. | Table 2 | Consensus AA sequence of HC FR3 | RFTISRDNSKNTLYLQMNSTRAEDTAVYYCAK |
| 10 | n.a. | Table 2 | Consensus AA sequence of HC FR4 | WG[A/Q]G[T/A][T/M][L/V] TVSS |
| 11 | n.a. | Table 2 | Consensus AA sequence of LC FR1 | [E/D]I[V/Q]MTQSP[D/S][S/T][L/V][A/S][V/A][S/T][L/V/R]G[E/D]R[A/V][T/S]I[N/T/Q/D/R/]C[K/R]SS |
| 12 | n.a. | Table 2 | Consensus AA sequence of LC FR2 | WYQQKPG[Q/K][P/A]PKLLIY |
| 13 | n.a. | Table 2 | Consensus AA sequence of LC FR3 | GVP[D/E/S]RFSGSGSGTDFTLTISSLQ[A/P]ED[V/F/K/D]A[V/T]YYC |
| 14 | n.a. | Table 2 | Consensus AA sequence of LC FR4 | FG[G/Q/T/S/N]GTK[L/V][D/E]IK |
| 15 | 15 VH15 | Table 3, Table 4A, FIG. 2 | AA sequence of HC VR of Ab A18; entire HC domain is in FIG. 1; ID version is in FIG. 13; NT sequence is in Example 1 | EVQLLESGGGLVKPGQSLKLSCAASGFTFTSYGMHWVRQPPGKGLEWVAVISYDGSYKYYADSVQGRFTISRDNSKNTLYLQMNSLRAEDTAVYYCAKDSRLRSLLYFEWLSQGYFNPWGAGTTLTVSS |
| 28 | 28 VL28 | Table 3, Table 4A, FIG. 3 | AA sequence of LC VR of Ab A18; entire LC domain is in FIG. 1; ID version is in FIG. 14; NT sequence is in Example 1 | EIVMTQSPDSLAVSLGERATINCKSSQSVTYNYKNYLAWYQQKPGQPPKLLIYWASTRESGVPDRFSGSGSGTDFTLTISSLQAEDVAVYYCQQYYRTPPTFGGGTKLDIK |
| 16 | 16 VH16 | Table 3, Table 4A, FIG. 2 | AA sequence of HC VR of Abs 014, 028; ID version is in FIG. 13; NT sequence is in Example 1 | EVQLLESGGGLVKPGQSLKLSCAASGFTFSSYGMHWVRQPPGKGLEWVAVVSYDGSNKYYADSVQGRFTISRDNSKNTLYLQMNSLRAEDTAVYYCAKDTKLRSLLYFEWLSSGLLDYWGQGAMVTVSS |
| 29 | 29 VL29 | Table 3, Table 4A, FIG. 3 | AA sequence of LC VR of Abs 014, 154, 157; ID version is in FIG. 14; NT sequence is in Example 1 | EIVMTQSPDSLAVSLGERATINCKSSQSVTFSYKNYLAWYQQKPGQPPKLLIYWASTRESGVPDRFSGSGSGTDFTLTISSLQAEDVAVYYCQQYYRTPPTFGGGTKLDIK |
| 30 | 30 VL30 | Table 3, Table 4A, FIG. 3 | AA sequence of LC VR of Abs 028, 155; ID version is in FIG. 14; NT sequence is in Example 1 | EIVMTQSPDSLAVSLGERATINCKSSQSVTFDYKNYLAWYQQKPGQPPKTLIYWASTRESGVPDRFSGSGSGTDFTLTISSLQAEDVAVYYCQQYYRTPPTFGGGTKLDIK |
| 17 | 17 VH17 | Table 3, Table 4A, FIG. 2 | AA sequence of HC VR of Abs 001, 009, 017, 025, 160, 186, 187, 188, 189, 190, 191, 192, 193, 202, 211; ID version is in FIG. 13; | EVQLLESGGGLVKPGQSLKLSCAASGFTFTSYGMHWVRQPPGKGLEWVAVVSYDGNYKYYADSVQGRFTISRDNSKNTLYLQMNSLRAEDTAVYYCAKDSRLRSLLYFEWLSQGYFNPWGAGTTLTVSS |
| 31 | 31 VL31 | Table 3, Table 4A, FIG. 3 | AA sequence of LC VR of Abs 001, 002, 003; ID version is in FIG. 14; | EIVMTQSPDSLAVSLGERATINCKSSQTVTFNYKNYLAWYQQKPGQPPKLLIYWASTRESGVPDRFSGSGSGTDFTLTISSLQAEDVAVYYCQQHYRTPPSFGGGTKLDIK |
| 18 | 18 VH18 | Table 3, Table 4A, FIG. 2 | AA sequence of HC VR of Abs 002, 010, B18, 026, 203, 212; ID version is in FIG. 13; | EVQLLESGGGLVKPGQSLKLSCAASGFTFTSYGMHWVRQPPGKGLEWVAVLSYDGNYKYYADSVQGRFTISRDNSKNTLYLQMNSLRAEDTAVYYCAKDSRLRSLLYFEWLSQGYFNPWGAGTTLTVSS |
| 19 | 19 VH19 | Table 3, Table 4A, FIG. 2 | AA sequence of HC VR of Abs 003, 011, 019, 027, 194, 195, 196, 197, 198, 199, 200, 204, 213; ID version is in FIG. 13; | EVQLLESGGGLVKPGQSLKLSCAASGFTFTTYAMHWVRQPPGKGLEWVAVLSYDGNYKYYADSVQGRFTISRDNSKNTLYLQMNSLRAEDTAVYYCAKDSRLRSLLYFEWLSQGYFNPWGAGTTLTVSS |
| 32 | 32 VL32 | Table 3, Table 4A, FIG. 3 | AA sequence of LC VR of Abs 009, 010, 011; ID version is in FIG. 14; | EIVMTQSPDSLAVSLGERATINCKSSQTLSFNYKNYLAWYQQKPGQPPKLLIYWASTRESGVPDRFSGSGSGTDFTLTISSLQAEDVAVYYCQQHYRTPPSFGGGTKLDIK |
| 33 | 33 VL33 | Table 3, Table 4A, FIG. 3 | AA sequence of LC VR of Abs 017, B18, 019; ID version is in FIG. 14; | EIVMTQSPDSLAVSLGERATINCKSSQTVTFNYKNYLAWYQQKPGQPPKLLIYFASTRESGVPDRFSGSGSGTDFTLTISSLQAEDVAVYYCQQHYRTPPSFGGGTKLDIK |
| 34 | 34 VL34 | Table 3, Table 4A, FIG. 3 | AA sequence of LC VR of Abs 025, 026, 027, 086; ID version is in FIG. 14; | EIVMTQSPDSLAVSLGERATINCKSSQTLSFNYKNYLAWYQQKPGQPPKLLIYFASTRESGVPDRFSGSGSGTDFTLTISSLQAEDVAVYYCQQHYRTPPSFGGGTKLDIK |
| 20 | 20 VH20 | Table 3, Table 4A, FIG. 2 | AA sequence of HC VR of Ab 086; ID version is in FIG. 13; | EVQLLESGGGLVKPGQSLKLSCAASGFTFTTYAMHWVRQPPGKGLEWVAVVSFDGNNRYYADSVQGDFTISRDNSKNTLYLQMNSLRAEDTAVYYCAKDSQLRSTLYFEWLSSGVLDYWGQGAMVTVSS |

TABLE 4C-continued

Nucleic acid and amino acid sequences

| SEQ ID NO. | Lab no. | Source | Comment | Sequence |
|---|---|---|---|---|
| 21 | 21 VH21 | Table 3 Table 4A FIG. 2 | AA sequence of HC VR of Abs 154, 155; ID version is in FIG. 13; | EVQLLESGGGLVKPGQSLKLSCAASGFTFSSYGMHWVRQPPGKGLEWVAV VSYDGNNKYYADSVQGRFTISRDNSKNTLYLQMNSLRAEDTAVYYCAKDS KLRSLLYFEWLSSGLLDYWGQGAMVTVSS |
| 22 | 22 VH22 | Table 3 Table 4A FIG. 2 | AA sequence of HC VR of Abs 157, 159; ID version is in FIG. 13; | EVQLLESGGGLVKPGQSLKLSCAASGFTFTTYAMHWVRQPPGKGLEWVAV VSYDGNNKYYADSVQGRFTISRDNSKNTLYLQMNSLRAEDTAVYYCAKDS KTRSLLYFEWLSSGLLDYWGQGAMVTVSS |
| 35 | 35 VL35 | Table 3 Table 4A FIG. 3 | AA sequence of LC VR of Ab 159; ID version is in FIG. 14; | EIVMTQSPDSLAVSLGERATINCKSSQSVTWSYKNYLAWYQQKPGQPPKL LIYWASTRESGVPDRFSGSGSGTDFTLTISSLQAEDVAVYYCQQYYRTTP TFGGGTKLDIK |
| 36 | 36 VL36 | Table 3 Table 4A FIG. 3 | AA sequence of LC VR of Ab 160; ID version is in FIG. 14; | EIVMSQSPDTLAVTLGERASINCKSSQTVTFNYKNYLAWYQQKPGQPPKV LIYWASARETGVPERFSGSGSGTDFTLTISSLQAEDVAVYYCQQHYRTPP SFGQGTKLEIK |
| 37 | 37 VL37 | Table 3 Table 4A FIG. 3 | AA sequence of LC VR of Abs 186, 194; ID version is in FIG. 14; | EIVMTQSPDSLAVSLGERATINCKSSQTVTFNYKNYLAWYQQKPGQPPKL LIYWASTRESGVPDRFSGSGSGTDFTLTISSLQAEDVAVYYCQQHYRTPP SFGTGTKLDIK |
| 38 | 38 VL38 | Table 3 Table 4A FIG. 3 | AA sequence of LC VR of Abs 187, 195; ID version is in FIG. 14; | EIVMTQSPDSLAVSLGERATINCKSSQTVTFNYKNYLAWYQQKPGQPPKL LIYWASTRESGVPDRFSGSGSGTDFTLTISSLQAEDVAVYYCQQHYRTPP SFGSGTKLDIK |
| 39 | 39 VL39 | Table 3 Table 4A FIG. 3 | AA sequence of LC VR of Abs 188, 196; ID version is in FIG. 14; | EIVMTQSPDSLAVSLGERATINCKSSQTVTFNYKNYLAWYQQKPGQPPKL LIYWASTRESGVPDRFSGSGSGTDFTLTISSLQAEDVAVYYCQQHYRTPP SFGQGTKLDIK |
| 40 | 40 VL40 | Table 3 Table 4A FIG. 3 | AA sequence of LC VR of Abs 189, 197; ID version is in FIG. 14; | EIVMTQSPDSLAVSLGERATINCKSSQTVTFNYKNYLAWYQQKPGQPPKL LIYWASTRESGVPDRFSGSGSGTDFTLTISSLQAEDVAVYYCQQHYRTPP SFGNGTKLDIK |
| 41 | 41 VL41 | Table 3 Table 4A FIG. 3 | AA sequence of LC VR of Abs 190, 198; ID version is in FIG. 14; | EIVMTQSPDSLAVSLGERATINCKSSQTLSFNYKNYLAWYQQKPGQPPKL LIYWASTRESGVPDRFSGSGSGTDFTLTISSLQAEDVAVYYCQQHYRTPP SFGTGTKLDIK |
| 42 | 42 VL42 | Table 3 Table 4A | AA sequence of LC VR of Abs 191, 199; ID version is in FIG. 14; | EIVMTQSPDSLAVSLGERATINCKSSQTLSFNYKNYLAWYQQKPGQPPKL LIYWASTRESGVPDRFSGSGSGTDFTLTISSLQAEDVAVYYCQQHYRTPP SFGSGTKLDIK |
| 43 | 43 VL43 | Table 3 Table 4A FIG. 3 | AA sequence of LC VR of Abs 192, 200; ID version is in FIG. 14; | EIVMTQSPDSLAVSLGERATINCKSSQTLSFNYKNYLAWYQQKPGQPPKL LIYWASTRESGVPDRFSGSGSGTDFTLTISSLQAEDVAVYYCQQHYRTPP SFGQGTKLDIK |
| 44 | 44 VL44 | Table 3 Table 4A FIG. 3 | AA sequence of LC VR of Abs 193; ID version is in FIG. 14; | EIVMTQSPDSLAVSLGERATINCKSSQTLSFNYKNYLAWYQQKPGQPPKL LIYWASTRESGVPDRFSGSGSGTDFTLTISSLQAEDVAVYYCQQHYRTPP SFGRGTKLDIK |
| 45 | 45 VL45 | Table 3 Table 4A FIG. 3 | AA sequence of LC VR of Abs 202, 203, 204, 210, 031, 032, 033, 034; ID version is in FIG. 14; NT sequence is in Example 1 | DIQMTQSPSSLSASVGDRVTITCRSSQSITFNYKNYLAWYQQKPGKAPKL LIYWGSYLESGVPSRFSGSGSGTDFTLTISSLQPEDFATYYCQQHYRTPP SFGQGTKVEIK |
| 46 | 46 VL46 | Table 3 Table 4A FIG. 3 | AA sequence of LC VR of Abs 211, 212, 213, 219, 037, 038, 039, 040; ID version is in FIG. 14; | DIQMTQSPSSLSASVGDRVTITCRSSQSITFNYKNYLGWYQQKPGKAPKL LIYWGSYLESGVPSRFSGSGSGTDFTLTISSLQPEDFATYYCQQHYRTPP SFGQGTKVEIK |
| 23 | 23 VH23 | Table 3 Table 4A FIG. 2 | AA sequence of HC VR of Abs 210, 219; ID version is in FIG. 13; | EVQLLESGGGLVKPGQSLKLSCAASGFTFTSYGMHWVRQPPGKGLEWVAV VSYDGNYKYYADSVQGDFTISRDNSKNTLYLQMNSLRAEDTAVYYCAKDS KLRSLLYFEWLSQGYFNPWGAGTTLTVSS |
| 24 | 24 VH24 | Table 3 Table 4A FIG. 2 | AA sequence of HC VR of Abs A001, A002, A003, A010, A011, 031, 037; ID version is in FIG. 13; NT sequence is in Example 1 | EVQLLESGGGLVKPGQSLKLSCAASGFTFTSYAMHWVRQPPGKGLEWVAV VSYDGNYKYYADSVQGDFTISRDNSKNTLYLQMNSLRAEDTAVYYCAKDS RLRSLLYFEWLSQGYFNPWGQGTTLTVSS |
| 47 | 47 VL47 | Table 3 Table 4A FIG. 3 | AA sequence of LC VR of Abs A001, 004, 007, 016; ID version is in FIG. 14; | DIVMTQSPDTLAVTLGERATIQCKSSQTVTFNYKNYLAWYQQKPGQPPKL LIYWASTRESGVPDRFSGSGSGTDFTLTITSLQAEDVAVYYCQQHYRTPP SFGQGTKLDIK |
| 48 | 48 VL48 | Table 3 Table 4A FIG. 3 | AA sequence of LC VR of Abs 002, 005, 008, A017; ID version is in FIG. 14; | DIVMTQSPDTVAVTVGERATINCKSSQTVTFNYKNYLAWYQQKPGQPPKL LIYWASTRESGVPDRFSGSGSGTDFTLTISSLQAEDVAVYYCQQHYRTPP SFGQGTKLDIK |

TABLE 4C-continued

Nucleic acid and amino acid sequences

| SEQ ID NO. | Lab no. | Source | Comment | Sequence |
|---|---|---|---|---|
| 25 | 25 VH25 | Table 3 Table 4A FIG. 2 | AA sequence of HC VR of Abs 004, 005, 006, 012, 013, 032, 038, 043, 044, 045, 046, 047, 048, 049, 050, 051, 052, 067, 068, 069, 070, 073, 074, 075, 076, 077; ID version is in FIG. 13; NT sequence is in Example 1 | QVQLLETGGGLVKPGQSLKLSCAASGFTFTSYAMHWVRQPPGKGLEWVAV VSYDGNYKYYADSVQGRFTISRDNSKNTLYLQMNSLRAEDTAVYYCAKDS RLRSLLYFEWLSQGYFNPWGQGTTLTVSS |
| 49 | 49 VL49 | Table 3 Table 4A FIG. 3 | AA sequence of LC VR of Abs A003, 006, A009, C18; ID version is in FIG. 14; | DIVMTQSPDTVAVTLGERATIDCKSSQTVTFNYKNYLAWYQQKPGQPPKL LIYWASTRESGVPDRFSGSGSGTDFTLTISSLQAEDVAVYYCQQHYRTPP SFGQGTKLDIK |
| 26 | 26 VH26 | Table 3 Table 4A FIG. 2 | AA sequence of HC VR of Abs 007, 008, A009, A14, 015, 033, 039; ID version is in FIG. 13; | EVQLLESGGGLVKPGQSLKLSCAASGFTFTSYAMHWVRQPPGKGLEWVAV VSYDGNYKYYADSVQGDFTISRDNSKNTLYLQMNSLRAEDTAVYYCAKDS QLRTLLYFEWLSQGYFNPWGQGTTLTVSS |
| 50 | 50 VL50 | Table 3 Table 4A FIG. 3 | AA sequence of LC VR of Abs A010 012, A14, A019; ID version is in FIG. 14; | DIVMTQSPDTLAVTVGERATIRCKSSQTVTFNYKNYLAWYQQKPGQPPKL LIYWASTRESGVPDRFSGSGSGTDFTLTISSLQAEDVAVYYCQQHYRTPP SFGQGTKLDIK |
| 51 | 51 VL51 | Table 3 Table 4A FIG. 3 | AA sequence of LC VR of Ab A011, 013, 015; ID version is in FIG. 14; | DIVMTQSPDTLAVSRGERATIDCKSSQTVTFNYKNYLAWYQQKPGQPPKL LIYWASTRESGVPDRFSGSGSGTDFTLTISSLQAEDEAVYYCQQHYRTPP SFGQGTKLDIK |
| 27 | 27 VH27 | Table 3 Table 4A FIG. 2 | AA sequence of HC VR of Abs 016, A017, C18, A019, 034, 040; ID version is in FIG. 13; | EVQLLESGGGLVKPGQSLKLSCAASGFTFTSYAMHWVRQPPGKGLEWVAV VSYDGNYKYYADSVQGDFTISRDNSKNTLYLQMNSLRAEDTAVYYCAKDS RLRTLLYFEWLSQGYFDPWGQGTTLTVSS |
| 60 | 60 VL60 | Table 3 Table 4A FIG. 3 | AA sequence of LC VR of Ab 043; ID version is in FIG. 14; | DIQMTQSPSSLSASVGDRVTITCRSSQSITFNYKNYLAWYQQKPGKAPKL LIYWGSYLESGVPSRFSGSGSGTDFTLTISSLQPEDFATYYCQQYYRTPP SFGQGTKVEIK |
| 52 | 52 VL52 | Table 3 Table 4A FIG. 3 | AA sequence of LC VR of Abs 044, 071, 072, 078; ID version is in FIG. 14; NT sequence is in Example 1 | DIQMTQSPSSLSASVGDRVTITCRSSQSITFDYKNYLAWYQQKPGKAPKL LIYWGSYLESGVPSRFSGSGSGTDFTLTISSLQPEDFATYYCQQYYRTPP SFGQGTKVEIK |
| 57 | 57 VL57 | Table 3 Table 4A FIG. 3 | AA sequence of LC VR of Ab 045; ID version is in FIG. 14; | DIQMTQSPSSLSASVGDRVTITCRSSQSITFNYKNYLAWYQQKPGKAPKL LIYWGSYLESGVPSRFSGSGSGTDFTLTISSLQPEDVATYYCQQYYRTPP SFGQGTKVEIK |
| 59 | 59 VL59 | Table 3 Table 4A FIG. 3 | AA sequence of LC VR of Ab 046; ID version is in FIG. 14; | DIQMTQSPSSLSASVGDRVTITCRSSQSITFNYKNYLAWYQQKPGKAPKL LIYWGSYLESGVPSRFSGSGSGTDFTLTISSLQPEDDATYYCQQYYRTPP SFGQGTKVEIK |
| 55 | 55 VL55 | Table 3 Table 4A FIG. 3 | AA sequence of LC VR of Ab 047; ID version is in FIG. 14; | DIQMTQSPSSLSASVGDRVTITCRSSQSITFNYKNYLAWYQQKPGKAPKL LIYWGSKLESGVPSRFSGSGSGTDFTLTISSLQPEDFATYYCQQYYRTPP SFGQGTKVEIK |
| 58 | 58 VL58 | Table 3 Table 4A FIG. 3 | AA sequence of LC VR of Ab 048; ID version is in FIG. 14; | DIQMTQSPSSLSASVGDRVTITCRSSQSITFNYKNYLAWYQQKPGKAPKL LIYWGSYLESGVPSRFSGSGSGTDFTLTISSLQPEDKATYYCQQYYRTPP SFGQGTKVEIK |
| 54 | 54 VL54 | Table 3 Table 4A FIG. 3 | AA sequence of LC VR of Ab 049; ID version is in FIG. 14; | DIQMTQSPSSLSASVGDRVTITCRSSQSITFNYKNYLAWYQQKPGKAPKL LIYWGSHLESGVPSRFSGSGSGTDFTLTISSLQPEDFATYYCQQYYRTPP SFGQGTKVEIK |
| 56 | 56 VL56 | Table 3 Table 4A FIG. 3 | AA sequence of LC VR of Ab 050; ID version is in FIG. 14; | DIQMTQSPSSLSASVGDRVTITCRSSQSITFNYKNYLAWYQQKPGKAPKL LIYWGSDLESGVPSRFSGSGSGTDFTLTISSLQPEDFATYYCQQYYRTPP SFGQGTKVEIK |
| 53 | 53 VLS3 | Table 3 Table 4A FIG. 3 | AA sequence of LC VR of Ab 051; ID version is in FIG. 14; | DIQMTQSPSSLSASVGDRVTITCRSSQSITFNYKNYLAWYQQKPGKAPKL LIYWGSTLESGVPSRFSGSGSGTDFTLTISSLQPEDFATYYCQQYYRTPP SFGQGTKVEIK |
| 61 | 61 VL61 | Table 3 Table 4A FIG. 3 | AA sequence of LC VR of Ab 052; ID version is in FIG. 14; | DIQMTQSPSSLSASVGDRVTITCRSSQSITFNYKNYLAWYQQKPGKAPKL LIYWGSTRESGVPSRFSGSGSGTDFTLTISSLQPEDFATYYCQQYYRTPP SFGQGTKVEIK |
| 153 | 153 VL153 | Table 3 Table 4A FIG. 3 | AA sequence of LC VR of Ab 067; ID version is in FIG. 14; | DIQMTQSPSSLSASVGDRVTITCRSSQSITFQYKNYLAWYQQKPGKAPKL LIYWGSYLESGVPSRFSGSGSGTDFTLTISSLQPEDFATYYCQQYYRTPP SFGQGTKVEIK |

TABLE 4C-continued

Nucleic acid and amino acid sequences

| SEQ ID NO. | Lab no. | Source | Comment | Sequence |
|---|---|---|---|---|
| 154 | 154 VL154 | Table 3 Table 4A FIG. 3 | AA sequence of LC VR of Ab 068; ID version is in FIG. 14; | DIQMTQSPSSLSASVGDRVTITCRSSQSITFRYKNYLAWYQQKPGKAPKL LIYWGSYLESGVPSRFSGSGSGTDFTLTISSLQPEDFATYYCQQHYRTPP SFGQGTKVEIK |
| 155 | 155 VL155 | Table 3 Table 4A | AA sequence of LC VR of Abs 069, 079; ID version is in FIG. 14; | DIQMTQSPSSLSASVGDRVTITCRSSQSITFEYKNYLAWYQQKPGKAPKL LIYWGSYLESGVPSRFSGSGSGTDFTLTISSLQPEDFATYYCQQHYRTPP SFGQGTKVEIK |
| 156 | 156 VL156 | Table 3 Table 4A FIG. 3 | AA sequence of LC VR of Ab 070; ID version is in FIG. 14; | DIQMTQSPSSLSASVGDRVTITCRSSQSITFDYKNYLAWYQQKPGKAPKL LIYWGSTRESGVPSRFSGSGSGTDFTLTISSLQPEDFATYYCQQHYRTPP SFGQGTKVEIK |
| 162 | 162 VL162 | Table 3 Table 4A FIG. 17 | AA sequence of HC VR of Ab 071 | EVQLLESGGGLVKPGQSLKLSCAASGFSFSTYAMHWVRQPPGKGLEWVAV VSYDGNYKYYADTVQGRFTISRDNSKNTLYLQMNSLRAEDTAVYYCAKDS RLRSLLYFEWLSQGYFNPWGQGTTLIVSS |
| 163 | 163 VL163 | Table 3 Table 4A FIG. 17 | AA sequence of HC VR of Ab 072 | EVQLLESGGGLRKPGQSLKLSCAASGFSFSTYAMHWVRQPPGKGLEWVAV VSYDGNYKYYADSVQGRFTISRDNSKNTLYLQMNSLRAEDTAVYYCAKDS RLRSLLYFEWLSQGYFNPWGQGTTLTVSS |
| 165 | 165 VL165 | Table 3 Table 4A FIG. 17 | AA sequence of LC VR of Ab 073 | DIQMTQSPSSLSASVGDRVTITCRSSQSITWNYKNYLAWYQQKPGKAPKL LIYWGSYLESGVPSRFSGSGSGTDFTLTISSLQPEDFATYYCQQHYRTPP SFGQGTKVEIK |
| 166 | 166 VL166 | Table 3 Table 4A FIG. 17 | AA sequence of LC VR of Abs 074, 080 | DIQMTQSPSSLSASVGDRVTITCRSSQSITWDYKNYLAWYQQKPGKAPKL LIYWGSYLESGVPSRFSGSGSGTDFTLTISSLQPEDFATYYCQQHYRTPP SFGQGTKVEIK |
| 167 | 167 VL167 | Table 3 Table 4A FIG. 17 | AA sequence of LC VR of Ab 075 | DIQMTQSPSSLSASVGDRVTITCRSSQSITWQYKNYLAWYQQKPGKAPKL LIYWGSYLESGVPSRFSGSGSGTDFTLTISSLQPEDFATYYCQQHYRTPP SFGQGTKVEIK |
| 168 | 168 VL168 | Table 3 Table 4A FIG. 17 | AA sequence of LC VR of Ab 076 | DIQMTQSPSSLSASVGDRVTITCRSSQSITWRYKNYLAWYQQKPGKAPKL LIYWGSYLESGVPSRFSGSGSGTDFTLTISSLQPEDFATYYCQQHYRTPP SFGQGTKVEIK |
| 169 | 169 VL169 | Table 3 Table 4A FIG. 17 | AA sequence of LC VR of Abs 077, 081 | DIQMTQSPSSLSASVGDRVTITCRSSQSITWEYKNYLAWYQQKPGKAPKL LIYWGSYLESGVPSRFSGSGSGTDFTLTISSLQPEDFATYYCQQHYRTPP SFGQGTKVEIK |
| 164 | 164 VL164 | Table 3 Table 4A FIG. 17 | AA sequence of HC VR of Abs 078, 079, 080, 081 | QVQLLETGGGLVKPGQSLKLSCAASGFTFTSYAMHWVRQPPGKGLEWVAV VSYDGNYKYYADSVQGRFTISRDNSKNTLYLQMNSLRAEDTAVYYCAKDS RLRSLLYFEWLSQGYFNPWGQGTTVTVSS |
| 161 | HC161 | Table 4A FIG. 2 | AA sequence of HC VR consensus; ID version is in FIG. 13; | EVQLLESGGGLVKPGQSLKLSCAASGFTFSSYGMHWVRQPPGKGLEWVAV VSYDGSNKYYADSVQGRFTISRDNSKNTLYLQMNSLRAEDTAVYYCAKDS KLRSLLYFEWLSSGLLDYWGQGAMVTSS |
| 62 | LC62 | Table 4A FIG. 3 | AA sequence of LC VR consensus; ID version is in FIG. 14; | DIQMTQSPSSLSASVGDRVTITCRSSQSITFNYKNYLAWYQQKPGKAPKL LIYWGSYLESGVPSRFSGSGSGTDFTLTISSLQPEDFATYYCQQHYRTPP SFGQGTKVEIK |
| 96 | 15-ID | Table 4B FIG. 13 | AA sequence of HC VR of Ab A18; non-ID version is in FIG. 2; | IDEVQLLESGGGLVKPGQSLKLSCAASGFTFTSYGMHWVRQPPGKGLEWV AVISYDGSYKYYADSVQGRFTISRDNSKNTLYLQMNSLRAEDTAVYYCAK DSRLRSLLYFEWLSQGYFNPWGAGTTLTVSS |
| 110 | 28-ID | Table 4B FIG. 14 | AA sequence of LC VR of Ab A18; non-ID version is in FIG. 3 | IDEIVMTQSPDSLAVSLGERATINCKSSQSVTYNYKNYLAWYQQKPGQPP KLLIYWASTRESGVPDPFSGSGSGTDFTLTISSLQAEDVAVYYCQQYYRT PPTFGGGTKLDIK |
| 97 | 16-ID | Table 4B FIG. 13 | AA sequence of HC VR of Abs 014, 028; non-ID version is in FIG. 2; | IDEVQLLESGGGLVKPGQSLKLSCAASGFTFSSYGMHWVRQPPGKGLEWV AVVSYDGSNKYYADSVQGRFTISRDNSKNTLYLQMNSLRAEDTAVYYCAK DTKLRSLLYFEWLSSGLLDYWGQGAMVTVSS |
| 111 | 29-ID | Table 4B FIG. 14 | AA sequence of LC VR of Abs 014, 154, 157; non-ID version is in FIG. 3; | IDEIVMTQSPDSLAVSLGERATINCKSSQSVTFSYKNYLAWYQQKPGQPP KLLIYWASTRESGVPDPFSGSGSGTDFTLTISSLQAEDVAVYYCQQYYRT PPTFGGGTKLDIK |
| 98 | 17-ID | Table 4B FIG. 13 | AA sequence of HC VR of Ab 001, 009, 017, 025, 160, 186, 187, 188, 189, 190, 191, 192, 193, 202, 211; non-ID version is in FIG. 2; | IDEVQLLESGGGLVKPGQSLKLSCAASGFTFTSYGMHWVRQPPGKGLEWV AVVSYDGNYKYYADSVQGRFTISRDNSKNTLYLQMNSLRAEDTAVYYCAK DSRLRSLLYFEWLSQGYFNPWGAGTTLTVSS |

TABLE 4C-continued

Nucleic acid and amino acid sequences

| SEQ ID NO. | Lab no. | Source | Comment | Sequence |
|---|---|---|---|---|
| 112 | 30-ID | Table 4B FIG. 14 | AA sequence of LC VR of Abs 028, 155; non-ID version is in FIG. 3; | IDEIVMTQSPDSLAVSLGERATINCKSSQSVTFDYKNYLAWYQQKPGQPPKLLIYWASTRESGVPDPFSGSGSGTDFTLTISSLQAEDVAVYYCQQYYRTPPTFGGGTKLDIK |
| 99 | 18-ID | Table 4B FIG. 13 | AA sequence of HC VR of Abs 002, 010, B18, 026, 203, 212; non-ID version is in FIG. 2; | IDEVQLLESGGGLVKPGQSLKLSCAASGFTFTSYGMHWVRQPPGKGLEWVAVLSYDGNYKYYADSVQGRFTISRDNSKNTLYLQMNSLRAEDTAVYYCAKDSRLRSLLYFEWLSQGYFNPWGAGTTLTVSS |
| 113 | 35-ID | Table 4B FIG. 14 | AA sequence of LC VR of Ab 159; non-ID version is in FIG. 3; | IDEIVMTQSPDSLAVSLGERATINCKSSQSVTWSYKNYLAWYQQKPGQPPKLLIYWASTRESGVPDPFSGSGSGTDFTLTISSLQAEDVAVYYCQQYYRTPPTFGGGTKLDIK |
| 100 | 19-ID | Table 4B FIG. 13 | AA sequence of HC VR of Abs 003, 011, 019, 027, 194, 195, 196, 197, 198, 199, 200, 204, 213; non-ID version is in FIG. 2; | IDEVQLLESGGGLVKPGQSLKLSCAASGFTFTTYAMHWVRQPPGKGLEWVAVLSYDGNYKYYADSVQGRFTISRDNSKNTLYLQMNSLRAEDTAVYYCAKDSRLRSLLYFEWLSQGYFNPWGAGTTLTVSS |
| 114 | 31-ID | Table 4B FIG. 14 | AA sequence of LC VR of Abs 001, 002, 003; non-ID version is in FIG. 3; | IDEIVMTQSPDSLAVSLGERATINCKSSQLVTFNYKNYLAWYQQKPGQPPKLLIYWASTRESGVPDPFSGSGSGTDFTLTISSLQAEDVAVYYCQQHYRTPPSFGGGTKLDIK |
| 101 | 21-ID | Table 4B FIG. 13 | AA sequence of HC VR of Abs 154,155; non-ID version is in FIG. 2; | IDEVQLLESGGGLVKPGQSLKLSCAASGFTFSSYGMHWVRQPPGKGLEWVAVVSYDGNNKYYADSVQGRFTISRDNSKNTLYLQMNSLRAEDTAVYYCAKDSKLRSLLYFEWLSSGLLDYWGQGAMVTVSS |
| 115 | 32-ID | Table 4B FIG. 14 | AA sequence of LC VR of Abs 009, 010, 011; non-ID version is in FIG. 3; | IDEIVMTQSPDSLAVSLGERATINCKSSQTLSFNYKNYLAWYQQKPGQPPKLLIYWASTRESGVPDPFSGSGSGTDFTLTISSLQAEDVAVYYCQQHYRTPPSFGGGTKLDIK |
| 102 | 22-ID | Table 4B FIG. 13 | AA sequence of HC VR of Abs 157, 159; non-ID version is in FIG. 2; | IDEVQLLESGGGLVKPGQSLKLSCAASGFTFTTYAMHWVRQPPGKGLEWVAVVSYDGNNKYYADSVQGRFTISRDNSKNTLYLQMNSLRAEDTAVYYCAKDSKLRSLLYFEWLSSGLLDYWGQGAMVTVSS |
| 116 | 33-ID | Table 4B FIG. 14 | AA sequence of LC VR of Abs 017, B18, 019; non-ID version is in FIG. 3; | IDEIVMTQSPDSLAVSLGERATINCKSSQLVTFNYKNYLAWYQQKPGQPPKLLIYFASTRESGVPDRFSGSGSGTDFTLTISSLQAEDVAVYYCQQHYRTPPSFGGGTKLDIK |
| 103 | 20-ID | Table 4B FIG. 13 | AA sequence of HC VR of Ab 086; non-ID version is in FIG. 2; | IDEVQLLESGGGLVKPGQSLKLSCAASGFTFTTYAMHWVRQPPGKGLEWVAVVSFDGNNRYYADSVQGRFTISRDNSKNTLYLQMNSLRAEDTAVYYCAKDSQLRSLLYFEWLSSGVLDYWGQGAMVTVSS |
| 117 | 34-ID | Table 4B FIG. 14 | AA sequence of LC VR of Abs 025, 026, 027, 086; non-ID version is in FIG. 3; | IDEIVMTQSPDSLAVSLGERATINCKSSQTLSFNYKNYLAWYQQKPGQPPKLLIYFASTRESGVPDRFSGSGSGTDFTLTISSLQAEDVAVYYCQQHYRTPPSFGGGTKLDIK |
| 104 | 23-ID | Table 4B FIG. 13 | AA sequence of HC VR of Abs 210, 219; non-ID version is in FIG. 2; | IDEVQLLESGGGLVKPGQSLKLSCAASGFTFTSYGMHWVRQPPGKGLEWVAVVSYDGNYKYYADSVQGRFTISRDNSKNTLYLQMNSLRAEDTAVYYCAKDSKLRSLLYFEWLSQGYFNPWGAGTTLTVSS |
| 118 | 36-ID | Table 4B FIG. 14 | AA sequence of LC VR of Ab 160; non-ID version is in FIG. 3; | IDEIVMSQSPDTLAVTLGERASINCKSSQTVTFNYKNYLAWYQQKPGQPPKVLIYWGASARETGVPERFSGSGSGTDFTLTISSLQAEDVAVYYCQQHYRTPPSFGQGTKLEIK |
| 105 | 24-ID | Table 4B FIG. 13 | AA sequence of HC VR of Abs A001, A002, A003, A010, A011, 031, 037; non-ID version is in FIG. 2; | IDEVQLLESGGGLVKPGQSLKLSCAASGFTFTSYAMHWVRQPPGKGLEWVAVVSYDGNYKYYADSVQGRFTISRDNSKNTLYLQMNSLRAEDTAVYYCAKDSRLRSLLYFEWLSQGYFNPWGQGTTLTVSS |
| 119 | 45-ID | Table 4B FIG. 14 | AA sequence of LC VR of Abs 202, 203, 204, 210, 031, 032, 033, 034 ; non-ID version is in FIG. 3; | IDDIQMTQSPSSLSASVGDRVTITCRSSQSITFNYKNYLAWYQQKPGKAPKLLIYWGSYLESGVPSRFSGSGSGTDFTLTISSLQPEDFATYYCQQHYRTPPSFGQGTKVEIK |
| 106 | 25-ID | Table 4B FIG. 13 | AA sequence of HC VR of Abs 004, 005, 006, 012, 013, 032, 038, 043, 044, 045, 046, 047, 048, 049, 050, 051, 052, 067, 068, 069, 070, 073, 074, 075, 076, 077; non-ID version is in FIG. 2; | IDQVQLLETGGGLVKPGQSLKLSCAASGFTFTSYAMHWVRQPPGKGLEWVAVVSYDGNYKYYADSVQGRFTISRDNSKNTLYLQMNSLRAEDTAVYYCAKDSRLRSLLYFEWLSQGYFNPWGQGTTLTVSS |
| 120 | 46-ID | Table 4B FIG. 14 | AA sequence of LC VR of Abs 211, 212, 213, 219, 037, 038, 039, 040; non-ID version is in FIG. 3; | IDDIQMTQSPSSLSASVGDRVTITCRSSQSITFNYKNYLGWYQQKPGKAPKLLIYWGSYLESGVPSRFSGSGSGTDFTLTISSLQPEDFATYYCQQHYRTPPSFGQGTKVEIK |

TABLE 4C-continued

Nucleic acid and amino acid sequences

| SEQ ID NO. | Lab no. | Source | Comment | Sequence |
|---|---|---|---|---|
| 107 | 26-ID | Table 4B FIG. 13 | AA sequence of HC VR of Abs 007, 008, A009, A14, 015, 033, 039; non-ID version is in FIG. 2; | IDEVQLLESGGGLVKPGQSLKLSCAASGFTFTSYAMHWVRQPPGKGLEWV AVVSYDGNYKYYADSVQGRFTISRDNSKNTLYLQMNSLRAEDTAVYYCAK DSQLRTLLYFEWLSQGYFNPWGQGTTLTVSS |
| 121 | 37-ID | Table 4B FIG. 14 | AA sequence of LC VR of Abs 186, 194; non-ID version is in FIG. 3; | IDEIVMTQSPDSLAVSLGERATINCKSSQLVTFNYKNYLAWYQQKPGQPP KLLIYWASTRESGVPDPFSGSGSGTDFTLTISSLQAEDVAVYYCQQHYRT PPSFGLGTKLDIK |
| 108 | 27-ID | Table 4B FIG. 13 | AA sequence of HC VR of Abs 016, A017, C18, A019, 034, 040; non-ID version is in FIG. 2; | IDEVQLLESGGGLVKPGQSLKLSCAASGFTFTSYAMHWVRQPPGKGLEWV AVVSYDGNYKYYADSVQGRFTISRDNSKNTLYLQMNSLRAEDTAVYYCAK DSRLRTLLYFEWLSQGYFDPWGQGTTLTVSS |
| 122 | 38-ID | Table 4B FIG. 14 | AA sequence of LC VR of Abs 187, 195; non-ID version is in FIG. 3; | IDEIVMTQSPDSLAVSLGERATINCKSSQTVTFNYKNYLAWYQQKPGQPP KLLIYWASTRESGVPDRFSGSGSGTDFTLTISSLQAEDVAVYYCQQHYRT PPSFGSGTKLDIK |
| 109 | 161-ID | Table 4B FIG. 13 | AA sequence of HC VR consensus ID; non-ID version is in FIG. 2; | IDEVQLLESGGGLVKPGQSLKLSCAASGFTFSSYGMHWVRQPPGKGLEWV AVVSYDGSNKYYADSVQGRFTISRDNSKNTLYLQMNSLRAEDTAVYYCAK DSKLRSLLYFEWLSSGLLDYWGQGAMVTVSS |
| 123 | 39-ID | Table 4B FIG. 14 | AA sequence of LC VR of Abs 188, 196; non-ID version is in FIG. 3; | IDEIVMTQSPDSLAVSLGERATINCKSSQTVTFNYKNYLAWYQQKPGQPP KLLIYWASTRESGVPDRFSGSGSGTDFTLTISSLQAEDVAVYYCQQHYRT PPSFGQGTKLDIK |
| 124 | 40-ID | Table 4B FIG. 14 | AA sequence of LC VR of Abs 189, 197; non-ID version is in FIG. 3; | IDEIVMTQSPDSLAVSLGERATINCKSSQTVTFNYKNYLAWYQQKPGQPP KLLIYWASTRESGVPDRFSGSGSGTDFTLTISSLQAEDVAVYYCQQHYRT PPSFGNGTKLDIK |
| 125 | 41-ID | Table 4B FIG. 14 | AA sequence of LC VR of Abs 190, 198; non-ID version is in FIG. 3; | IDEIVMTQSPDSLAVSLGERATINCKSSQTLSFNYKNYLAWYQQKPGQPP KLLIYWASTRESGVPDRFSGSGSGTDFTLTISSLQAEDVAVYYCQQHYRT PPSFGTGTKLDIK |
| 126 | 42-ID | Table 4B FIG. 14 | AA sequence of LC VR of Abs 191, 199; non-ID version is in FIG. 3; | IDEIVMTQSPDSLAVSLGERATINCKSSQTLSFNYKNYLAWYQQKPGQPP KLLIYWASTRESGVPDRFSGSGSGTDFTLTISSLQAEDVAVYYCQQHYRT PPSFGSGTKLDIK |
| 127 | 43-ID | Table 4B FIG. 14 | AA sequence of LC VR of Abs 192, 200; non-ID version is in FIG. 3; | IDEIVMTQSPDSLAVSLGERATINCKSSQTLSFNYKNYLAWYQQKPGQPP KLLIYWASTRESGVPDRFSGSGSGTDFTLTISSLQAEDVAVYYCQQHYRT PPSFGQGTKLDIK |
| 128 | 44-ID | Table 4B FIG. 14 | AA sequence of LC VR of Abs 193; non-ID version is in FIG. 3; | IDEIVMTQSPDSLAVSLGERATINCKSSQTLSFNYKNYLAWYQQKPGQPP KLLIYWASTRESGVPDRFSGSGSGTDFTLTISSLQAEDVAVYYCQQHYRT PPSFGNGTKLDIK |
| 129 | 47-ID | Table 4B FIG. 14 | AA sequence of LC VR of Abs A001, 004, 007, 016 | IDDIVMTQSPDTLAVTLGERATIQCKSSQTVTFNYKNYLAWYQQKPGQPP KLLIYWASTRESGVPDRFSGSGSGTDFTLTITSLQAEDVAVYYCQQHYRT PPSFGQGTKLDIK |
| 130 | 48-ID | Table 4B FIG. 14 | AA sequence of LC VR of Abs 002, 005, 008, A017; non-ID version is in FIG. 3; | IDDIVMTQSPDTVAVTVGERATINCKSSQTVTFNYKNYLAWYQQKPGQPP KLLIYWASTRESGVPDRFSGSGSGTDFTLTISSLQAEDVAVYYCQQHYRT PPSFGQGTKLDIK |
| 131 | 49-ID | Table 4B FIG. 14 | AA sequence of LC VR of Abs A003, 006, A009, C18; non-ID version is in FIG. 3; | IDDIVMTQSPDTVAVTLGERATIDCKSSQTVTFNYKNYLAWYQQKPGQPP KLLIYWASTRESGVPDRFSGSGSGTDDTLTISSLQAEDVAVYYCQQHYRT PPSFGQGTKLDIK |
| 132 | 50-ID | Table 4B FIG. 14 | AA sequence of LC VR of Abs A010 012, A14, A019; non-ID version is in FIG. 3; | IDDIVMTQSPDTLAVTVGERATIRCKSSQTVTFNYKNYLAWYQQKPGQPP KLLIYWASTRESGVPDRFSGSGSGTDFTLTISSLQAEDVAVYYCQQHYRT PPSFGQGTKLDIK |
| 133 | 51-ID | Table 4B FIG. 14 | AA sequence of LC VR of Ab A011, 013, 015; non-ID version is in FIG. 3; | IDDIVMTQSPDTLAVSRGERATIDCKSSQTVTFNYKNYLAWYQQKPGQPP KLLIYWASTRESGVPDRFSGSGSGTDFTLTISSLQAEDEAVYYCQQHYRT PPSFGQGTKLDIK |
| 134 | 52-ID | Table 4B FIG. 14 | AA sequence of LC VR of Abs 044, 071, 072, 078; non-ID version is in FIG. 3; | IDDIQMTQSPSSLSASVGDRVTITCRSSQSITFDYKNYLAWYQQKPGKAP KLLIYWGSYLESGVPSRFSGSGSGTDFTLTISSLQPEDFATYYCQQHYRT PPSFGQGTKVEIK |
| 135 | 53-ID | Table 4B FIG. 14 | AA sequence of LC VR of Ab 051; non-ID version is in FIG. 3; | IDDIQMTQSPSSLSASVGDRVTITCRSSQSITFNYKNYLAWYQQKPGKAP KLLIYWGSTLESGVPSRFSGSGSGTDFTLTISSLQPEDFATYYCQQHYRT PPSFGQGTKVEIK |

TABLE 4C-continued

Nucleic acid and amino acid sequences

| SEQ ID NO. | Lab no. | Source | Comment | Sequence |
|---|---|---|---|---|
| 136 | 54-ID | Table 4B FIG. 14 | AA sequence of LC VR of Ab 049; non-ID version is in FIG. 3; | IDDIQMTQSPSSLSASVGDRVTITCRSSQSITFNYKNYLAWYQQKPGKAP KLLIYWGSHLESGVPSRFSGSGSGTDFTLTISSLQPEDFATYYCQQHYRT PPSFGQGTKVEIK |
| 137 | 55-ID | Table 4B FIG. 14 | AA sequence of LC VR of Ab 047; non-ID version is in FIG. 3; | IDDIQMTQSPSSLSASVGDRVTITCRSSQSITFNYKNYLAWYQQKPGKAP KLLIYWGSKLESGVPSRFSGSGSGTDFTLTISSLQPEDFATYYCQQHYRT PPSFGQGTKVEIK |
| 138 | 56-ID | Table 4B FIG. 14 | AA sequence of LC VR of Ab 050; non-ID version is in FIG. 3; | IDDIQMTQSPSSLSASVGDRVTITCRSSQSITFNYKNYLAWYQQKPGKAP KLLIYWGSDLESGVPSRFSGSGSGTDFTLTISSLQPEDFATYYCQQHYRT PPSFGQGTKVEIK |
| 139 | 57-ID | Table 4B FIG. 14 | AA sequence of LC VR of Ab 045; non-ID version is in FIG. 3; | IDDIQMTQSPSSLSASVGDRVTITCRSSQSITFNYKNYLAWYQQKPGKAP KLLIYWGSYLESGVPSRFSGSGSGTDFTLTISSLQPEDVATYYCQQHYRT PPSFGQGTKVEIK |
| 140 | 58-ID | Table 4B FIG. 14 | AA sequence of LC VR of Ab 048; non-ID version is in FIG. 3; | IDDIQMTQSPSSLSASVGDRVTITCRSSQSITFNYKNYLAWYQQKPGKAP KLLIYWGSYLESGVPSRFSGSGSGTDFTLTISSLQPEDKATYYCQQHYRT PPSFGQGTKVEIK |
| 141 | 59-ID | Table 4B FIG. 14 | AA sequence of LC VR of Ab 046; non-ID version is in FIG. 3; | IDDIQMTQSPSSLSASVGDRVTITCRSSQSITFNYKNYLAWYQQKPGKAP KLLIYWGSYLESGVPSRFSGSGSGTDFTLTISSLQPEDDATYYCQQHYRT PPSFGQGTKVEIK |
| 142 | 60-ID | Table 4B FIG. 14 | AA sequence of LC VR of Ab 043; non-ID version is in FIG. 3; | IDDIQMTQSPSSLSASVGDRVTITCRSSQSITFNYKNYLAWYQQKPGKAP KLLIYWGSYLESGVPSRFSGSGSGTDFTLTISSLQPEDFATYYCQQYYRT PPSFGQGTKVEIK |
| 143 | 61-ID | Table 4B FIG. 14 | AA sequence of LC VR of Ab 052; non-ID version is in FIG. 3; | IDDIQMTQSPSSLSASVGDRVTITCRSSQSITFNYKNYLAWYQQKPGKAP KLLIYWGSTRESGVPSRFSGSGSGTDFILTISSLQPEDFATYYCQQHYRT PPSFGQGTKVEIK |
| 157 | 153-ID | Table 4B FIG. 14 | AA sequence of LC VR of Ab 067; non-ID version is in FIG. 3; | IDDIQMTQSPSSLSASVGDRVTITCRSSQSITFQYKNYLAWYQQKPGKAP KLLIYWGSYLESGVPSRFSGSGSGTDFTLTISSLQPEDFATYYCQQHYRT PPSFGQGTKVEIK |
| 158 | 154-ID | Table 4B FIG. 14 | AA sequence of LC VR of Ab 068; non-ID version is in FIG. 3; | IDDIQMTQSPSSLSASVGDRVTITCRSSQSITFRYKNYLAWYQQKPGKAP KLLIYWGSYLESGVPSRFSGSGSGTDFTLTISSLQPEDFATYYCQQHYRT PPSFGQGTKVEIK |
| 159 | 155-ID | Table 4B FIG. 14 | AA sequence of LC VR of Abs 069, 079; non-ID version is in FIG. 3; | IDDIQMTQSPSSLSASVGDRVTITCRSSQSITFEYKNYLAWYQQKPGKAP KLLIYWGSYLESGVPSRFSGSGSGTDFTLTISSLQPEDFATYYCQQHYRT PPSFGQGTKVEIK |
| 160 | 156-ID | Table 4B FIG. 14 | AA sequence of LC VR of Ab 070; non-ID version is in FIG. 3; | IDDIQMTQSPSSLSASVGDRVTITCRSSQSITFDYKNYLAWYQQKPGKAP KLLIYWGSTRESGVPSRFSGSGSGTDFTLTISSLQPEDFATYYCQQHYRT PPSFGQGTKVEIK |
| 144 | 62-ID | Table 4B FIG. 14 | AA sequence of LC VR consensus ID; non-ID version is in FIG. 3; | IDDIQMTQSPSSLSASVGDRVTITCRSSQSITFNYKNYLAWYQQKPGKAP KLLIYWGSYLESGVPSRFSGSGSGTDFTLTISSLQPEDFATYYCQQHYRT PPSFGQGTKVEIK |
| 63 | VH16 | Example 1 | NT sequence of HC VR of Abs 014, 028 | GAGGTACAGCTCCTCGAATCGGGAGGGGGACTGGTCAAACCCGGTCAATC GCTCAAACTCTCGTGTGCAGCGTCAGGTTTTACGTTCAGCTCATATGGGA TGCACTGGGTCCGCCAGCCTCCGGGAAAGGGACTGGAGTGGGTGGCAGTC GTGTCGTATGACGGGAGCAATAAGTACTACGCCGATTCAGTGCAAGGTCG GTTTACCATTTCGAGGGATAACAGCAAGAACACGCTCTACTTGCAGATGA ACTCACTTAGAGCGGAAGATACGGCTGTGTACTATTGCGCCAAAGACACA AAGCTGCGATCCCTGTTGTACTTCGAATGGTTGTCCTCGGGCTTGCTTGA CTATTGGGGGCAGGGCGCCATGGTCACAGTATCCAGCGCGTCGACTAAGG GGCCC |
| 64 | VL29 | Example 1 | NT sequence of LC VR of Abs 014, 154, 157 | GAGATCGTGATGACGCAGAGCCCCGATAGCCTCGCTGTCTCATTGGGGGA ACGGGCCACGATTAACTGCAAATCCTCACAGTCGGTGACTTTCAGCTATA AGAATTACCTGGCATGGTATCAGCAGAAGCCGGGTCAACCCCCAAAACTG TTGATCTACTGGGCCTCCACACGCGAGTCGGGAGTCCCGGACCGATTTTC GGGTTCAGGGTCCGGCACTGACTTTACCCTCACAATTTCATCGCTTCAAG CGGAGGATGTAGCAGTGTACTATTGTCAGCAGTATTACGAACACCTCCC ACCTTCGGAGGGGGAACGAAACTTGACATCAAGGGATCC |
| 65 | VL30 | Example 1 | NT sequence of LC VR of Abs 028, 155 | NT: GAGATCGTGATGACGCAGAGCCCCGATAGCCTCGCTGTCTCATTGGGGGA ACGGGCCACGATTAACTGCAAATCCTCACAGTCGGTGACTTTCGACTATA |

TABLE 4C-continued

Nucleic acid and amino acid sequences

| SEQ ID NO. | Lab no. | Source | Comment | Sequence |
|---|---|---|---|---|
| | | | | AGAATTACCTGGCATGGTATCAGCAGAAGCCGGGTCAACCCCCAAAACTG TTGATCTACTGGGCCTCCACACGCGAGTCGGGAGTCCCGGACCGATTTTC GGGTTCAGGGTCCGGCACTGACTTTACCCTCACAATTTCATCGCTTCAAG CGGAGGATGTAGCAGTGTACTATTGTCAGCAGTATTACAGAACACCTCCC ACCTTCGGAGGGGGAACGAAACTTGACATCAAGGGATCC |
| 66 | VH15 | Example 1 | NT sequence of HC VR of Ab A18 | GAAGTGCAACTCCTCGAGTCAGGAGGAGGTTTGGTGAAACCGGGTCAGTC CTTGAAACTGAGCTGTGCAGCAAGCGGGTTCACGTTTACGTCGTACGGCA TGCACTGGGTACGGCAGCCTCCCGGGAAGGGACTTGAATGGGTCGCCGTC ATCTCATACGACGGGTCGTACAAATACTATGCGGATAGCGTGCAAGGTCG CTTCACAATTTCCCGGGACAATTCGAAGAATACACTGTATCTTCAGATGA ACTCGCTCAGGGCTGAGGACACGGCGGTCTATTACTGCGCGAAGGATTCG CGACTCAGATCCCTTTTGTACTTTGAGTGGCTGTCGCAGGGGTATTTCAA CCCATGGGGAGCCGGAACCACTTTGACCGTATCAAGCGCGTCAACAAAGG GGCCC |
| 187 | VL28 | Example 1 | NT sequence of LC VR of Ab A18 | GAAATTGTAATGACGCAGAGCCCTGATAGCCTTGCCGTGTCCCTGGGTGA GAGGGCGACAATCAATTGTAAGTCATCACAGTCGGTCACGTACAACTACA AGAACTACCTGGCGTGGTATCAACAGAAACCCGGGCAGCCGCCCAAATTG CTCATCTATTGGGCTTCGACACGGGAGTCGGGTGTGCCAGACCGCTTCTC CGGGTCAGGATCGGGAACTGACTTCACGTTGACTATTTCGTCCCTCCAGG CAGAAGATGTAGCCGTCTACTATTGCCAACAGTATTACAGAACGCCGCCT ACATTTGGAGGCGGGACCAAACTTGACATCAAGGGATCCGTGGCCGCCCC CAGCGTCTTCATCTTCCCGCCCAGCGACGAGCAGCTGAAGTCGGGCACGG CCAGCGTGGTGTGCCTCCTGAACAACTTCTACCCCCGCGAGGCGAAGGTC CAGTGGAAGGTGGACAACGCCCTGCAGAGCGGGAACAGCCAGGAGAGCGT GACCGAGCAGGACTCGAAGGACAGCACCTACAGCCTCAGCAGCACCCTGA CGCTGAGCAAGGCCGACTACGAGAAGCACAAGGTCTACGCCTGCGAGGTG ACCCACCAGGGGCTCTCGAGCCCCGTGACCAAGAGCTTCAACCGGGGCGA GTG |
| 149 | VL52 | Example 1 | NT sequence of LC VR of Abs 044, 071, 072, 078 | GACATTCAGATGACTCAGTCGCCTTCGTCATTGTCCGCCTCCGTGGGTGA TAGGGTCACGATCACGTGCCGGAGCAGCCAGTCCATCACCTTCAATTACA AAACTATTTGGCATGGTATCAACAGAAACCCGGAAAGGCGCCGAAGCTC CTGATCTACTGGGGTTCATATCTTGAGTCGGGGGTGCCGTCGAGATTTTC GGGCAGCGGATCAGGGACGGATTTCACGCTGACCATTTCGTCACTCCAGC CCGAGGACTTTGCGACATATTACTGTCAACAGCACTACAGGACACCCCCA TCTTTCGGACAGGGGACTAAAGTAGAAATCAAGGGATCCGTGGCCGCCCC CAGCGTCTTCATCTTCCCGCCCAGCGACGAGCAGCTGAAGTCGGGCACGG CCAGCGTGGTGTGCCTCCTGAACAACTTCTACCCCCGCGAGGCGAAGGTC CAGTGGAAGGTGGACAACGCCCTGCAGAGCGGGAACAGCCAGGAGAGCGT GACCGAGCAGGACTCGAAGGACAGCACCTACAGCCTCAGCAGCACCCTGA CGCTGAGCAAGGCCGACTACGAGAAGCACAAGGTCTACGCCTGCGAGGTG ACCCACCAGGGGCTCTCGAGCCCCGTGACCAAGAGCTTCAACCGGGGCGA GTGCTGA |
| 150 | VL45 | Example 1 | NT sequence of LC VR of Abs 202, 203, 204, 210, 031, 032, 033, 034 | GACATTCAGATGACTCAGTCGCCTTCGTCATTGTCCGCCTCCGTGGGTGA TAGGGTCACGATCACGTGCCGGAGCAGCCAGTCCATCACCTTCAATTACA AAACTATTTGGCATGGTATCAACAGAAACCCGGAAAGGCGCCGAAGCTC CTGATCTACTGGGGTTCATATCTTGAGTCGGGGGTGCCGTCGAGATTTTC GGGCAGCGGATCAGGGACGGATTTCACGCTGACCATTTCGTCACTCCAGC CCGAGGACTTTGCGACATATTACTGTCAACAGCACTACAGGACACCCCCA TCTTTCGGACAGGGGACTAAAGTAGAAATCAAGGGATCCGTGGCCGCCCC CAGCGTCTTCATCTTCCCGCCCAGCGACGAGCAGCTGAAGTCGGGCACGG CCAGCGTGGTGTGCCTCCTGAACAACTTCTACCCCCGCGAGGCGAAGGTC CAGTGGAAGGTGGACAACGCCCTGCAGAGCGGGAACAGCCAGGAGAGCGT GACCGAGCAGGACTCGAAGGACAGCACCTACAGCCTCAGCAGCACCCTGA CGCTGAGCAAGGCCGACTACGAGAAGCACAAGGTCTACGCCTGCGAGGTG ACCCACCAGGGGCTCTCGAGCCCCGTGACCAAGAGCTTCAACCGGGGCGA GTGCTGAGAATTC |
| 151 | VH25 | Example 1 | NT sequence of HC VR of Abs 004, 005, 006, 012, 013, 032, 038, 043, 044, 045, 046, 047, 048, 049, 050, 051, 052, 067, 068, 069, 070, 073, 074, 075, 076, 077 | CAGGTACAATTGCTTGAGACAGGTGGAGGACTCGTGAAGCCAGGTCAGTC ATTGAAACTGAGCTGTGCCGCATCCGGGTTCACATTCACTTCCTACGCGA TGCACTGGGTCCGCCAGCCTCCCGGAAAGGGACTTGAGTGGGTCGCTGTG GTATCGTATGATGGGAATTACAAATACTATGCAGACTCCGTGCAAGGCCG GTTTACGATTAGCAGGGACAACTCGAAGAATACCCTTTACCTCCAAATGA ACTCGCTCCGAGCGGAGGACACGGCGGTGTATTACTGCGCGAAGGATTCA CGGTTGAGATCGCTGCTCTATTTTGAATGGTTGTCACAGGGGTACTTCAA CCCGTGGGGTCAGGGAACAACTGTCCGTCAGCTCAGCCTCGACTAAAG GGCCCAGCGTGTTCCCGCTGGCCCCCAGCAGCAAGAGCACCAGCGGCGGG ACCGCCGCCCTGGGCTGCCTCGTCAAGGACTACTTCCCCGAGCCCGTGAC CGTGTCGTGGAACAGCGGCGCGCTGACGAGCGGGGTCCACACCTTCCCGG CCGTGCTGCAGAGCAGCGGCCTCTACTCGCTGAGCAGCGTGGTCACCGTG CCCAGCAGCAGCCTGGGGACCCAGACGTACATCTGCAACGTGAACCACAA |

TABLE 4C-continued

Nucleic acid and amino acid sequences

| SEQ ID NO. | Lab no. | Source | Comment | Sequence |
|---|---|---|---|---|
| | | | | GCCCTCGAACACCAAGGTCGACAAGAAGGTGGAGCCCCCGAAGAGCTGCG<br>ACAAAACTCACACATGCCCACCGTGCCCAGGTACTGAACTCCTGGGGGGA<br>CCGTCAGTCTTCCTCTTCCCCCCAAAACCCAAGGACACCCTCATGATCTC<br>CCGGACCCCTGAGGTCACATGCGTGGTGGTGGACGTGAGCCACGAAGACC<br>CTGAGGTCAAGTTCAACTGGTACGTGGACGGCGTGGAGGTGCATAATGCC<br>AAGACAAAGCCGCGGGAGGAGCAGTACAACAGCACGTACCGTGTGGTCAG<br>CGTCCTCACCGTCCTGCACCAGGACTGGCTGAATGGCAAGGAGTACAAGT<br>GCAAGGTCTCCAACAAAGCCCTCCCAGCCCCCATCGAGAAAACCATCTCC<br>AAAGCCAAAGGTGAGCCCCGAGAACCACAGGTGTACACCCTGCCCCCATC<br>CCGGGATGAGCTGACCAAGAACCAGGTCAGCCTGACCTGCCTGGTCAAAG<br>GCTTCTATCCCAGCGACATCGCCGTGGAGTGGGAGAGCAATGGGCAGCCG<br>GAGAACAACTACAAGACCACGCCTCCCGTGCTGGACTCCGACGGCTCCTT<br>CTTCCTCTACAGCAAGCTCACCGTGGACAAGAGCAGGTGGCAGCAGGGGA<br>ACGTCTTCTCATGCTCCGTGATGCATGAGGCTCTGCACAACCACTACACG<br>CAGAAGAGCCTCTCCCTGTCTCCGGGTAAATGA |
| 152 | VH24 | Example 1 | NT sequence of HC VR of Abs A001, A002, A003, A010, A011, 031, 037 | GAAGTACAATTGCTTGAGTCGGGTGGAGGACTCGTGAAGCCAGGTCAGTC<br>ATTGAAACTGAGCTGTGCCGCATCCGGGTTCACATTCACTTCCTACGCGA<br>TGCACTGGGTCCGCCAGCCTCCCGGAAAGGGACTTGAGTGGGTCGCTGTG<br>GTATCGTATGATGGGAATTACAAATACTATGCAGACTCCGTGCAAGGCCG<br>GTTTACGATTAGCAGGGACAACTCGAAGAATACCCTTTACCTCCAAATGA<br>ACTCGCTCCGAGCGGAGGACACGGCGGTGTATTACTGCGCGAAGGATTCA<br>CGGTTGAGATCGCTGCTCTATTTTGAATGGTTGTCACAGGGGTACTTCAA<br>CCCGTGGGGTCAGGGAACAACACTGACCGTCAGCTCAGCCTCGACTAAAG<br>GCCCAGCGTGTTCCCGCTGGCCCCCAGCAGCAAGAGCACCAGCGGCGGG<br>ACCGCCGCCCTGGGCTGCCTCGTCAAGGACTACTTCCCCGAGCCCGTGAC<br>CGTGTCGTGGAACAGCGGCGCGCTGACGAGCGGGGTCCACACCTTCCCGG<br>CCGTGCTGCAGAGCAGCGGCCTCTACTCGCTGAGCAGCGTGGTCACCGTG<br>CCCAGCAGCAGCCTGGGGACCCAGACGTACATCTGCAACGTGAACCACAA<br>GCCCTCGAACACCAAGGTCGACAAGAAGGTGGAGCCCCCGAAGAGCTGCG<br>ACGGTACCCACACATGCCCACCGTGCCCAGGTACTGAACTCCTGGGGGGA<br>CCGTCAGTCTTCCTCTTCCCCCCAAAACCCAAGGACACCCTCATGATCTC<br>CCGGACCCCTGAGGTCACATGCGTGGTGGTGGACGTGAGCCACGAAGACC<br>CTGAGGTCAAGTTCAACTGGTACGTGGACGGCGTGGAGGTGCATAATGCC<br>AAGACAAAGCCGCGGGAGGAGCAGTACAACAGCACGTACCGTGTGGTCAG<br>CGTCCTCACCGTCCTGCACCAGGACTGGCTGAATGGCAAGGAGTACAAGT<br>GCAAGGTCTCCAACAAAGCCCTCCCAGCCCCCATCGAGAAAACCATCTCC<br>AAAGCCAAAGGTGAGCCCCGAGAACCACAGGTGTACACCCTGCCCCCATC<br>CCGGGATGAGCTGACCAAGAACCAGGTCAGCCTGACCTGCCTGGTCAAAG<br>GCTTCTATCCCAGCGACATCGCCGTGGAGTGGGAGAGCAATGGGCAGCCG<br>GAGAACAACTACAAGACCACGCCTCCCGTGCTGGACTCCGACGGCTCCTT<br>CTTCCTCTACAGCAAGCTCACCGTGGACAAGAGCAGGTGGCAGCAGGGGA<br>ACGTCTTCTCATGCTCCGTGATGCATGAGGCTCTGCACAACCACTACACG<br>TCAGAAGAGCCTCTCCCTGTCTCCGGGAAATGA |
| 94 | 15 | FIG. 1 | AA sequence of HC of Ab A18 | EVQLLESGGGLVKPGQSLKLSCAASGFTFTSYGMHWVRQPPGKGLEWVAV<br>ISYDGSYKYYADSVQGDFTISRDNSKNTLYLQMNSLRAEDTAVYYCAKDS<br>RLRSLLYFEWLSQGYFNPWGAGTTLTVSSASTKGPSVFPLAPSSKSTSGG<br>TAALGCLVKDYFPEPVTVSWNSGALTSGVHTFPAVLQSSGLYSLSSVVTV<br>PSSSLGTQTYICNVNHKPSNTKVDKKVEPPKSCDKTHTCPPCPGTELLGG<br>PSVFLFPPKPKDTLMISRTPEVTCVVVDVSHEDPEVKFNWYVDGVEVHNA<br>KTKPREEQYNSTYRVVSVLTVLHQDWLNGKEYKCKVSNKALPAPIEKTIS<br>KAKGEPREPQVYTLPPSRDELTKNQVSLTCLVKGFYPSDIAVEWESNGQP<br>ENNYKTTPPVLDSDGSFFLYSKLTVDKSRWQQGNVFSCSVMHEALHNHYT<br>QKSLSLSPGK |
| 188 | 28 | FIG. 1 | AA sequence of LC of Ab A18 | EIVMTQSPDSLAVSLGERATINCKSSQSVTYNYKNYLAWYQQKPGQPPKL<br>LIYWASTRESGVPDRFSGSGSGTDFTLTISSLQAEDVAVYYCQQYYRTPP<br>TFGGGTKLDIKGSVAAPSVFIFPPSDEQLKSGTASVVCLLNNFYPREAKV<br>QWKVDNALQSGNSQESVTEQDSKDSTYSLSSTLTLSKADYEKHKVYACEV<br>THQGLSSPVTKSFNRGE |
| 145 | n.a. | see text | AA sequence of LC CDR1 of Ab 044 | QSITFDYKNYLA |
| 146 | n.a. | see text | AA sequence of LC CDR1 of F16 VK | KSSQSVTFNYKNYLA |
| 147 | n.a. | see text | AA sequence of LC CDR2 of F16 VK | WASARES |
| 148 | n.a. | see text | AA sequence of LC CDR3 of F16 VK | QQHYRTPPT |
| 68 | n.a. | see text | AA sequence of HC CDR1 of Abs 044, 069, 032, 031 | SYAMH |

TABLE 4C-continued

Nucleic acid and amino acid sequences

| SEQ ID NO. | Lab no. | Source | Comment | Sequence |
|---|---|---|---|---|
| 69 | n.a. | see text | AA sequence of HC CDR2 of Abs 044, 069, 032, 031 | VVSYDGNYKYYADSVQG |
| 70 | n.a. | see text | AA sequence of HC CDR3 of Abs 044, 069, 032, 031 | DSRLRSLLYFEWLSQGYFNP |
| 71 | n.a. | see text | AA sequence of LC CDR1 of Abs 032, 031 | QSITFNYKNYLA |
| 72 | n.a. | see text | AA sequence of LC CDR2 of Abs 044, 069, 032, 031 | WGSYLES |
| 73 | n.a. | see text | AA sequence of LC CDR3 of Abs 044, 069, 032, 031 | QQHYRTPPS |
| 74 | n.a. | see text | AA sequence of HC FR1 of Ab 069 | QVQLLETGGGLVKPGQSLKLSCAASGFTFT |
| 75 | n.a. | see text | AA sequence of HC FR2 of Ab 069 | WVRQPPGKGLEWVA |
| 76 | n.a. | see text | AA sequence of HC FR3 of Ab 069 | RFTISRDNSKNTLYLQMNSLRAEDTAVYYCAK |
| 77 | n.a. | see text | AA sequence of HC FR4 of Ab 069 | WGQGTTLTVSS |
| 78 | n.a. | see text | AA sequence of LC FR1 of Ab 069 | DIQMTQSPSSLSASVGDRVTITCRSS |
| 79 | n.a. | see text | AA sequence of LC FR2 of Ab 069 | WYQQKPGKAPKLLIY |
| 80 | n.a. | see text | AA sequence of LC FR3 of Ab 069 | GVPSRFSGSGSGTDFTLTISSLQPEDFATYYC |
| 81 | n.a. | see text | AA sequence of LC FR4 of Ab 069 | FGQGTKVEIK |
| 82 | n.a. | see text | AA sequence of HC FR1 of Ab 031 | EVQLLESGGGLVKPGQSLKLSCAASGFTFT |
| 83 | n.a. | see text | AA sequence of LC CDR1 of Ab A18 et al. | KSSQSVTYNYKNYLA |
| 84 | n.a. | see text | AA sequence of LC CDR2 of Ab A18 et al. | WASTRES |
| 85 | n.a. | see text | AA sequence of LC CDR3 of Ab A18 et al. | QQYYRTPPT |
| 86 | n.a. | see text | AA sequence of HC CDR1 of Ab A18 et al. | SYGMH |
| 87 | n.a. | see text | AA sequence of HC CDR2 of Ab A18 et al. | VISYDGSYKYYADSVQG |
| 88 | n.a. | see text | AA sequence of an HC CDR3 | DSELRSLLYFEWLSQGYFNP |
| 89 | n.a. | see text | AA sequence of HC FR4 of Ab A18 et al. | WGAGTTLTVSS |
| 90 | n.a. | see text | AA sequence of LC FR1 of Ab A18 et al. | EIVMTQSPDSLAVSLGERATINC |
| 91 | n.a. | see text | AA sequence of LC FR2 of Ab A18 et al. | WYQQKPGQPPKLLIY |
| 92 | n.a. | see text | AA sequence of LC FR3 of Ab A18 et al. | GVPDRFSGSGSGTDFTLTISSLQAEDVAVYYC |
| 93 | n.a. | see text | AA sequence of LC FR4 of Ab A18 et al. | FGGGTKLDIK |
| 171 | n.a. | see text | AA sequence of HC FR4 of Ab 078 et al | WGQGTTVTVSS |
| 172 | n.a. | see text | AA sequence of LC CDR1 of Ab 069 | QSITFEYKNYLA |
| 173 | n.a. | see text | AA sequence of H3 HA1 | QDLPGNDNSTATLCLGHHAVPNGTLVKTITDDQIEVTNATELVQSSSTGK ICNNPHRILDGIDCTLIDALLGDPHCDVFQNETWDLFVERSKAFSNCYPY DVPDYASLRSLVASSGTLEFITEGFTWTGVTQNGGSNACKRGPGSGFFSR |

TABLE 4C-continued

Nucleic acid and amino acid sequences

| SEQ ID NO. | Lab no. | Source | Comment | Sequence |
|---|---|---|---|---|
| | | | | LNWLTKSGSTYPVLNVTMPNNDNFDKLYIWGIHHPSTNQEQTSLYVQASG RVTVSTRRSQQTIIPNIGSRPWVRGLSSRISIYWTIVKPGDVLVINSNGN LIAPRGYFKMRTGKSSIMRSDAPIDTCISECITPNGSIPNDKPFQNVNKI TYGACPKYVKQNTLKLATGMRNVPEKQTR |
| 174 | n.a. | see text | AA sequence of H3 HA2 | GLFGAIAGFIENGWEGMIDGWYGFRHQNSEGTGQAADLKSTQAAIDQING KLNRVIEKTNEKFHQIEKEFSEVEGRIQDLEKYVEDTKIDLWSYNAELLV ALENQHTIDLTDSEMNKLFEKTRRQLRENAEEMGNGCFKIYHKCDNACIE SIRNGTYDHDVYRDEALNNRFQIKG |
| 175 | n.a. | FIG. 12 | AA sequence of HC VR of FI6 | QVQLVQSGGGVVQPGRSLRLSCVASGFTFSTYAMHWVRQAPGRGLEWVAV ISYDGNYKYYADSVKGRFSISRDNSNNTLHLEMNTLRTEDTALYYCAKDS QLRSLLYFEWLSQGYFDPWGQGTLVTVTS |
| 176 | n.a. | FIG. 12 | AA sequence of HC VR of FI370 | QVQLVQSGGGVVPPGRSLRLSCAASGFTFSTYGMHWVRQAPGKGLEWVAV ISYDGNYKYYADSVRGRFTISRDNSKNTLNLDMNSLRTEDTALYYCAKDS QLRSLLYFDWLSQGYFDHWGQGTLVTVSS |
| 177 | n.a. | FIG. 12 | AA sequence of HC VR of FI6 variant 1 | QVQLVESGGGVVQPGRSLRLSCAASGFTFSSYGMHWVRQAPGKGLEWVAV ISYDGSNKYYADSVKGRFTISRDNSKNTLYLQMNSLRAEDTAVYYCAKDS QLRSLLYFDWLSQGYFDYWGQGTLVTVSS |
| 178 | n.a. | FIG. 12 | AA sequence of HC VR of FI6 variant 3 | QVQLVESGGGVVQPGRSLRLSCAASGFTFSTYAMHWVRQAPGKGLEWVAV ISYDANYKYYADSVKGRFTISRDNSKNTLYLQMNSLRAEDTAVYYCAKDS QLRSLLYFEWLSQGYFDYWGQGTLVTVSS |
| 179 | n.a. | FIG. 12 | AA sequence of HC VR of FI6/370 | QVQLVQSGGGVVQPGRSLRLSCAASGFTFSTYGMHWVRQAPGKGLEWVAV ISYDGNYKYYADSVKGRFTISRDNSKNTLYLEMNSLRTEDTALYYCAKDS QLRSLLYFDWLSQGYFDHWGQGTLVTVSS |
| 180 | n.a. | FIG. 12 | AA sequence of kappa LC VR of FI6 | DIQMTSQPDSLAVSLGARATINCKSSQSVTFNYKNYLAWYQQKPGQPPKV LIYWASARESGVPDRFSGSGSGTDFTLTISSLQAEDVAVYYCQQHYRTPP TFGQGTKVEIK |
| 181 | | See text | AA sequence of H1 HA1 | TNADTICIGYHANNSTDTVDTVLEKNVTVTHSVNLLEDSHNGKLCKLKGI APLQLGKCNIAGWLLGNPECDLLLTASSWSYIVETSNSENGTCYPGDFID YEELREQLSSVSSFEKFEIFPKTSSWPNHETTKGVTAACSYAGASSFYRN LLWLTKKGSSYPKLSKSYVNNKGKEVLVLWGVHHPPTGTDQQSLYQNADA YVSVGSSKYNRRFTPEIAARPKVRDQAGRMNYYWTLLEPGDTITFEATGN LIAPWYAFALNRGSGSGIITSDAPVHDCNTKCQTPHGAINSSLPFQNIHP VTIGECPKYVRSTKLRMATGLRNIPSIQS |
| 182 | | See text | AA sequence of H1 HA2 | GLFGAIAGFIEGGWTGMIDGWYGYHHQNEQGSGYAADQKSTQNAIDGITN KVNSVIEKMNTQFTAVGKEFNNLERRIENLNKKVDDGFLDIWTYNAELLV LLENERTLDFHDSNVRNLYEKVKSQLKNNAKEIGNGCFEFYHKCDDACME SVRNGTYDYPKYSEESKLNREEIDGVKLESMGVYQILAIYSTVASSLVLL VSLGAISFWMCSNGSLQCRICI |

EXAMPLES

Example 1

Designing of Anti-HA Antibodies

Human antibodies (IgG) targeting viral hemagglutinin (HA) were computationally designed. HA mediates viral binding to host cell surface receptor, and cell membrane fusion to the viral envelope, resulting in viral entry. The antibody molecules described herein were designed to block HA's fusogenic activity.

All antibody constructs were based on human IgG1 structure (γ1 heavy chain and κ light chain). Point mutations in the $V_H$ (variable heavy domain) and $V_L$ (variable light domain) were computationally designed. These mutations are located within or outside the CDRs (Complementarity Determining Regions). The mutations were designed, e.g., to modify antigen binding properties (e.g., for stronger or weaker binding affinity), or to stabilize structure, or to improve expression properties, etc.

The heavy and light chain sequences of one antibody, called A18 is provided in FIG. 1.

The heavy and light chain pairings for exemplary computationally designed antibodies are shown in Table 3, above in Detailed Description.

DNA sequences for the variable heavy chain and variable light chain for each of antibodies Ab A18, Ab 031, Ab 032, Ab 044, Ab 014 and Ab 028 are provided below.

VH16:

(SEQ ID NO: 63)

GAGGTACAGCTCCTCGAATCGGGAGGGGGACTGGTCAAACCCGGTCAATC

GCTCAAACTCTCGTGTGCAGCGTCAGGTTTTACGTTCAGCTCATATGGGA

TGCACTGGGTCCGCCAGCCTCCGGGAAAGGGACTGGAGTGGGTGGCAGTC

GTGTCGTATGACGGGAGCAATAAGTACTACGCCGATTCAGTGCAAGGTCG

GTTTACCATTTCGAGGGATAACAGCAAGAACACGCTCTACTTGCAGATGA

ACTCACTTAGAGCGGAAGATACGGCTGTGTACTATTGCGCCAAAGACACA
AAGCTGCGATCCCTGTTGTACTTCGAATGGTTGTCCTCGGGCTTGCTTGA
CTATTGGGGCAGGGCGCCATGGTCACAGTATCCAGCGCGTCGACTAAGG
GGCCC VL29:
(SEQ ID NO: 64)
GAGATCGTGATGACGCAGAGCCCCGATAGCCTCGCTGTCTCATTGGGGGA
ACGGGCCACGATTAACTGCAAATCCTCACAGTCGGTGACTTTCAGCTATA
AGAATTACCTGGCATGGTATCAGCAGAAGCCGGGTCAACCCCCAAAACTG
TTGATCTACTGGGCCTCCACACGCGAGTCGGGAGTCCCGGACCGATTTTC
GGGTTCAGGGTCCGGCACTGACTTTACCCTCACAATTTCATCGCTTCAAG
CGGAGGATGTAGCAGTGTACTATTGTCAGCAGTATTACAGAACACCTCCC
ACCTTCGGAGGGGGAACGAAACTTGACATCAAGGGATCC VL30:
(SEQ ID NO: 65)
GAGATCGTGATGACGCAGAGCCCCGATAGCCTCGCTGTCTCATTGGGGGA
ACGGGCCACGATTAACTGCAAATCCTCACAGTCGGTGACTTTCGACTATA
AGAATTACCTGGCATGGTATCAGCAGAAGCCGGGTCAACCCCCAAAACTG
TTGATCTACTGGGCCTCCACACGCGAGTCGGGAGTCCCGGACCGATTTTC
GGGTTCAGGGTCCGGCACTGACTTTACCCTCACAATTTCATCGCTTCAAG
CGGAGGATGTAGCAGTGTACTATTGTCAGCAGTATTACAGAACACCTCCC
ACCTTCGGAGGGGGAACGAAACTTGACATCAAGGGATCC VH15:
(SEQ ID NO: 66)
GAAGTGCAACTCCTCGAGTCAGGAGGAGGTTTGGTGAAACCGGGTCAGTC
CTTGAAACTGAGCTGTGCAGCAAGCGGGTTCACGTTTACGTCGTACGGCA
TGCACTGGGTACGGCAGCCTCCCGGGAAGGGACTTGAATGGGTCGCCGTC
ATCTCATACGACGGGTCGTACAAATACTATGCGGATAGCGTGCAAGGTCG
CTTCACAATTTCCCGGGACAATTCGAAGAATACACTGTATCTTCAGATGA
ACTCGCTCAGGGCTGAGGACACGGCGGTCTATTACTGCGCGAAGGATTCG
CGACTCAGATCCCTTTTGTACTTTGAGTGGCTGTCGCAGGGGTATTTCAA
CCCATGGGGAGCCGGAACCACTTTGACCGTATCAAGCGCGTCAACAAAGG
GGCCC VL28:
(SEQ ID NO: 67)
GAAATTGTAATGACGCAGAGCCCTGATAGCCTTGCCGTGTCCCTGGGTGA
GAGGGCGACAATCAATTGTAAGTCATCACAGTCGGTCACGTACAACTACA
AGAACTACCTGGCGTGGTATCAACAGAAACCCGGGCAGCCGCCCAAATTG
CTCATCTATTGGGCTTCGACACGGGAGTCGGGTGTGCCAGACCGCTTCTC
CGGGTCAGGATCGGGAACTGACTTCACGTTGACTATTTCGTCCCTCCAGG
CAGAAGATGTAGCCGTCTACTATTGCCAACAGTATTACAGAACGCCGCCT
ACATTTGGAGGCGGGACCAAACTTGACATCAAGGGATCCGTGGCCGCCCC
CAGCGTCTTCATCTTCCCGCCCAGCGACGAGCAGCTGAAGTCGGGCACGG
CCAGCGTGGTGTGCCTCCTGAACAACTTCTACCCCCGCGAGGCGAAGGTC
CAGTGGAAGGTGGACAACGCCCTGCAGAGCGGGAACAGCCAGGAGAGCGT
GACCGAGCAGGACTCGAAGGACAGCACCTACAGCCTCAGCAGCACCCTGA
CGCTGAGCAAGGCCGACTACGAGAAGCACAAGGTCTACGCCTGCGAGGTG
ACCCACCAGGGGCTCTCGAGCCCCGTGACCAAGAGCTTCAACCGGGGCGA
GTGC VL52:
(SEQ ID NO: 149)
GACATTCAGATGACTCAGTCGCCTTCGTCATTGTCCGCCTCCGTGGGTGA
TAGGGTCACGATCACGTGCCGGAGCAGCCAGTCCATCACCTTCAATTACA
AAAACTATTTGGCATGGTATCAACAGAAACCCGGAAAGGCGCCGAAGCTC
CTGATCTACTGGGGTTCATATCTTGAGTCGGGGGTGCCGTCGAGATTTTC
GGGCAGCGGATCAGGGACGGATTTCACGCTGACCATTTCGTCACTCCAGC
CCGAGGACTTTGCGACATATTACTGTCAACAGCACTACAGGACACCCCA
TCTTTCGGACAGGGGACTAAAGTAGAAATCAAGGGATCCGTGGCCGCCCC
CAGCGTCTTCATCTTCCCGCCCAGCGACGAGCAGCTGAAGTCGGGCACGG
CCAGCGTGGTGTGCCTCCTGAACAACTTCTACCCCCGCGAGGCGAAGGTC
CAGTGGAAGGTGGACAACGCCCTGCAGAGCGGGAACAGCCAGGAGAGCGT
GACCGAGCAGGACTCGAAGGACAGCACCTACAGCCTCAGCAGCACCCTGA
CGCTGAGCAAGGCCGACTACGAGAAGCACAAGGTCTACGCCTGCGAGGTG
ACCCACCAGGGGCTCTCGAGCCCCGTGACCAAGAGCTTCAACCGGGGCGA
GTGCTGA VL45:
(SEQ ID NO: 150)
GACATTCAGATGACTCAGTCGCCTTCGTCATTGTCCGCCTCCGTGGGTGA
TAGGGTCACGATCACGTGCCGGAGCAGCCAGTCCATCACCTTCAATTACA
AAAACTATTTGGCATGGTATCAACAGAAACCCGGAAAGGCGCCGAAGCTC
CTGATCTACTGGGGTTCATATCTTGAGTCGGGGGTGCCGTCGAGATTTTC
GGGCAGCGGATCAGGGACGGATTTCACGCTGACCATTTCGTCACTCCAGC
CCGAGGACTTTGCGACATATTACTGTCAACAGCACTACAGGACACCCCA
TCTTTCGGACAGGGGACTAAAGTAGAAATCAAGGGATCCGTGGCCGCCCC
CAGCGTCTTCATCTTCCCGCCCAGCGACGAGCAGCTGAAGTCGGGCACGG
CCAGCGTGGTGTGCCTCCTGAACAACTTCTACCCCCGCGAGGCGAAGGTC
CAGTGGAAGGTGGACAACGCCCTGCAGAGCGGGAACAGCCAGGAGAGCGT
GACCGAGCAGGACTCGAAGGACAGCACCTACAGCCTCAGCAGCACCCTGA
CGCTGAGCAAGGCCGACTACGAGAAGCACAAGGTCTACGCCTGCGAGGTG
ACCCACCAGGGGCTCTCGAGCCCCGTGACCAAGAGCTTCAACCGGGGCGA
GTGCTGAGAATTC VH25:
(SEQ ID NO: 151)
CAGGTACAATTGCTTGAGACAGGTGGAGGACTCGTGAAGCCAGGTCAGTC
ATTGAAACTGAGCTGTGCCGCATCCGGGTTCACATTCACTTCCTACGCGA
TGCACTGGGTCCGCCAGCCTCCCGGAAAGGGACTTGAGTGGGTCGCTGTG
GTATCGTATGATGGGAATTACAAATACTATGCAGACTCCGTGCAAGGCCG
GTTTACGATTAGCAGGGACAACTCGAAGAATACCCTTTACCTCCAAATGA -continued
```
ACTCGCTCCGAGCGGAGGACACGGCGGTGTATTACTGCGCGAAGGATTCA

CGGTTGAGATCGCTGCTCTATTTTGAATGGTTGTCACAGGGGTACTTCAA

CCCGTGGGGTCAGGGAACAACACTGACCGTCAGCTCAGCCTCGACTAAAG

GGCCCAGCGTGTTCCCGCTGGCCCCCAGCAGCAAGAGCACCAGCGGCGGG

ACCGCCGCCCTGGGCTGCCTCGTCAAGGACTACTTCCCCGAGCCCGTGAC

CGTGTCGTGGAACAGCGGCGCGCTGACGAGCGGGGTCCACACCTTCCCGG

CCGTGCTGCAGAGCAGCGGCCTCTACTCGCTGAGCAGCGTGGTCACCGTG

CCCAGCAGCAGCCTGGGGACCCAGACGTACATCTGCAACGTGAACCACAA

GCCCTCGAACACCAAGGTCGACAAGAAGGTGGAGCCCCGAAGAGCTGCG

ACAAAACTCACACATGCCCACCGTGCCCAGGTACTGAACTCCTGGGGGA

CCGTCAGTCTTCCTCTTCCCCCCAAAACCCAAGGACACCCTCATGATCTC

CCGGACCCCTGAGGTCACATGCGTGGTGGTGGACGTGAGCCACGAAGACC

CTGAGGTCAAGTTCAACTGGTACGTGGACGGCGTGGAGGTGCATAATGCC

AAGACAAAGCCGCGGGAGGAGCAGTACAACAGCACGTACCGTGTGGTCAG

CGTCCTCACCGTCCTGCACCAGGACTGGCTGAATGGCAAGGAGTACAAGT

GCAAGGTCTCCAACAAAGCCCTCCCAGCCCCCATCGAGAAAACCATCTCC

AAAGCCAAAGGTGAGCCCCGAGAACCACAGGTGTACACCCTGCCCCCATC

CCGGGATGAGCTGACCAAGAACCAGGTCAGCCTGACCTGCCTGGTCAAAG

GCTTCTATCCCAGCGACATCGCCGTGGAGTGGGAGAGCAATGGGCAGCCG

GAGAACAACTACAAGACCACGCCTCCCGTGCTGGACTCCGACGGCTCCTT

CTTCCTCTACAGCAAGCTCACCGTGGACAAGAGCAGGTGGCAGCAGGGGA

ACGTCTTCTCATGCTCCGTGATGCATGAGGCTCTGCACAACCACTACACG

CAGAAGAGCCTCTCCCTGTCTCCGGGTAAATGA
```

VH24:

(SEQ ID NO: 152)
```
GAAGTACAATTGCTTGAGTCGGGTGGAGGACTCGTGAAGCCAGGTCAGTC

ATTGAAACTGAGCTGTGCCGCATCCGGGTTCACATTCACTTCCTACGCGA

TGCACTGGGTCCGCCAGCCTCCCGAAAGGGACTTGAGTGGGTCGCTGTG

GTATCGTATGATGGGAATTACAAATACTATGCAGACTCCGTGCAAGGCCG

GTTTACGATTAGCAGGGACAACTCGAAGAATACCCTTTACCTCCAAATGA

ACTCGCTCCGAGCGGAGGACACGGCGGTGTATTACTGCGCGAAGGATTCA

CGGTTGAGATCGCTGCTCTATTTTGAATGGTTGTCACAGGGGTACTTCAA

CCCGTGGGGTCAGGGAACAACACTGACCGTCAGCTCAGCCTCGACTAAAG

GGCCCAGCGTGTTCCCGCTGGCCCCCAGCAGCAAGAGCACCAGCGGCGGG

ACCGCCGCCCTGGGCTGCCTCGTCAAGGACTACTTCCCCGAGCCCGTGAC

CGTGTCGTGGAACAGCGGCGCGCTGACGAGCGGGGTCCACACCTTCCCGG

CCGTGCTGCAGAGCAGCGGCCTCTACTCGCTGAGCAGCGTGGTCACCGTG

CCCAGCAGCAGCCTGGGGACCCAGACGTACATCTGCAACGTGAACCACAA

GCCCTCGAACACCAAGGTCGACAAGAAGGTGGAGCCCCGAAGAGCTGCG

ACGGTACCCACACATGCCCACCGTGCCCAGGTACTGAACTCCTGGGGGA

CCGTCAGTCTTCCTCTTCCCCCCAAAACCCAAGGACACCCTCATGATCTC

CCGGACCCCTGAGGTCACATGCGTGGTGGTGGACGTGAGCCACGAAGACC

CTGAGGTCAAGTTCAACTGGTACGTGGACGGCGTGGAGGTGCATAATGCC

AAGACAAAGCCGCGGGAGGAGCAGTACAACAGCACGTACCGTGTGGTCAG

CGTCCTCACCGTCCTGCACCAGGACTGGCTGAATGGCAAGGAGTACAAGT

GCAAGGTCTCCAACAAAGCCCTCCCAGCCCCCATCGAGAAAACCATCTCC

AAAGCCAAAGGTGAGCCCCGAGAACCACAGGTGTACACCCTGCCCCCATC

CCGGGATGAGCTGACCAAGAACCAGGTCAGCCTGACCTGCCTGGTCAAAG

GCTTCTATCCCAGCGACATCGCCGTGGAGTGGGAGAGCAATGGGCAGCCG

GAGAACAACTACAAGACCACGCCTCCCGTGCTGGACTCCGACGGCTCCTT

CTTCCTCTACAGCAAGCTCACCGTGGACAAGAGCAGGTGGCAGCAGGGGA

ACGTCTTCTCATGCTCCGTGATGCATGAGGCTCTGCACAACCACTACACG

CAGAAGAGCCTCTCCCTGTCTCCGGGTAAATGA
```

Each of the above sequences can be modified to include an ATCGAT nucleotide sequence at the 5' end, which will encode a variable heavy chain or light chain polypeptide comprising Ile-Asp at the amino terminus Example 2

Binding of Anti-HA Antibodies to Hemagglutinins from a Variety of Influenza Viruses as Measured by ELISA The antibodies were tested for binding to hemagglutinins (HAs) from different influenza strains by ELISA assay. The antibodies were also assayed for BSA binding to test for non-specific binding. There is not necessarily a direct correlation between the binding affinity and the level of effectiveness in in vivo studies.

Binding affinity of antibodies was measured by ELISA. To perform the ELISA, a 96-well flat bottom NUNC Maxisorp plates (Cat#439454), was coated with the indicated hemagglutinins (HAs) diluted to 2 μg/mL in 1×PBS, 100 μL per well. The plate was sealed with a plate cover, and allowed to incubate overnight at 4° C. static. The plates were then washed three times with 1×PBS+0.05% Tween-20 (PBST). The HA-coated plates were blocked with 200 μL of 5% Blotto (Santa Cruz Biotechnology Cat#sc-2325) in 1×PBS and incubated at room temperature for 1 hour. Subsequently, the plates were washed three times with PBST. Once washed, the antibodies (described in the disclosure) were diluted to the desired starting concentration in PBST and loaded on the plate with serial dilution. No sample was added to the last well in the set to get the antigen blank reading. The plates were incubated at room temperature for 2 hours, static, and then washed three times with PBST, and tapped to dry. Anti-human HRP-conjugated antibody was diluted in PBST, and 100 μL of HRP-antibody was loaded per well to all wells. After incubation for 1 hour at room temperature, the plates were washed three times with PBST. TMB solution (KPL, Gaithersburg, Md., Cat#50-76-00) was prepared prior to use and allowed to warm to room temperature. The TMB solution was then added to the plate and developed until max OD is between 2 and 3 absorbance units at 650 nm as read on a 96-well plate reader (SpectraMax M2e or similar), or 4 minutes, upon attainment of desired OD, quench the reaction with 1N $H_2SO_4$ and OD at 450 nm on same plate reader was read on the plate. The OD was plotted as a function of concentration and the relative Kd was calculated using a four-parametric fit.

Antibody Ab 018.

Antibody Ab 018 was found to have picomolar binding affinity to Group 1 strains (H1 (A/Solomon Islands/3/2006), H5 (A/Vietnam/1203/2004) and H9 (A/Hong Kong/1073/99)), and at least one Group 2 strain (H7 (A/Netherlands/219/2003) but not at least one strain of H3 (A/Wyoming/03/2003)) when measured by ELISA. See Table 5.

TABLE 5

Antibody Binding Assays

| Antibody | ELISA Kd (pM) | | | | | |
|---|---|---|---|---|---|---|
| | H1 | H3 Bris 07 | H3 Wy03 | H5 | H7 | H9 |
| Ab 018 | 144 | 459 | VLB | 68 | 845 | 67 |

VLB = "Very Low Binding"

Figure 5:
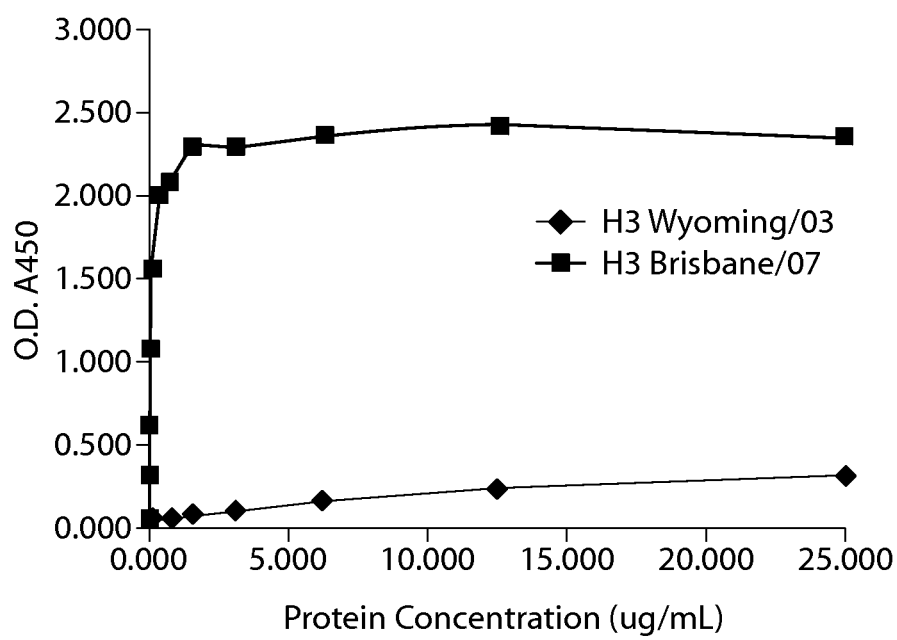
FIG. 5 is a graph of ELISA results depicting stronger binding of A18 to H3 Brisbane/07, and much weaker binding to H3 Wyoming/03.

Ab 018 also bound with high affinity to H3 from A/Brisbane/10/2007. The binding affinity was comparable to H7 HA. Extending the dose range revealed low affinity binding of A18 to A/Wyoming/03/2003 (FIG. 5).

Figure 6:
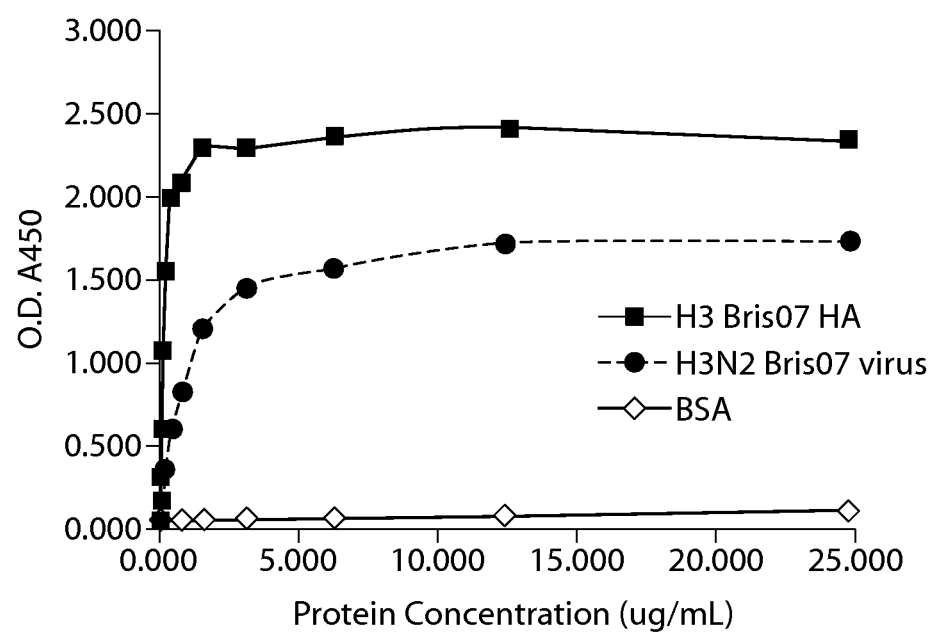
FIG. 6 is a graph of ELISA results depicting binding of A18 to H3Bris07 HA, H3N2 Bris07 virus, and weak binding to the negative control, BSA (bovine serum albumin)

Ab 018 also bound with high affinity to both $HA_0$ and intact virus (FIG. 6). The epitope that Ab 018 binds is therefore present on both cleaved and uncleaved HA.

Antibodies Ab 004, Ab 005, Ab 031, Ab 032, Ab 037, and Ab 038.

Binding affinities for select antibodies (Ab 004, Ab 005, Ab 031, Ab 032, Ab 037, and Ab 038), as determined by ELISA, are shown in Table 6 below.

TABLE 6

Antibody Binding Assays

| Antiody | ELISA Kd (pM) | | | | | | | | Expression Rate (mg/L) |
|---|---|---|---|---|---|---|---|---|---|
| | H1 | H3 (Wyo3) | H3 (Bri07) | H3 (NY04) | H3 (Wis05) | H5 | H7 | H9 | |
| Ab 004 | <80 | 272 | <80 | 66 | 713 | 60 | 73 | 60 | 5.8 |
| Ab 005 | <80 | 311 | 52 | 65 | 1093 | 38 | 64 | 35 | 4.0 |
| Ab 031 | <25 | 331 | 68 | 59 | 253 | <25 | 91 | <25 | 7.4 |
| Ab 032 | <25 | 262 | <25 | 94 | 208 | <25 | 106 | 79 | 23.7 |
| Ab 037 | 75 | 512 | 87 | 140 | 313 | 59 | 114 | 75 | 15.1 |
| Ab 038 | 64 | 515 | <25 | 102 | 199 | 87 | 119 | <25 | 12.0 |

Antibodies Ab 014 and Ab 028.

Antibodies Ab 014 and Ab 028 were found to have broad specificity, as measured by ELISA assay (see FIGS. 10A to 10D).

Antibody Ab 044.

Antibody Ab 044 was found to have less than 500 μM binding affinity (Kd) to hemagglutinins (HAs) from a variety of influenza strains of different groups, clades, and subtypes, including Group 1 strains ("the H1a cluster" (H1 (A/Solomon Islands/20/1999, A/Puerto Rico/8/34), H2 (A/chicken/PA/2004), H5 (A/Vietnam/1203/2004)); "the H9 cluster" (H9 (A/Hong Kong/1073/1999, A/Guinea fowl/HK/WF10/99)); "the H1b cluster" (H16 (A/black headed gull/Mongolia/1756/2006))) and Group 2 strains ("the H3 cluster" (H3 (A/Brisbane/10/2007, A/New York/55/2004, A/Wyoming/3/2003, A/Wisconsin/67/2005, A/Moscow/10/1999, A/Perth/16/2006, A/Uruguay/716/2007)); "the H7 cluster" (H7 (A/Netherlands/219/2003))), when measured by ELISA.

Antibody Ab 044 was also found to have less than 500 pM binding affinity (Kd) to an HA from influenza B (B/Wisconsin/1/2010) as measured by ELISA.

Example 3

Binding of Anti-HA Antibody Ab 032 to Hemagglutinins from Various Influenza Strains as Measured by Surface Plasmon Resonance (SPR)

The GE Biacore™ Biotin CAPture Kit (Amersham Biosciences, Pittsburgh, Pa.) has been successfully used to measure the on-rate ($k_{on}$) and off-rate ($k_{off}$), from which the dissociation constant ($K_D=k_{off}/k_{on}$) was obtained between two partners. Specifically, the interaction of Ab 032 against sub-stoichiometrically biotinylated and immobilized H3 (A/Brisbane/10/07), H7 (A/Netherlands/219/03), H1 (A/California/07/09), and H5 (A/Vietnam/1203/2004) hemagglutinins from Protein Sciences (Meriden, Conn.) were assessed using surface-plasmon resonance on a Biacore® 3000 (Amersham Biosciences, Pittsburgh, Pa.). The kit contains a chip whose surface is covalently modified with single-stranded DNA. The kit also contains complementary DNA modified with streptavidin, which is captured by the surface through hybridization. Biotinylated hemagglutinin targets that have been passaged through two Zeba Spin Desalting Columns and Devices 7k MWCO (Thermo Fisher Scientific, Rockford, Ill.) to remove unincorporated biotin were applied at the desired RU level (~100 RU of different hemagglutinin ligands on flow cells 2, 3, or 4). The biotinylated target ligand was immobilized by the strong, non-covalent biotin-streptavidin interaction, and modification of target lysines with an activated NHS ester of biotin (#21338 EZ-Link Sulfo-NHS-LC-LC-Biotin from Thermo Fisher Scientific, Rockford, Ill.) was performed sub-stoichiometrically with respect to the hemagglutinin ~72 kDa monomer to aid in uniform ligand presentation. The kinetic parameters were based on global fitting of 4 or more curves generated by sequential 30 μL/min injections of Ab 032 antibody analyte of increasing concentration (500 sec of on-rate data to fit) and accumulation of the decay data when the injection was stopped (1200 sec of off-rate data to fit), using double reference subtraction and a 1:1 binding with mass transfer model with a docked chip that was normalized with 40% glycerol prior to the experiment. Running buffer and diluent for Ab 032 was 1×PBS (Gibco®, Life Technologies Corporation, Grand Island, N.Y.) in 3 mM EDTA (pH 8.5) and 0.005% Surfactant P-20 (GE # BR-1000-54, Amersham Biosciences, Pittsburgh, Pa.). The BIAevaluation software (version 4.1.1) was used in the 'Kinetics Simultaneous ka/kd . . . ' module in which the refractive index was set to 0, the Rmax was fit locally, and the 1:1 binding with mass transfer was employed. The data were 'double reference subtracted' before processing, in which the signal from the reference flow cell (containing the streptavidin surface but no hemagglutinin) was subtracted from the hemagglutinin-containing flow cell of interest; from the curves within this set were then subtracted the curve from the running buffer injection (no antibody). The surface was regenerated by DNA denaturation with an injection of 0.25M NaOH and 6 M guanidine-HCl prior to the next cycle of applying fresh DNA-streptavidin and biotinylated hemagglutinin target for the next Ab 032 concentration injection. Three blank injection full run cycles were performed followed by low to high concentrations of Ab 032 analyte, and the third blank injection was used for double reference subtracting using flow cell 1, which contained hybridized DNA-streptavidin conjugate, but without being charged with biotinylated material.

Binding of Ab 032 antibody analyte was measured against sub-stoichiometrically biotinylated and immobilized hemagglutinin H7 Netherlands target. Two-fold serial dilutions of Ab 032 from 8 nM to 0.5 nM were used against 85 RU H7 deposited.

In a separate experiment, binding of Ab 032 antibody analyte was measured against sub-stoichiometrically biotinylated and immobilized hemagglutinin H1 California 07 target. Two-fold serial dilutions of Ab 032 from 8 nM to 0.5 nM were used against 111 RU H1 deposited.

The results are shown in Table 7 below.

TABLE 7

Binding Affinity of Ab 032 as Measured by SPR

| Antibody:Target | $k_{on}$ ($M^{-1}s^{-1}$) | $k_{on}$ (error) | $k_{off}$ ($s^{-1}$) | $k_{off}$ (error) | $K_D$ (pM) | $K_D$ (error) | Chi$^2$ (error) |
|---|---|---|---|---|---|---|---|
| Ab 032:H3 (A/Brisbane/10/07) | $1.61 \times 10^6$ | 1.24% | $3.76 \times 10^{-4}$ | 0.56% | 234 | 1.36% | 0.4 |
| Ab 032:H7 (A/Netherlands/219/03) | $1.13 \times 10^6$ | 0.34% | $1.61 \times 10^{-4}$ | 0.52% | 145 | 0.62% | 0.5 |
| Ab 032:H1 (A/California/07/09) | $1.55 \times 10^6$ | 0.24% | $2.45 \times 10^{-5}$ | 2.28% | 16 | 2.29% | 0.8 |
| Ab 032:H5 (A/Vietnam/1203/2004) | $9.88 \times 10^5$ | 0.23% | NA | NA | NA | NA | 0.4 |

The off-rate ($k_{off}$) for Ab 032 interacting with H5 Vietnam was so slow, that it fell outside of the range of Biacore measurement specifications ($<5 \times 10^{-6}$ s$^{-1}$), and is therefore designated as not available (NA) in Table 7. Since the dissociation constant ($K_D$) is determined by the off-rate divided by the on-rate, it also bears the NA designation.

Example 4

In Vitro Antiviral Activity of Anti-HA Antibodies

MIC Assay, CPE Assay, and qRT-PCR.

The antibodies were tested to determine minimum inhibitory concentration (MIC). Despite the results of the ELISA assay (shown in Example 2) indicating that A18 does not bind a strain of H3 (A/Wyoming/03/2003), A18 neutralized strains of both H1N1 (PR8) and a different strain of H3N2 (X-31) in vitro in a MIC assay. MIC of A18 with PR8 was about 26 µg/mL, and MIC of A18 with X-31 was about 421 µg/mL.

The antibodies described in Table 6 also neutralized H1N1 and H3N2 viruses in vitro. See below in Table 8.

TABLE 8

Results of MIC Assays

| | MIC (µg/mL) | |
|---|---|---|
| Antibody | H1N1 (PR8) | H3N2 (X-31) |
| Ab 004 | 12 | 6 |
| Ab 005 | 10 | 10 |
| Ab 031 | 1 | 20 |
| Ab 032 | 3 | 2 |
| Ab 037 | 4 | 8 |
| Ab 038 | 2 | 4 |

In a cytopathic effect (CPE) assay, A18 at 10 µg/mL and 50 µg/mL demonstrated near complete inhibition of X-31 infection while the AB1 anti-HA control antibody at 10 µg/mL and 50 µg/mL showed little or no inhibition of X-31 infection (FIG. 4). AB1 binds the stem region of the HA trimer.

A qPCR assay quantification of X-31 viral RNA further indicated that the IC$_{50}$ of A18 is likely significantly lower than 10 µg/mL.

RT-PCR experiments revealed that A18 could neutralize multiple H3N2 strains, including Vic75 (IC$_{50}$=2 µg/mL), X-31 (IC$_{50}$=0.4 µg/mL) and Bris07 (IC$_{50}$=~7 µg/mL).

Visual and Neutral Red Assays.

External validation of in vitro neutralization potential of Ab 032 was confirmed by visual and neutral red assays.

Briefly, the antibodies were prepared in MEM solution with 50 µg/mL gentamicin. Starting at 500 µg/mL as the highest concentration, half-log dilutions were prepared and added to 5 wells each on a 96-well plate with MDCK cells in confluency. Three wells of each dilution were infected with a low titer of virus, and two wells remained uninfected as toxicity controls. Plates were incubated 3-6 days until virus control wells reached maximum cytopathic effect (CPE). Plates were either evaluated by visual scoring of CPE or stained with neutral red dye for approximately 2 hours, then supernatant dye was removed from the wells and the incorporated dye was extracted in 50:50 Sorensen citrate buffer/ethanol, then the optical density (O.D.) was read on a spectrophotometer. O.D. were then converted to percent of cell controls and normalized to the virus control, then the concentration of test compound required to inhibit CPE by 50% (EC50) was calculated by regression analysis. The concentration of compound that would cause 50% CPE in the absence of virus was similarly calculated (CC50). The selectivity index (SI) is the CC50 divided by EC50.

The results are shown below in Table 9.

TABLE 9

Results of Visual and Neutral Red assays for Ab 032

| Virus | Visual | | | Neutral Red | | |
|---|---|---|---|---|---|---|
| | $EC_{50}$ | $CC_{50}$ | SI | $EC_{50}$ | $CC_{50}$ | SI[a] |
| H1N1 Ca04 | <0.059 | >180 | >3100 | 0.2 | >180 | >900 |
| H1N1 SI | <0.059 | >180 | >3100 | 0.08 | >180 | >2200 |
| H3N2 Bris07 | <0.059 | >180 | >3100 | 0.076 | >180 | >2400 |
| H3N2 Fujian03 | <0.059 | >180 | >3100 | 2.2 | >180 | >82 |
| H3N2 Pan99 | 19 | >180 | >9.5 | 38 | >180 | >4.9 |
| H3N2 Shangdong93 | 0.35 | >180 | >510 | 1.5 | >180 | >120 |
| H3N2 Vic75 | 1.1 | >180 | >160 | 1.3 | >180 | >140 |
| H3N2 Wyo03 | 5.3 | >180 | >34 | >180 | >180 | 0 |
| H5N1 Duck81 | <0.059 | >180 | >3100 | <0.059 | >180 | >3100 |

[a]SI is selectivity index (CC50:EC50)

The in vitro antiviral effect of Ab 044 was also examined by the assay described above. The results are shown in Table 10. In vitro, Ab 044 demonstrated dose-dependent viral inhibition in vitro with an $EC_{50}$ in the range of 0.3-6.8 ug/ml against all Group 1 and Group 2 virus strains tested.

TABLE 10

Results of Neutral Red Assay for Ab 044.

| | | | Ab 044 (µg/mL) | | |
|---|---|---|---|---|---|
| Virus | | Inoc.[a] | $EC_{50}$[b] | $CC_{50}$[c] | SI[d] |
| H1N1 | California 04/2009 | 300 | 5.1 | >500 | >98 |
| H1N1 | Solomon Islands | 160 | 1.2 | >500 | >420 |
| H3N2 | Brisbane/10/2007 | 40 | 0.3 | >500 | >1700 |
| H3N2 | Fujian/411/2003 | 65 | 0.3 | >500 | >1800 |
| H3N2 | Panama/2007/99[e] | 13 | 11 | >500 | >45 |
| H3N2 | Shangdong/09/93 | 100 | 0.6 | >500 | >890 |
| H3N2 | Victoria/3/75[e] | 12 | 4.9 | >500 | >100 |
| H3N2 | Wyoming/03/2003 | 10 | 6.8 | >500 | >74 |
| H5N1 | Duck/MN/1525/81 | 160 | 1.5 | >500 | >330 |

[a]Inoculum, 50% cell culture infectious dose (CCID50) of virus per well
[b]$CC_{50}$ = 50% toxic concentration of compound without virus added (µg/mL)
[c]$EC_{50}$ = 50% effective antiviral concentration (µg/mL)
[d]SI = CC50/EC50
[e]Mouse-adapted strain Example 5

In Vitro Drug Resistance Assay

The emergence of drug resistance was evaluated after continuous exposure of the H1N1 influenza strain PR8 to anti-influenza HA-targeting antibodies described herein. In brief, PR8 was pre-incubated with an antibody at the $IC_{50}$ for 40 minutes prior to infecting confluent MDCK cells in a 96 well plate format. Infection occurred for 1 h, at which time antibody and virus containing media was removed and replaced with virus-free media containing the antibody at the $IC_{50}$. After 48 hours incubation at 37° C., 5% $CO_2$, the supernatant was removed and viral titer was quantified by real time PCR using primers specific for the virus M protein. Once titered, viral supernatants were diluted and used to re-infect MDCK cells at the same PFU/mL following pre-incubation with drug at the $IC_{50}$. As each round of re-infection continues under drug pressure, there is an increased likelihood of selecting for resistant populations. C179 was evaluated as a control agent since it is a known anti-influenza agent that targets the stem region of HA (Okuna et al., J Virol 1993).

An example using two control anti-HA stem antibodies, AB1 and C179 (Takara), is shown in FIG. 11. Concentration of both antibodies was maintained at 1 μg/mL (starting IC50 levels for both). After 5 rounds of passaging in the presence of C179, but not in the presence of AB1, PR8 viral titers recovered, suggesting that under given conditions PR8 is resistant to escape from AB1 inhibition but not from that of C179.

Both AB1 and C179 inhibited PR8 propagation in MDCK cells, however this inhibition was lost over five rounds of passaging with C179 treatment while it was retained during AB1 treatment. Drug passaged PR8 was plaque purified to isolate ten plaques which were sequenced for HA to confirm that AB1 was not generating minority resistant populations.

These results indicated that treatment of cells with AB1 prevented production of escape mutants for at least five rounds of infectivity.

Example 6

Inhibitions of H5-Mediated Cell Fusion by Anti-HA Antibodies

Ab 032 and Ab 044 were evaluated for their abilities to block cell-cell fusion. Briefly, the assay utilizes HEK293 cells that stably express and display H5 (Viet04). The membrane-anchored hemagglutinin can be induced to convert to its fusion conformation by a brief (3 minute) exposure to low pH (5.0). A 3-hour incubation period follows to allow the cells to recover and fuse to form syncytia. A nuclear stain is used to aid in the visualization of these fusion products, and their count is used as a gauge of fusion activity. The test antibody is added either before or after the low pH treatment to determine with which stage of the fusion process it interferes.

Ab 032 or Ab 044 was added at the indicated levels to 96-well plate cultures of HEK293 cells displaying surface H5 (Viet04) either 1 hour before or immediately after induction of HA into its fusion conformation by a 3 minute low pH (5.0) or neutral pH (7.0; control). After the 3-minute induction to stimulate cell fusion, the buffer was replaced with full culture medium (pH 7.4), and the cells were allowed to recover and fuse during a 2-3-hour incubation period. Cell cultures were treated with Ab 032 at either 0, 10 or 100 μg/mL or with Ab 044 at 0, 0.2, 0.78, 3.13, 12.5, or 50 μg/mL, either before or after fusion induction by low pH or treatment with control buffer at neutral pH. The cells were then fixed and their nuclei stained with Hema-3. The degree of cell fusion was measured by the number of syncytia observed under the microscope lens (20×) per field (FIG. 15).

As shown in FIG. 15, Ab 032 is effective in inhibiting cell fusion only when added to the cell culture before the activation of HA by low pH.

As shown in FIG. 18, syncytia formation between HA-expressing cells was inhibited with pre-treatment of Ab 044 in a dose responsive manner. The result indicated that Ab 044 was able to block HA-mediated fusion if present prior to exposure to low pH buffer, presumably by binding to HA and preventing its conversion to the active/fusogenic conformation. Ab044 does not inhibit agglutination of tRBC by H1N1 virus.

Example 7

Prophylactic and Therapeutic Effect of Anti-HA Antibodies in a Murine Co-Infection Model Therapeutic administration of Ab 032 and Ab 028 rescued mice challenged with H1N1 and H3N2.

To test the effect of anti-HA antibodies in vivo, a mouse model of co-infection was used (McCullers, "Effect of Antiviral Treatment on the Outcome of Secondary Bacterial Pneumonia after Influenza" Jour. Infect. Dis. 190:519-526, 2004). Briefly, on day zero, mice were anaesthetized under isoflurane and challenged intranasally with influenza H1N1 at 100 PFU/head in a volume of 50 μL PBS. On day 7 after viral infection, mice were anesthetized under isoflurane and challenged intranasally with *Streptococcus pneumoniae* at a dose of 200 CFU/head in a volume of 50 μL PBS Animals were administered drug by intraperitoneal (IP) treatment in a 200 μL volume on the days as indicated in Table 11. Because the anaesthesia regimen may contribute to the disease state, all mice were anaesthetized at both infection steps. Lungs were harvested on day four post-viral infection for the determination of viral load and on day eleven post-viral infection for the determination of bacterial load. Lungs were stored at −80° C. until such time as all samples could be analyzed for viral and microbial loads respectively. Weight and body score of the animals were recorded daily. Animals were euthanized upon loss of considerable weight (>20%) in conjunction with physical indicators of illness such as piloerection.

A schematic of the experimental design is provided in Table 11 below. The negative control group was co-infected but received no agent other than PBS. Ribavirin, a known inhibitor of H1N1, was used as the positive control for antiviral activity. Azithromycin, a known inhibitor of *Streptococcus pneumoniae*, was used as the positive control for antibacterial activity. Ab 032 was administered as prophylaxis in a single dose 24 h prior to infection at 10 mg/kg or as therapy in a single dose 48 h after infection at 10 mg/kg. Ab 028 at 10 mg/kg was administered as therapy in a single dose 48 h post infection.

TABLE 11

Experimental Design for Murine Co-Infection Model

| Day | Negative control | Ab 032 (mg/kg) | Ab 032 (mg/kg) | Ribavarin (mg/kg) | Azithromycin (mg/kg) | Ab 028 (mg/kg) |
|---|---|---|---|---|---|---|
| −1 | — | 10 | — | — | — | — |
| 0 (H1N1 Challenge) | — | — | — | 75 | — | — |
| 1 | — | — | — | 75 | — | — |
| 2 | — | — | 10 | 75 | — | 10 |
| 3 | — | — | — | — | — | — |
| 4 (Lung Harvest) | — | — | — | — | — | — |
| 5 | — | — | — | — | — | — |
| 6 | — | — | — | — | — | — |
| 7 (Strep Challenge) | — | — | — | — | 10 | — |
| 8 | — | — | — | — | 5 | — |
| 9 | — | — | — | — | 5 | — |
| 10 | — | — | — | — | 5 | — |
| 11 (Lung Harvest) | — | — | — | — | 5 | — |
| 12 | — | — | — | — | 5 | — |
| 13 | — | — | — | — | 5 | — |
| 14 | — | — | — | — | 5 | — |

Figure 9A:
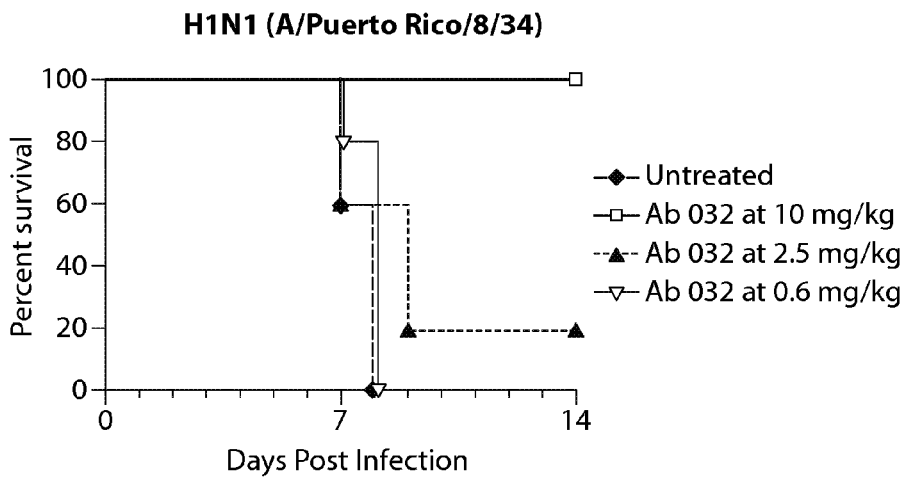
FIGS. 9A, 9B and 9C are graphs depicting percent survival of mice infected with H1N1 (A/Puerto Rico/8/34) (FIG. 9A), H3N2 (A/Victoria/03/75) (FIG. 9B) or H1N1 (A/California/04/09) (FIG. 9C). Mice were treated with various dosages of Ab 032 antibody.
Figure 9B:
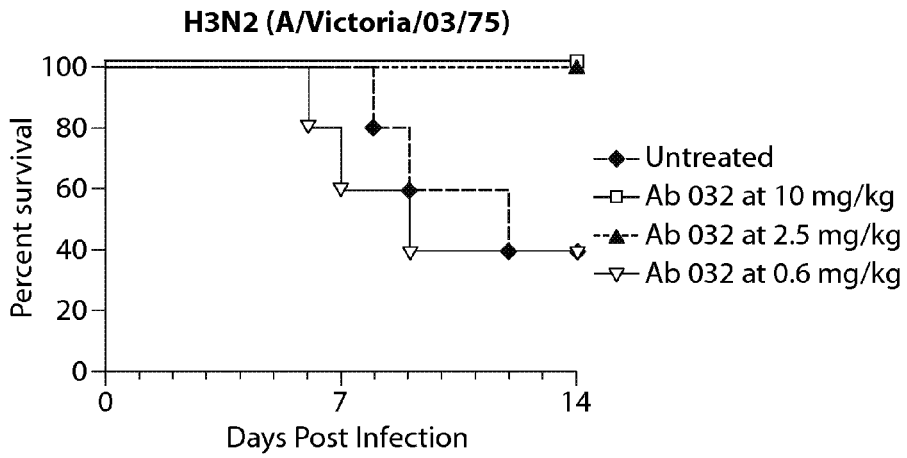
Figure 9C:
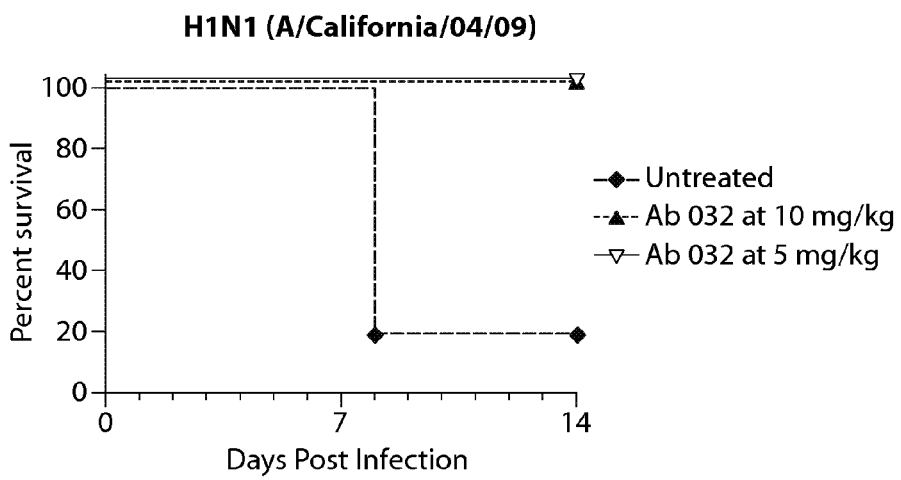
Figure 10A:
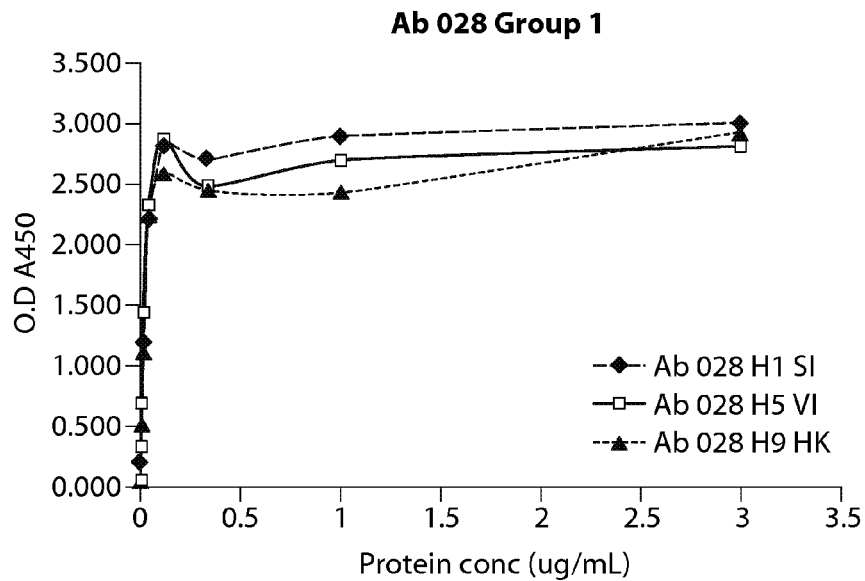
FIGS. 10A to 10D are graphs of ELISA results depicting the broad specificity of antibodies Ab 014 and Ab 028. Both antibodies are shown to bind to influenza subtypes from Group 1 (subtypes H1, H5, and H9) and from Group 2 (subtypes H3 and H7).
Figure 10B:
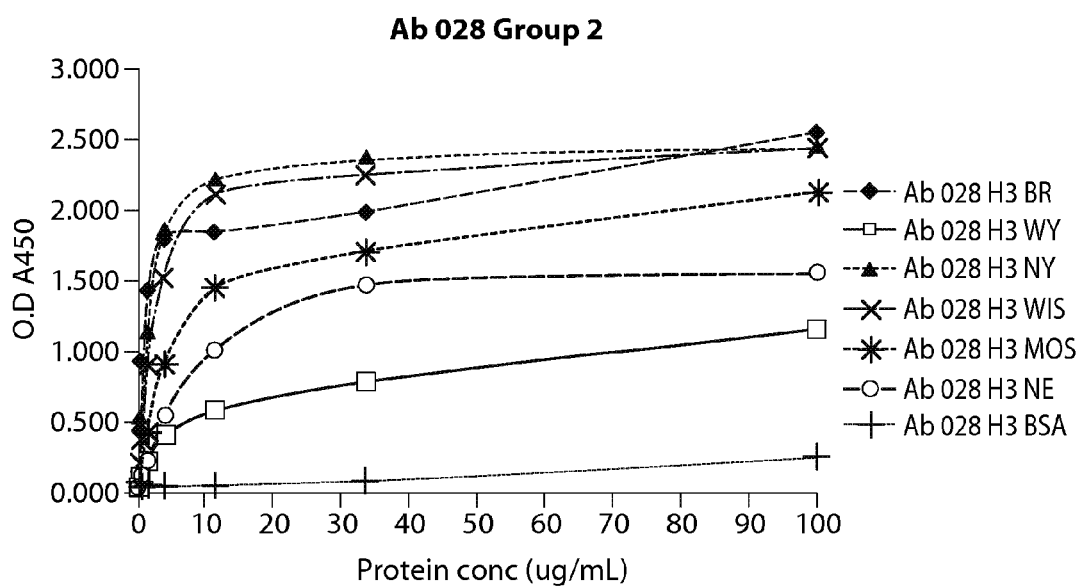
Figure 10C:
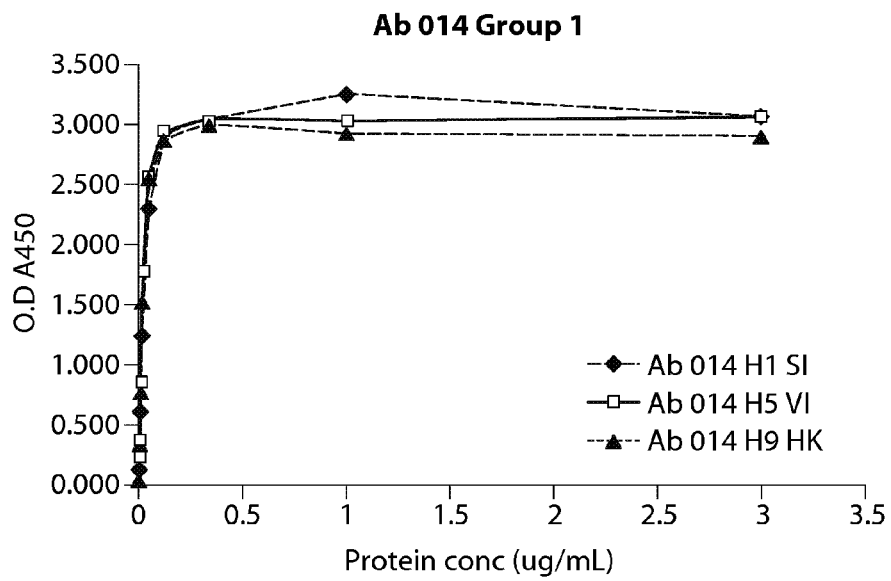
Figure 10D:
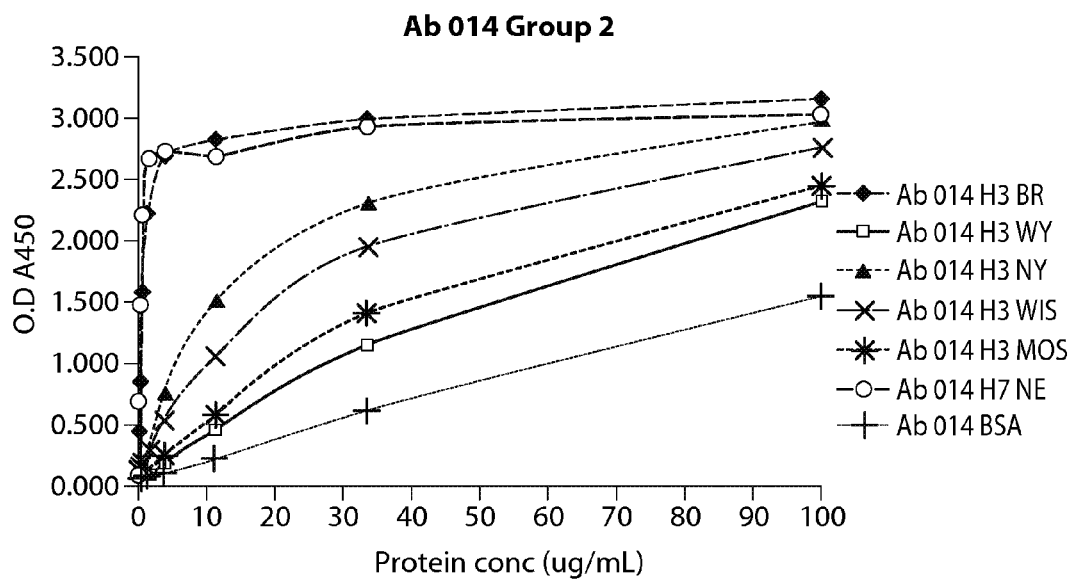
Figure 11:
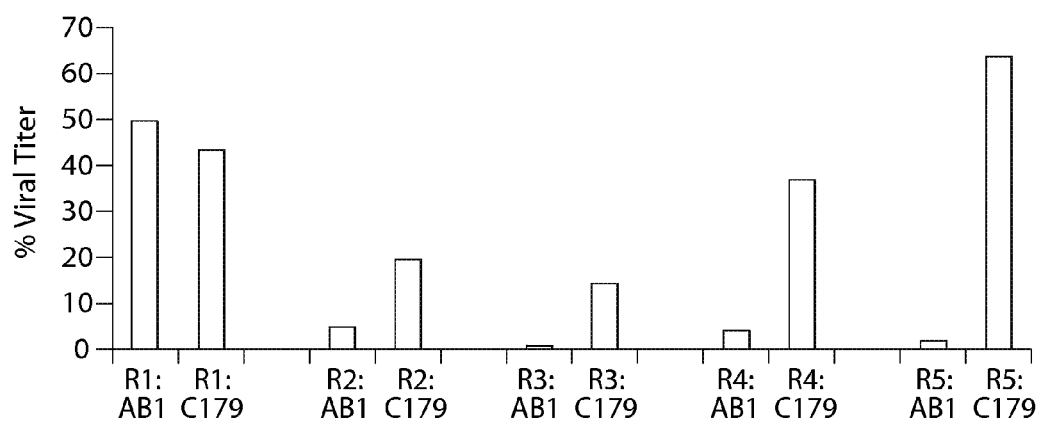
FIG. 11 is a graph depicting the inability of the influenza strain PR8 (H1N1) to overcome neutralization by AB1 after 5 rounds (R5) of propagation in the presence of AB1. On the other hand, PR8 does develop resistance to the control neutralizing antibody C179 seen by titer recovery after 4 round of selection in the presence of C179.
Figure 15:
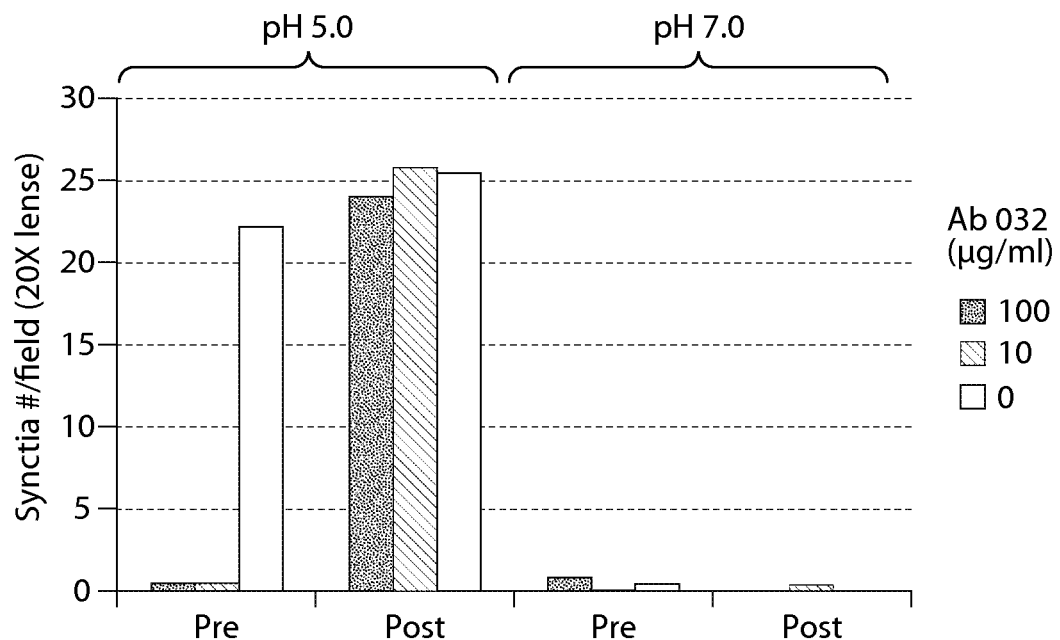
FIG. 15 is a graph depicting the number of syncytia observed after treatment of HA infected HEK293 cells with Ab 032 antibody. "Pre" and "Post" indicates treatment of the cells with antibody before induction of fusion conditions by low pH (5.0), or after induction by low pH.
Figure 16:
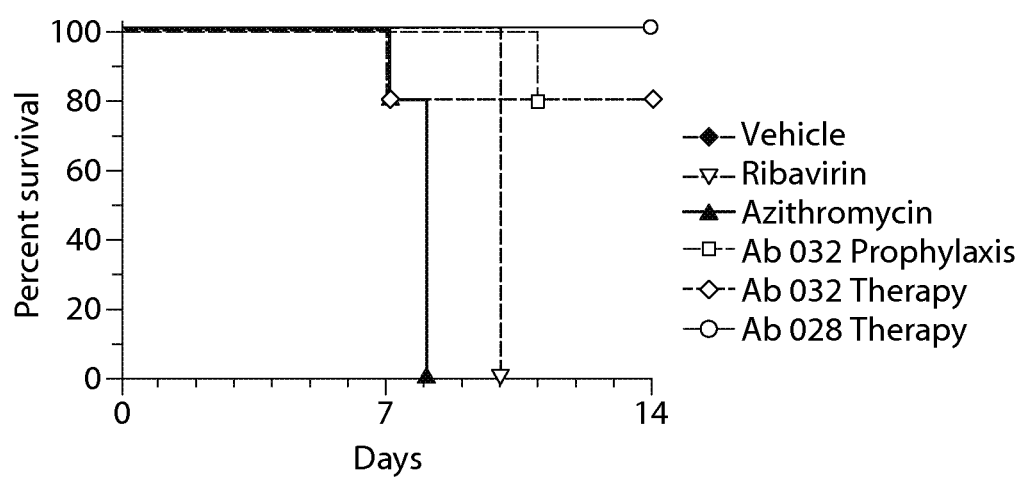
FIG. 16 is a graph depicting percent survival of mice infected with H1N1 and subsequently infected with the bacteria S. pneumococcus. Mice were treated with antibiotic or anti-HA antibody.
Figure 18:
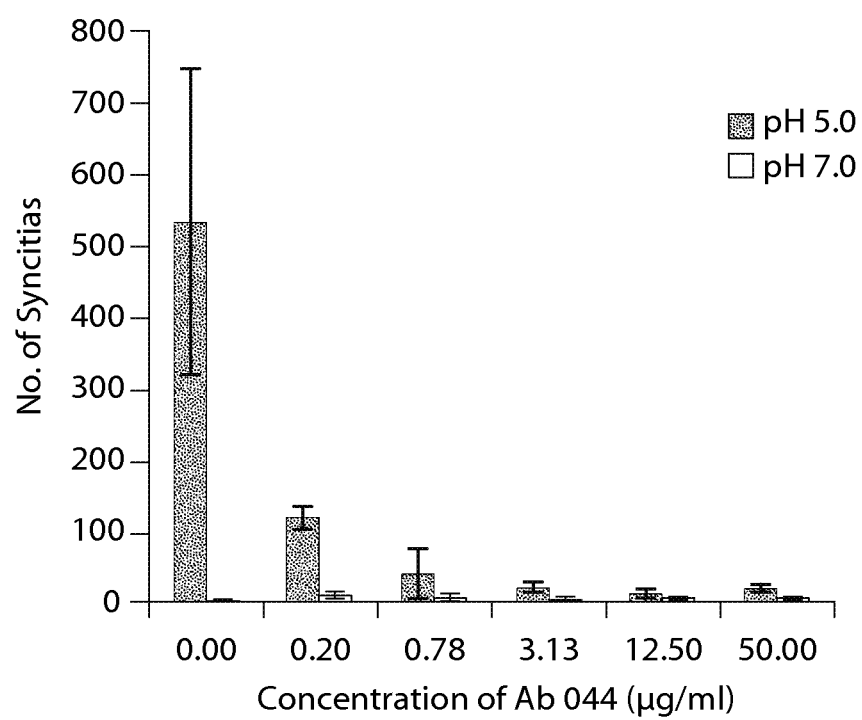
FIG. 18 is a graph depicting the number of syncytia observed after treatment of HA infected HEK293 cells with Ab 044 antibody. Left bar=pH 5.0; right bar=pH 7.0.

Survival curves were generated to describe the experimental outcome. Ribavirin treatment failed to rescue animals from death while Ab 028 therapy resulted in 100% survival (FIG. 16). Ab 032 either as prophylaxis or as therapy at 10 mg/kg protected 80% of mice from death due to secondary pneumococcal infection, despite comprising no direct antibacterial inhibitory activity (FIGS. 9A, 9B and 9C).

Taken together, Ab 028 and Ab 032 can not only impact viral-induced damage but also prevent complications from secondary, opportunistic bacterial infections, such as from *Streptococcus pneumonia*.

Example 8

Prophylactic and Therapeutic Efficacy of Anti-HA Antibodies AB1 and A18 in H1N1 and H3N2 Mouse Models The prophylactic and therapeutic efficacy of anti-HA antibodies AB1 and A18 was investigated in the H1N1 and H3N2 mouse models in essentially the same way as described in Example 10.

Figure 7A:
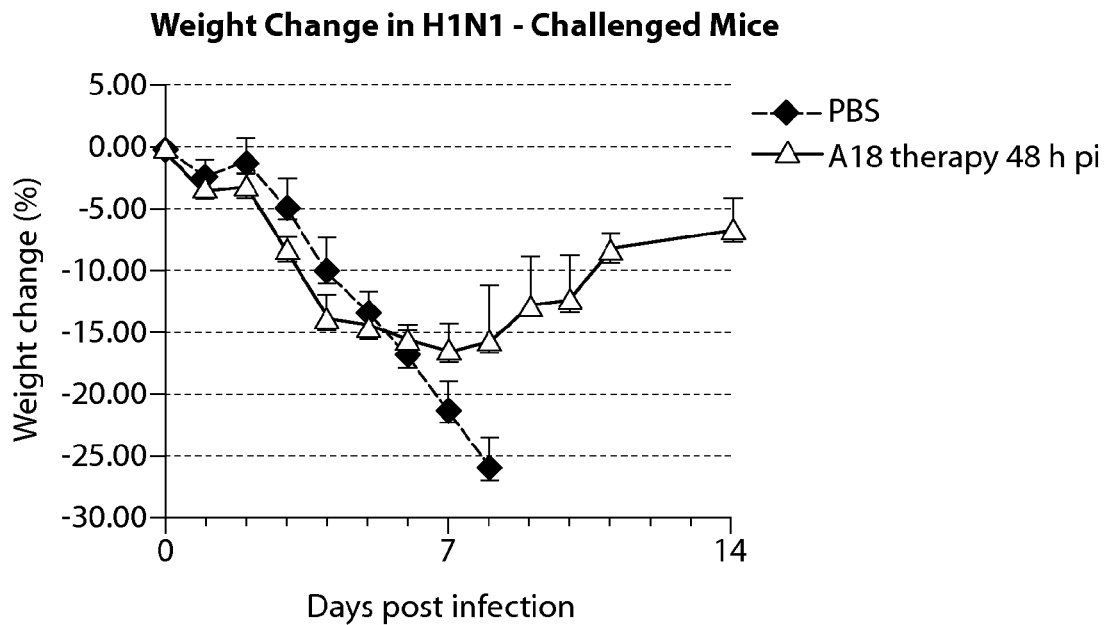
FIGS. 7A and 7B are graphs depicting the ability of the A18 antibody to protect infected mice from weight loss. The mice were infected either with H1N1 (FIG. 7A) or with H3N2 (FIG. 7B) influenza strains.
Figure 7B:
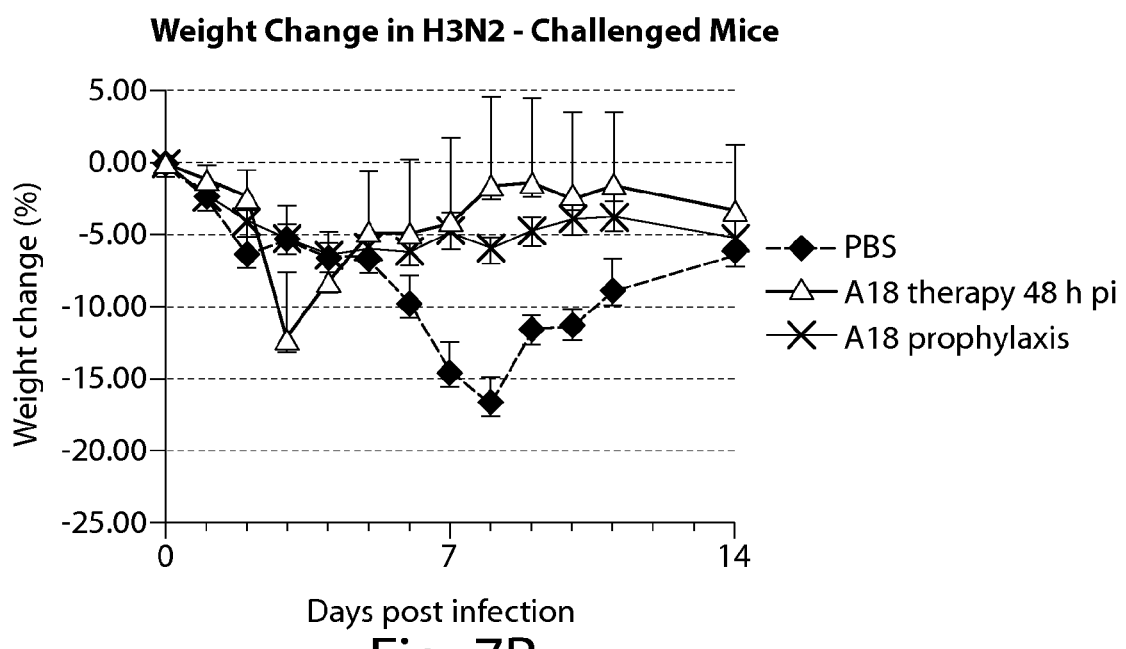

The results are shown in FIGS. 7A-7B. AB1 and A18 were efficacious at 10 mg/kg against H1N1 (PR8) when administered to mice 48 h post infection (FIG. 7A).

A18 was also efficacious at 10 mg/kg against H3N2 (Vic75) when administered to mice as prophylaxis or 48 h post infection (FIG. 7B).

Example 9

Prophylactic and Therapeutic Efficacy of Anti-HA Antibodies Ab 028, Ab 031, and Ab 032 in H1N1 and H3N2 Mouse Models The prophylactic and therapeutic efficacy of anti-HA antibodies Ab 028, Ab 031, and Ab 032 was investigated in the H1N1 and H3N2 mouse models in essentially the same way as described in Example 10.

Figure 8A:
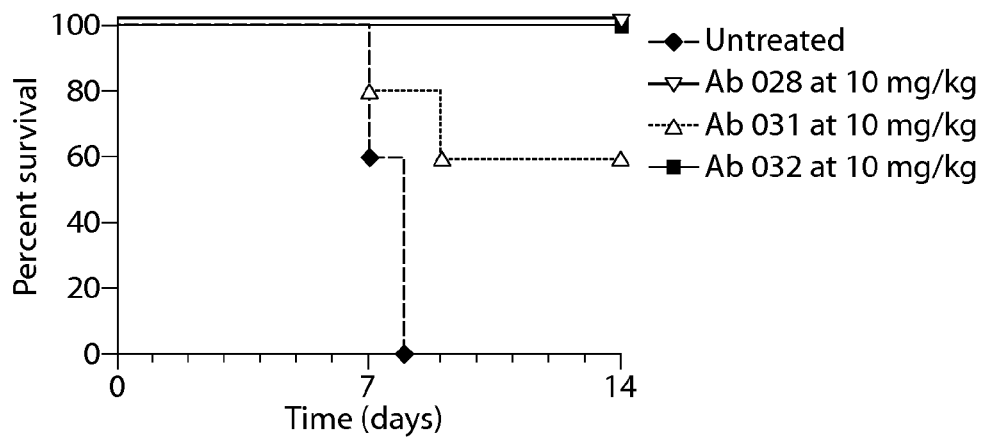
FIGS. 8A and 8B are graphs depicting percent survival of mice infected with H1N1 (FIG. 8A) or H3N2 (FIG. 8B), and treated 48 hours later with either Ab 028, Ab 031, or Ab 032 antibodies.
Figure 8B:
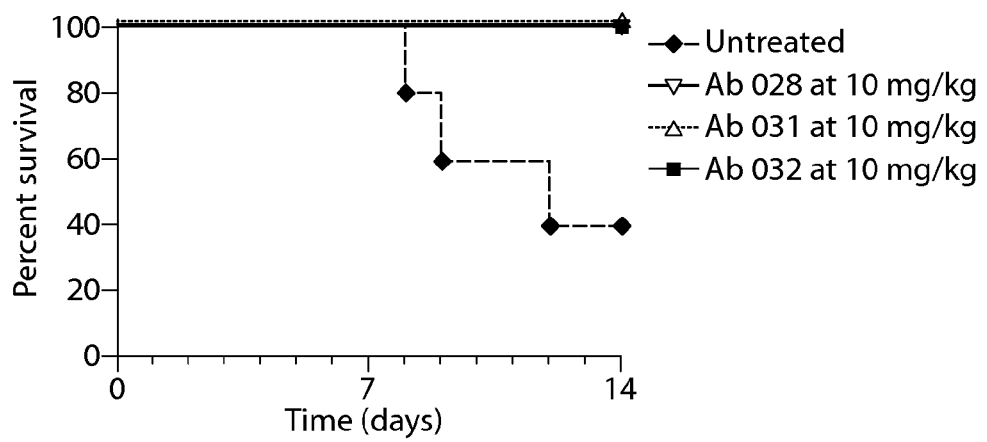

The results are shown in FIGS. 8A-8B. FIG. 8A indicates the survival time of H1N1-infected mice that were administered HA-antibody therapy 48 hours after infection. FIG. 8B indicates survival time of H3N2-infected mice administered HA-antibody therapy 48 hours after infection.

Example 10

Prophylactic and Therapeutic Efficacy of Anti-HA Antibody Ab 044 in H1N1 and H3N2 Mouse Models In vivo experiments were performed to investigate the potential of agent Ab 044 as both therapy and prophylaxis in the H1N1 and H3N2 lethal mouse models. A dose response design was utilized to discriminate the minimum amounts of drug required for therapeutic efficacy. Ab 044 is sometimes referred to herein as G044, G44, or Ab044, Briefly, both the H1N1 and H3N2 mouse models were lethal with a challenge dose of PR8 at 100 PFU/head and of Victoria at 10,000 PFU/head. Mice were anaesthetized under isoflurane and challenged IN with 50 ul viral suspension. Animals were administered agent IP in a volume of 200 ul, (a) as prophylaxis one day prior to infection, (b) as therapy two days post infection, or (c) as therapy three days post infection. Weight and appearance of the animals were recorded daily. Animals were euthanized upon loss of considerable weight (>20%) in conjunction with high body score indicating illness. Lungs were harvested from some animals on day four post infection for the determination of viral load by plaque assay. In addition, lungs on day eight were submitted for histological examination. The study was completed as follows (Table 12).

TABLE 12

Experimental Design

| Influenza Strain | Agent | Dose (mg/kg) | Time of Administration |
|---|---|---|---|
| H1N1 PR8 | PBS (Vehicle) | — | 48 h post infection |
| H1N1 PR8 | Ribavirin (+) | 75 | 3 days treatment |
| H1N1 PR8 | Ab 044 | 10 | 24 h prior to infection |
| H1N1 PR8 | Ab 044 | 2.5 | 24 h prior to infection |
| H1N1 PR8 | Ab 044 | 0.6 | 24 h prior to infection |
| H1N1 PR8 | Ab 044 | 10 | 48 h post infection |
| H1N1 PR8 | Ab 044 | 2.5 | 48 h post infection |
| H1N1 PR8 | Ab 044 | 0.6 | 48 h post infection |
| H1N1 PR8 | Ab 044 | 20 | 72 h post infection |
| H3N2 Victoria | PBS (Vehicle) | — | 48 h post infection |
| H3N2 Victoria | Ribavirin (+) | 75 | 3 days treatment |
| H3N2 Victoria | Ab 044 | 10 | 24 h prior to infection |
| H3N2 Victoria | Ab 044 | 10 | 48 h post infection |
| H3N2 Victoria | Ab 044 | 2.5 | 48 h post infection |
| H3N2 Victoria | Ab 044 | 0.6 | 48 h post infection |
| H3N2 Victoria | Ab 044 | 20 | 72 h post infection |

Summary of Results

In lethal influenza challenge models against H1N1 (A/Puerto Rico/08/1934; Group 1 virus) or H3N2 (A/Victoria/03/1975; Group 2 virus), a single injection of Ab 044 at 10 mg/kg (48 hours post infection) or 20 mg/kg (72 hours post infection) leads to 100% survival of mice (n=5 per arm) if administered therapeutically. Survival is correlated with secondary metrics, including drop in viral titer and reduction in viral-induced weight loss and body score.

In lethal influenza challenge models against H1N1 (A/Puerto Rico/08/1934) or H3N2 (A/Victoria/03/1975), a single injection of Ab 044 at up to 10 mg/kg (24 hours pre infection) leads to 100% protection of mice (n=5 per arm) if administered prophylactically. Survival is correlated with secondary metrics, including drop in viral titer and reduction in viral-induced weight loss and body score.

The detailed experimental results are presented below.

H1N1 Results

Visual Cues.

Animals were monitored for signs of illness (ruffled fur, hunching) daily. The visual score reflects the average of the group; here, lines without point markers reflect the average of recovering survivor(s).

Mice that were challenged with H1N1 appeared sick three days post infection and were euthanized on day seven, as expected. Mice that were challenged with H1N1 and treated with ribavirin exhibited negligible sign of illness and recovered fully. Mice that were treated with Ab 044 one day prior to challenge at 2.5 mg/kg or 10 mg/kg exhibited no sign of illness. Mice that were treated with Ab 044 one day prior to challenge at 0.6 mg/kg exhibited signs of illness; 60% recovered.

Agent Ab 044 was administered in a dose response manner two days post infection. Animals that received 10 mg/kg exhibited little sign of illness while animals that received 2.5 mg/kg or 0.6 mg/kg became quite ill with some deaths counted in both groups. Agent Ab 044 was also administered at 20 mg/kg three days post infection; those animals benefited from therapy, with a clear difference between treated and untreated animals on day six, and full recovery by day seven.

Animals were also monitored for weight loss. The weight change reflects the average of the group; here, lines without point markers reflect the average of recovering survivor(s).

Figure 19A:
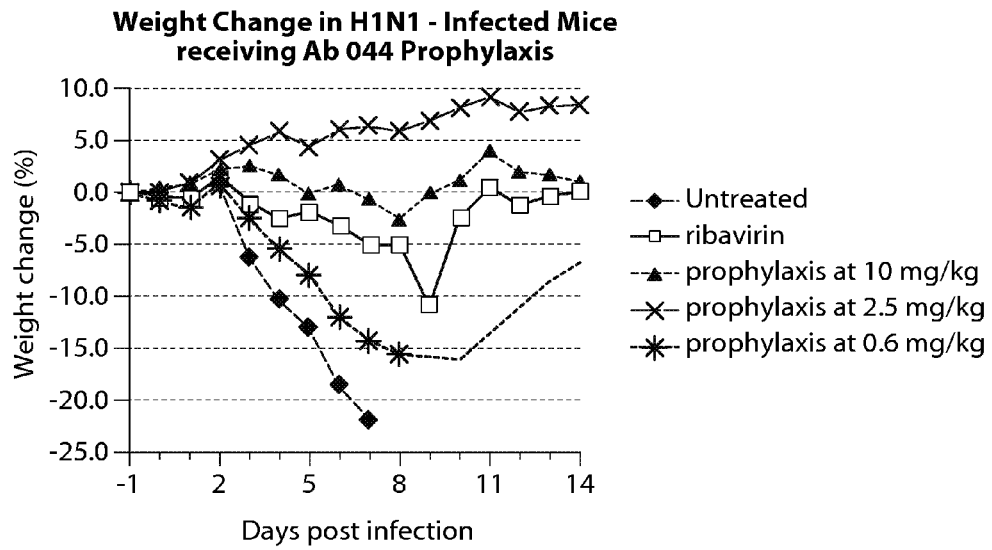
FIG. 19A shows the weight changes of mice after challenge with H1N1 strain PR8 and administration of vehicle, ribavirin, Ab 044 prophylaxis at 10 mg/kg, Ab 044 prophylaxis at 2.5 mg/kg, or Ab 044 prophylaxis at 0.6 mg/kg.

Mice that were challenged with H1N1 lost >20% weight by day seven and were euthanized, as expected. Mice that were challenged but treated with ribavirin at 75 mg/kg once per day for three days exhibited <10% weight loss and recovered. Mice that were treated with Ab 044 one day prior to challenge at 2.5 mg/kg or 10 mg/kg exhibited no weight loss or gained weight over time. Mice that were treated with Ab 044 prophylaxis at 0.6 mg/kg lost a substantial amount of weight, with three of five animals losing ≥16% body weight; two of five animals were euthanized (FIG. 19A).

Figure 19B:
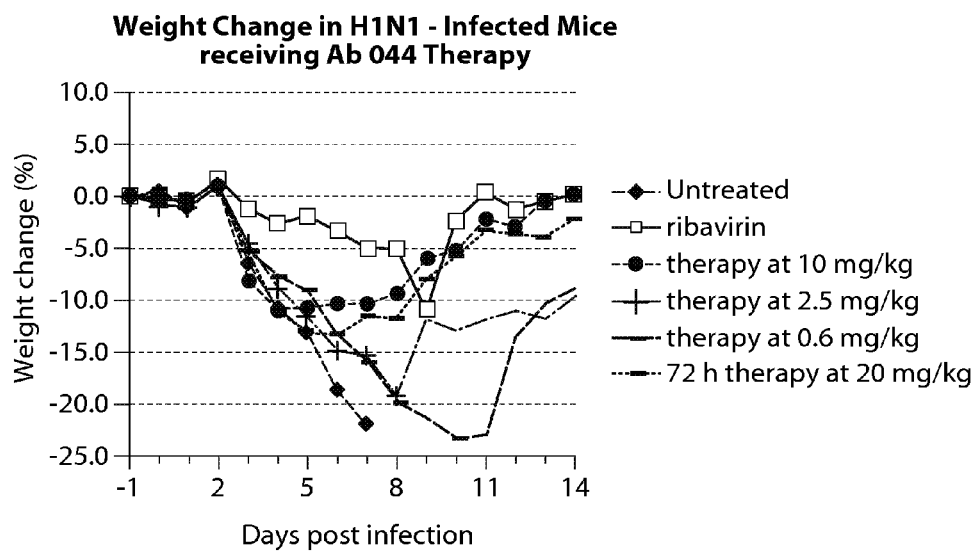
FIG. 19B shows the weight change of mice after challenge with H1N1 strain PR8 and administration of Ab 044 therapy two days post infection at 10 mg/kg, 2.5 mg/kg, or 0.6 mg/kg; or Ab 044 therapy three days post infection at 20 mg/kg.

Ab 044 therapy was administered in a dose response manner. Animals that received 10 mg/kg exhibited 10% weight loss and recovered. Animals that received 2.5 mg/kg lost substantial weight with four of five animals losing >16% body weight; three animals were euthanized. All but one animal that received 0.6 mg/kg lost >20% body weight and were euthanized (FIG. 19B).

In summary, Ab 044 prophylaxis one day prior to challenge prevented death from H1N1 infection when administered at >2.5 mg/kg. Ab 044 therapy two days post infection rescued mice from death when administered at 10 mg/kg while Ab 044 therapy three days post infection at 20 mg/kg was fully efficacious.

Viral Load.

The lung viral loads four days after H1N1 infection were assessed in a single plaque assay (Table 13). The reductions in lung viral load were more substantial than expected in three groups: ribavirin, Ab 044 prophylaxis at 10 mg/kg, and Ab 044 prophylaxis at 2.5 mg/kg. The viral loads in the samples were confirmed by a repeat plaque assay then again by qPCR (data not shown) and thus reported here.

TABLE 13

Lung Viral Load in Mice Four Days after Challenge with H1N1 PR8

| Treatment Group | Dose (mg/kg) | Lung Viral Load H1N1 (PFU/ml) | Log Reduction from Untreated |
|---|---|---|---|
| Untreated | — | 6.03 | — |
| Ribavirin | 75 | 4.38 | 1.65 |
| Ab 044 prophylaxis | 10 | 4.45 | 1.58 |
| Ab 044 prophylaxis | 2.5 | 4.08 | 1.95 |
| Ab 044 prophylaxis | 0.6 | 5.38 | 0.65 |
| Ab 044 therapy at 48 h | 10 | 5.34 | 0.69 |
| Ab 044 therapy at 48 h | 2.5 | 5.49 | 0.54 |
| Ab 044 therapy at 48 h | 0.6 | 5.74 | 0.29 |
| Ab 044 therapy at 72 h | 20 | 5.29 | 0.74 |

Comparisons were made between treatment groups to assess the significance of the reductions in lung viral load. Significance ($p<0.05$) was determined Mann Whitney U test. The lung viral load in all treatment arms was significantly different from that in the untreated group, with the exception of the Ab 044 therapy at 0.6 mg/kg at 48 h which was no different from untreated.

H3N2 Results

Visual Cues.

Animals were monitored for signs of illness (piloerection, hunching) daily.

Mice that were challenged with H3N2 appeared sick three days post infection and were euthanized on day seven, as expected. Mice that were challenged with H3N2 and treated with ribavirin exhibited no sign of illness and recovered fully, as expected. Mice that were treated with Ab 044 one day prior to challenge at 10 mg/kg exhibited no sign of illness.

Agent Ab 044 was administered in a dose response manner two days post infection. Animals that received therapy at ≥2.5 mg/kg exhibited negligible illness and recovered fully. Mice that received therapy 0.6 mg/kg were indistinguishable from mice in the untreated group, with severe illness and euthanasia required by day seven. Agent Ab 044 was also administered at 20 mg/kg three days post infection; those animals benefited from therapy, with a clear difference between treated and untreated animals on day four, and full recovery by day six.

Figure 20A:
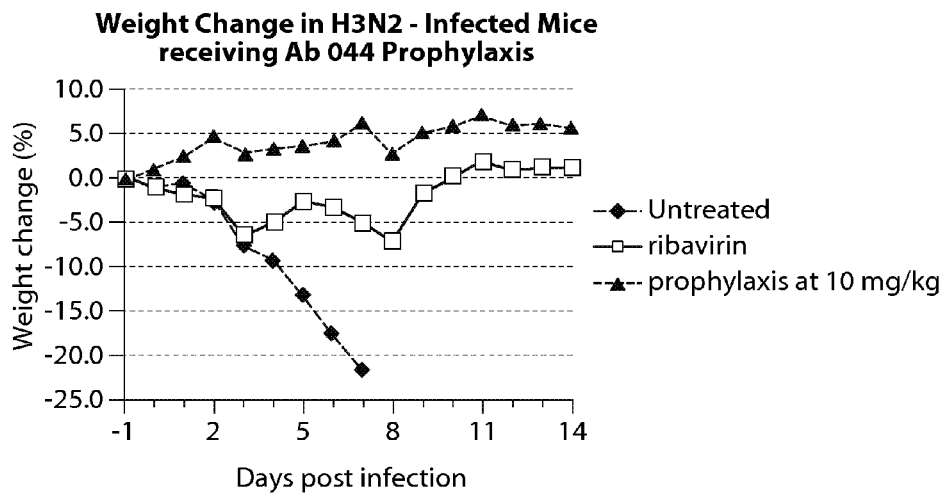
FIG. 20A shows the weight changes of mice after challenge with H3N2 strain Victoria and administration of vehicle, ribavirin, or AB 044 prophylaxis at 10 mg/kg.
Figure 20B:
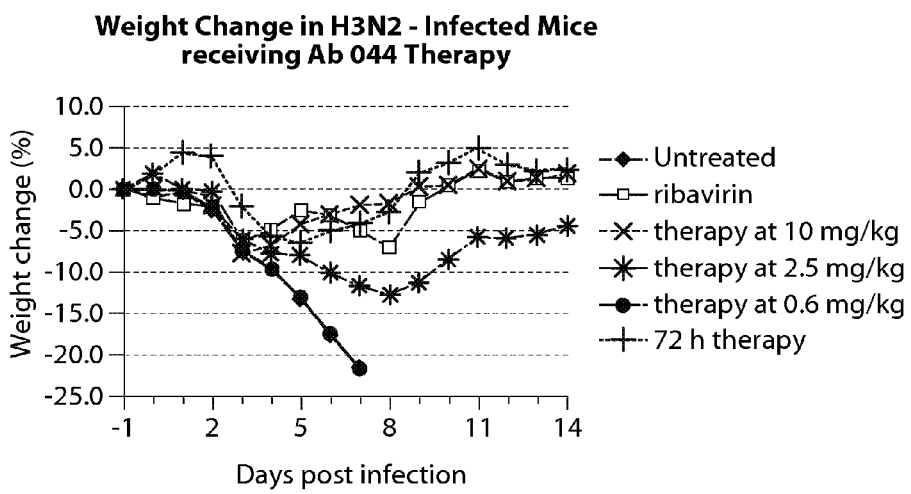
FIG. 20B shows the weight changes of mice after challenge with H3N2 and administration of Ab 044 therapy two days post infection at 10 mg/kg, 2.5 mg/kg, or 0.6 mg/kg; or Ab 044 therapy three days post infection at 20 mg/kg.

Animals were also monitored for weight loss (FIGS. 20A-20B).

All mice that were challenged with H3N2 lost >10% weight by day five and were euthanized with >20% weight loss on day seven. Mice that were challenged but treated with ribavirin at 75 mg/kg once per day for three days exhibited <10% weight loss and recovered. Mice that were treated with Ab 044 one day prior to challenge at 10 mg/kg gained weight over time (FIG. 20A).

Ab 044 therapy was administered in a dose response manner. Animals that received 10 mg/kg exhibited ≤10% weight loss and recovered. Animals that received 2.5 mg/kg lost >10% weight but recovered. Animals that received 0.6 mg/kg lost >20% body weight and were euthanized (FIG. 20B).

Viral Load.

The lung viral loads four days after H3N2 infection were assessed in a single plaque assay (Table 15).

TABLE 15

Lung Viral Load in Mice Four Days after Challenge with H3N2

| Treatment Group | Dose (mg/kg) | Lung Viral Load H3N2 (PFU/ml) | Log Reduction from Untreated |
|---|---|---|---|
| Untreated | — | 6.48 | — |
| Ribavirin | 75 | 5.66 | 0.82 |
| Ab 044 prophylaxis | 10 | 5.42 | 1.06 |
| Ab 044 therapy at 48 h | 10 | 5.46 | 1.02 |
| Ab 044 therapy at 48 h | 2.5 | 5.99 | 0.49 |
| Ab 044 therapy at 48 h | 0.6 | 6.44 | 0.04 |
| Ab 044 therapy at 72 h | 20 | 5.64 | 0.84 |

Comparisons were made between treatment groups to assess the significance of the reductions in lung viral load. Significance ($p<0.05$) was determined Mann Whitney U test. The lung viral load in all treatment arms was significantly different from that in the untreated group, with two exceptions. The lung viral loads after Ab 044 therapy at 48 h at 2.5 mg/kg or 0.6 mg/kg were no different from untreated.

Correlation Between In Vitro and In Vivo Activities.

Agent Ab 044 exhibited reproducible in vitro activity against H1N1 PR8 and H3N2 X31 (Table 17).

TABLE 17

In vitro activity of Agent Ab 044 as Measured by CPE

| Assay # | NB Ref | Agent | Lot # | H1N1 PR8 | H3N2 X31 |
|---|---|---|---|---|---|
| 27 | 56-33 | Ab 044 | 202165 | 13 | 13 |
| 27 | 56-33 | Ab 044 | 202175 | 12 | 12 |
| 27 | 56-33 | Ab 044 | 202176 | 18 | 9 |
| 27 | 56-33 | Ab 044 | 202177 | 14 | 14 |
| 28 | 56-56 | Ab 044 | 202188 | 8 | 14 |

In vitro activity has translated into in vivo activity in both models. The lung viral load on day four provided a snapshot of the infection state (FIGS. 21A-21B) and demonstrated a significant ($p<0.05$) reduction in viral load attributable to various treatment strategies with Ab 044.

A second snapshot of the infection was taken when lungs were harvested for histological examination on day eight (Tables 14 and 16). Administration of Ab 044 at 10 mg/kg as prophylaxis one day prior to challenge substantially decreased the severity of necrosis and inflammation attributable to H1N1 infection. Therapeutic administration of Ab 044 at 10 mg/kg two days after infection had no clear effect on the disruption of fine lung structure attributable to H1N1 or H3N2 infections. The expectation was that both Ab 044 prophylaxis and therapy would visibly reduce the inflammation and necrosis associated with influenza infection. Instead, there appears to be a timing component, such that delivery of Ab 044 in advance of the infection alters the cytokine cascade with its recruitment of white cells and resulting inflammation and necrosis while delivery of Ab 044 after infection minimally impacts the outcome.

Survival Curves Generated for the H1N1 Model.

Figure 22A:
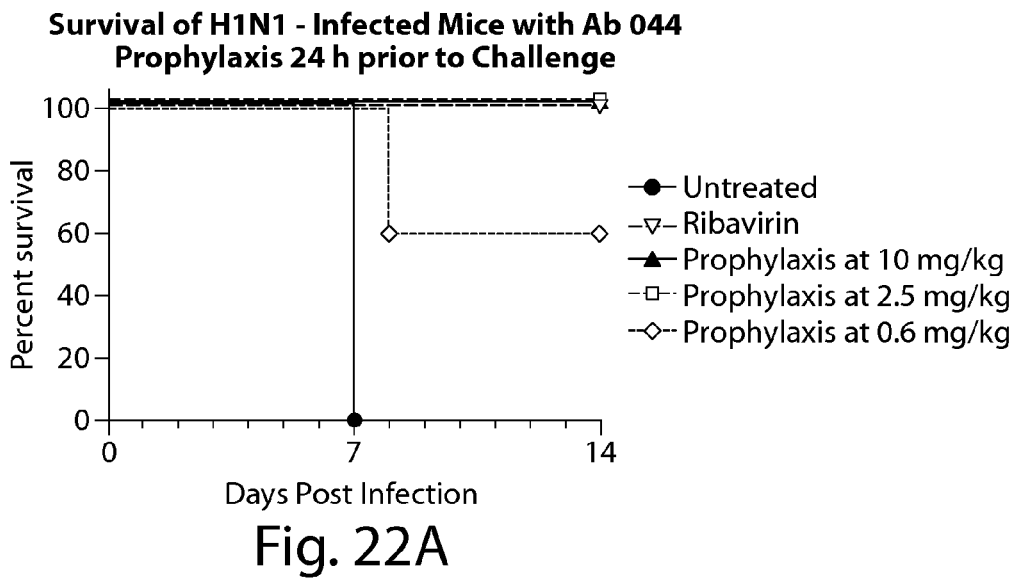
FIG. 22A shows the survival curves of mice after H1N1 challenge and administration of vehicle, ribavirin, Ab 044 prophylaxis at 10 mg/kg, 2.5 mg/kg, or 0.6 mg/kg.
Figure 22B:
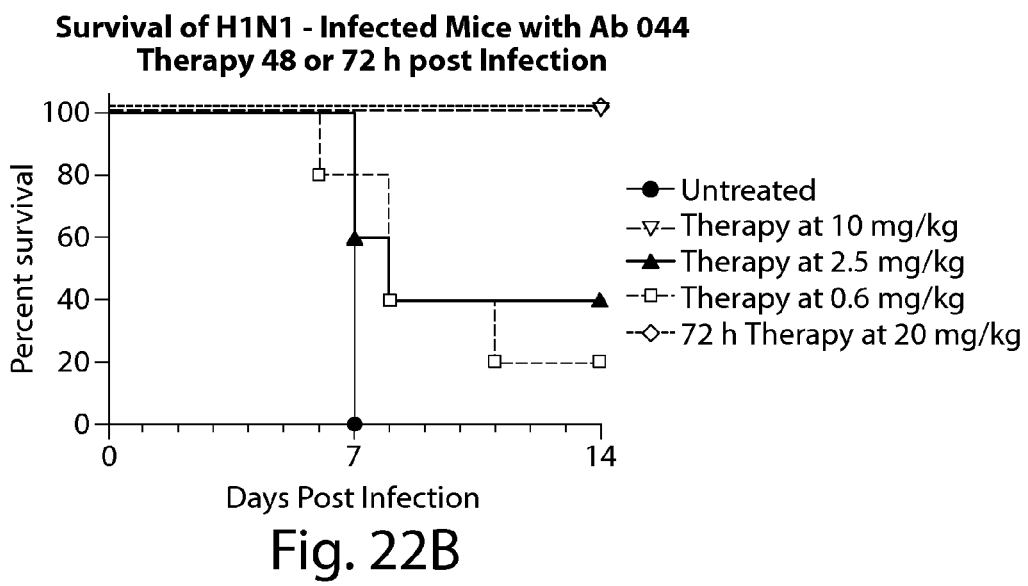
FIG. 22B shows the survival curves of mice after H1N1 challenge and administration of vehicle, Ab 044 therapy at 48 h at 10 mg/kg, at 2.5 mg/kg, at 0.6 mg/kg, or Ab 044 therapy at 72 h at 20 mg/kg.

Ab 044 prophylaxis resulted in 100% survival despite lethal challenge when administered at ≥2.5 mg/kg one day prior to infection (FIG. 22A). 100% survival of lethally infected animals was observed with Ab 044 therapy two days post infection at 10 mg/kg or Ab 044 therapy three days post infection at 20 mg/kg (FIG. 22B).

Survival Curves Generated for the H3N2 Model.

Figure 23A:
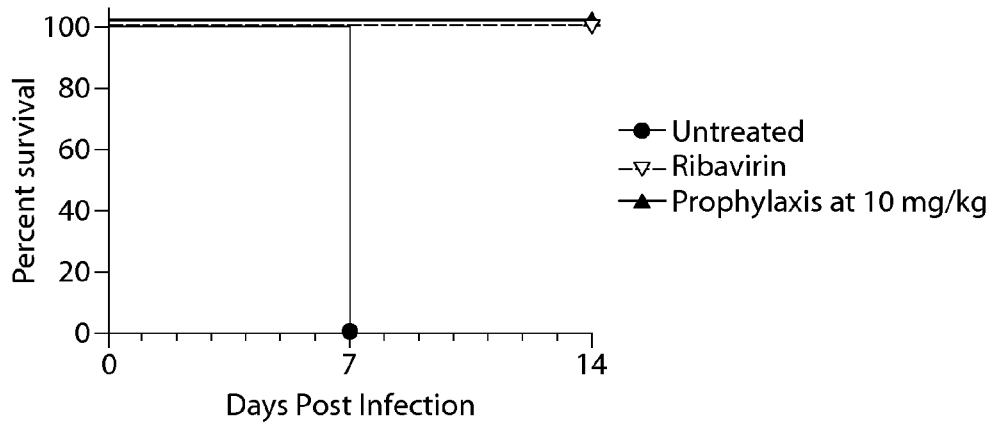
FIG. 23A shows the survival curves of mice after H3N2 challenge and administration of vehicle, ribavirin, or Ab 044 prophylaxis at 10 mg/kg.
Figure 23B:
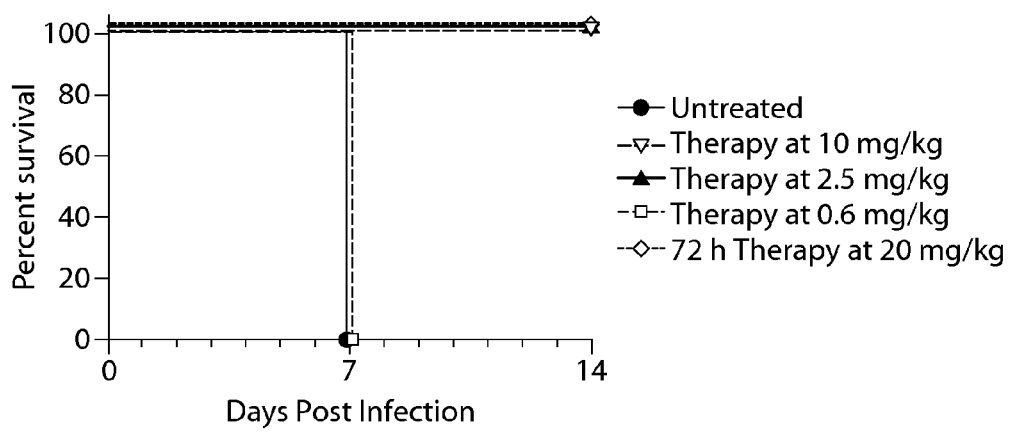
FIG. 23B shows the survival curves of mice after H3N2 challenge and administration of vehicle, Ab 044 therapy at 48 h post infection at 10 mg/kg, at 2.5 mg/kg, at 0.6 mg/kg, or Ab 044 therapy at 72 h post infection at 20 mg/kg.

Ab 044 prophylaxis at 10 mg/kg resulted in 100% survival (FIG. 23A). 100% survival of lethally infected animals was observed with Ab 044 therapy two days post infection at ≥2.5 mg/kg or Ab 044 therapy three days post infection at 20 mg/kg (FIG. 23B).

In summary, Ab 044 was efficacious in both the H1N1 and H3N2 mouse models (Table 18). Administration of Ab 044 prophylaxis at 2.5 mg/kg or higher resulted in 100% survival in the H1N1 model, a dose that would likely also achieve 100% survival in the H3N2 model. Administration of Ab 044 therapy at 48 h post infection at 10 mg/kg against the H1N1 infection and at ≥2.5 mg/kg against the H3N2 infection achieved 100% survival. Administration of Ab 044 therapy at 20 mg/kg three days post infection rescued 100% of H1N1- and H3N2-infected animals.

TABLE 18

In vivo Efficacy of Agent Ab 044 in Lethal Mouse Models

| | | | Survival (%) | |
|---|---|---|---|---|
| Agent | Administration | Dose (mg/kg) | H1N1 (PR8) | H3N2 (Vic75) |
| Untreated | — | | 0 | 0 | 0 |
| Ribavirin | Days 0, 1, 2 | 75 | 100 | 100 |
| Ab 044 | 24 h prior to infection | 10 | 100 | 100 |
| | | 2.5 | 100 | nd |
| | | 0.6 | 60 | nd |
| Ab 044 | 48 h post infection | 10 | 100 | 100 |
| | | 2.5 | 40 | 100 |
| | | 0.6 | 20 | 0 |
| Ab 044 | 72 h post infection | 20 | 100 | 100 |

Example 11

Prophylactic and Therapeutic Efficacy of Anti-HA Antibody Ab 044 in a Highly Pathogenic Avian Influenza A Virus Mouse Model Ab 044 was tested to determine its efficacy in a highly pathogenic avian influenza A H5N1 mouse model.

The objective of this study was to evaluate both prophylactic and therapeutic dosing regimens of Ab 044 for efficacy. The parameters/endpoints to be assessed included: weight loss (assessed every day for 21), virus lung titer reduction at day 4 post virus exposure, and mortality.

Materials and Methods

Animals: Female 17-20 g BALB/c mice were obtained from Charles River Laboratories (Wilmington, Mass.) for this study. They were maintained on Wayne Lab Blox and tap water ad libitum. They were quarantined for 24 h prior to use.

Viruses: Influenza A/Vietnam/1203/2004 (H5N1) virus was obtained from Dr. Jackie Katz of Centers for disease control. Mice exposed to lethal dose of the virus (5 MLD50, 5 PFU/mouse) generally die from days 8-13.

Experimental design: Groups of mice were intraperitoneally (i.p.) administered Ab 044 one time (qd) 24 h before virus exposure with doses of Ab 044 at 20, 10, or 5 mg/kg. Five of those mice were sacrificed on day 4 to determine the extent of observable gross lung pathology, the extent of lung edema in the form of increased lung weights, and to determine virus lung titers. The remaining mice were observed for mortality or for adverse events until day 21 following virus exposure. Thirteen mice were treated with 20 mg/kg Ab 044 24 h after virus exposure and 13 mice were treated with 20 mg/kg Ab 044 48 h after virus exposure with 4 mice from each group being sacrificed on day 4 post virus exposure as described of above, the remaining kept for observation of death or adverse events until day 21 following exposure to virus. An additional 7 mice received oseltamivir at 30 mg/kg/d, twice a day for five days (bid×5) beginning at time 0; being observed for mortality or adverse events until day 21 after virus exposure. Twenty mice were also treated with PSS 48 h after virus exposure, and 5 of these were sacrificed for lung titers on day 4. These mice represented the placebo controls. Mice were weighed every day up to day 21, or until death, beginning just prior to virus exposure.

Lung virus titer determination: Each mouse lung was homogenized in MEM solution and assayed in triplicate for infectious virus in MDCK cells. Samples from each test group were titered in triplicate.

Statistical analysis: Normality of the animal weights was assessed by D'Agostino & Pearson omnibus normality test. Upon finding that the weight data fit a Gaussian distribution, statistical inferences were made by two way analysis of variance followed by pairwise comparisons using Bonferroni's post-tests to compare each treatment group to the placebo treatment. Survival analysis was done using the Kaplan-Meier graphing method and a Logrank test. That analysis revealed significant differences among the treatment groups. Therefore, pairwise comparisons of survivor curves (PSS vs. any treatment) were analyzed by the Gehan-Breslow-Wilcoxon test to determine which treatment group differed significantly from the placebo group, and the relative significance was adjusted to a Bonferroni-corrected significance threshold for the number of treatment comparisons done.

Hazard ratios (HR), which compare how rapidly groups of treated mice are dying relative to untreated control groups of mice, were determined by the Mantel-Haenszel tests as part of the survival analysis program used above (GraphPad Prism® for MAC v5). The Kruskal-Wallis test, followed by Dunn's posttest for evaluating significant pairwise comparisons, was used to detect significant differences in mean day of death between treatment groups and the placebo-treated mice. Differences in the ratios of live mice/total mice for treatment groups were analyzed using contingency table analysis, and pairwise comparisons to the placebo-treated group were made by Fisher's exact tests.

Virus lung titers from each treatment group were compared to untreated controls using the analysis of variance on log-transformed values assuming equal variance and normal distribution. When significance at $P<0.05$ was achieved by ANOVA analysis of all treatments, individual treatment values were then compared to the PSS control using Newman-Keuls pair-wise comparison tests.

Summary of Results

In a lethal influenza challenge model against H5N1 (A/Vietnam/1203/2004; Group 1 virus), a single injection of Ab 044 at 10-20 mg/kg (24 hours pre-infection) or 20 mg/kg (up to 72 hours post infection) leads to 100% survival of mice (n=5 per arm) if administered therapeutically. Survival is correlated with secondary metrics, including drop in viral titer and reduction in viral-induced weight loss and body score. In this same experiment, 30 mg/kg of oseltamivir, administered twice daily for 5 days, resulted in only 60% survival.

Mice treated with Ab 044 at 10 mg/kg were observed for 14 days. Ab 044-treated mice did not lose weight or show any visible signs of stress. Histological analysis was performed on lungs harvested on day 8, where tissues were scored on the basis of observed necrosis or signs of inflammation. Neither necrosis nor inflammation was observed in the tissues of mice treated with Ab 044.

The detailed experimental results are presented below.

Results

The weight data shown in FIG. 24 suggest that the compound was well tolerated even in infected mice, since mice treated with Ab 044 did not lose significant amounts of weight compared to the starting weights of these treated mice. In addition, the Ab 044-treated, infected mice were significantly protected against weight loss due to virus infection at all concentrations of Ab 044 used from days 7 to 12 post virus exposure regardless of the dosing regimen used (FIG. 24, Table 19; P<0.01-P<0.001). The only exception to this generalization was the group of mice that was treated with Ab044 at 5 mg/kg/d (qd×1, beg. −24 h) on day 12 post virus exposure. Especially notable about the lack of weight loss was the fact that mice treated with the 20 mg/kg doses did not lose weight at all and most mice even had gained weight compared to their starting weight by the end of the experiment. This correlated very well with the fact that mice receiving Ab 044 at 20 mg/kg post virus exposure all survived the infection (FIG. 25). In fact, significant numbers (90-100%) of mice survived the infection in each treatment group receiving Ab 044 regardless of dose and treatment regimen used (P<0.0001).

TABLE 19

Table of Significant Weight Differences Illustrated in FIG. 24.

| Treatment vs. PSS | Level of Significance | | | | | | | |
|---|---|---|---|---|---|---|---|---|
| | Day 7 | Day 8 | Day 9 | Day 10 | Day 11 | Day 12 | Day 13 | Day 14 |
| Ab 044 (20 mg/kg/d, qd X 1, −24 h) | P < 0.001 | P < 0.001 | P < 0.001 | P < 0.001 | P < 0.001 | P < 0.001 | P < 0.001 | P < 0.001 |
| Ab 044 (10 mg/kg/d, qd X 1, −24 h) | P < 0.01 | P < 0.001 | P < 0.001 | P < 0.001 | P < 0.001 | P < 0.01 | P < 0.001 | P < 0.001 |
| Ab 044 (5 mg/kg/d, qd X 1, −24 h) | P < 0.01 | P < 0.01 | P < 0.001 | P < 0.001 | P < 0.001 | NS[a] | P < 0.001 | P < 0.001 |
| Ab 044 (20 mg/kg/d, qd X 1, +24 h) | P < 0.001 | P < 0.001 | P < 0.001 | P < 0.001 | P < 0.001 | P < 0.001 | P < 0.001 | P < 0.001 |

TABLE 19-continued

Figure 24:
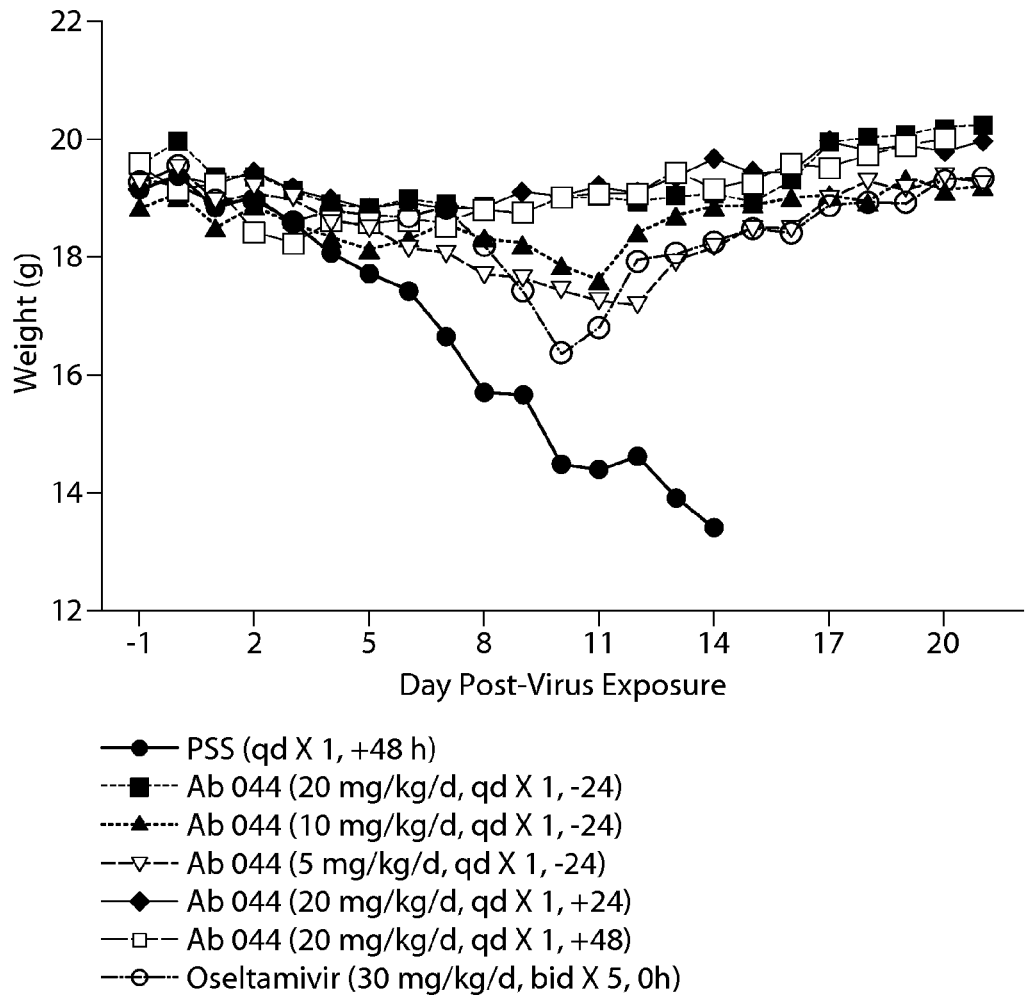
FIG. 24 depicts the effects of prophylactic and therapeutic administration of Ab 044 on the weight of BALB/c mice infected with influenza A/Vietnam/1203/2004 H5N1 virus.

Table of Significant Weight Differences Illustrated in FIG. 24.

| Treatment vs. PSS | Level of Significance | | | | | | | |
|---|---|---|---|---|---|---|---|---|
| | Day 7 | Day 8 | Day 9 | Day 10 | Day 11 | Day 12 | Day 13 | Day 14 |
| Ab 044 (20 mg/kg/d, qd X 1, +48 h) | P < 0.01 | P < 0.001 | P < 0.001 | P < 0.001 | P < 0.001 | P < 0.001 | P < 0.001 | P < 0.001 |
| Oseltamivir (30 mg/kg/d, bid X 5, 0 h) | P < 0.01 | P < 0.001 | NS | NS | P < 0.05 | NS | P < 0.01 | P < 0.001 |

[a]Not Significant (P > 0.05).

Although only 60% of mice treated with oseltamivir survived the infection, this survival rate was significantly different from the infected untreated group of mice (P=0.0055). In the past, when H5N1-infected mice have been treated with oseltamivir at 30 mg/kg/d for eight days instead of the five days as was done in the current study, 90-100% of mice treated for the longer period of time survived the virus infection with little or no weight loss. The weight loss in past studies was significantly less than for untreated, infected mice, unlike the weight loss detected at days 9, 10, and 12 post virus exposure in the current study (FIG. 24, Table 19).

Figure 25:
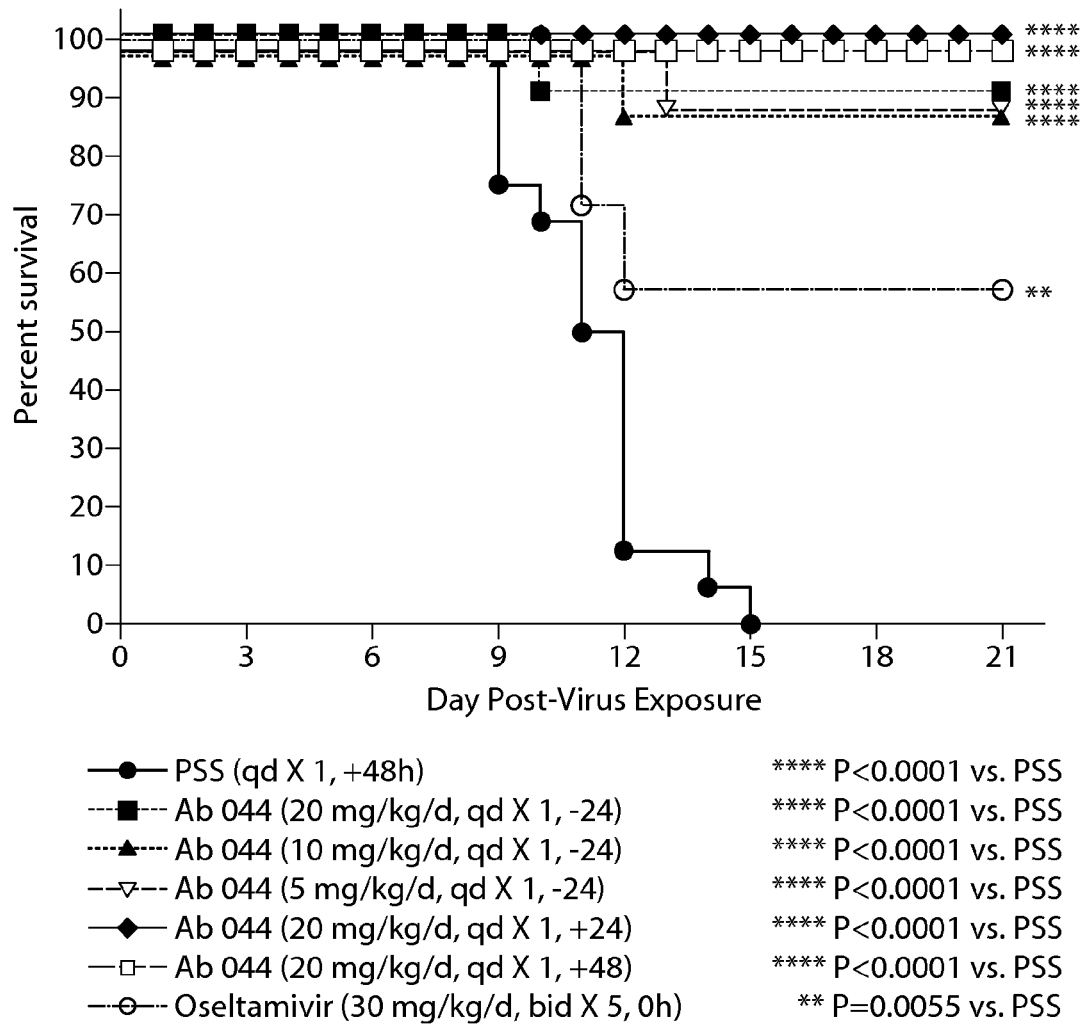
FIG. 25 depicts the effects of prophylactic and therapeutic administration of Ab 044 on survival of BALB/c mice infected with influenza A/Vietnam/1203/2004 H5N1 virus.
Figure 26:
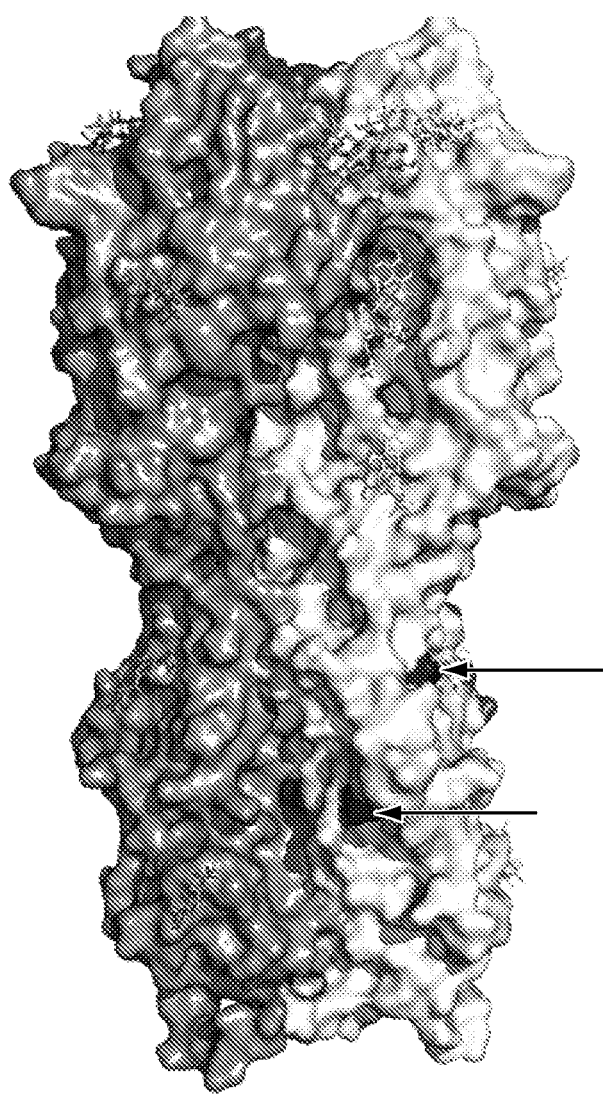
FIG. 26 is a three dimensional representation of H3 HA with the amino acids residues that are predicted to be part of Ab044 epitope but not part of FI6's epitope highlighted. That is, the highlighted amino acids are unique to Ab044's epitope.
Figure 27:
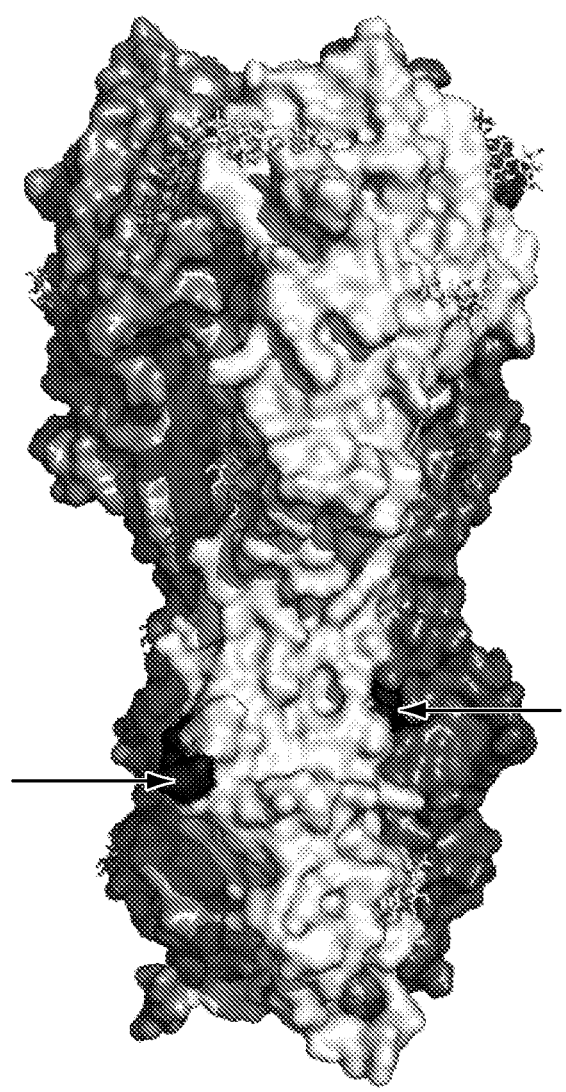
FIG. 27 is a three dimensional representation of H3 HA with the amino acid residues that are part of FI6's epitope but not predicted to be part of Ab044's epitope highlighted.

Interestingly, it was during the time period of days 9-12 post virus exposure that mice in the oseltamivir-treated group of mice succumbed to the virus infection in the current study (FIG. 25).

Not only did treatment of mice with Ab 044 significantly protect mice against death as measured by total survivors (Table 20, Live/Total column, P≤0.0019), but the treatments also profoundly affected the kinetics of death; mice treated with Ab 044 were 11-38 times less likely to die as rapidly from virus infection, if at all, than untreated, infected mice (Table 20, hazards ratios). In addition, for most Ab 044 treatment regimens the one mouse that did succumb to infection in each group did so one to two days later compared to mice that died in the placebo (PSS) group (Table 20, see mean day of death).

TABLE 20

Effects of Ab 044 on Various Mortality Parameters Measured for BALB/c Mice Infected with a Lethal Dose of Influenza A/Vietnam/1203/2004 H5N1 Virus

| Animals: Female 17-20 g BALB/c Mice | Treatment Schedule: Variable |
|---|---|
| Virus: Ia/Vietnam/1203/2004 | Treatments: |
| (H5N1) 1 LD90 | Ab044 |
| Virus route: i.n. | Oseltamivir |
| Duration of Experiment: 21 days | Treatment route: i.p. |

| Treatment | Live/Total | Mean Day of Death ± SD[a] | Median Survival (days)[b] | Hazard Ratio (95% CI)[c] |
|---|---|---|---|---|
| PSS | 0/15 | 11.3 ± 1.8 | 11.5 | — |
| Ab 044 (20 mg/kg/d, qd X 1, −24 h) | 9/10** | 10.0 ± 0.0 | Undefined | 10.9 (3.9-32.3) |
| Ab 044 (10 mg/kg/d, qd X 1, −24 h) | 9/10** | 12.0 ± 0.0 | Undefined | 14.2 (4.7-42.6) |
| Ab 044 (5 mg/kg/d, qd X 1, −24 h) | 9/10** | 13.0 ± 0.0 | Undefined | 15.74 (5.3-46.7) |
| Ab 044 (20 mg/kg/d, qd X 1, +24 h) | 9/9[††] | >21*** | Undefined | 38.0 (12.2-116.6) |
| Ab 044 (20 mg/kg/d, qd X 1, +48 h) | 9/9[††] | >21*** | Undefined | 38.0 (12.2-116.6) |
| Oseltamivir (30 mg/kg/d, bid X 5, 0 h) | 4/7* | 11.3 ± 0.6 | Undefined | 4.8 (1.6-14.3) |

[a]The average time to death among animals succumbing to the infection.
[b]The time at which fractional survival equals 50%. (i.e., the calculated time at which half the subjects have died and half are still alive.)
[c]Hazard ratios are calculated relative to the placebo.
Live/Total:
*P = 0.02,
**P = 0.0019 vs. Placebo,
[††]P = 0.0014 vs. Placebo.
Mean Day of Death:
***P < 0.001 vs. Placebo.

No gross lung pathology or edema was detected at day 4 post virus exposure, because these infection related phenomena are usually observed at day 8 or later after virus exposure in the H5N1 mouse model. However, the virus lung titers were significantly for reduced in mice treated doses of Ab 044 at 10 mg/kg or greater regardless of when Ab 044 was administered (Table 21, P<0.05, P<0.01). The virus lung titers from mice treated with 5 mg/kg of Ab 044 were lower, but statistically similar to the virus lung titers detected in the lungs of mice from the placebo group.

Thus, reduction of virus lung titers early in the infection by Ab 044 treatment at 24 h post virus exposure likely reduced the amount of antigen produced that was capable of inducing a pathogenic hyperinflammatory response characteristic of H5N1 pulmonary infections in mice (Otte et al., Am J Pathol 179:230-239 (2011)). However, the virus titer data from the treatment beginning at 48 h post virus exposure seemingly could contradict that hypothesis, since day 4 titers for that group of mice were near the levels of the placebo-treated mice. It may be that treatment at 48 h kept the titers sufficiently low for the next 24 h to avoid a hyper-inflammatory response to the original insult. It is also possible that the compound did not have sufficient time to exert its antiviral effect between 48 hrs and the 4-day virus titer assay, but it had sufficient activity by day 9 when deaths began to protect the mice from death.

TABLE 21

Effects of Ab 044 on Lung Virus Titer Measured for BALB/c Mice Infected with a Lethal Dose of Influenza A/Vietnam/1203/2004 H5N1 Virus

| Animals: Female 17-20 g BALB/c Mice | Treatment Schedule: Variable |
|---|---|
| Virus: Ia/Vietnam/1203/2004 | Treatments: |
| (H5N1) 1 LD90 | Ab044 |
| Virus route: i.n. | Oseltamivir |
| Duration of Experiment: 21 days | Treatment route: i.p. |

| Treatment | Lung Virus Titers ± SD |
|---|---|
| PSS | 5.67 ± 0.49 |
| Ab 044 (20 mg/kg/d, qd X 1, −24 h) | 3.54 ± 0.91** |

TABLE 21-continued

Effects of Ab 044 on Lung Virus Titer Measured for BALB/c Mice Infected with a Lethal Dose of Influenza A/Vietnam/1203/2004 H5N1 Virus

| | |
|---|---|
| Ab 044 (10 mg/kg/d, qd X 1, −24 h) | 3.01 ± 1.05** |
| Ab 044 (5 mg/kg/d, qd X 1, −24 h) | 4.40 ± 0.62 |
| Ab 044 (20 mg/kg/d, qd X 1, +24 h) | 3.98 ± 0.98* |
| Ab 044 (20 mg/kg/d, qd X 1, +48 h) | 5.24 ± 0.88 |

*$P < 0.05$,
**$P < 0.01$ vs. Placebo.

In conclusion, at doses of 2.5 and 10 mg/kg, Ab 044 gives 100% protection from lethal challenge of H1N1 and H3N2, respectively. Furthermore, when the monoclonal antibody was administered up to 72 hours after infection, it was completely effective in treating the infection with 100% survival for both H1N1 and H3N2 virus subtypes. Ab 044, regardless of the dose or dosing regimen used (prophylactic or therapeutic), was extremely efficacious in protecting BALB/c mice against death due to an extremely lethal infection with a highly pathogenic avian influenza A H5N1 virus. Moreover, the same Ab 044 treatment regimens were extremely effective in preventing weight loss due to virus infection and in significantly reducing day 4 virus lung titers.

Example 12

Competition Assays for Antibody Epitope Mapping

Competition ELISA is used to test whether a monoclonal antibody (mAb1) alters the ability of another antibody (e.g., mAb2, or test antibody) to bind the target. To perform the assay, a 96-well flat bottom NUNC Maxisorp plates (Cat#439454) is coated with the desired hemagglutinin (HA) diluted to 2 μg/mL in 1×PBS, 100 μL per well. The plate is sealed with a plate cover, and allowed to incubate overnight at 4° C. static. The plates are then washed thrice with 1×PBS+0.05% Tween-20 (PBST). The HA-coated plates are blocked with 200 μL of 5% Blotto (Santa Cruz Biotechnology Cat#sc-2325) in 1×PBS and incubated at room temperature for 1 hour. Subsequently, the plates are washed thrice with PBST. One hundred microliters of mAb1 is then added to the wells at saturation concentration (determined previously) and incubated for 2 hours at room temperature. Post-incubation, the plates are washed to remove unbound mAb1 and the test antibody (mAb2) is diluted to the desired starting concentration in PBST and loaded on the plate. The plates are incubated at room temperature for 2 hours, static and then washed thrice with PBST, and tapped to dry. Appropriate HRP-conjugated antibody at desired concentration is diluted in PBST, and 100 μL of HRP-antibody is loaded per well to all wells. After incubation for 1 hour at room temperature, the plates are washed thrice with PBST. TMB solution (KPL Cat#50-76-00) is prepared prior to use and allowed to warm to room temperature. The TMB solution in then added to the plate and developed until max OD is between 2 and 3 absorbance units at 650 nm as read on a 96-well plate reader (SpectraMax M2e or similar). Upon attainment of desired OD, the reaction quenched with 1N $H_2SO_4$ and the OD at 450 nm is read. The OD is plotted as a function of concentration and the Kd is calculated using a four-parametric fit. The existence of an overlapping epitope between mAb1 and mAb2 will be indicated by a significant drop in binding of mAb2 to HA in the presence of mAb1 relative to that observed in its (mAb1) absence in control wells.

Example 13

Making and Testing of Candidate Antibodies

Recombinant Expression of Antibody:

For recombinant expression of an IgG1, the $V_H$ and $V_L$ regions of the antibody can be either isolated from B-cells, hybridomas or synthesized and sub-cloned into plasmids containing $C_{H1-H2-H3}$ and $C_L$ respectively. Recombinant expression of antibody can be carried out in mammalian cells such as HEK 293-F FreeStyle suspension cells (Invitrogen, Carlsbad, Calif.) cultured in 293-F FreeStyle Expression Medium (Invitrogen, Carlsbad, Calif.) maintained at 37° C., 80% humidity and 8% $CO_2$. Cells (with >95% viability) are transfected with Poly-ethylene-imine Max (PEI-MAX, Poly-Sciences) with equivalent amounts of HC and LC containing plasmids. Seven days post-infection, the cells are harvested by spinning the cells at 4000 rpm for 15 min at 4° C. and filtered through a 0.45 μm filter system (Nalgene) and supplemented with 1:1000 diluted protease inhibitor cocktail (Calbiochem).

The antibody is purified from the supernatant using a Protein A resin (Pierce) filled column on a AKTA Purifier FPLC system. The antibody is eluted with a 100 mM Glycine-HCl buffer (pH 2.5) buffer and pH neutralized by the addition of 10% 1M Tris-base 2.5 M NaCl (pH 8.5). The purified sample is then buffer exchanged into 1×PBS (pH 7.4) and concentrated by ultrafiltration/diafiltration (UF/DF) using a 30 KDa MWCO spin filter (Millipore). Purified antibody is quantified using NanoDrop spectrophotometer.

ELISA Binding Assays

Recombinant hemagglutinin is diluted to 2 μg/mL in PBS and 100 μl is used to coat 96-well microtiter plates (Immuno™ Maxisorp, Nunc). The plates are incubated at 4° C. overnight. The plates are subsequently washed thrice with 1×PBS+0.05% Tween-20 (PBST) and then blocked with 200 μL of 5% Blotto (Santa Cruz Biotechnology) in 1×PBS for 1 hr. The plates are then thrice washed with PBST and antibody serially diluted in PBST is added and incubated for 2 hrs at room temperature. The wells are subsequently washed with PBST and the bound IgG1 is detected using 100 μl of 1:1000 HRP-conjugated anti-hIgG1. After 1 hr incubation, the plates are washed and the reaction was developed using TMB solution (KPL) and stopped by addition of 1N $H_2SO_4$. The absorbance at 450 nm is measured using d TMB on a SpectraMax M2e plate reader.

Microneutralisation Assays

In vitro neutralization assay is performed using the protocol described by Sidwell and Huffman to test the ability of the antibody to inhibit infectivity of influenza virus in MDCK cells. Briefly, the antibody is prepared in half-log dilutions starting with 500 μg/mL in MEM solution with 50 μg/mL of gentamicin. Each dilution is added to 5 wells of a 96-well plate with confluent cells. Three wells of each dilution is infected with a low titer of virus, and two wells remain uninfected as toxicity controls. Ribavirin is included as a control. Plates are incubated 3-6 days until virus control wells reached maximum cytopathic effect (CPE). Plates are then stained with neutral red dye for approximately 2 hours, then supernatant dye is removed from the wells and the incorporated dye is extracted in 50:50 Sorensen citrate buffer/ethanol, and the optical density is read on a spectrophotometer. Optical densities are converted to percent of cell controls and normalized to the virus control, and the concentration of test compound required to inhibit CPE by 50% ($EC_{50}$) is calculated by regression analysis. The concentration of compound that would cause 50% CPE in the absence of virus was similarly calculated ($CC_{50}$). The selective index (SI) is the $CC_{50}$ divided by $EC_{50}$.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

EQUIVALENTS

Those skilled in the art will recognize, or be able to ascertain using no more than routine experimentation, many equivalents to the specific embodiments of the invention described herein. Such equivalents are intended to be encompassed by the following claims

We claim:

1. An isolated antibody molecule comprising:
   (a) a heavy chain immunoglobulin variable region segment comprising:
      a CDR1 comprising the sequence S-Y-A-M-H (SEQ ID NO:68);
      a CDR2 comprising the sequence V-V-S-Y-D-G-N-Y-K-Y-Y-A-D-S-V-Q-G (SEQ ID NO:69); and
      a CDR3 comprising the sequence D-S-R-L-R-S-L-L-Y-F-E-W-L-S-Q-G-Y-F-N-P (SEQ ID NO:70); and
   (b) a light chain variable region segment comprising
      a CDR1 comprising the sequence Q-S-I-T-F-D-Y-K-N-Y-L-A (SEQ ID NO:145);
      a CDR2 comprising the sequence W-G-S-Y-L-E-S (SEQ ID NO:72); and
      a CDR3 comprising the sequence Q-Q-H-Y-R-T-P-P-S (SEQ ID NO:73).

2. The isolated antibody molecule of claim 1, comprising a heavy chain immunoglobulin variable region segment that comprises SEQ ID NO: 25.

3. The isolated antibody molecule of claim 1, comprising a light chain immunoglobulin variable region segment that comprises SEQ ID NO: 52.

4. The isolated antibody molecule of claim 1, comprising:
   a heavy chain immunoglobulin variable region segment that comprises SEQ ID NO: 25 and
   a light chain immunoglobulin variable region segment that comprises SEQ ID NO: 52.

5. The isolated antibody molecule of claim 1, comprising a tetramer of:
   two heavy chain immunoglobulin variable region segments, each comprising SEQ ID NO: 25 and
   two light chain immunoglobulin variable region segments, each comprising SEQ ID NO: 52.

6. The isolated antibody molecule of claim 1, wherein said antibody molecule comprises a full length antibody.

7. The isolated antibody molecule of claim 1, wherein said antibody molecule comprises a humanized antibody molecule.

8. The isolated antibody molecule of claim 7, wherein said antibody molecule comprises two heavy claim variable regions and two light chain variable regions.

9. The isolated antibody molecule of claim 7, wherein said antibody molecule is an IgG antibody.

* * * * *